United States Patent
McDevitt et al.

(10) Patent No.: US 6,649,403 B1
(45) Date of Patent: Nov. 18, 2003

(54) METHOD OF PREPARING A SENSOR ARRAY

(75) Inventors: John T. McDevitt, Travis, TX (US); Eric V. Anslyn, Austin, TX (US); Jason B. Shear, Austin, TX (US); Dean P. Neikirk, Travis, TX (US)

(73) Assignee: Board of Regents, The University of Texas Systems, Austin, TX (US)

( * ) Notice: Subject to any disclaimer, the term of this patent is extended or adjusted under 35 U.S.C. 154(b) by 0 days.

(21) Appl. No.: 09/775,353

(22) Filed: Jan. 31, 2001

Related U.S. Application Data

(60) Provisional application No. 60/179,369, filed on Jan. 31, 2000, provisional application No. 60/179,424, filed on Jan. 31, 2000, provisional application No. 60/179,294, filed on Jan. 31, 2000, provisional application No. 60/179,380, filed on Jan. 31, 2000, provisional application No. 60/179,292, filed on Jan. 31, 2000, and provisional application No. 60/179,293, filed on Jan. 31, 2000.

(51) Int. Cl.[7] .................. C12M 1/34; G01N 33/543; G01N 33/551
(52) U.S. Cl. ................ 435/288.5; 435/287.1; 435/287.3; 435/288.2; 435/288.4; 436/518; 436/524; 436/531
(58) Field of Search ............ 422/68.1, 67, 82.07, 422/55, 58; 435/6, 7.1, 286.1, 287.1, 288.2, 288.4, 288.5, 287.3; 436/518, 524, 531

(56) References Cited

U.S. PATENT DOCUMENTS

| | | |
|---|---|---|
| 3,696,932 A | 10/1972 | Rosenberg |
| 3,701,433 A | 10/1972 | Krakauer et al. |
| 3,709,868 A | 1/1973 | Spector |
| 3,843,696 A | 10/1974 | Wagner et al. |
| 3,856,469 A | 12/1974 | Schneider et al. |
| 3,876,504 A | 4/1975 | Koffler |
| 3,954,623 A | 5/1976 | Hammer et al. |
| 3,964,974 A | 6/1976 | Banauch et al. |
| 4,036,946 A | 7/1977 | Kleinerman |
| 4,050,898 A | 9/1977 | Goffe, deceased et al. |
| 4,069,017 A | 1/1978 | Wu et al. |
| 4,115,277 A | 9/1978 | Swank |
| 4,189,382 A | 2/1980 | Zine, Jr. |
| 4,200,613 A | 4/1980 | Alfrey et al. |
| 4,245,041 A | 1/1981 | Denney |

(List continued on next page.)

FOREIGN PATENT DOCUMENTS

| | | |
|---|---|---|
| EP | 439182 | 4/1996 |
| WO | 90/01069 | 2/1990 |
| WO | 92/0880 | 1/1992 |
| WO | 97/35189 | 9/1997 |
| WO | 98/40726 | 9/1998 |
| WO | 98/53300 | 11/1998 |
| WO | 99/17139 | 4/1999 |
| WO | 99/18434 | 4/1999 |
| WO | 00/04372 | 1/2000 |

OTHER PUBLICATIONS

Lavigne et al., "Solution–Based Analysis of Multiple Analytes by a Sensor Array: Toward the Development of an "Electronic Tongue"", J. Am. Chem., 1998, 120:25, 6429–6430.*

Adler, M; Nicholson, J.D.; Hackley, B.E., Jr. "Efficacy of a novel metalloprotease inhibitor on bot

U.S. PATENT DOCUMENTS

| | | | |
|---|---|---|---|
| 4,246,107 A | 1/1981 | Takenaka et al. | |
| 4,294,817 A | 10/1981 | Burgett | |
| 4,344,743 A | 8/1982 | Bessman et al. | |
| 4,378,429 A | 3/1983 | Modrovich | |
| 4,477,575 A | 10/1984 | Vogel et al. | |
| 4,567,149 A | 1/1986 | Sell et al. | |
| 4,596,657 A | 6/1986 | Wisdom | |
| 4,623,461 A | 11/1986 | Hossom et al. | |
| 4,661,445 A | 4/1987 | Saxinger et al. | |
| 4,672,028 A | 6/1987 | Olson | |
| 4,683,195 A | 7/1987 | Mullis et al. | |
| 4,683,202 A | 7/1987 | Mullis | |
| 4,753,776 A | 6/1988 | Hillman et al. | |
| 4,795,698 A | 1/1989 | Owen et al. | |
| 4,810,378 A | 3/1989 | Carmen et al. | |
| 4,813,277 A | 3/1989 | Miller et al. | |
| 4,828,386 A | 5/1989 | Matkovich et al. | |
| 4,855,225 A | 8/1989 | Fung et al. | |
| 4,908,112 A | 3/1990 | Pace | |
| 4,925,800 A | 5/1990 | Kovacs | |
| 4,938,742 A | 7/1990 | Smits | |
| 4,965,188 A | 10/1990 | Mullis et al. | |
| 4,997,577 A | 3/1991 | Stewart | |
| 5,053,197 A | 10/1991 | Bowen | |
| 5,071,076 A | 12/1991 | Chagnon et al. | |
| 5,108,933 A | 4/1992 | Liberti et al. | |
| 5,130,238 A | 7/1992 | Malek et al. | |
| 5,143,853 A | 9/1992 | Walt | |
| 5,147,606 A | 9/1992 | Charlton et al. | |
| 5,156,810 A * | 10/1992 | Ribi | 435/287.2 |
| 5,162,863 A | 11/1992 | Ito | |
| 5,168,044 A | 12/1992 | Joyce et al. | |
| 5,182,366 A | 1/1993 | Huebner et al. | |
| 5,188,934 A | 2/1993 | Menchen et al. | |
| 5,209,904 A | 5/1993 | Forney et al. | |
| 5,211,850 A | 5/1993 | Shettigar et al. | |
| 5,219,763 A | 6/1993 | Van Hoegaerden | |
| 5,235,028 A | 8/1993 | Barany et al. | |
| 5,244,636 A | 9/1993 | Walt et al. | |
| 5,244,813 A | 9/1993 | Walt et al. | |
| 5,250,264 A | 10/1993 | Walt et al. | |
| 5,252,294 A * | 10/1993 | Kroy et al. | 422/68.1 |
| 5,252,494 A | 10/1993 | Walt et al. | |
| 5,278,303 A | 1/1994 | Krepinsky et al. | |
| 5,288,214 A | 2/1994 | Fukuda et al. | |
| 5,307,144 A | 4/1994 | Hiroshi et al. | |
| 5,366,860 A | 11/1994 | Bergot et al. | |
| 5,374,530 A | 12/1994 | Nuzzolo et al. | |
| 5,382,512 A | 1/1995 | Smethers et al. | |
| 5,405,784 A | 4/1995 | Van Hoegaerden | |
| 5,480,723 A | 1/1996 | Klainer et al. | |
| 5,491,097 A | 2/1996 | Ribi et al. | |
| 5,499,909 A | 3/1996 | Yamada et al. | |
| 5,503,985 A | 4/1996 | Cathey et al. | |
| 5,512,490 A | 4/1996 | Walt et al. | |
| 5,518,887 A | 5/1996 | Parsons et al. | |
| 5,563,042 A | 10/1996 | Phillips et al. | |
| 5,567,627 A | 10/1996 | Lehnen | |
| 5,611,676 A | 3/1997 | Ooumi et al. | |
| 5,616,698 A | 4/1997 | Krepinsky et al. | |
| 5,631,130 A | 5/1997 | Leckie et al. | |
| 5,632,876 A | 5/1997 | Zanzucchi et al. | |
| 5,654,497 A | 8/1997 | Hoffheins et al. | |
| 5,677,196 A | 10/1997 | Herron et al. | |
| 5,698,089 A | 12/1997 | Lewis et al. | |
| 5,700,897 A | 12/1997 | Klainer et al. | |
| 5,705,018 A | 1/1998 | Hartley | |
| 5,707,502 A | 1/1998 | McCaffrey et al. | |
| 5,755,942 A | 5/1998 | Zanzucchi et al. | |
| 5,759,015 A | 6/1998 | Van Lintel et al. | |
| 5,788,814 A * | 8/1998 | Sun et al. | 279/128 |
| 5,797,898 A | 8/1998 | Santini, Jr. et al. | |
| 5,814,524 A | 9/1998 | Walt et al. | |
| 5,827,748 A * | 10/1998 | Golden | 436/518 |
| 5,834,318 A | 11/1998 | Buettner | |
| 5,840,256 A | 11/1998 | Demers et al. | |
| 5,843,655 A | 12/1998 | McGall | |
| 5,846,396 A | 12/1998 | Zanzucchi et al. | |
| 5,846,708 A * | 12/1998 | Hollis et al. | 435/6 |
| 5,854,141 A | 12/1998 | Cronin et al. | |
| 5,856,174 A * | 1/1999 | Lipshutz et al. | 435/287.2 |
| 5,858,804 A | 1/1999 | Zanzucchi et al. | |
| 5,863,957 A * | 1/1999 | Li et al. | 521/141 |
| 5,866,430 A | 2/1999 | Grow | |
| 5,869,241 A | 2/1999 | Edwards et al. | |
| 5,872,170 A | 2/1999 | Mine et al. | |
| 5,876,605 A | 3/1999 | Kitajima et al. | |
| 5,891,656 A | 4/1999 | Zarling et al. | |
| 5,914,042 A | 6/1999 | Ball et al. | |
| 5,922,617 A * | 7/1999 | Wang et al. | 422/82.05 |
| 5,965,590 A | 10/1999 | Rossignol | |
| 5,965,695 A | 10/1999 | Simon et al. | |
| 5,981,297 A | 11/1999 | Baselt | |
| 5,992,820 A | 11/1999 | Fare et al. | |
| 6,008,031 A | 12/1999 | Modrich et al. | |
| 6,013,440 A | 1/2000 | Lipshutz et al. | |
| 6,023,540 A | 2/2000 | Walt et al. | |
| 6,037,137 A | 3/2000 | Komoriya et al. | |
| 6,045,579 A | 4/2000 | Hochshuler et al. | |
| 6,048,732 A | 4/2000 | Anslyn et al. | |
| 6,063,581 A | 5/2000 | Sundrehagen | |
| 6,083,763 A * | 7/2000 | Balch | 435/6 |
| 6,103,479 A * | 8/2000 | Taylor | 216/11 |
| 6,151,973 A * | 11/2000 | Geysen et al. | 73/865.8 |
| 6,171,780 B1 * | 1/2001 | Pham et al. | 422/102 |
| 6,331,441 B1 * | 12/2001 | Balch et al. | 435/6 |

OTHER PUBLICATIONS

Khanna, P.L., Ullman, E.F. "4', 5'–Dimethoxyl–6–carboxyfluorescein; A novel dipoledipole coupled fluorescence energy transfer acceptor useful for fluorescence immunoassays", Anal. Biochem. 1980, 108, 156.

Morrison, L.E. "Time resolved Detection of Energy Transfer: Theory and Application to Immunoassays", Anal. Biochem. 1998, 174, 101.

Schmidt, J.J.; Stafford, R.G.; Bostian, K.A.; "Type A botulinum neurotoxin proteolytic activity: development of competitive inhibitors and implicatins for substrate specificity at the $S_1$ binding subsite", FEBS Lett., 1998, 435, 61–64.

Shone, C.C.; Roberts, A.K., "Peptide substrate specificity and properties of the zincendopetidase activity of botulinum type B neurotoxin", Eur. J. Biochem., 1994, 225, 263–270.

Soleihac, J.–M.; Cornille, F.; Martin, L.; Lenoir, C.; Fournie–Zaluski, M.–C.; Roques, B.P. A sensitive and rapid fluorescence–based assay for determination of tetnus toxin peptidase activity: Anal. Biochem., 1996, 241, 120–127.

Stimpson, D.I.; Haijer, J.V.; Hsieh, W.; Jou, C.; Gardon, J.; Theriault, T.; Gamble, R.; Baldeschwieler, J.D.; Proc. Natl. Acad. Sci. USA 1995, 92, 6379.

Niikura, K.; Metzger, A.; Anslyn, E.V., "A Sensing Ensemble with Selectivity for Iositol Triphosphate", J. Am. Chem. Soc., 1998, 120, 0000.

Kaiser, E.; Colescott, R.L.; Bossinger, C.D.; Cook, P.I.; "Color Test for Detection of Free Terminal Amino Groups in the Solid–Phase Synthesis of Peptides", Anal. Biochem., 1970, 34, 595–598.

Hamasaki, K.; Ikeda, H.; Nakamura, A.; Ueno, A.; Toda, F.: Suzuki, I.; Osa, T. "Fluorescent Sensors of Molecular Recognition. Modified Cyclodextrins Capable of Exhibiting Guest–Responsive Twisted Intramolecular Charge Transfer Fluorescence", J. Am. Chem. Soc., 1993, 115, 5035. And reference 5 therein.

Youil R; Kemper, B; Cotton, RGH, "Detection of 81 of 81 Known Mouse Beta–Globin Promoter Mutations with T4 Endonuclease–VII–The EMC Method", Genomics, 1996, 32, 431–5.

Pabo and Sauer, 1992, Annu. Rev. Biochem, 61, 1053–1095.

Harrison, 1991, Nature, (London) 353, 715–719.

Klug, 1993, Gene, 135–83–92.

Hsu, I.C.; Yang, Q.P.; Kahng, M.W.; Xu, J.F.; "Detection of DNA Point Mutations with DNA Mismatch Repaire Enzymes", Carcinogenesis, 1994, 15, 1657–1662.

Saiki, et al., 1985, Science, 230, 1350–1354.

Mullis, et al., 1986 Cold Springs Harbor Symp. Quant. Biol., 51, 263–273.

Mullis and Faloona, 1987, Methods Enzymol., 155, 335–350.

Barany, 1991, PCR Methods and Applications 1:5–16.

Wu and Wallace, 1989, Genomics, 4:560–569.

Barany, 1991, Proc. Natl. Acad. Sci. USA, 88:189–193.

Kwoh, et al., 1989, Proc. Natl. Acad. Sci., USA, 86:1173–1177.

Guatelli, et al. 1990, Proc. Natl. Acad, Sci., USA, 87:1874–1878.

Goldrick, M.M.; Kimball, G.R.; Liu, Q.: Martin, L.A.; Sommer, S.S.: Tseng, J.Y.H.; "Nirca™–A Rapid Robust Method for Screening for Unknown Point Mutations", Biotechniques, 1996, 21, 106–112.

Stanley, "UT scientists engineer a tiny arbiter of taste," Austin American Statesman, July 26, 1988.

"Biosensors respond with colored light," Science News, Vol. 152, Nov. 15, 1997, p. 317.

Ricco et al, Accounts of Chemical Research, 1998, 31, pp. 289–296.

Grate et al., Analytical Chemistry, 1999, 71, pp. 1033–1040.

Johnson et al., Analytical Chemistry 1997, 69, pp. 4641–4648.

Healey et al., Analytical Chemistry, 1997, 69, pp. 2213–2216.

White et al., Analytical Chemistry, 1996, 68, pp. 2191–2202.

Potyrailo et al., Analytical Chemistry, 1998, 70, pp. 3407–3412.

Holtz et al., Analytical Chemistry, 1998, 70, pp. 780–791.

Lavigne et al., J. Am. Chem. Soc., 1998, 120, pp. 6429–6430.

Han et al., "Fabrication and characterization of a Fabry–Perot based chemical sensor," Microelectronics Research Center and Department of Electrical and Computer Engineering, Feb. 7, 1997.

Han et al, "Deflection behavior of Fabry–Perot pressure sensors having planar and corrugated diaphragms," Microelectronics Research Center and Department of Electrical and Computer Engineering, Feb. 4, 1997.

* cited by examiner

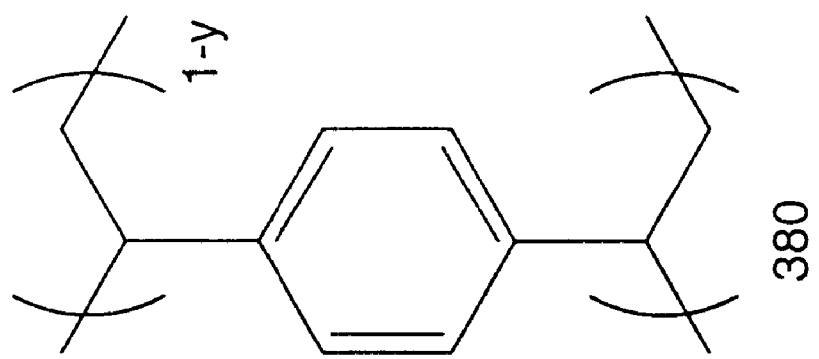
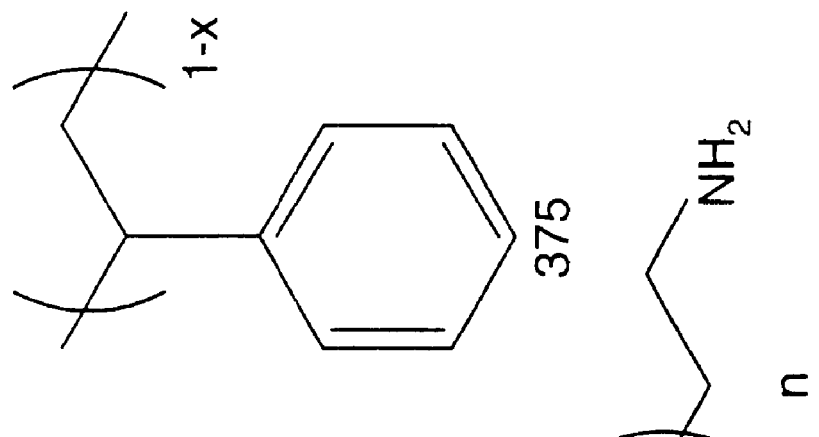
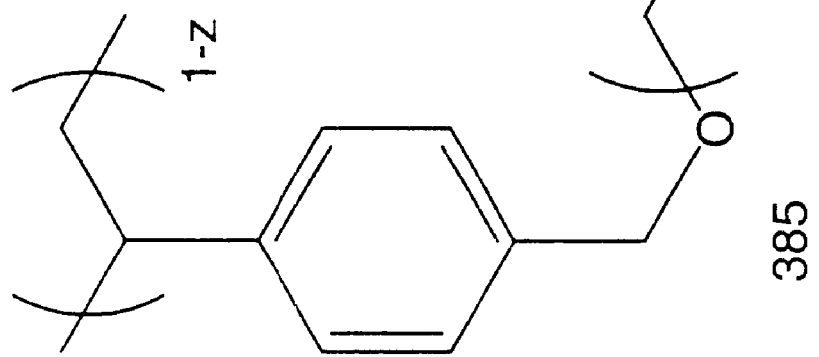
FIG. 5

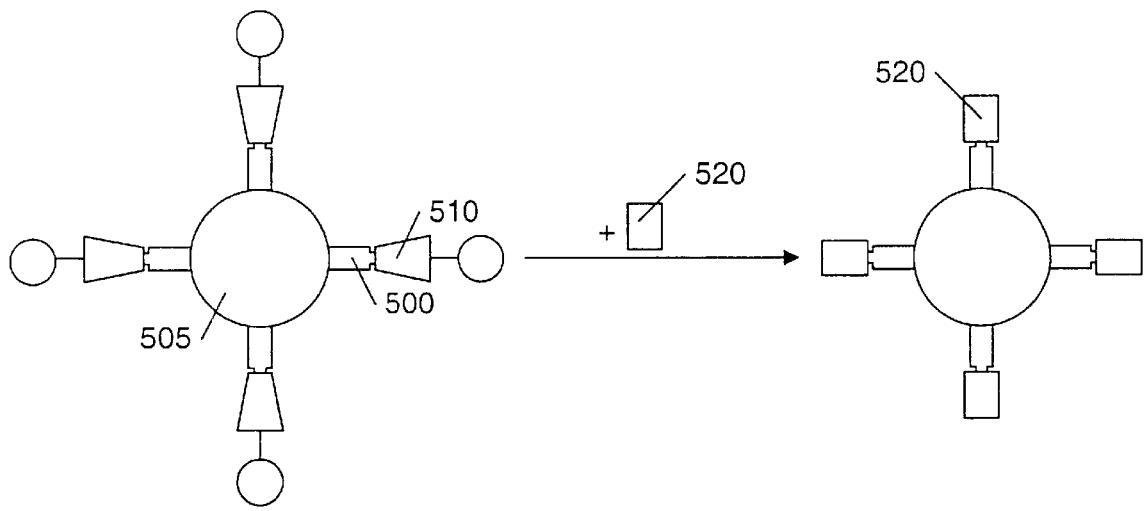
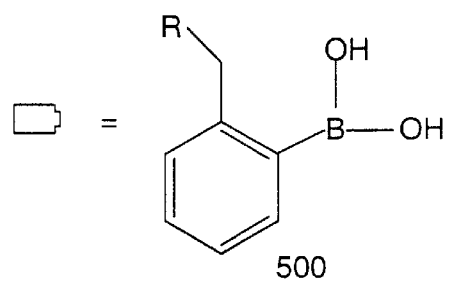
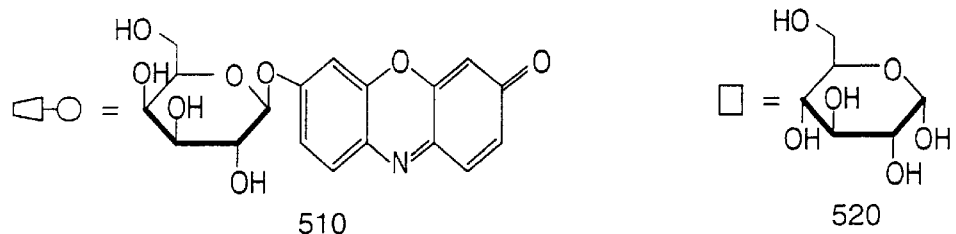
FIG. 9

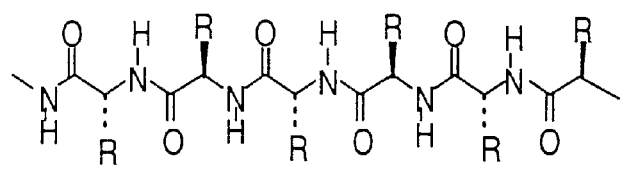
Peptides
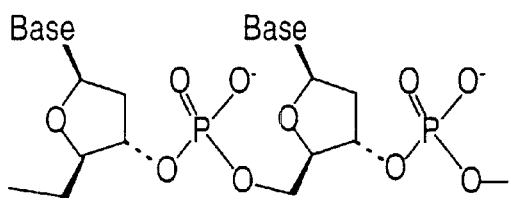
Nucleotides
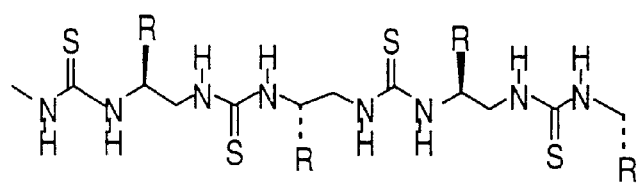
Polythioureas
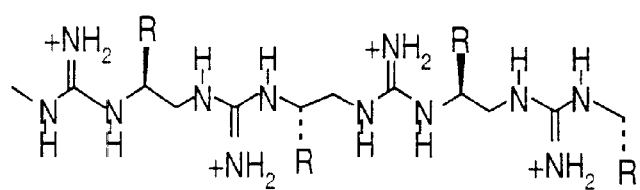
Polyguanidiniums
FIG. 10

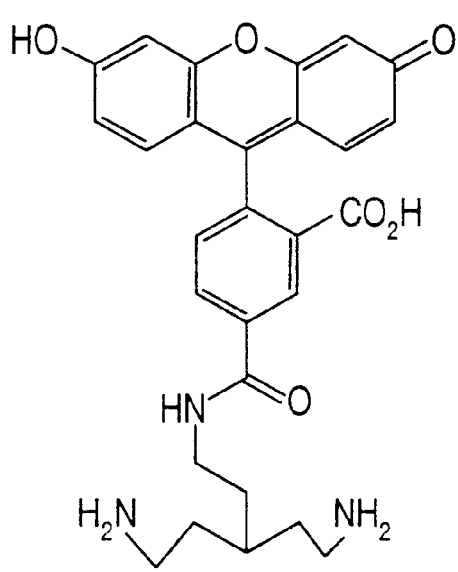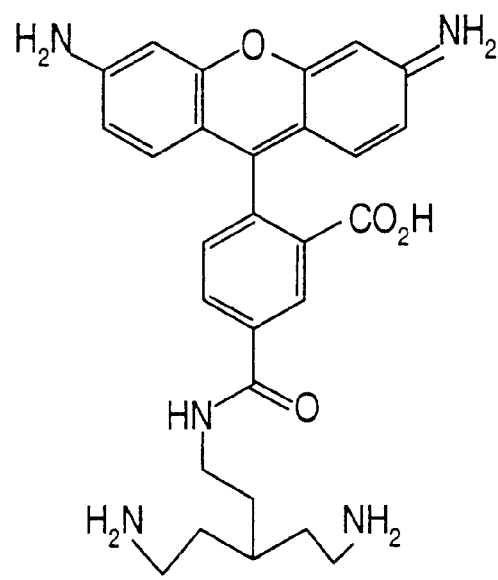
FIG. 14

| RESIN: pH | Ion | Blank | Alizarin | o-Cresol-phthalein | Fluorescein | Alizarin-Ce$^{3+}$ complex |
|---|---|---|---|---|---|---|
| 2 | none | R G B | R G B | R G B | R G B | R G B |
| 2 | Ca$^{2+}$ | R G B | R G B | R G B | R G B | R G B |
| 7 | none | R G B | R G B | R G B | R G B | R G B |
| 7 | Ca$^{2+}$ | R G B | R G B | R G B | R G B | R G B |
| 7 | F$^-$ | R G B | R G B | R G B | R G B | R G B |
| 12 | none | R G B | R G B | R G B | R G B | R G B |
| 12 | Ca$^{2+}$ | R G B | R G B | R G B | R G B | R G B |
| 12 | F$^-$ | R G B | R G B | R G B | R G B | R G B |

FIG. 16

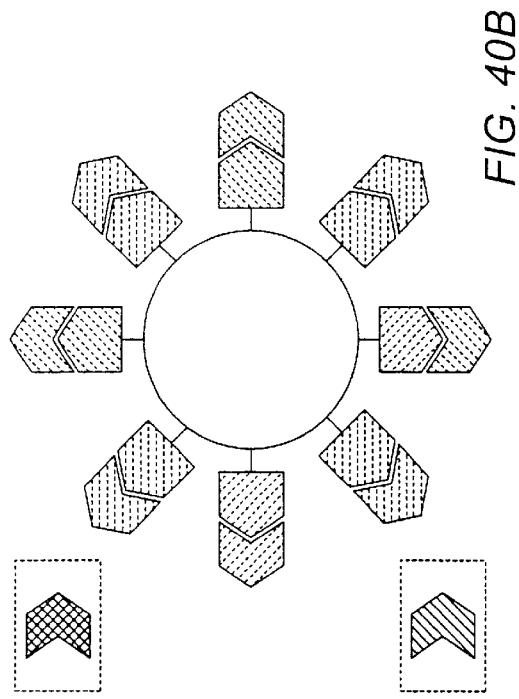
FIG. 40A
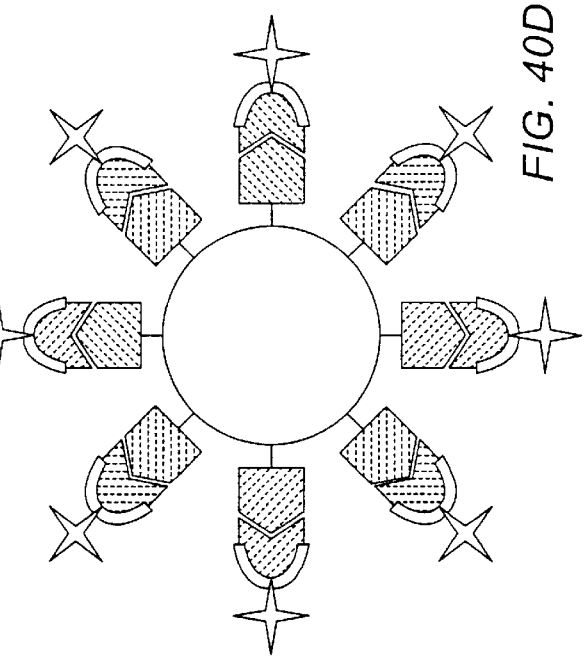
FIG. 40B
FIG. 40C
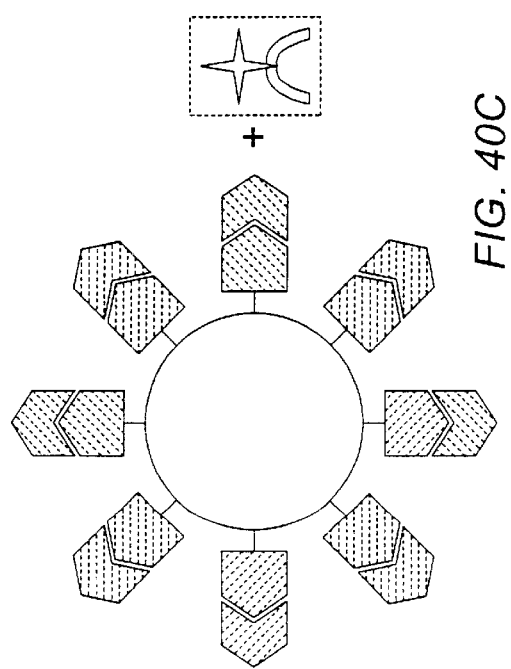
FIG. 40D

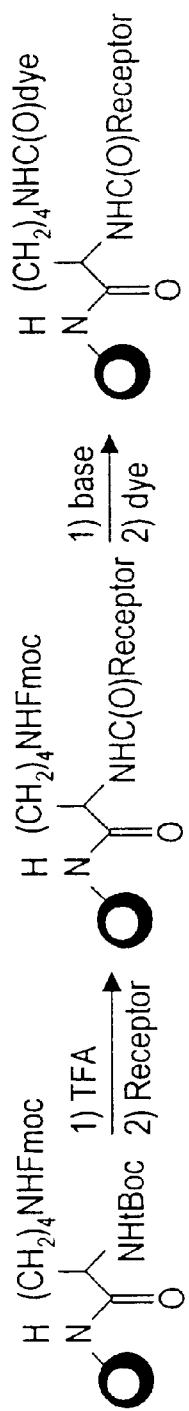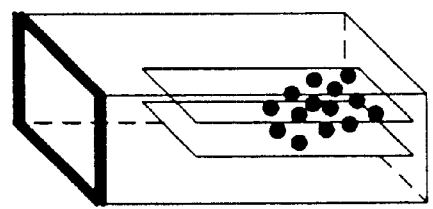
FIG. 45D
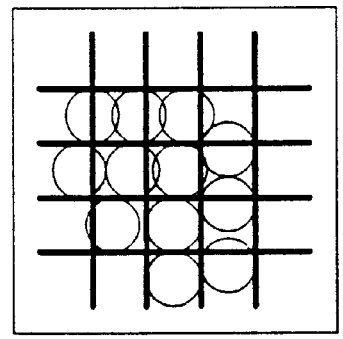
FIG. 46B
FIG. 46A

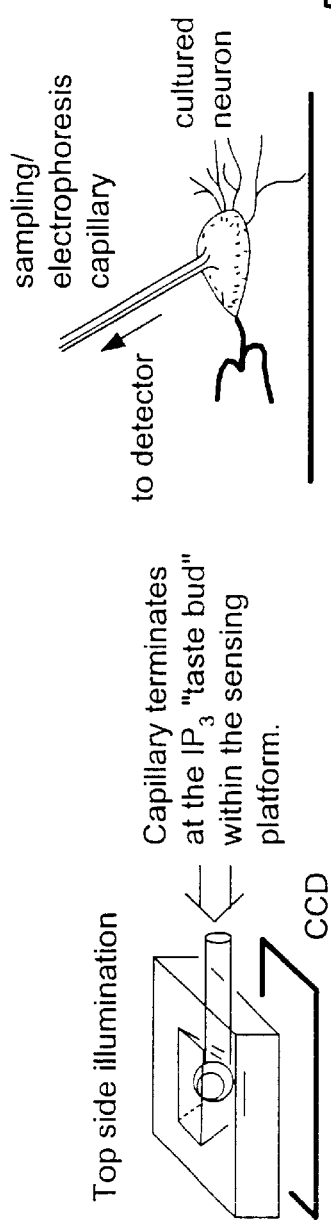
FIG. 49
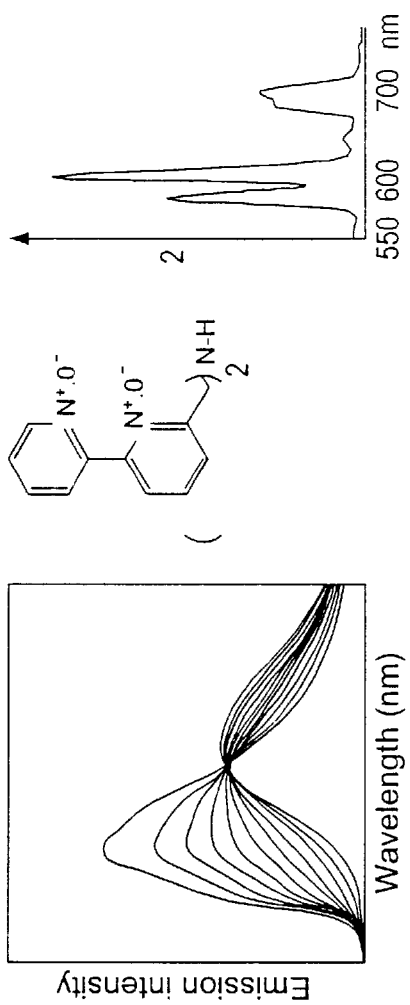
FIG. 50
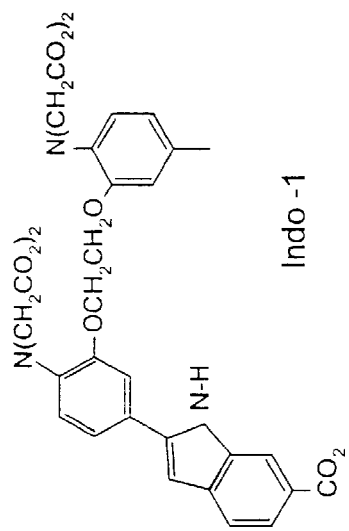

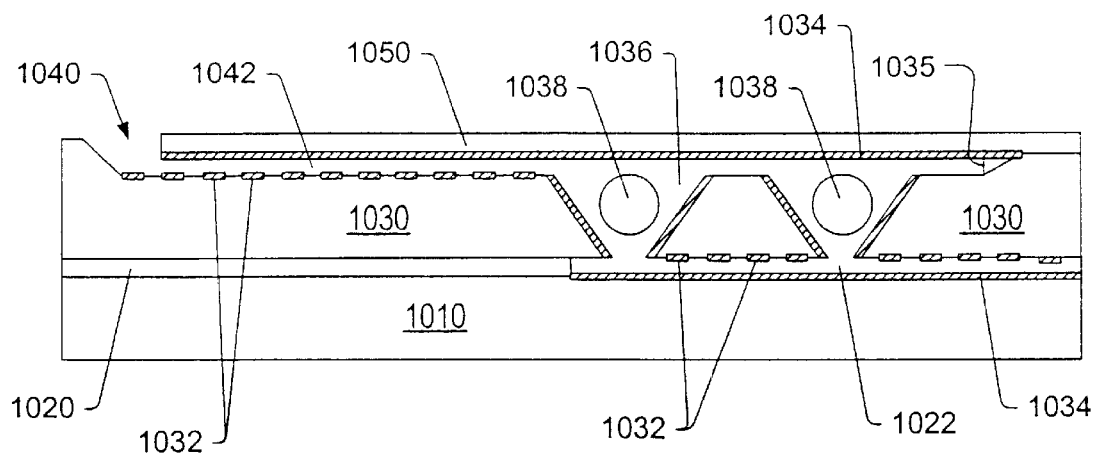
FIG. 73
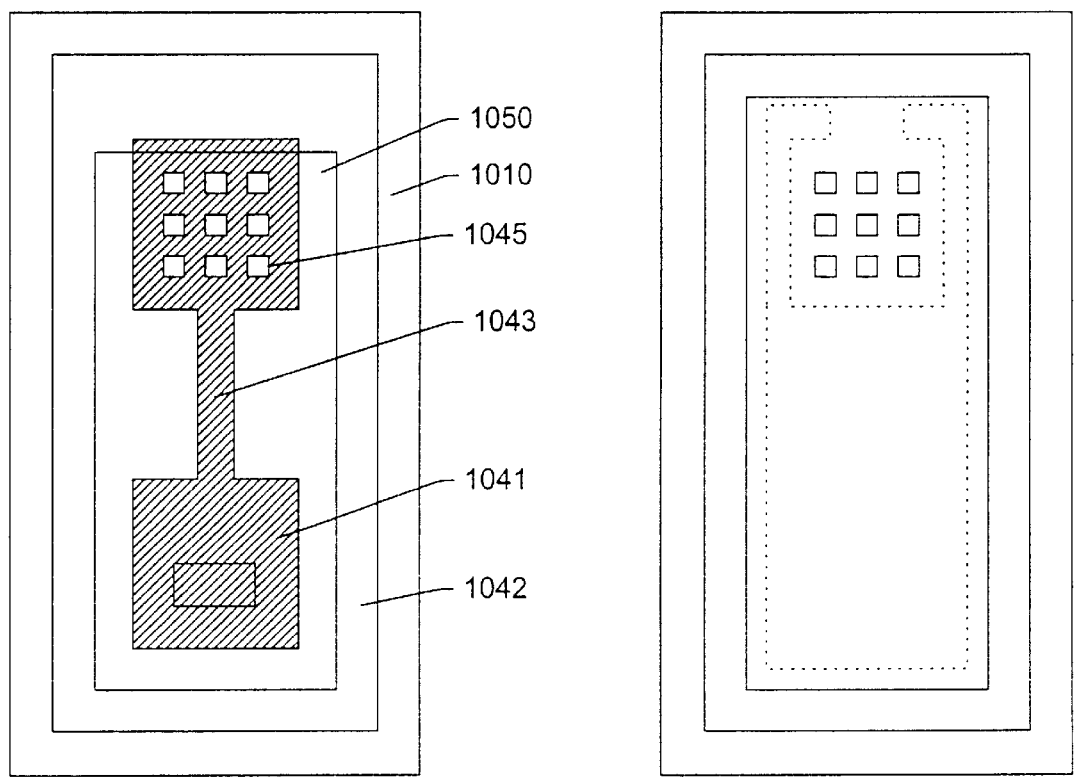
FIG. 74A                  FIG. 74B

METHOD OF PREPARING A SENSOR ARRAY

PRIORITY CLAIM

This application claims priority to U.S. Provisional Application No. 60/179,369 entitled "METHOD AND SYSTEM FOR COLLECTING AND TRANSMITTING CHEMICAL INFORMATION," filed Jan. 31, 2000, U.S. Provisional Application No. 60/179,424 entitled "SYSTEM AND METHOD FOR THE ANALYSIS OF BODILY FLUIDS" filed Jan. 31, 2000, U.S. Provisional Application No. 60/179,294 entitled "SYSTEM AND METHOD FOR IDENTIFYING NUCLEIC ACIDS IN A FLUID SAMPLE," filed Jan. 31, 2000, U.S. Provisional Application No. 60/179,380 entitled "METHOD OF PREPARING A SENSOR ARRAY," filed Jan. 31, 2000, U.S. Provisional Application No. 60/179,292 entitled "SYSTEM FOR TRANSFERRING FLUID SAMPLES THROUGH A SENSOR ARRAY," filed Jan. 31, 2000 and U.S. Provisional Application No. 60/179,293 entitled "PORTABLE SENSOR ARRAY SYSTEM," filed Jan. 31, 2000.

STATEMENT REGARDING FEDERALLY SPONSORED RESEARCH OR DEVELOPMENT

Research leading to this invention was federally supported, in part, by grant No. 1R01GM57306-01 entitled "The Development of an Electronic Tongue" from the National Institute of Health and the U.S. Government has certain rights to this invention.

BACKGROUND OF THE INVENTION

1. Field of the Invention

The present invention relates to a method and device for the detection of analytes in a fluid. More particularly, the invention relates to the development of a sensor array system capable of discriminating mixtures of analytes, toxins, and/or bacteria in medical, food/beverage, and environmental solutions.

2. Brief Description of the Related Art

The development of smart sensors capable of discriminating different analytes, toxins, and bacteria has become increasingly important for clinical, environmental, health and safety, remote sensing, military, food/beverage and chemical processing applications. Although many sensors capable of high sensitivity and high selectivity detection have been fashioned for single analyte detection, only in a few selected cases have array sensors been prepared which display solution phase multi-analyte detection capabilities. The advantages of such array systems are their utility for the analysis of multiple analytes and their ability to be "trained" to respond to new stimuli. Such on site adaptive analysis capabilities afforded by the array structures make their utilization promising for a variety of future applications. Array based sensors displaying the capacity to sense and identify complex vapors have been demonstrated recently using a number of distinct transduction schemes. For example, functional sensors based on Surface Acoustic Wave (SAW), tin oxide ($SnO_2$) sensors, conductive organic polymers, and carbon black/polymer composites have been fashioned. The use of tin oxide sensors, for example, is described in U.S. Pat. No. 5,654,497 to Hoffheins et al. These sensors display the capacity to identify and discriminate between a variety of organic vapors by virtue of small site-to-site differences in response characteristics. Pattern recognition of the overall fingerprint response for the array serves as the basis for an olfaction-like detection of the vapor phase analyte species. Indeed, several commercial "electronic noses" have been developed recently. Most of the well established sensing elements are based on $SnO_2$ arrays which have been derivatized so as to yield chemically distinct response properties. Arrays based on SAW crystals yield extremely sensitive responses to vapor, however, engineering challenges have prevented the creation of large SAW arrays having multiple sensor sites. To our knowledge, the largest SAW device reported to date possesses only 12 sensor elements. Additionally, limited chemical diversity and the lack of understanding of the molecular features of such systems makes their expansion into more complex analysis difficult.

Other structures have been developed that are capable of identifying and discriminating volatile organic molecules. One structure involves a series of conductive polymer layers deposited onto metal contacting layers. When these sensors are exposed to volatile reagents, some of the volatile reagents adsorb into the polymer layers, leading to small changes in the electrical resistance of these layers. It is the small differences in the behavior of the various sites that allows for a discrimination, identification, and quantification of the vapors. The detection process takes only a few seconds, and sensitivities of part-per-billion can be achieved with this relatively simple approach. This "electronic nose" system is described in U.S. Pat. No. 5,698,089 to Lewis et al. which is incorporated herein by reference as if set forth herein.

Although the above described electronic nose provides an impressive capability for monitoring volatile reagents, the system possesses a number of undesirable characteristics that warrant the development of alternative sensor array systems. For example, the electronic nose can be used only for the identification of volatile reagents. For many environmental, military, medical, and commercial applications, the identification and quantification of analytes present in liquid or solid-phase samples is necessary. Moreover, the electronic nose systems are expensive (e.g., the Aromascan system costs about $50,000/unit) and bulky ($\geq 1$ $ft^3$). Furthermore, the functional elements for the currently available electronic nose are composed of conductive polymer systems which possess little chemical selectivity for many of the analytes which are of interest to the military and civilian communities.

One of the most commonly employed sensing techniques has exploited colloidal polymer microspheres for latex agglutination tests (LATs) in clinical analysis. Commercially available LATs for more than 60 analytes are used routinely for the detection of infectious diseases, illegal drugs, and early pregnancy tests. The vast majority of these types of sensors operate on the principle of agglutination of latex particles (polymer microspheres) which occurs when the antibody-derivatized microspheres become effectively "cross-linked" by a foreign antigen resulting in the attachment to, or the inability to pass through a filter. The dye-doped microspheres are then detected calorimetrically upon removal of the antigen carrying solution. However, the LATs lack the ability to be utilized for multiple, real time analyte detection schemes as the nature of the response intrinsically depends on a cooperative effect of the entire collection of microspheres.

Similar to the electronic nose, array sensors that have shown great analytical promise are those based on the "DNA on a chip" technology. These devices possess a high density of DNA hybridization sites that are affixed in a two-dimensional pattern on a planar substrate. To generate nucleotide sequence information, a pattern is created from unknown DNA fragments binding to various hybridization sites. Both radiochemical and optical methods have provided excellent detection limits for analysis of limited quantities of DNA. (Stimpson, D. I.; Hoijer, J. V.; Hsieh, W.; Jou, C.; Gardon, J.; Theriault, T.; Gamble, R.; Baldeschwieler, J. D. Proc. Natl. Acad. Sci. USA 1995, 92, 6379). Although quite promising for the detection of DNA fragments, these arrays are generally not designed for non-DNA molecules, and accordingly show very little sensitivity to smaller organic molecules. Many of the target molecules of interest to civilian and military communities, however, do not possess DNA components. Thus, the need for a flexible, non-DNA based sensor is still desired. Moreover, while a number of prototype DNA chips containing up to a few thousand different nucleic acid probes have been described, the existing technologies tend to be difficult to expand to a practical size. As a result, DNA chips may be prohibitively expensive for practical uses.

Systems for analyzing fluid samples using an array formed of heterogeneous, semi-selective thin films which function as sensing receptor units are described in U.S. Pat. Nos. 6,023,540; 5,814,524; 5,700,897; 5,512,490; 5,480,723; 5,252,494; 5,250,264; 5,244,813; 5,244,636; and 5,143,853 which are incorporated herein by reference as if set forth herein. These systems appears to describe the use of covalently attached polymeric "cones" which are grown via photopolymerization onto the distal face of fiber optic bundles. These sensor probes appear to be designed with the goal of obtaining unique, continuous, and reproducible responses from small localized regions of dye-doped polymer. The polymer appears to serve as a solid support for indicator molecules that provide information about test solutions through changes in optical properties. These polymer supported sensors have been used for the detection of analytes such as pH, metals, and specific biological entities. Methods for manufacturing large numbers of reproducible sensors, however, has yet to be developed. Moreover, no methods for acquisitions of data streams in a simultaneous manner are commercially available with this system. Optical alignment issues may also be problematic for these systems.

A method of rapid sample analysis for use in the diagnostic microbiology field is also desirable. The techniques now used for rapid microbiology diagnostics detect either antigens or nucleic acids. Rapid antigen testing is based on the use of antibodies to recognize either the single cell organism or the presence of infected cell material. Inherent to this approach is the need to obtain and characterize the binding of the antibody to unique structures on the organism being tested. Since the identification and isolation of the appropriate antibodies is time consuming, these techniques are limited to a single agent per testing module and there is no opportunity to evaluate the amount of agent present.

Most antibody methods are relatively insensitive and require the presence of $10^5$ to $10^7$ organisms. The response time of antibody-antigen reactions in diagnostic tests of this type ranges from 10 to 120 minutes, depending on the method of detection. The fastest methods are generally agglutination reactions, but these methods are less sensitive due to difficulties in visual interpretation of the reactions. Approaches with slower reaction times include antigen recognition by antibody conjugated to either an enzyme or chromophore. These test types tend to be more sensitive, especially when spectrophotometric methods are used to determine if an antigen-antibody reaction has occurred. These detection schemes do not, however, appear to allow the simultaneous detection of multiple analytes on a single detector platform.

The alternative to antigen detection is the detection of nucleic acids. An approach for diagnostic testing with nucleic acids uses hybridization to target unique regions of the target organism. These techniques require fewer organisms ($10^3$ to $10^5$), but require about five hours to complete. As with antibody-antigen reactions this approach has not been developed for the simultaneous detection of multiple analytes.

The most recent improvement in the detection of microorganisms has been the use of nucleic acid amplification. Nucleic acid amplification tests have been developed that generate both qualitative and quantitative data. However, the current limitations of these testing methods are related to delays caused by specimen preparation, amplification, and detection. Currently, the standard assays require about five hours to complete. The ability to complete much faster detection for a variety of microorganisms would be of tremendous importance to military intelligence, national safety, medical, environmental, and food areas.

It is therefore desirable that new sensors capable of discriminating different analytes, toxins, and bacteria be developed for medical/clinical diagnostic, environmental, health and safety, remote sensing, military, food/beverage, and chemical processing applications. It is further desired that the sensing system be adaptable to the simultaneous detection of a variety of analytes to improve throughput during various chemical and biological analytical procedures.

SUMMARY OF THE INVENTION

Herein we describe a system and method for the analysis of a fluid containing one or more analytes. The system may be used for either liquid or gaseous fluids. The system, in some embodiments, may generate patterns that are diagnostic for both the individual analytes and mixtures of the analytes. The system in some embodiments, is made of a plurality of chemically sensitive particles, formed in an ordered array, capable of simultaneously detecting many different kinds of analytes rapidly. An aspect of the system is that the array may be formed using a microfabrication process, thus allowing the system to be manufactured in an inexpensive manner.

In an embodiment of a system for detecting analytes, the system, in some embodiments, includes a light source, a sensor array, and a detector. The sensor array, in some embodiments, is formed of a supporting member which is configured to hold a variety of chemically sensitive particles (herein referred to as "particles") in an ordered array. The particles are, in some embodiments, elements which will create a detectable signal in the presence of an analyte. The particles may produce optical (e.g., absorbance or reflectance) or fluorescence/phosphorescent signals upon exposure to an analyte. Examples of particles include, but are not limited to functionalized polymeric beads, agarous beads, dextrose beads, polyacrylamide beads, control pore glass beads, metal oxides particles (e.g., silicon dioxide ($SiO_2$) or aluminum oxides ($Al_2O_3$)), polymer thin films, metal quantum particles (e.g., silver, gold, platinum, etc.), and semiconductor quantum particles (e.g., Si, Ge, GaAs, etc.). A detector (e.g., a charge-coupled device "CCD") in one embodiment is positioned below the sensor array to allow for the data acquisition. In another embodiment, the detector may be positioned above the sensor array to allow for data acquisition from reflectance of the light off of the particles.

Light originating from the light source may pass through the sensor array and out through the bottom side of the sensor array. Light modulated by the particles may pass through the sensor array and onto the proximally spaced detector. Evaluation of the optical changes may be completed by visual inspection or by use of a CCD detector by itself or in combination with an optical microscope. A microprocessor may be coupled to the CCD detector or the microscope. A fluid delivery system may be coupled to the supporting member of the sensor array. The fluid delivery system, in some embodiments, is configured to introduce samples into and out of the sensor array.

In an embodiment, the sensor array system includes an array of particles. The particles may include a receptor molecule coupled to a polymeric bead. The receptors, in some embodiments, are chosen for interacting with analytes. This interaction may take the form of a binding/association of the receptors with the analytes. The supporting member may be made of any material capable of supporting the particles, while allowing the passage of the appropriate wavelengths of light. The supporting member may include a plurality of cavities. The cavities may be formed such that at least one particle is substantially contained within the cavity.

In an embodiment, the optical detector may be integrated within the bottom of the supporting member, rather than using a separate detecting device. The optical detectors may be coupled to a microprocessor to allow evaluation of fluids without the use of separate detecting components. Additionally, a fluid delivery system may also be incorporated into the supporting member. Integration of detectors and a fluid delivery system into the supporting member may allow the formation of a compact and portable analyte sensing system.

A high sensitivity CCD array may be used to measure changes in optical characteristics which occur upon binding of the biological/chemical agents. The CCD arrays may be interfaced with filters, light sources, fluid delivery and micromachined particle receptacles, so as to create a functional sensor array. Data acquisition and handling may be performed with existing CCD technology. CCD detectors may be configured to measure white light, ultraviolet light or fluorescence. Other detectors such as photomultiplier tubes, charge induction devices, photo diodes, photodiode arrays, and microchannel plates may also be used.

A particle, in some embodiments, possess both the ability to bind the analyte of interest and to create a modulated signal. The particle may include receptor molecules which posses the ability to bind the analyte of interest and to create a modulated signal. Alternatively, the particle may include receptor molecules and indicators. The receptor molecule may posses the ability to bind to an analyte o f interest. Upon binding the analyte of interest, the receptor molecule may cause the indicator molecule to produce the modulated signal. The receptor molecules may be naturally occurring or synthetic receptors formed by rational design or combinatorial methods. Some examples of natural receptors include, but are not limited to, DNA, RNA, proteins, enzymes, oligopeptides, antigens, and antibodies. Either natural or synthetic receptors may be chosen for their ability to bind to the analyte molecules in a specific manner.

In one embodiment, a naturally occurring or synthetic receptor is bound to a polymeric bead in order to create the particle. The particle, in some embodiments, is capable of both binding the analyte(s) of interest and creating a detectable signal. In some embodiments, the particle will create an optical signal when bound to an analyte of interest.

A variety of natural and synthetic receptors may be used. The synthetic receptors may come from a variety of classes including, but not limited to, polynucleotides (e.g., aptamers), peptides (e.g., enzymes and antibodies), synthetic receptors, polymeric unnatural biopolymers (e.g., polythioureas, polyguanidiniums), and imprinted polymers. Polynucleotides are relatively small fragments of DNA which may be derived by sequentially building the DNA sequence. Peptides include natural peptides such as antibodies or enzymes or may be synthesized from amino acids. Unnatural biopolymers are chemical structure which are based on natural biopolymers, but which are built from unnatural linking units. For example, polythioureas and polyguanidiniums have a structure similar to peptides, but may be synthesized from diamines (i.e., compounds which include at least two amine functional groups) rather than amino acids. Synthetic receptors are designed organic or inorganic structures capable of binding various analytes.

In an embodiment, a large number of chemical/biological agents of interest to the military and civilian communities may be sensed readily by the described array sensors. Bacteria may also be detected using a similar system. To detect, sense, and identify intact bacteria, the cell surface of one bacteria may be differentiated from other bacteria, or genomic material may be detected using oligonucleic receptors. One method of accomplishing this differentiation is to target cell surface oligosaccharides (i.e., sugar residues). The use of synthetic receptors which are specific for oligosaccharides may be used to determine the presence of specific bacteria by analyzing for cell surface oligosaccharides.

In one embodiment, a receptor may be coupled to a polymeric resin. The receptor may undergo a chemical reaction in the presence of an analyte such that a signal is produced. Indicators may be coupled to the receptor or the polymeric bead. The chemical reaction of the analyte with the receptor may cause a change in the local microenvironment of the indicator to alter the spectroscopic properties of the indicator. This signal may be produced using a variety of signalling protocols. Such protocols may include absorbance, fluorescence resonance energy transfer, and/or fluorescence quenching. Receptor-analyte combination may include, but are not limited to, peptides-proteases, polynucleotides-nucleases, and oligosaccharides- oligosaccharide cleaving agents.

In one embodiment, a receptor and an indicator may be coupled to a polymeric resin. The receptor may undergo a conformational change in the presence of an analyte such that a change in the local microenvironment of the indicator occurs. This change may alter the spectroscopic properties of the indicator. The interaction of the receptor with the indicator may be produce a variety of different signals depending on the signalling protocol used. Such protocols may include absorbance, fluorescence resonance energy transfer, and/or fluorescence quenching.

In an embodiment, the sensor array system includes an array of particles. The particles may include a receptor molecule coupled to a polymeric bead. The receptors, in some embodiments, are chosen for interacting with analytes. This interaction may take the form of a binding/association of the receptors with the analytes. The supporting member may be made of any material capable of supporting the particles, while allowing the passage of the appropriate wavelengths of light. The supporting member may include a plurality of cavities. The cavities may be formed such that at least one particle is substantially contained within the cavity. A vacuum may be coupled to the cavities. The vacuum may be applied to the entire sensor array. Alternatively, a vacuum apparatus may be coupled to the cavities to provide a vacuum to the cavities. A vacuum apparatus is any device capable of creating a pressure differential to cause fluid movement. The vacuum apparatus may apply a pulling force to any fluids within the cavity. The vacuum apparatus may pull the fluid through the cavity. Examples of vacuum apparatuss include pre-sealed vacuum chamber, vacuum pumps, vacuum lines, or aspirator-type pumps.

BRIEF DESCRIPTION OF THE DRAWINGS

The above brief description as well as further objects, features and advantages of the methods and apparatus of the present invention will be more fully appreciated by reference to the following detailed description of presently preferred but nonetheless illustrative embodiments in accordance with the present invention when taken in conjunction with the accompanying drawings in which:

FIG. 5 depicts the chemical constituents of a particle;

FIG. 9 depicts a schematic of the interaction of a sugar molecule with a boronic acid based receptor.

FIG. 10 depicts various synthetic receptors;

FIG. 14 depicts fluorescent diamino monomers;

FIG. 16 depicts the color responses of a variety of sensing particles to solutions of $Ca^{+2}$ and various pH levels;

FIG. 40 depicts a general scheme for the testing of an antibody analyte;

FIG. 45D depicts the attachment of differentially protected lysine to a bead;

FIG. 46 depicts a system for measuring the absorbance or emission of a sensing particle;

FIG. 49 depicts a device for the analysis of $IP_3$ in cells;

FIG. 50 depicts the structure of Indo-1 and compound 2 and the emission spectra of Indo-1 and compound 2 in the presence of Ca(II) and Ce(III), respectively;

FIG. 73 depicts a cross section view of a sensor array which includes a passive pump system;

FIG. 74A depicts a top view of the sensor array of FIG. 57;

FIG. 74B depicts a bottom view of the sensor array of FIG. 57;

DETAILED DESCRIPTION OF PREFERRED EMBODIMENTS

Herein we describe a system and method for the simultaneous analysis of a fluid containing multiple analytes. The system may be used for either liquid or gaseous fluids. The system may generate patterns that are diagnostic for both individual analytes and mixtures of the analytes. The system, in some embodiments, is made of a combination of chemically sensitive particles, formed in an ordered array, capable of simultaneously detecting many different kinds of analytes rapidly. An aspect of the system is that the array may be formed using a microfabrication process, thus allowing the system to be manufactured in an inexpensive manner.

System for Analysis of Analytes

Figure 1:
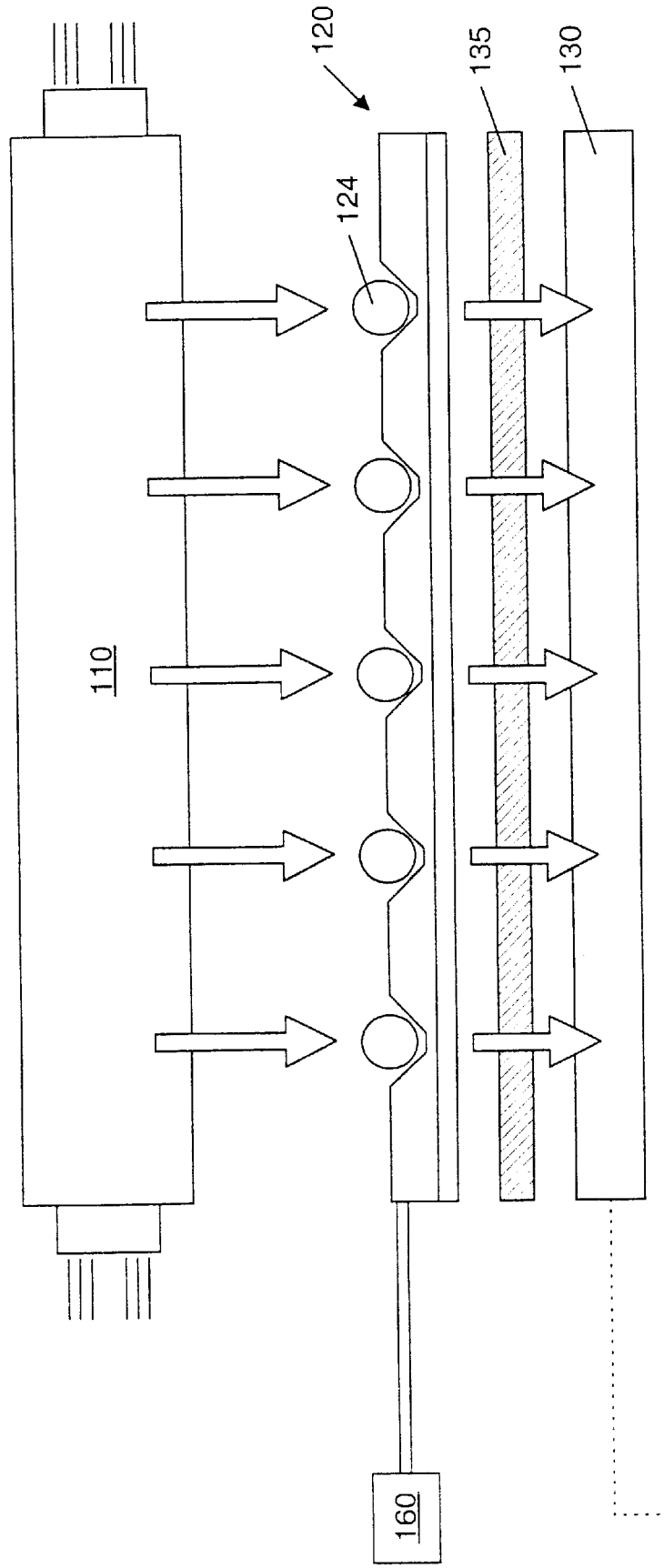
FIG. 1 depicts a schematic of an analyte detection system.

Shown in FIG. 1 is an embodiment of a system for detecting analytes in a fluid. The system, in some embodiments, includes a light source 110, a sensor array 120 and a detector 130. The light source 110 may be a white light source or light emitting diodes (LED). In one embodiment, light source 110 may be a blue light emitting diode (LED) for use in systems relying on changes in fluorescence signals. For colorimetric (e.g., absorbance) based systems, a white light source may be used. The sensor array 120, in some embodiments, is formed of a supporting member which is configured to hold a variety of particles 124. A detecting device 130 (e.g., a charge-coupled device "CCD") may be positioned below the sensor array to allow for data acquisition. In another embodiment, the detecting device 130 may be positioned above the sensor array.

Light originating from the light source 110, in some embodiments, passes through the sensor array 120 and out through the bottom side of the sensor array. The supporting member and the particles together, in some embodiments, provide an assembly whose optical properties are well matched for spectral analyses. Thus, light modulated by the particles may pass through the sensor array and onto the proximally spaced detector 130. Evaluation of the optical changes may be completed by visual inspection (e.g., with a microscope) or by use of a microprocessor 140 coupled to the detector. For fluorescence measurements, a filter 135 may be placed between supporting member 122 and detector 130 to remove the excitation wavelength. A fluid delivery system 160 may be coupled to the supporting member. The fluid delivery system 160 may be configured to introduce samples into and out of the sensor array.

In an embodiment, the sensor array system includes an array of particles. Upon the surface and within the interior region of the particles are, in some embodiments, located a variety of receptors for interacting with analytes. The supporting member, in some embodiments, is used to localize these particles as well as to serve as a microenvironment in which the chemical assays can be performed. For the chemical/biological agent sensor arrays, the particles used for analysis are about 0.05–500 microns in diameter, and may actually change size (e.g., swell or shrink) when the chemical environment changes. Typically, these changes occur when the array system is exposed to the fluid stream which includes the analytes. For example, a fluid stream which comprises a non-polar solvent, may cause non-polar particles to change in volume when the particles are exposed to the solvent. To accommodate these changes, it is preferred that the supporting member consist of an array of cavities which serve as micro test-tubes.

The supporting member may be made of any material capable of supporting the particles, while allowing the passage of the appropriate wavelength of light. The supporting member is also made of a material substantially impervious to the fluid in which the analyte is present. A variety of materials may be used including plastics, glass, silicon based materials (e.g., silicon, silicon dioxide, silicon nitride, etc.) and metals. In one embodiment, the supporting member includes a plurality of cavities. The cavities may be formed such that at least one particle is substantially contained within the cavity. Alternatively, a plurality of particles may be contained within a single cavity.

In an embodiment, the supporting member may consist of a strip of plastic which is substantially transparent to the wavelength of light necessary for detection. A series of cavities may be formed within the strip. The cavities may be configured to hold at least one particle. The particles may be contained within the strip by a transparent cover which is configured to allow passage of the analyte containing fluid into the cavities.

Figure 2:
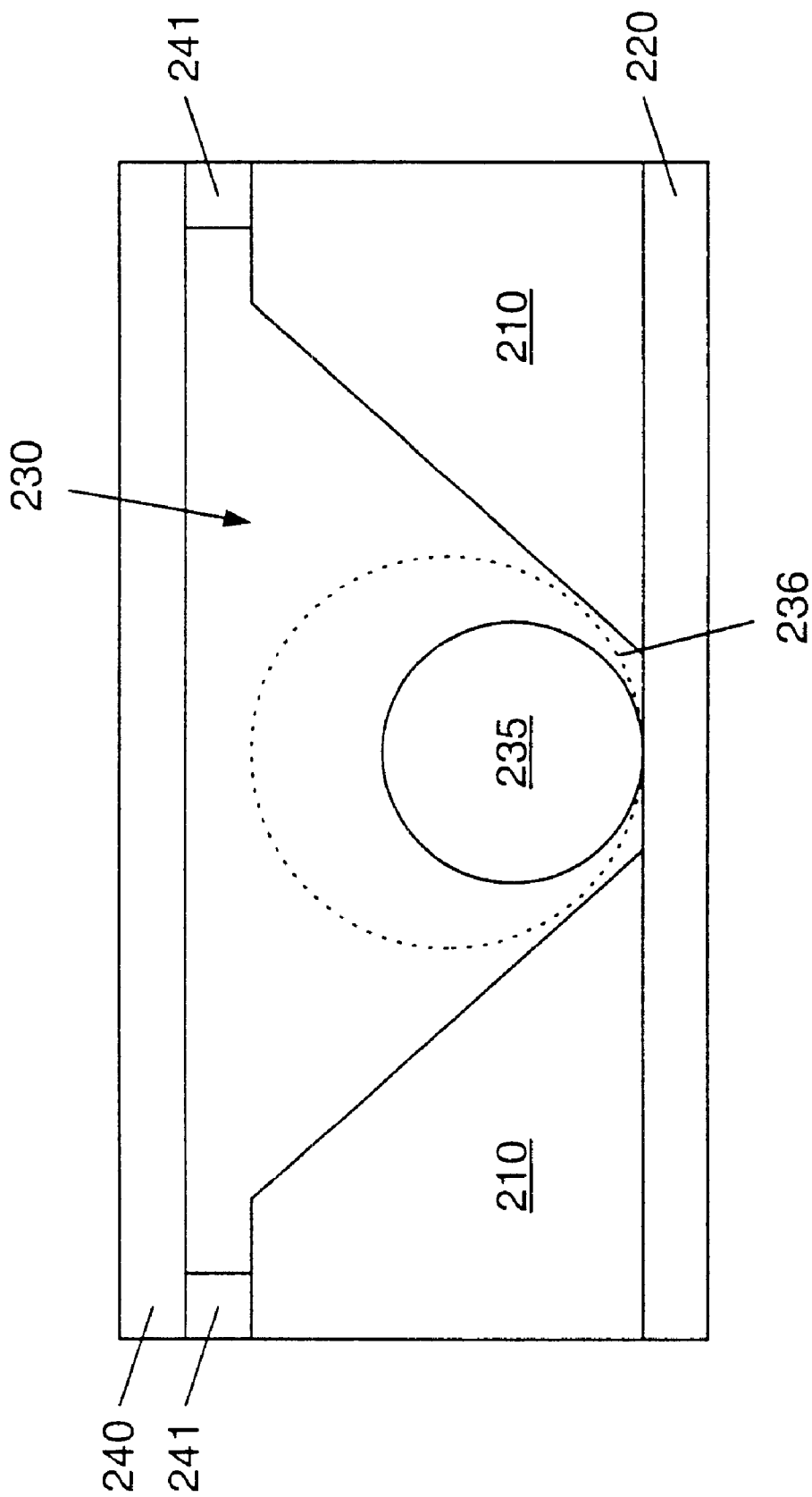
FIG. 2 depicts a particle disposed in a cavity.

In another embodiment, the supporting member may be formed using a silicon wafer as depicted in FIG. 2. The silicon wafer 210 may include a substantially transparent layer 220 formed on the bottom surface of the wafer. The cavities 230, in one embodiment, are formed by an anisotropic etch process of the silicon wafer. In one embodiment, anisotropic etching of the silicon wafer is accomplished using a wet hydroxide etch. Photolithographic techniques may be used to define the locations of the cavities. The cavities may be formed such that the sidewalls of the cavities are substantially tapered at an angle of between about 50 to 60 degrees. Formation of such angled cavities may be accomplished by wet anisotropic etching of <100> silicon. The term "<100> silicon" refers to the crystal orientation of the silicon wafer. Other types of silicon, (e.g., <110> and <111> silicon) may lead to steeper angled sidewalls. For example, <111> silicon may lead to sidewalls formed at about 90 degrees. The angled sides of the cavities in some embodiments, serve as "mirror layers" which may improve the light collection efficiency of the cavities. The etch process may be controlled so that the formed cavities extend through the silicon wafer to the upper surface of transparent layer 220. While depicted as pyramidal, the cavities may be formed in a number of shapes including but not limited to, spherical, oval, cubic, or rectangular. An advantage to using a silicon wafer for the support member, is that the silicon material is substantially opaque to the light produced from the light source. Thus, the light may be inhibited from passing from one cavity to adjacent cavities. In this manner, light from one cavity may be inhibited from influencing the spectroscopic changes produced in an adjacent cavity.

The silicon wafer, in some embodiments, has an area of approximately 1 cm$^2$ to about 100 cm$^2$ and includes about $10^1$ to about $10^6$ cavities. In an embodiment, about 100 cavities are formed in a ten by ten matrix. The center to center distance between the cavities, in some embodiments, is about 500 microns. Each of the cavities may include at least one particle.

The transparent layer 220 may serve as a window, allowing light of a variety of wavelengths to pass through the cavities 230 and to the detector. Additionally, the transparent layer may serve as a platform onto which the individual particles 235 may be positioned. The transparent layer may be formed of silicon dioxide ($SiO_2$), silicon nitride ($Si_3N_4$) or silicon dioxide/silicon nitride multi-layer stacks. The transparent layer, in some embodiments, is deposited onto the silicon wafer prior to the formation of the cavities.

The cavities 230 may be sized to substantially contain a particle 235. The cavities are, in some embodiments, larger than a particle. The cavities are, in some embodiments, sized to allow facile placement and removal of the particle within the cavities. The cavity may be substantially larger than the particle, thus allowing the particle to swell during use. For example, a particle may have a size as depicted in FIG. 2 by particle 235. During use, contact with a fluid (e.g., a solvent) may cause the particle to swell, for example, to a size depicted as circle 236. In some embodiments, the cavity is sized to allow such swelling of the particle during use. A particle may be positioned at the bottom of a cavity using, e.g., a micromanipulator. After a particle has been placed within the cavity, a transparent cover plate 240 may be placed on top of the supporting member to keep the particle in place.

When forming an array which includes a plurality of particles, the particles may be placed in the array in an ordered fashion using the micromanipulator. In this manner, a ordered array having a predefined configuration of particles may be formed. Alternatively, the particles may be randomly placed within the cavities. The array may subsequently undergo a calibration test to determine the identity of the particle at any specified location in the supporting member.

The transparent cover plate 240, in some embodiments, is coupled to the upper surface of the silicon wafer 220 such that the particles are inhibited from becoming dislodged from the cavity. The transparent cover plate, in some embodiments, is positioned a fixed distance above the silicon wafer, as depicted in FIG. 2, to keep the particle in place, while allowing the entrance of fluids into the cavities. The transparent cover plate, in some embodiments, is positioned at a distance above the substrate which is substantially less than a width of the particle. The transparent cover plate may be made of any material which is substantially transparent to the wavelength of light being utilized by the detector. The transparent cover plate may be made of plastic, glass, quartz, or silicon dioxide/silicon nitride.

In one embodiment, the transparent cover plate 240 is a thin sheet of glass (e.g., a microscope slide cover slip). The slide may be positioned a fixed distance above the silicon wafer. Support structures 241 (See FIG. 2) may be placed upon the silicon wafer 210 to position the transparent cover plate 240. The support structures may be formed from a polymer or a silicon based material. In another embodiment, a polymeric substrate is coupled to the silicon wafer to form the support structures 241 for the transparent cover plate 240. In an embodiment, a plastic material with an adhesive backing (e.g., cellophane tape) is positioned on the silicon wafer 210. After the support structures 241 are placed on the wafer, the transparent cover plate 240 is placed upon the support structures. The support structures inhibit the transparent cover sheet from contacting the silicon wafer 210. In this manner, a channel is formed between the silicon wafer and the transparent cover plate, which allow the fluid to pass into the cavity, while inhibiting displacement of the particle by the fluid.

Figure 3:
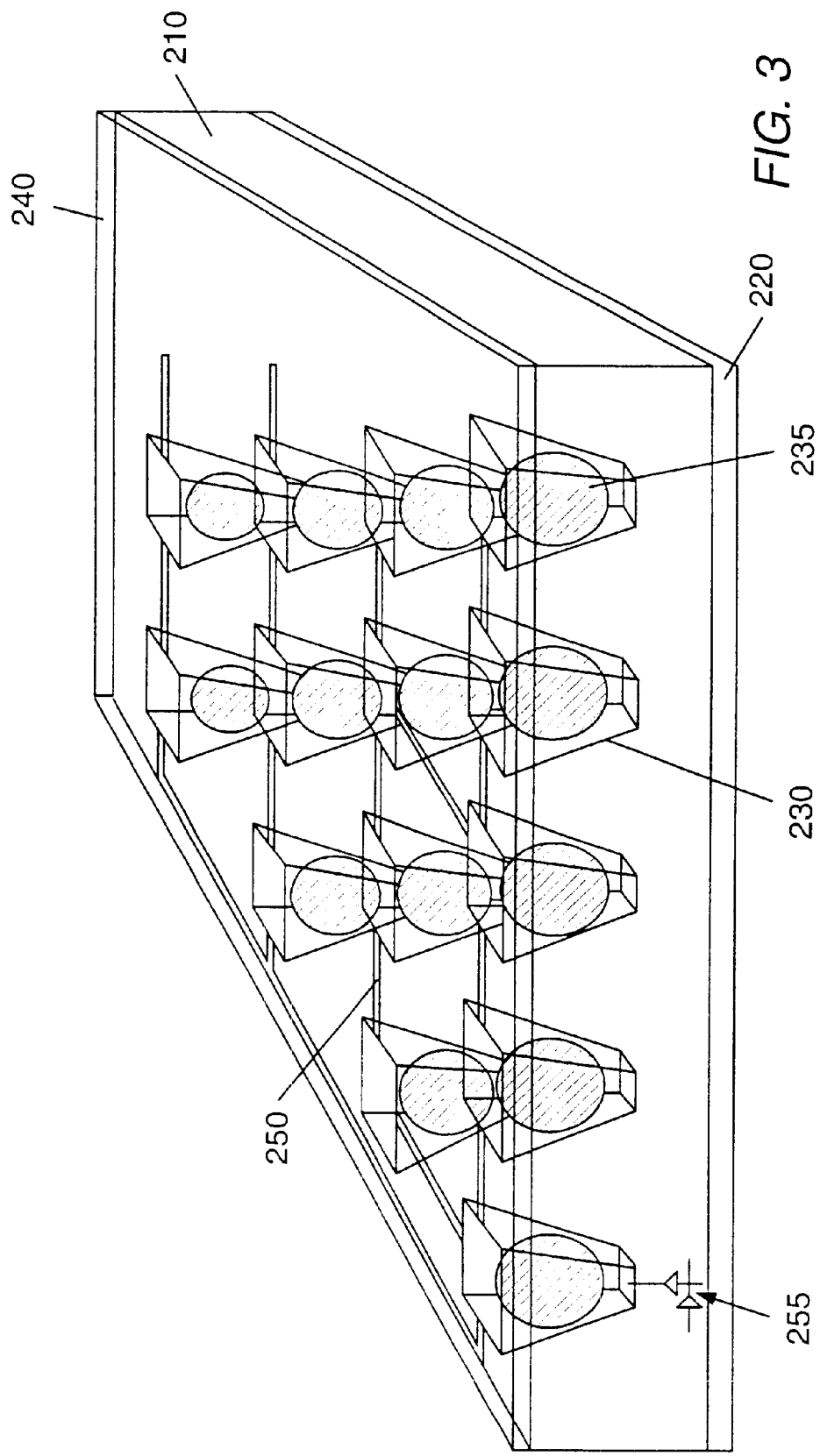
FIG. 3 depicts a sensor array.

In another embodiment, the transparent cover plate 240 may be fastened to the upper surface of the silicon wafer, as depicted in FIG. 3. In this embodiment, the fluid may be inhibited from entering the cavities 230 by the transparent cover plate 240. To allow passage of the fluid into the cavities, a number of channels 250 may be formed in the silicon wafer. The channels, in one embodiment, are oriented to allow passage of the fluid into substantially all of the cavities. When contacted with the fluid, the particles may swell to a size which may plug the channels. To prevent this plugging, the channels may be formed near the upper portion of the cavities, as depicted in FIG. 3. The channels, in one embodiment, are formed using standard photolithographic masking to define the regions where the trenches are to be formed, followed by the use of standard etching techniques. A depth of the cavity may be such that the particle resides substantially below the position of the channel. In this way, the plugging of the channels due to swelling of the particle may be prevented.

The inner surfaces of the cavities may be coated with a material to aid the positioning of the particles within the cavities. In one embodiment, a thin layer of gold or silver may be used to line the inner surface of the cavities. The gold or silver layer may act as an anchoring surface to anchor particles (e.g., via alkylthiol bonding). In addition, the gold or silver layer may also increase the reflectivity of the inner surface of the cavities. The increased reflectance of the surface may enhance the analyte detection sensitivity of the system. Alternatively, polymer layers and self-assembled monolayers formed upon the inner surface of the cavities may be used to control the particle adhesion interactions. Additional chemical anchoring methods may be used for silicon surfaces such as those based on siloxane type reagents, which may be attached to Si—OH functionalities. Similarly, monomeric and polymeric reagents attached to an interior region of the cavities can be used to alter the local wetting characteristics of the cavities. This type of methodology can be used to anchor the particles as well as to alter the fluid delivery characteristics of the cavity. Furthermore, amplification of the signals for the analytes may be accomplished with this type of strategy by causing preconcentration of appropriate analytes in the appropriate type of chemical environment.

In another embodiment, the optical detector may be integrated within the bottom transparent layer 220 of the supporting member, rather than using a separate detecting device. The optical detectors may be formed using a semiconductor-based photodetector 255. The optical detectors may be coupled to a microprocessor to allow evaluation of fluids without the use of separate detecting components. Additionally, the fluid delivery system may also be incorporated into the supporting member. Micro-pumps and micro-valves may also be incorporated into the silicon wafer to aid passage of the fluid through the cavities. Integration of detectors and a fluid delivery system into the supporting member may allow the formation of a compact and portable analyte sensing system. Optical filters may also be integrated into the bottom membrane of the cavities. These filters may prevent short wavelength excitation from producing "false" signals in the optical detection system (e.g., a CCD detector array) during fluorescence measurements.

A sensing cavity may be formed on the bottom surface of the support substrate. An example of a sensing cavity that may be used is a Fabry-Perot type cavity. Fabry-Perot cavity-based sensors may be used to detect changes in optical path length induced by either a change in the refractive index or a change in physical length of the cavity. Using micromachining techniques, Fabry-Perot sensors may be formed on the bottom surface of the cavity.

Figure 4A:
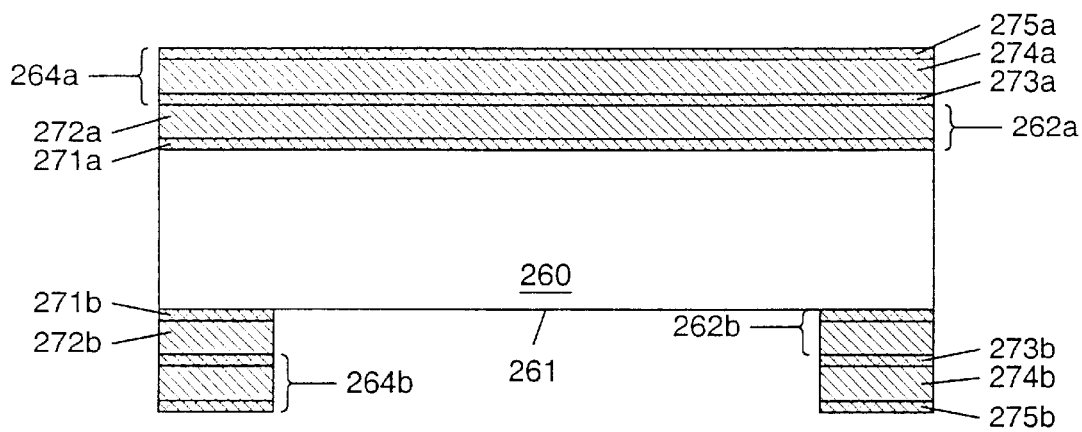
FIGS. 4A–F depict the formation of a Fabry-Perot cavity on the back of a sensor array.

FIGS. 4A–F depict a sequence of processing steps for the formation of a cavity and a planar top diaphragm Fabry-Perot sensor on the bottom surface of a silicon based supporting member. A sacrificial barrier layer 262a/b is deposited upon both sides of a silicon supporting member 260. The silicon supporting member 260 may be a double-side polished silicon wafer having a thickness ranging from about 100 $\mu$m to about 500 $\mu$m, preferably from about 200 $\mu$m to about 400 $\mu$m, and more preferably of about 300 $\mu$m. The barrier layer 262a/b may be composed of silicon dioxide, silicon nitride, or silicon oxynitride. In one embodiment, the barrier layer 262a/b is composed of a stack of dielectric materials. As depicted in FIG. 4A, the barrier layer 262a/b is composed of a stack of dielectric materials which includes a silicon nitride layer 271a/b and a silicon dioxide layer 272a/b. Both layers may be deposited using a low pressure chemical vapor deposition ("LPCVD") process. Silicon nitride may be deposited using an LPCVD reactor by reaction of ammonia ($NH_3$) and dichlorosilane ($SiCl_2H_2$) at a gas flow rate of about 3.5:1, a temperature of about 800° C., and a pressure of about 220 mTorr. The silicon nitride layer 271a/b is deposited to a thickness in the range from about 100 Å to about 500 Å, preferably from 200 Å to about 400 Å, and more preferably of about 300 Å. Silicon dioxide is may be deposited using an LPCVD reactor by reaction of silane ($SiH_4$) and oxygen ($O_2$) at a gas flow rate of about 3:4, a temperature of about 450° C., and a pressure of about 110 mTorr. The silicon dioxide layer 272a/b is deposited to a thickness in the range from about 3000 Å to about 7000 Å, preferably from 4000 Å to about 6000 Å, and more preferably of about 5000 Å. The front face silicon dioxide layer 272a, in one embodiment, acts as the main barrier layer. The underlying silicon nitride layer 271a acts as an intermediate barrier layer to inhibit overetching of the main barrier layer during subsequent KOH wet anisotropic etching steps.

A bottom diaphragm layer 264a/b is deposited upon the barrier layer 262a/b on both sides of the supporting member 260. The bottom diaphragm layer 264a/b may be composed of silicon nitride, silicon dioxide, or silicon oxynitride. In one embodiment, the bottom diaphragm layer 264a/b is composed of a stack of dielectric materials. As depicted in FIG. 4A, the bottom diaphragm layer 264a/b is composed of a stack of dielectric materials which includes a pair of silicon nitride layers 273a/b and 275a/b surrounding a silicon dioxide layer 274a/b. All of the layers may be deposited using an LPCVD process. The silicon nitride layers 273a/b and 275a/b have a thickness in the range from about 500 Å to about 1000 Å, preferably from 700 Å to about 800 Å, and more preferably of about 750 Å. The silicon dioxide layer 274*a/b* has a thickness in the range from about 3000 Å to about 7000 Å, preferably from 4000 Å to about 6000 Å, and more preferably of about 4500 Å.

Figure 4B:
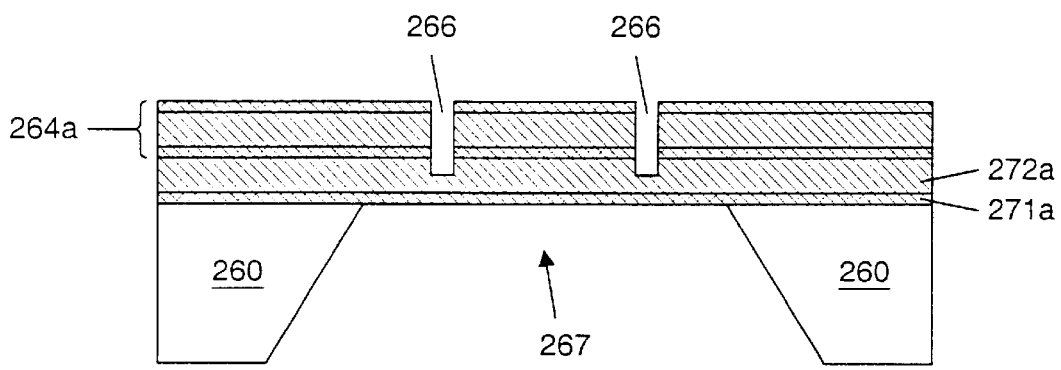

A cavity which will hold the particle may now be formed in the supporting member 260. The bottom diaphragm layer 264*b* and the barrier layer 262*b* formed on the back side 261 of the silicon supporting member 260 are patterned and etched using standard photolithographic techniques. In one embodiment, the layers are subjected to a plasma etch process. The plasma etching of silicon dioxide and silicon nitride may be performed using a mixture of carbontetrafluoride ($CF_4$) and oxygen ($O_2$). The patterned back side layers 262*b* and 264*b* may be used as a mask for anisotropic etching of the silicon supporting member 260. The silicon supporting member 260, in one embodiment, is anisotropically etched with a 40% potassium hydroxide ("KOH") solution at 80° C. to form the cavity. The etch is stopped when the front side silicon nitride layer 271*a* is reached, as depicted in FIG. 4B. The silicon nitride layer 271*a* inhibits etching of the main barrier layer 272*a* during this etch process. The cavity 267 may be formed extending through the supporting member 260. After formation of the cavity, the remaining portions of the back side barrier layer 262*b* and the diaphragm layer 264*b* may be removed.

Etch windows 266 are formed through the bottom diaphragm layer 264*a* on the front side of the wafer. A masking layer (not shown) is formed over the bottom diaphragm layer 264*a* and patterned using standard photolithographic techniques. Using the masking layer, etch windows 266 may be formed using a plasma etch. The plasma etching of silicon dioxide and silicon nitride may be performed using a mixture of carbontetrafluoride ($CF_4$) and oxygen ($O_2$). The etching is continued through the bottom diaphragm layer 264*a* and partially into the barrier layer 262*a*. In one embodiment, the etching is stopped at approximately half the thickness of the barrier layer 262*a*. Thus, when the barrier layer 262*a* is subsequently removed the etch windows 266 will extend through the bottom diaphragm layer 264*a*, communicating with the cavity 267. By stopping the etching at a midpoint of the barrier layer, voids or discontinuities may be reduced since the bottom diaphragm is still continuous due to the remaining barrier layer.

Figure 4C:
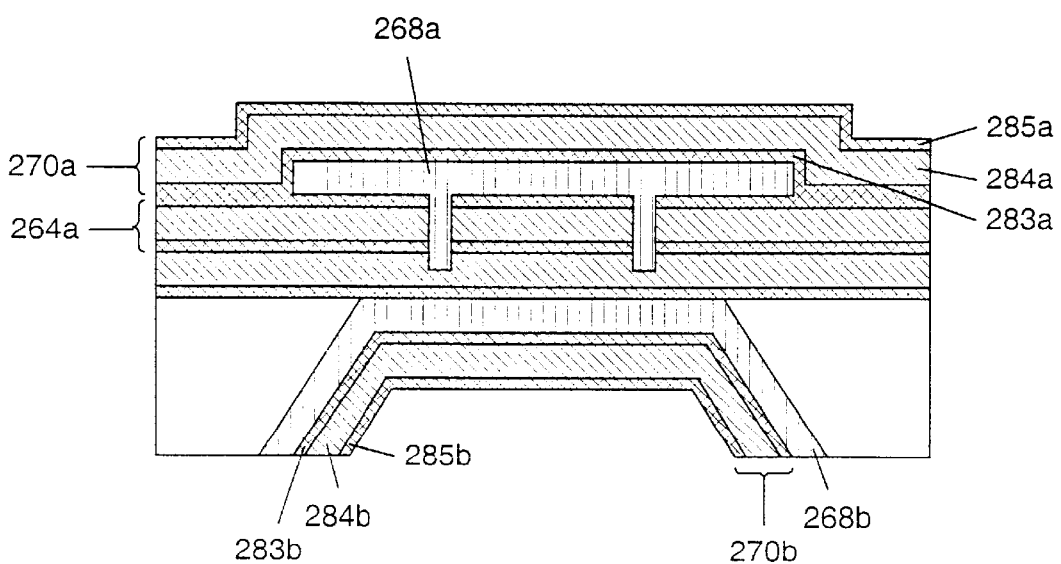

After the etch windows 266 are formed, a sacrificial spacer layer 268*a/b* is deposited upon the bottom diaphragm layer 264*a* and within cavity 267, as depicted in FIG. 4C. The spacer layer may be formed from LPCVD polysilicon. In one embodiment, the front side deposited spacer layer 268*a* will also at least partially fill the etch windows 266. Polysilicon may be deposited using an LPCVD reactor using silane ($SiH_4$) at a temperature of about 650° C. The spacer layer 268*a/b* is deposited to a thickness in the range from about 4000 Å to about 10,000 Å, preferably from 6000 Å to about 8000 Å, and more preferably of about 7000 Å. The preferred thickness of the spacer layer 268*a* is dependent on the desired thickness of the internal air cavity of the Fabry-Perot detector. For example, if a Fabry-Perot detector which is to include a 7000 Å air cavity between the top and bottom diaphragm layer is desired, a spacer layer having a thickness of about 7000 Å would be formed. After the spacer layer has been deposited, a masking layer for etching the spacer layer 268*a* (not shown) is used to define the etch regions of the spacer layer 268*a*. The etching may be performed using a composition of nitric acid ($HNO_3$), water, and hydrogen fluoride (HF) in a ratio of 25:13:1, respectively, by volume. The lateral size of the subsequently formed cavity is determined by the masking pattern used to define the etch regions of the spacer layer 268*a*.

After the spacer layer 268*a* has been etched, the top diaphragm layer 270*a/b* is formed. The top diaphragm 270*a/b*, in one embodiment, is deposited upon the spacer layer 268*a/b* on both sides of the supporting member. The top diaphragm 270*a/b* may be composed of silicon nitride, silicon dioxide, or silicon oxynitride. In one embodiment, the top diaphragm 270*a/b* is composed of a stack of dielectric materials. As depicted in FIG. 4C, the top diaphragm 270*a/b* is composed of a stack of dielectric materials which includes a pair of silicon nitride layers 283*a/b* and 285*a/b* surrounding a silicon dioxide layer 284*a/b*. All of the layers may be deposited using an LPCVD process. The silicon nitride layers 283*a/b* and 285*a/b* have a thickness in the range from about 1000 Å to about 2000 Å, preferably from 1200 Å to about 1700 Å, and more preferably of about 1500 Å. The silicon dioxide layer 284*a/b* has a thickness in the range from about 5000 Å to about 15,500 Å, preferably from 7500 Å to about 12,000 Å, and more preferably of about 10,500 Å.

Figure 4D:
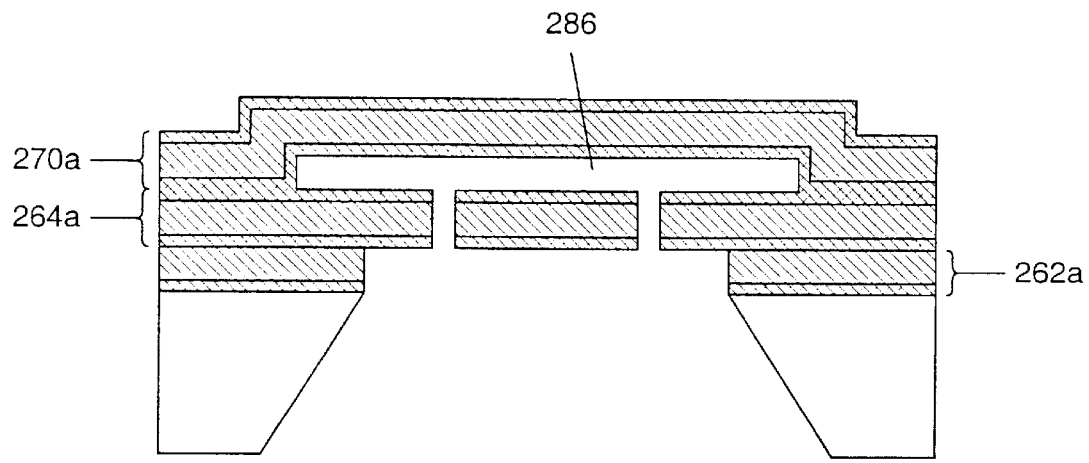

After depositing the top diaphragm 270*a/b*, all of the layers stacked on the bottom face of the supporting member (e.g., layers 268*b*, 283*b*, 284*b*, and 285*b*) are removed by multiple wet and plasma etching steps, as depicted in FIG. 4D. After these layers are removed, the now exposed portions of the barrier layer 262*a* are also removed. This exposes the spacer layer 268*a* which is present in the etch windows 266. The spacer layer 268 may be removed from between the top diaphragm 270*a* and the bottom diaphragm 264*a* by a wet etch using a KOH solution, as depicted in FIG. 4D. Removal of the spacer material 268*a*, forms a cavity 286 between the top diaphragm layer 270*a* and the bottom diaphragm layer 264*a*. After removal of the spacer material, the cavity 286 may be washed using deionized water, followed by isopropyl alcohol to clean out any remaining etching solution.

Figure 4E:
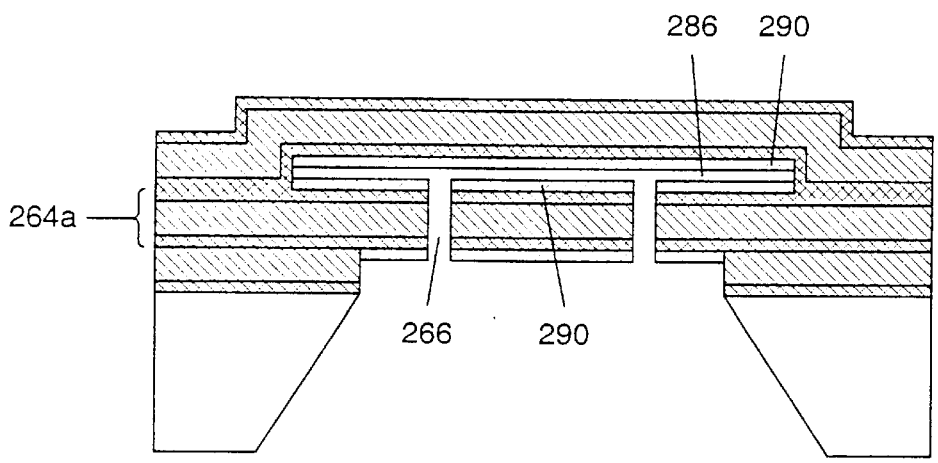

The cavity 286 of the Fabry-Perot sensor may be filled with a sensing substrate 290, as depicted in FIG. 4E. To coat the cavity 286 with a sensing substrate 290, the sensing substrate may be dissolved in a solvent. A solution of the sensing substrate is applied to the supporting member 260. The solution is believed to rapidly enter the cavity 286 through the etched windows 266 in the bottom diaphragm 264*a*, aided in part by capillary action. As the solvent evaporates, a thin film of the sensing substrate 290 coats the inner walls of the cavity 286, as well as the outer surface of the bottom diaphragm 264*a*. By repeated treatment of the supporting member with the solution of the sensing substrate, the thickness of the sensing substrate may be varied.

In one embodiment, the sensing substrate 290 is poly(3-dodecylthiophene) whose optical properties change in response to changes in oxidation states. The sensing substrate poly(3-dodecylthiophene) may be dissolved in a solvent such as chloroform or xylene. In one embodiment, a concentration of about 0.1 g of poly(3-dodecylthiophene)/mL is used. Application of the solution of poly(3-dodecylthiophene) to the supporting member causes a thin film of poly(3-dodecylthiophene) to be formed on the inner surface of the cavity.

Figure 4F:
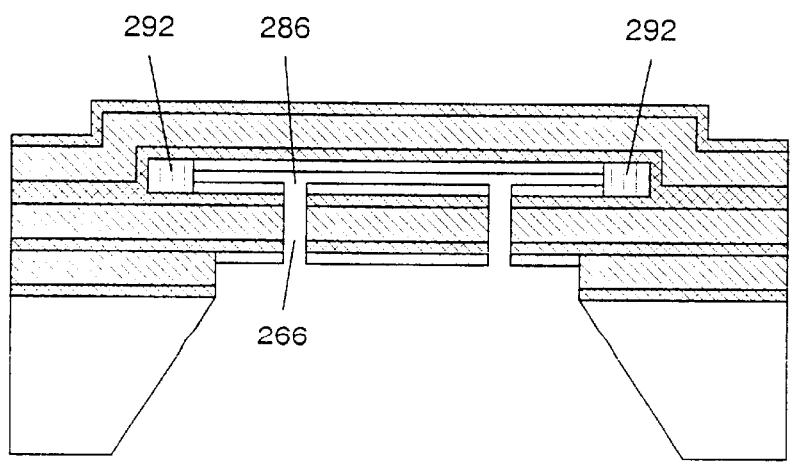

In some instances, the sensing substrate, when deposited within a cavity of a Fabry-Perot type detector, may cause stress in the top diaphragm of the detector. It is believed that when a sensing polymer coats a planar top diaphragm, extra residual stress on the top diaphragm causes the diaphragm to become deflected toward the bottom diaphragm. If the deflection becomes to severe, sticking between the top and bottom diaphragms may occur. In one embodiment, this stress may be relieved by the use of supporting members 292 formed within the cavity 286, as depicted in FIG. 4F. The supporting members 292 may be formed without any extra processing steps to the above described process flow. The formation of supporting members may be accomplished by deliberately leaving a portion of the spacer layer within the cavity. This may be accomplished by underetching the spacer layer (e.g., terminating the etch process before the entire etch process is finished). The remaining spacer will behave as a support member to reduce the deflection of the top diaphragm member. The size and shape of the support members may be adjusted by altering the etch time of the spacer layer, or adjusting the shape of the etch windows 266.

In another embodiment, a high sensitivity CCD array may be used to measure changes in optical characteristics which occur upon binding of the biological/chemical agents. The CCD arrays may be interfaced with filters, light sources, fluid delivery and micromachined particle receptacles, so as to create a functional sensor array. Data acquisition and handling may be performed with existing CCD technology. Data streams (e.g., red, green, blue for calorimetric assays; gray intensity for fluorescence assays) may be transferred from the CCD to a computer via a data acquisition board. Current CCDs may allow for read-out rates of $10^5$ pixels per second. Thus, the entire array of particles may be evaluated hundreds of times per second allowing for studies of the dynamics of the various host-guest interaction rates as well as the analyte/polymer diffusional characteristics. Evaluation of this data may offer a method of identifying and quantifying the chemical/biological composition of the test samples. CCD detectors may be configured to measure white light, ultraviolet light or fluorescence. Other detectors such as photomultiplier tubes, charge induction devices, photodiode, photodiode arrays, and microchannel plates may also be used. It should be understood that while the detector is depicted as being positioned under the supporting member, the detector may also be positioned above the supporting member. It should also be understood that the detector typically includes a sensing element for detecting the spectroscopic events and a component for displaying the detected events. The display component may be physically separated from the sensing element. The sensing element may be positioned above or below the sensor array while the display component is positioned close to a user.

In one embodiment, a CCD detector may be used to record color changes of the chemical sensitive particles during analysis. As depicted in FIG. 1, a CCD detector 130 may be placed beneath the supporting member 120. The light transmitted through the cavities is captured and analyzed by the CCD detector. In one embodiment, the light is broken down into three color components, red, green and blue. To simplify the data, each color is recorded using 8 bits of data. Thus, the data for each of the colors will appear as a value between 0 and 255. The color of each chemical sensitive element may be represented as a red, blue and green value. For example, a blank particle (i.e., a particle which does not include a receptor) will typically appear white. For example, when broken down into the red, green and blue components, it is found that a typical blank particle exhibits a red value of about 253, a green value of about 250, and a blue value of about 222. This signifies that a blank particle does not significantly absorb red, green or blue light. When a particle with a receptor is scanned, the particle may exhibit a color change, due to absorbance by the receptor. For example, it was found that when a particle which includes a 5-carboxyfluorescein receptor is subjected to white light, the particle shows a strong absorbance of blue light. The CCD detector values for the 5-carboxyfluorescein particle exhibits a red value of about 254, a green value of about 218, and a blue value of about 57. The decrease in transmittance of blue light is believed to be due to the absorbance of blue light by the 5-carboxyfluorescein. In this manner, the color changes of a particle may be quantitatively characterized. An advantage of using a CCD detector to monitor the color changes is that color changes which may not be noticeable to the human eye may now be detected.

The support array may be configured to allow a variety of detection modes to be practiced. In one embodiment, a light source is used to generate light which is directed toward the particles. The particles may absorb a portion of the light as the light illuminates the particles. The light then reaches the detector, reduced in intensity by the absorbance of the particles. The detector may be configure to measure the reduction in light intensity (i.e., the absorbance) due to the particles. In another embodiment, the detector may be placed above the supporting member. The detector may be configured to measure the amount of light reflected off of the particles. The absorbance of light by the particles is manifested by a reduction in the amount of light being reflected from the cavity. The light source in either embodiment may be a white light source or a fluorescent light source.

Chemically Sensitive Particles

A particle, in some embodiments, possess both the ability to bind the analyte of interest and to create a modulated signal. The particle may include receptor molecules which posses the ability to bind the analyte of interest and to create a modulated signal. Alternatively, the particle may include receptor molecules and indicators. The receptor molecule may posses the ability to bind to an analyte o f interest. Upon binding the analyte of interest, the receptor molecule may cause the indicator molecule to produce the modulated signal. The receptor molecules may be naturally occurring or synthetic receptors formed by rational design or combinatorial methods. Some examples of natural receptors include, but are not limited to, DNA, RNA, proteins, enzymes, oligopeptides, antigens, and antibodies. Either natural or synthetic receptors may be chosen for their ability to bind to the analyte molecules in a specific manner. The forces which drive association/recognition between molecules include the hydrophobic effect, anion-cation attraction, and hydrogen bonding. The relative strengths of these forces depend upon factors such as the solvent dielectric properties, the shape of the host molecule, and how it complements the guest. Upon host-guest association, attractive interactions occur and the molecules stick together. The most widely used analogy for this chemical interaction is that of a "lock and key". The fit of the key molecule (the guest) into the lock (the host) is a molecular recognition event.

A naturally occurring or synthetic receptor may be bound to a polymeric resin in order to create the particle. The polymeric resin may be made from a variety of polymers including, but not limited to, agarous, dextrose, acrylamide, control pore glass beads, polystyrene-polyethylene glycol resin, polystyrene-divinyl benzene resin, formylpolystyrene resin, trityl-polystyrene resin, acetyl polystyrene resin, chloroacetyl polystyrene resin, aminomethyl polystyrene-divinylbenzene resin, carboxypolystyrene resin, chloromethylated polystyrene-divinylbenzene resin, hydroxymethyl polystyrene-divinylbenzene resin, 2-chlorotrityl chloride polystyrene resin, 4-benzyloxy-2'4'-dimethoxybenzhydrol resin (Rink Acid resin), triphenyl methanol polystyrene resin, diphenylmethanol resin, benzhydrol resin, succinimidyl carbonate resin, p-nitrophenyl carbonate resin, imidazole carbonate resin, polyacrylamide resin, 4-sulfamylbenzoyl-4'-methylbenzhydrylamine-resin (Safety-catch resin), 2-amino-2-(2'-nitrophenyl) propionic acid-aminomethyl resin (ANP Resin), p-benzyloxybenzyl alcohol-divinylbenzene resin (Wang resin), p-methylbenzhydrylamine-divinylbenzene resin (MBHA resin), Fmoc-2,4-dimethoxy-4'-(carboxymethyloxy)-benzhydrylamine linked to resin (Knorr resin), 4-(2',4'-Dimethoxyphenyl-Fmoc-aminomethyl)-phenoxy resin (Rink resin), 4-hydroxymethyl-benzoyl-4'-methylbenzhydrylamine resin (HMBA-MBHA Resin), p-nitrobenzophenone oxime resin (Kaiser oxime resin), and amino-2,4-dimethoxy-4'-(carboxymethyloxy)-benzhydrylamine handle linked to 2-chlorotrityl resin (Knorr-2-chlorotrityl resin). In one embodiment, the material used to form the polymeric resin is compatible with the solvent in which the analyte is dissolved. For example, polystyrene-divinyl benzene resin will swell within non-polar solvents, but does not significantly swell within polar solvents. Thus, polystyrene-divinyl benzene resin may be used for the analysis of analytes within non-polar solvents. Alternatively, polystyrene-polyethylene glycol resin will swell with polar solvents such as water. Polystyrene-polyethylene glycol resin may be useful for the analysis of aqueous fluids.

In one embodiment, a polystyrene-polyethylene glycol-divinyl benzene material is used to form the polymeric resin. The polystyrene-polyethylene glycol-divinyl benzene resin is formed from a mixture of polystyrene 375, divinyl benzene 380 and polystyrene-polyethylene glycol 385, see FIG. 5. The polyethylene glycol portion of the polystyrene-polyethylene glycol 385, in one embodiment, may be terminated with an amine. The amine serves as a chemical handle to anchor both receptors and indicator dyes. Other chemical functional groups may be positioned at the terminal end of the polyethylene glycol to allow appropriate coupling of the polymeric resin to the receptor molecules or indicators.

The chemically sensitive particle, in one embodiment, is capable of both binding the analyte(s) of interest and creating a detectable signal. In one embodiment, the particle will create an optical signal when bound to an analyte of interest. The use of such a polymeric bound receptors offers advantages both in terms of cost and configurability. Instead of having to synthesize or attach a receptor directly to a supporting member, the polymeric bound receptors may be synthesized en masse and distributed to multiple different supporting members. This allows the cost of the sensor array, a major hurdle to the development of mass-produced environmental probes and medical diagnostics, to be reduced. Additionally, sensor arrays which incorporate polymeric bound receptors may be reconfigured much more quickly than array systems in which the receptor is attached directly tot he supporting member. For example, if a new variant of a pathogen or a pathogen that contains a genetically engineered protein is a threat, then a new sensor array system may be readily created to detect these modified analytes by simply adding new sensor elements (e.g., polymeric bound receptors) to a previously formed supporting member.

Figure 6:
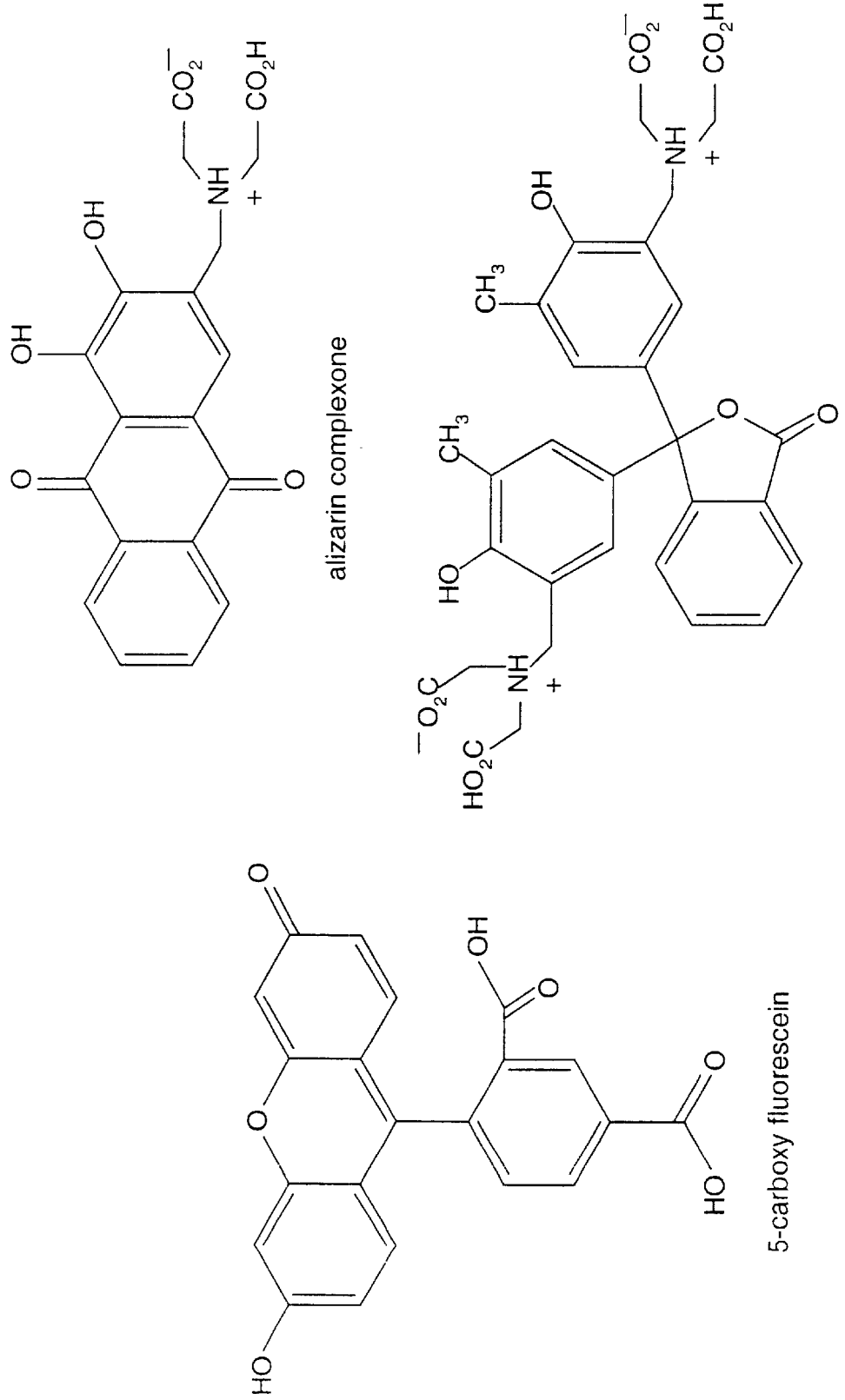
FIG. 6 depicts the chemical formulas of some receptor compounds.

In one embodiment, a receptor, which is sensitive to changes in the pH of a fluid sample is bound to a polymeric resin to create a particle. That is, the receptor is sensitive to the concentration of hydrogen cations ($H^+$). The receptor in this case is typically sensitive to the concentration of $H^+$ in a fluid solution. The analyte of interest may therefore be $H^+$. There are many types of molecules which undergo a color change when the pH of the fluid is changed. For example, many types of dyes undergo significant color changes as the pH of the fluid medium is altered. Examples of receptors which may be used to monitor the pH of a fluid sample include 5-carboxyfluorescein and alizarin complexone, depicted in FIG. 6. Each of these receptors undergoes significant color changes as the pH of the fluid is altered. 5-carboxyfluorescein undergoes a change from yellow to orange as the pH of the fluid is increased. Alizarin complexone undergoes two color changes, first from yellow to red, then from red to blue as the pH of the fluid increases. By monitoring the change in color caused by dyes attached to a polymeric particle, the pH of a solution may be qualitatively and, with the use of a detector (e.g., a CCD detector), quantitatively monitored.

In another embodiment, a receptor which is sensitive to presence of metal cations is bound to a polymeric particle to create a particle. The receptor in this case is typically sensitive to the concentration of one or more metal cations present in a fluid solution. In general, colored molecules which will bind cations may be used to determine the presence of a metal cation in a fluid solution. Examples of receptors which may be used to monitor the presence of cations in a fluid sample include alizarin complexone and o-cresolphthalein complexone, see FIG. 6. Each of these receptors undergoes significant color changes as the concentration of a specific metal ion in the fluid is altered. Alizarin complexone is particularly sensitive to lanthanum ions. In the absence of lanthanum, alizarin complexone will exhibit a yellow color. As the concentration of lanthanum is increased, alizarin complexone will change to a red color. o-Cresolphthalein complexone is particularly sensitive to calcium ions. In the absence of calcium, o-cresolphthalein complexone is colorless. As the concentration of calcium is increased, o-cresolphthalein complexone will change to a blue color. By monitoring the change in color of metal cation sensitive receptors attached to a polymeric particle, the presence of a specific metal ion may be qualitatively and, with the use of a detector (e.g., a CCD detector), quantitatively monitored.

Figure 7:
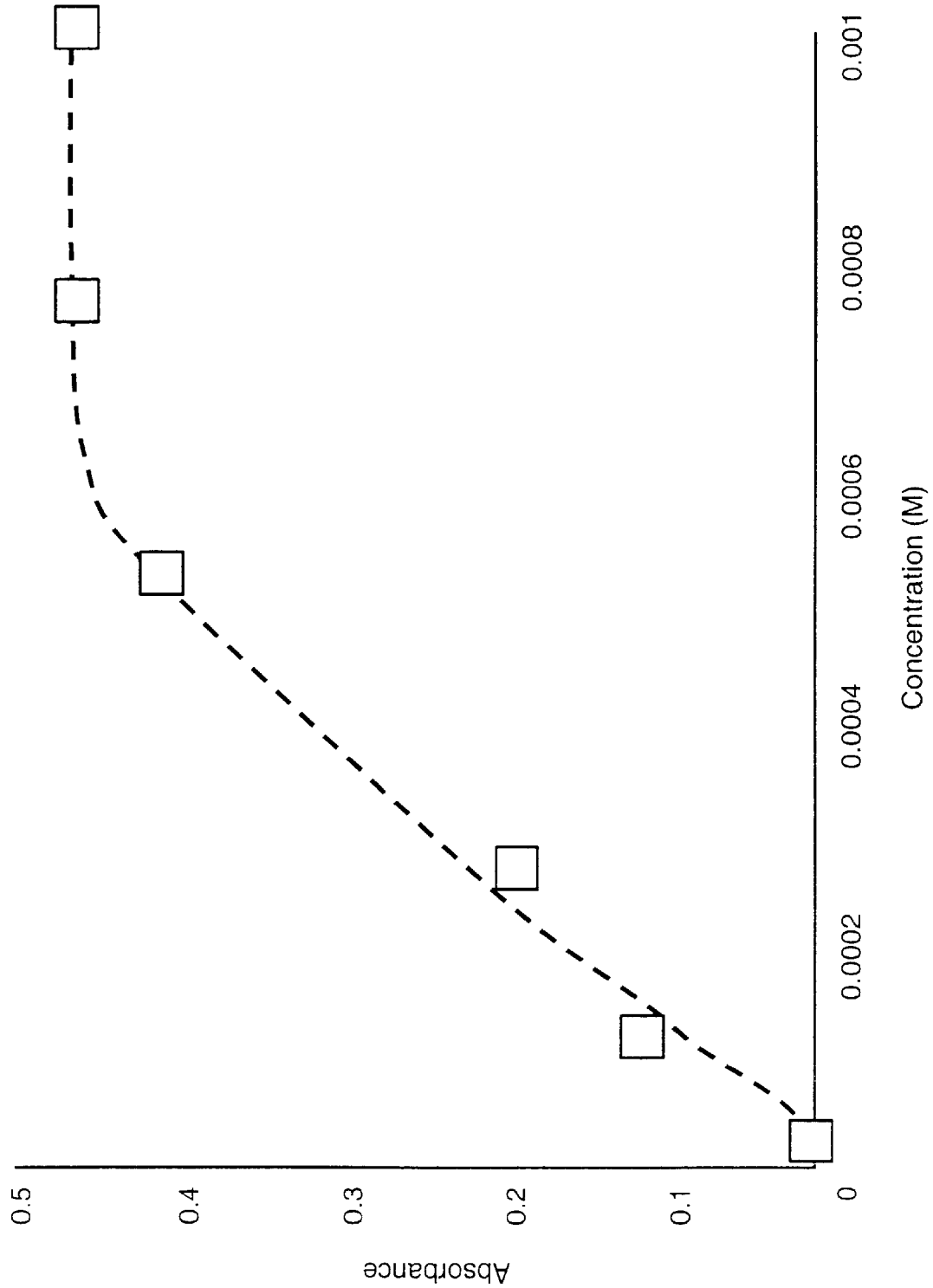
FIG. 7 depicts a plot of the absorbance of green light vs. concentration of calcium ($Ca^{+2}$) for a particle which includes an o-cresolphthalein complexone receptor.

Referring to FIG. 7, a graph of the absorbance of green light vs. concentration of calcium ($Ca^{+2}$) is depicted for a particle which includes an o-cresolphthalein complexone receptor. As the concentration of calcium is increased, the absorbance of green light increases in a linear manner up to a concentration of about 0.0006 M. A concentration of 0.0006 M is the solubility limit of calcium in the fluid, thus no significant change in absorbance is noted after this point. The linear relationship between concentration and absorbance allows the concentration of calcium to be determined by measuring the absorbance of the fluid sample.

In one embodiment, a detectable signal may be caused by the altering of the physical properties of an indicator ligand bound to the receptor or the polymeric resin. In one embodiment, two different indicators are attached to a receptor or the polymeric resin. When an analyte is captured by the receptor, the physical distance between the two indicators may be altered such that a change in the spectroscopic properties of the indicators is produced. A variety of fluorescent and phosphorescent indicators may be used for this sensing scheme. This process, known as Forster energy transfer, is extremely sensitive to small changes in the distance between the indicator molecules.

Figure 8:
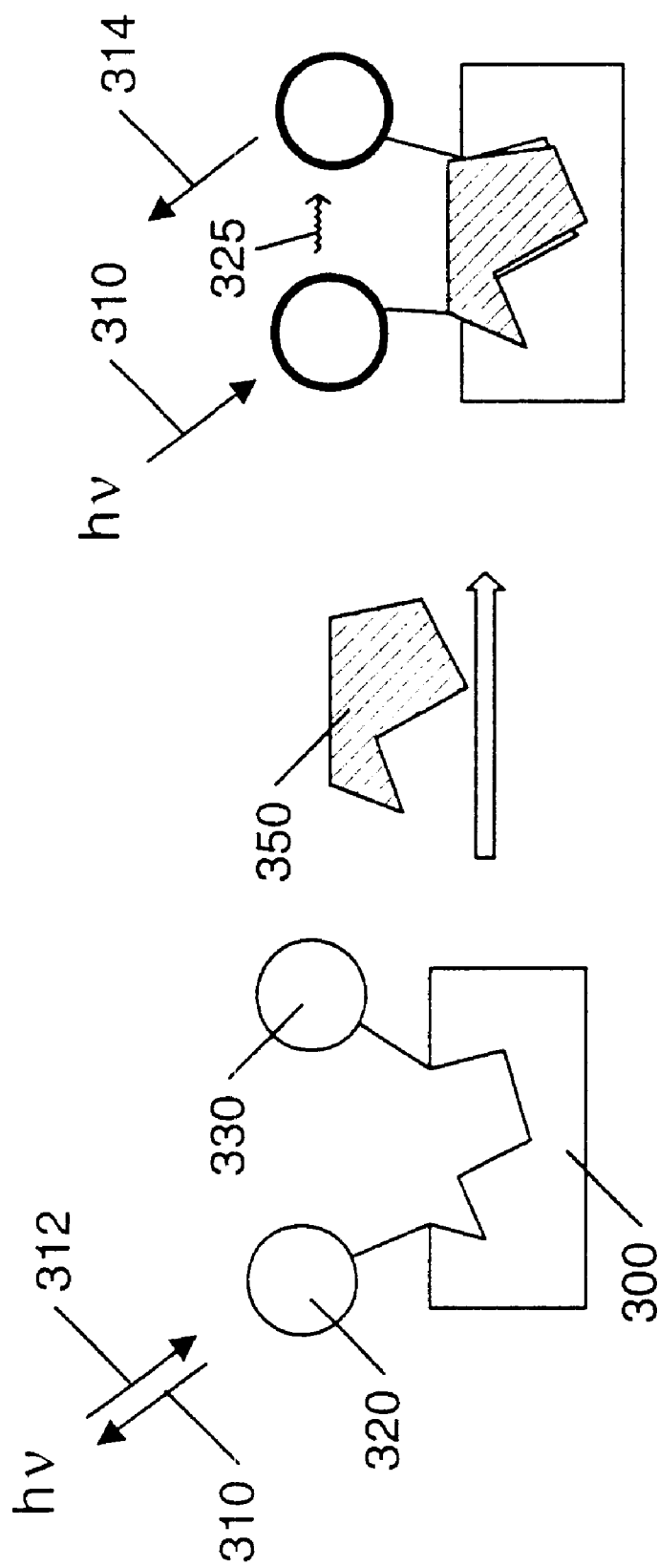
FIG. 8 depicts a schematic view of the transfer of energy from a first indicator to a second indicator in the presence of an analyte.

For example, a first fluorescent indicator 320 (e.g., a fluorescein derivative) and a second fluorescent indictor 330 (e.g., a rhodamine derivative) may be attached to a receptor 300, as depicted in FIG. 8. When no analyte is present short wavelength excitation 310 may excite the first fluorescent indicator 320, which fluoresces as indicated by 312. The short wavelength excitation, however, may cause little or no fluorescence of the second fluorescent indicator 330. After binding of analyte 350 to the receptor, a structural change in the receptor molecule may bring the first and second fluorescent indicators closer to each other. This change in intermolecular distance may allow the excited first indicator 320 to transfer a portion of its fluorescent energy 325 to the second fluorescent indicator 330. This transfer in energy may be measured by either a drop in energy of the fluorescence of the first indicator molecule 320, or the detection of increased fluorescence 314 by the second indicator molecule 330.

Alternatively, the first and second fluorescent indicators may initially be positioned such that short wavelength excitation, may cause fluorescence of both the first and second fluorescent indicators, as described above. After binding of analyte 350 to the receptor, a structural change in the receptor molecule may cause the first and second fluorescent indicators to move further apart. This change in intermolecular distance may inhibit the transfer of fluorescent energy from the first indicator 320 to the second fluorescent indicator 330. This change in the transfer of energy may be measured by either a drop in energy of the fluorescence of the second indicator molecule 330, or the detection of increased fluorescence by the first indicator molecule 320.

In another embodiment, an indicator ligand may be preloaded onto the receptor. An analyte may then displace the indicator ligand to produce a change in the spectroscopic properties of the particles. In this case, the initial background absorbance is relatively large and decreases when the analyte is present. The indicator ligand, in one embodiment, has a variety of spectroscopic properties which may be measured. These spectroscopic properties include, but are not limited to, ultraviolet absorption, visible absorption, infrared absorption, fluorescence, and magnetic resonance. In one embodiment, the indicator is a dye having either a strong fluorescence, a strong ultraviolet absorption, a strong visible absorption, or a combination of these physical properties. Examples of indicators include, but are not limited to, carboxyfluorescein, ethidium bromide, 7-dimethylamino-4-methylcoumarin, 7-diethylamino-4-methylcoumarin, eosin, erythrosin, fluorescein, Oregon Green 488, pyrene, Rhodamine Red, tetramethylrhodamine, Texas Red, Methyl Violet, Crystal Violet, Ethyl Violet, Malachite green, Methyl Green, Alizarin Red S, Methyl Red, Neutral Red, o-cresolsulfonephthalein, o-cresolphthalein, phenolphthalein, Acridine Orange, B-naphthol, coumarin, and α-naphthionic acid. When the indicator is mixed with the receptor, the receptor and indicator interact with each other such that the above mentioned spectroscopic properties of the indicator, as well as other spectroscopic properties may be altered. The nature of this interaction may be a binding interaction, wherein the indicator and receptor are attracted to each other with a sufficient force to allow the newly formed receptor-indicator complex to function as a single unit. The binding of the indicator and receptor to each other may take the form of a covalent bond, an ionic bond, a hydrogen bond, a van der Waals interaction, or a combination of these bonds.

The indicator may be chosen such that the binding strength of the indicator to the receptor is less than the binding strength of the analyte to the receptor. Thus, in the presence of an analyte, the binding of the indicator with the receptor may be disrupted, releasing the indicator from the receptor. When released, the physical properties of the indicator may be altered from those it exhibited when bound to the receptor. The indicator may revert back to its original structure, thus regaining its original physical properties. For example, if a fluorescent indicator is attached to a particle that includes a receptor, the fluorescence of the particle may be strong before treatment with an analyte containing fluid. When the analyte interacts with the particle, the fluorescent indicator may be released. Release of the indicator may cause a decrease in the fluorescence of the particle, since the particle now has less indicator molecules associated with it.

An example of this type of system is illustrated by the use of a boronic acid substituted resin 505 as a particle. Prior to testing, the boronic acid substituted resin 505 is treated with a sugar 510, which is tagged with an indicator (e.g., resorufin) as depicted in FIG. 9. The tagged sugar 510 binds to the boronic acid receptor 500 imparting a color change to the boronic substituted resin 505 (yellow for the resorufin tagged sugar). When the boronic acid resin 505 is treated with a fluid sample, which includes a sugar 520, the tagged sugar 510 may be displaced, causing a decrease in the amount of color produced by the boronic acid substituted resin 505. This decrease may be qualitatively or, with the use of a detector (e.g., a CCD detector), quantitatively monitored.

In another embodiment, a designed synthetic receptor may be used. In one embodiment, a polycarboxylic acid receptor may be attached to a polymeric resin. The polycarboxylic receptors are discussed in U.S. patent application Ser. No. 08/950,712 which is incorporated herein by reference.

In an embodiment, the analyte molecules in the fluid may be pretreated with an indicator ligand. Pretreatment may involve covalent attachment of an indicator ligand to the analyte molecule. After the indicator has been attached to the analyte, the fluid may be passed over the sensing particles. Interaction of the receptors on the sensing particles with the analytes may remove the analytes from the solution. Since the analytes include an indicator, the spectroscopic properties of the indicator may be passed onto the particle. By analyzing the physical properties of the sensing particles after passage of an analyte stream, the presence and concentration of an analyte may be determined.

For example, the analytes within a fluid may be derivatized with a fluorescent tag before introducing the stream to the particles. As analyte molecules are adsorbed by the particles, the fluorescence of the particles may increase. The presence of a fluorescent signal may be used to determine the presence of a specific analyte. Additionally, the strength of the fluorescence may be used to determine the amount of analyte within the stream.

Receptors

A variety of natural and synthetic receptors may be used. The synthetic receptors may come from a variety of classes including, but not limited to, polynucleotides (e.g., aptamers), peptides (e.g., enzymes and antibodies), synthetic receptors, polymeric unnatural biopolymers (e.g., polythioureas, polyguanidiniums), and imprinted polymers., some of which are generally depicted. in FIG. 10. Natural based synthetic receptors include receptors which are structurally similar to naturally occurring molecules. Polynucleotides are relatively small fragments of DNA which may be derived by sequentially building the DNA sequence. Peptides may be synthesized from amino acids. Unnatural biopolymers are chemical structure which are based on natural biopolymers, but which are built from unnatural linking units. Unnatural biopolymers such as polythioureas and polyguanidiniums may be synthesized from diamines (i.e., compounds which include at least two amine functional groups). These molecules are structurally similar to naturally occurring receptors, (e.g., peptides). Some diamines may, in turn, be synthesized from amino acids. The use of amino acids as the building blocks for these compounds allow a wide variety of molecular recognition units to be devised. For example, the twenty natural amino acids have side chains that possess hydrophobic residues, cationic and anionic residues, as well as hydrogen bonding groups. These side chains may provide a good chemical match to bind a large number of targets, from small molecules to large oligosaccharides. Amino acid based peptides, polythioureas, and polyguanidiniums are depicted in FIG. 10.

Figure 11:
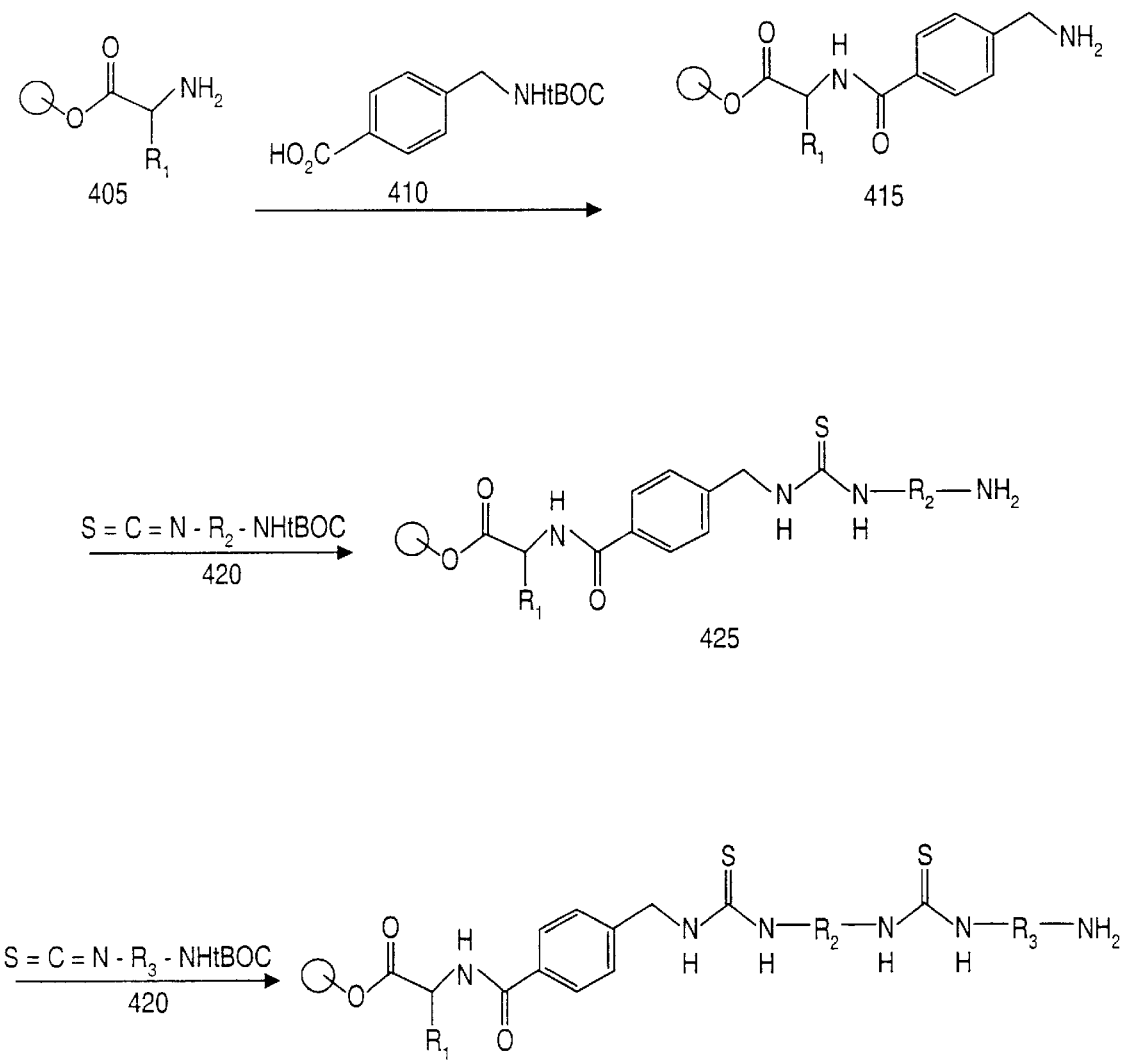
FIG. 11 depicts a synthetic pathway for the synthesis of polythioureas.

Techniques for the building of DNA fragments and polypeptide fragments on a polymer particle are well known. Techniques for the immobilization of naturally occurring antibodies and enzymes on a polymeric resin are also well known. The synthesis of polythioureas upon a resin particle may be accomplished by the synthetic pathway depicted in FIG. 11. The procedure may begin by deprotection of the terminal tBoc protecting group on an amino acid coupled to a polymeric particle, resulting in amine 405. Removal of the protecting group is followed by coupling of the rigid spacer 410 to amine 405 using diisopropylcarbodiimide (DIC) and 1-hydroxybenzotriazole hydrate (HOBT). The spacer group may inhibit formation of a thiazolone by reaction of the first amino acids with subsequently formed thioureas. After the spacer group is coupled to the amino acid, another tBoc deprotection is performed to remove the spacer protecting group, giving amine 415. At this point, monomer may be added incrementally to the growing chain, each time followed by a tBoc deprotection. The addition of a derivative of the diamine 420 (e.g., an isothiocyanate) to amine 415 gives the mono-thiourea 425. The addition of a second thiourea substituent is also depicted. After the addition of the desired number of monomers, a solution of benzylisothiocyanate or acetic anhydride may be added to cap any remaining amines on the growing oligomers. Between 1 to 20 thioureas groups may be formed to produce a synthetic polythiourea receptor.

Figure 12:
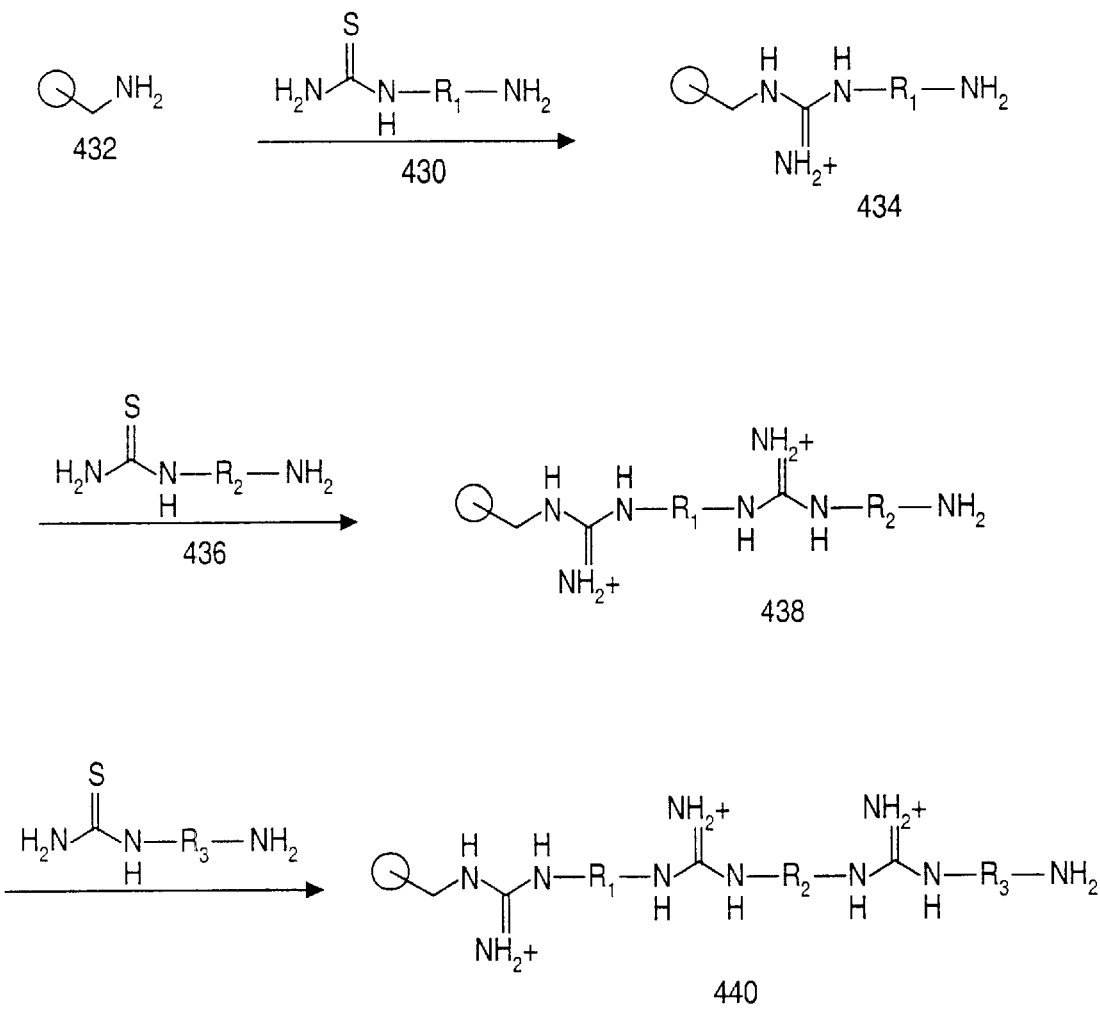
FIG. 12 depicts a synthetic pathway for the synthesis of polyguanidiniums.

The synthesis of polyguanidiniums may be accomplished as depicted in FIG. 12. In order to incorporate these guanidinium groups into the receptor, the coupling of a thiourea with a terminal amine in the presence of Mukaiyama's reagent may be utilized. The coupling of the first thiourea diamine 430 with an amino group of a polymeric particle gives the mono-guanidinium 434. Coupling of the resulting mono-guanidinium with a second thiourea diamine 436 gives a di-guanidinium 438. Further coupling may create a tri-guanidinium 440. Between 1 to 20 guanidinium groups may be formed to produce a synthetic polyguanidinium receptor.

Figure 13:
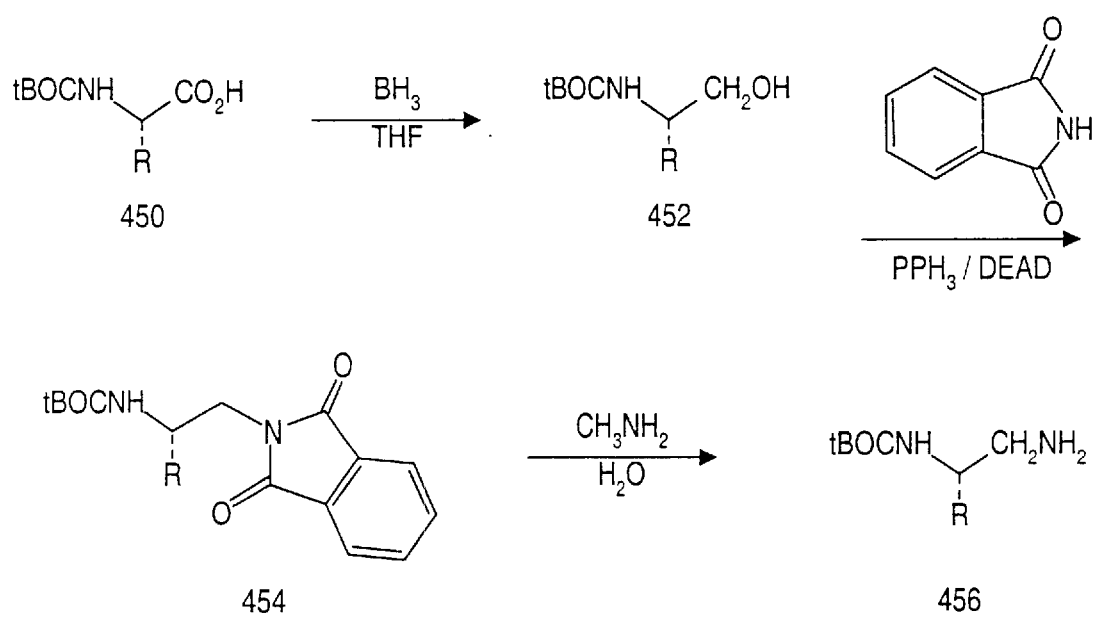
FIG. 13 depicts a synthetic pathway for the synthesis of diamines from amino acids.

The above described methods for making polythioureas and polyguanidiniums are based on the incorporation of diamines (i.e., molecules which include at least two amine functional groups) into the oligomeric receptor. The method may be general for any compound having at least two amino groups. In one embodiment, the diamine may be derived from amino acids. A method for forming diamines from amino acids is shown in FIG. 13. Treatment of a protected amino acid 450 with borane-THF reduces the carboxylic acid portion of the amino acid to the primary alcohol 452. The primary alcohol is treated with phthalimide under Mitsunobu conditions (PPh$_3$/DEAD). The resulting compound 454 is treated with aqueous methylamine to form the desired monoprotected diamine 456. The process may be accomplished such that the enantiomeric purity of the starting amino acid is maintained. Any natural or synthetic amino acid may be used in the above described method.

The three coupling strategies used to form the respective functional groups may be completely compatible with each other. The capability to mix linking groups (amides, thioureas, and guanidiniums) as well as the side chains (hydrophobic, cationic, anionic, and hydrogen bonding) may allow the creation of a diversity in the oligomers that is beyond the diversity of receptors typically found with natural biological receptors. Thus, we may produce ultra-sensitive and ultra-selective receptors which exhibit interactions for specific toxins, bacteria, and environmental chemicals. Additionally, these synthetic schemes may be used to build combinatorial libraries of particles for use in the sensor array.

In an embodiment, the indicator ligand may be incorporated into synthetic receptors during the synthesis of the receptors. The ligand may be incorporated into a monomeric unit, such as a diamine, that is used during the synthesis of the receptor. In this manner, the indicator may be covalently attached to the receptor in a controlled position. By placing the indicator within the receptor during the synthesis of the receptor, the positioning of the indicator ligand within the receptor may be controlled. This control may be difficult to achieve after synthesis of the receptor is completed.

In one embodiment, a fluorescent group may be incorporated into a diamine monomer for use in the synthetic sequences. Examples of monomeric units which may be used for the synthesis of a receptor are depicted in FIG. 14. The depicted monomers include fluorescent indicator groups. After synthesis, the interaction of the receptor with the analyte may induce changes in the spectroscopic properties of the molecule. Typically, hydrogen bonding or ionic substituents on the fluorescent monomer involved in analyte binding have the capacity to change the electron density and/or rigidity of the fluorescent ring system, thereby causing observable changes in the spectroscopic properties of the indicator. For fluorescent indicators such changes may be exhibited as changes in the fluorescence quantum yield, maximum excitation wavelength, and/or maximum emission wavelength. This approach does not require the dissociation of a preloaded fluorescent ligand, which may be limited in response time by $k_{(off)}$. While fluorescent ligands are shown here, it is to be understood that a variety of other ligand may be used including calorimetric ligands.

In another embodiment, two fluorescent monomers for signaling may be used for the synthesis of the receptor. For example, compound 470 (a derivative of fluorescein) and compound 475 (a derivative of rhodamine), depicted in FIG. 14, may both be incorporated into a synthetic receptor. Compound 470 contains a common colorimetric/fluorescent probe that will, in some embodiments, send out a modulated signal upon analyte binding. The modulation may be due to resonance energy transfer to compound 475. When an analyte binds to the receptor, structural changes in the receptor may alter the distance between monomeric units 470 and 475. It is well known that excitation of fluorescein can result in emission from rhodamine when these molecules are oriented correctly. The efficiency of resonance energy transfer from monomers 470 to 475 will depend strongly upon the presence of analyte binding; thus, measurement of rhodamine fluorescence intensity (at a substantially longer wavelength than fluorescein fluorescence) may serve as an indicator of analyte binding. To greatly improve the likelihood of a modulatory fluorescein-rhodamine interaction, multiple rhodamine tags may be attached at different sites along a receptor molecule without substantially increasing background rhodamine fluorescence (only rhodamine very close to fluorescein will yield appreciable signal). This methodology may be applied to a number of alternate fluorescent pairs.

In an embodiment, a large number of chemical/biological agents of interest to the military and civilian communities may be sensed readily by the described array sensors including both small and medium size molecules. For example, it is known that nerve gases typically produce phosphate structures upon hydrolysis in water. The presence of molecules which contain phosphate functional groups may be detected using polyguanidiniums. Nerve gases which have contaminated water sources may be detected by the use of the polyguanidinium receptors described above.

In order to identify, sense, and quantitate the presence of various bacteria using the proposed micro-machined sensor, two strategies may be used. First, small molecule recognition and detection may be exploited. Since each bacteria possesses a unique and distinctive concentration of the various cellular molecules, such as DNA, proteins, metabolites, and sugars, the fingerprint (i.e., the concentration and types of DNA, proteins, metabolites, and sugars) of each organism is expected to be unique. Hence, the analytes obtained from whole bacteria or broken down bacteria may be used to determine the presence of specific bacteria. A series of receptors specific for DNA molecules, proteins, metabolites, and sugars may be incorporated into an array. A solution containing bacteria, or more preferably broken down bacteria, may be passed over the array of particles. The individual cellular components of the bacteria may interact in a different manner with each of the particles. This interaction will provide a pattern within the array which may be unique for the individual bacteria. In this manner, the presence of bacteria within a fluid may be determined.

In another embodiment, bacteria may be detected as whole entities, as found in ground water, aerosols, or blood. To detect, sense, and identify intact bacteria, the cell surface of one bacteria may be differentiated from other bacteria. One method of accomplishing this differentiation is to target cell surface oligosaccharides (i.e. sugar residues). Each bacterial class (gram negative, gram positive, etc.) displays a different oligosaccharide on their cell surfaces. The oligosaccharide, which is the code that is read by other cells giving an identification of the cell, is part of the cell-cell recognition and communication process. The use of synthetic receptors which are specific for oligosaccharides may be used to determine the presence of specific bacteria by analyzing for the cell surface oligosaccharides.

In another embodiment, the sensor array may be used to optimize which receptor molecules should be used for a specific analyte. An array of receptors may be placed within the cavities of the supporting member and a stream containing an analyte may be passed over the array. The reaction of each portion of the sensing array to the known analyte may be analyzed and the optimal receptor determined by determining which particle, and therefore which receptor, exhibits the strongest reaction toward the analyte. In this manner, a large number of potential receptors may be rapidly scanned. The optimal receptor may then be incorporated into a system used for the detection of the specific analyte in a mixture of analytes.

It should be emphasized that although some particles may be purposefully designed to bind to important species (biological agents, toxins, nerve gasses, etc.), most structures will possess nonspecific receptor groups. One of the advantages associated with the proposed sensor array is the capacity to standardize each array of particles via exposure to various analytes, followed by storage of the patterns which arise from interaction of the analytes with the particles. Therefore, there may not be a need to know the identity of the actual receptor on each particle. Only the characteristic pattern for each array of particles is important. In fact, for many applications it may be less time consuming to place the various particles into their respective holders without taking precautions to characterize the location associated with the specific particles. When used in this manner, each individual sensor array may require standardization for the type of analyte to be studied.

On-site calibration for new or unknown toxins may also be possible with this type of array. Upon complexation of an analyte, the local microenvironment of each indicator may change, resulting in a modulation of the light absorption and/or emission properties. The use of standard pattern recognition algorithms completed on a computer platform may serves as the intelligence factor for the analysis. The "fingerprint" like response evoked from the simultaneous interactions occurring at multiple sites within the substrate may be used to identify the species present in unknown samples.

The above described sensor array system offers a number of distinct advantages over exiting technologies. One advantage is that "real time" detection of analytes may be performed. Another advantage is that the simultaneous detection of multiple analytes may be realized. Yet another advantage is that the sensor array system allows the use of synthetic reagents as well as biologically produced reagents. Synthetic reagents typically have superior sensitivity and specificity toward analytes when compared to the biological reagents. Yet another advantage is that the sensor array system may be readily modified by simply changing the particles which are placed within the sensor array. This interchangability may also reduce production costs.

EXAMPLES

1. The Determination of pH Using a Chemically Sensitive Particle

Figure 15:
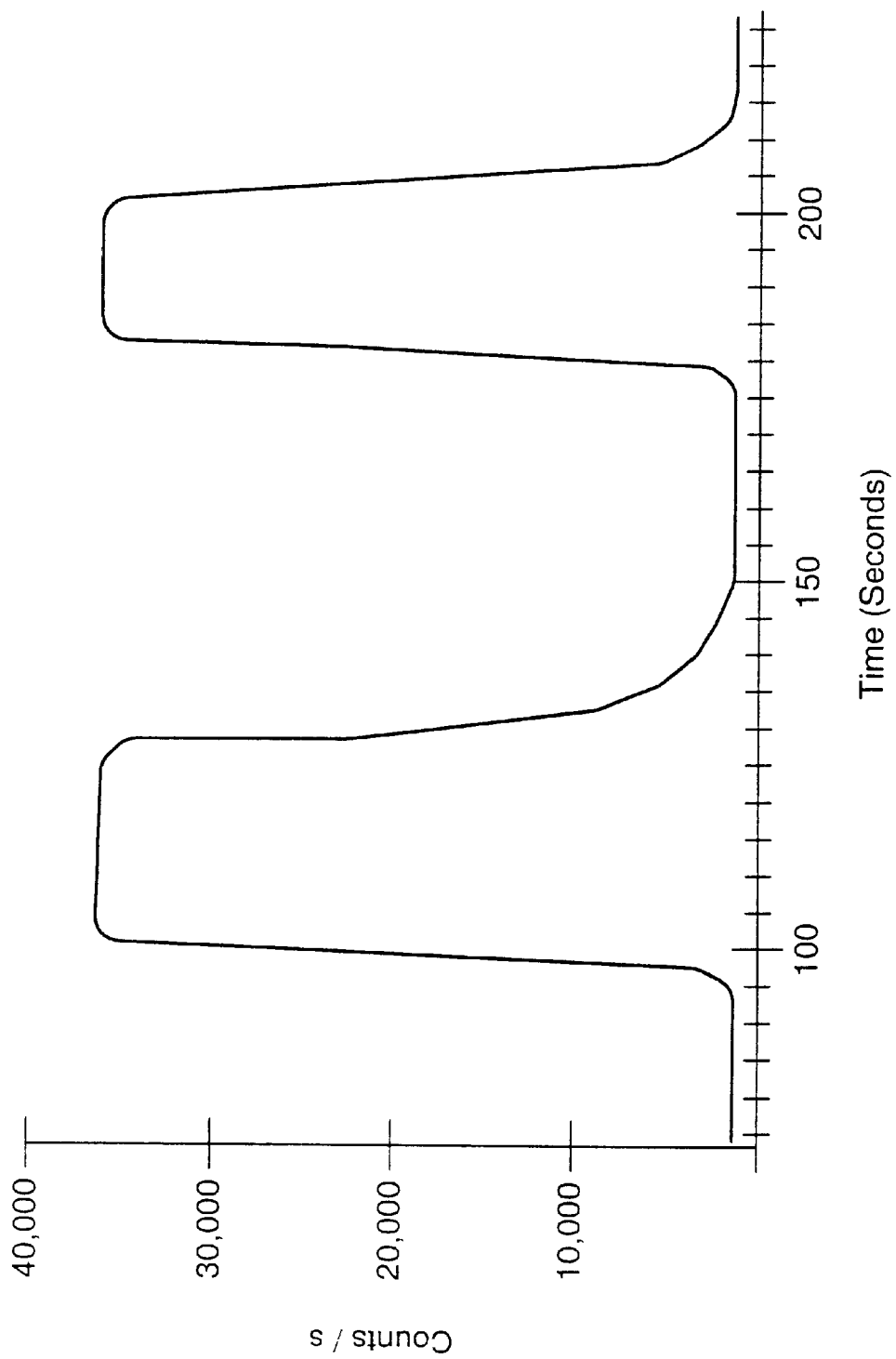
FIG. 15 depicts a plot of counts/sec. (i.e., intensity) vs. time as the pH of a solution surrounding a particle coupled to o-cresolphthalein is cycled from acidic to basic conditions.

Shown in FIG. 15 is the magnitude of the optical signal transmitted through a single polymer particle derivatized with o-cresolphthalein. Here, a filter is used to focus the analysis on those wavelengths which the dye absorbs most strongly (i.e., about 550 nm). Data is provided for the particle as the pH is cycled between acid and basic environments. In acidic media (i.e., at times of 100–150 seconds and 180–210 seconds), the particle is clear and the system yields large signals (up to greater than 300,000 counts) at the optical detector. Between times of 0–100 and 150–180 seconds, the solution was made basic. Upon raising the pH (i.e., making the solution more basic), the particle turns purple in color and the transmitted green light is greatly diminished. Large signal reductions are recorded under such circumstances. The evolution of the signal changes show that the response time is quite rapid, on the order of 10 seconds. Furthermore, the behavior is highly reproducible.

2. The Simultaneous Detection of $Ca^{+2}$, $Ce^{+3}$, and pH by a Sensor Array System The synthesis of four different particles was accomplished by coupling a variety of indictor ligands to a polyethylene glycol-polystyrene ("PEG-PS") resin particle. The PEG-PS resin particles were obtained from Novabiochem Corp., La Jolla, Calif. The particles have an average diameter of about 130 $\mu$m when dry and about 250 $\mu$m when wet. The indicator ligands of fluorescein, o-cresolphthalein complexone, and alizarin complexone were each attached to PEG-PS resin particles using a dicyclohexylcarbodiimide (DCC) coupling between a terminal resin bound amine and a carboxylic acid on the indicator ligand.

These synthetic receptors, localized on the PEG-PS resin to create sensing particles, were positioned within micromachined wells formed in silicon/silicon nitride wafers, thus confining the particles to individually addressable positions on a multicomponent chip. These wells were sized to hold the particles in both swollen and unswollen states. Rapid introduction of the test fluids can be accomplished using these structures while allowing spectrophotometric assays to probe for the presence of analytes. For the identification and quantification of analyte species, changes in the light absorption and light emission properties of the immobilized resin particles can be exploited, although only identification based upon absorption properties are discussed here. Upon exposure to analytes, color changes for the particles were found to be 90% complete within one minute of exposure, although typically only seconds were required. To make the analysis of the colorimetric changes efficient, rapid, and sensitive, a charge-coupled-device (CCD) was directly interfaced with the sensor array. Thus, data streams composed of red, green, and blue (RGB) light intensities were acquired and processed for each of the individual particle elements. The red, blue, and green responses of the particles to various solutions are graphically depicted in FIG. 16.

The true power of the described bead sensor array occurs when simultaneous evaluation of multiple chemically distinct bead structures is completed. A demonstration of the capacity of five different beads is provided in FIG. 16. In this case, blank, alizarin, o-cresol phthalein, fluorescein, and alizarin-Ce3+ complex derivatized beads serve as a matrix for subtle differentiation of chemical environments. The blank bead is simply a polystyrene sphere with no chemical derivatization. The bead derivatized with o-cresolphthalein responds to Ca+2 at pHs values around 10.0. The binding of calcium is noted from the large green color attenuation noted for this dye while exposed to the cation. Similarly, the fluorescein derivatized bead acts as a pH sensor. At pHs below 7.4 it is light yellow, but at higher pHs it turns dark orange. Interesting, the alizarin complexone plays three distinct roles. First, it acts as a proton sensor yielding a yellow color at pHs below 4.5, orange is noted at pHs between 4.5 and 11.5, and at pHs above 11.5 a blue hue is observed. Second, it functions as a sensor for lanthanum ions at lower parts by turning yellow to orange. Third, the combination of both fluoride and lanthanum ions results in yellow/orange coloration.

The analysis of solutions containing various amount of $Ca^{+2}$ or $F^-$ at various pH levels was performed using alizarin complexone, o-cresolphthalein complexone, 5-carboxy fluorescein, and alizarin-$Ce^{3+}$ complex. A blank particle in which the terminal amines of a PEG-PS resin particle have been acylated was also used. In this example, the presence of $Ca^{+2}$ (0.1 M Ca(NO$_3$)$_2$) was analyzed under conditions of varying pH. The pH was varied to values of 2, 7, and 12, all buffered by a mixture of 0.04 M phosphate, 0.04 M acetate, and 0.04 M borate. The RGB patterns for each sensor element in all environments were measured. The bead derivatized with o-cresolphthalein responds to $Ca^{+2}$ at pH values around 12. Similarly, the 5-carboxy fluorescein derivatized bead acts as a pH sensor. At pHs below 7.4 it is light yellow, but at higher pHs it turns dark orange. Interesting, the alizarin complexone plays three distinct roles. First, it acts as a proton sensor yielding a yellow color at pHs below 4.5, orange is noted at pHs between 4.5 and 11.5, and at pHs above 11.5 a blue hue is observed. Second, it functions as a sensor for lanthanum ions at lower pHs by turning yellow to orange. Third, the combination of both fluoride and lanthanum ions results in yellow/orange coloration.

This example demonstrates a number of important factors related to the design, testing, and functionality of micromachined array sensors for solution analyses. First, derivatization of polymer particles with both colorimetric and fluorescent dyes was completed. These structures were shown to respond to pH and $Ca^+$. Second, response times well under 1 minute were found. Third, micromachined arrays suitable both for confinement of particles, as well as optical characterization of the particles, have been prepared. Fourth, integration of the test bed arrays with commercially available CCD detectors has been accomplished. Finally, simultaneous detection of several analytes in a mixture was made possible by analysis of the RGB color patterns created by the sensor array.

3. The Detection of Sugar Molecules Using a Boronic Acid Based Receptor

A series of receptors were prepared with functionalities that associate strongly with sugar molecules, as depicted in FIG. 9. In this case, a boronic acid sugar receptor 500 was utilized to demonstrate the functionality of a new type of sensing scheme in which competitive displacement of tagged sugar molecule (e.g., resorufin derivatized galactose) 510 was used to assess the presence (or lack thereof) of other sugar molecules. The boronic acid receptor 500 was formed via a substitution reaction of a benzylic bromide. The boronic acid receptor was attached to a polyethylene glycol-polystyrene ("PEG-PS") resin particle at the "R" position. Initially, the boronic acid derivatized particle was loaded with resorufin-derivatized galactose 510. Upon exposure of the particle to a solution containing sugar 520 (e.g., glucose), the resorufin derivatized galactose molecule 510 is displaced from the particle receptor sites. Visual inspection of the optical photographs taken before and after exposure to the sugar solution show that the boron substituted resin is capable of sequestering sugar molecules from an aqueous solution. Moreover, the subsequent exposure of the colored particles to a solution of a non-tagged sugar (e.g., glucose) leads to a displacement of the bound colored sugar reporter molecule. Displacement of this molecule leads to a change in the color of the particle. The sugar sensor turns from dark orange to yellow in solutions containing glucose. The particles were also tested in conditions of varying pH. It was noted that the color of the particles changes from dark orange to yellow as the pH is varied from low pH to high pH.

Further Improvements

1. System Improvements

Figure 17:
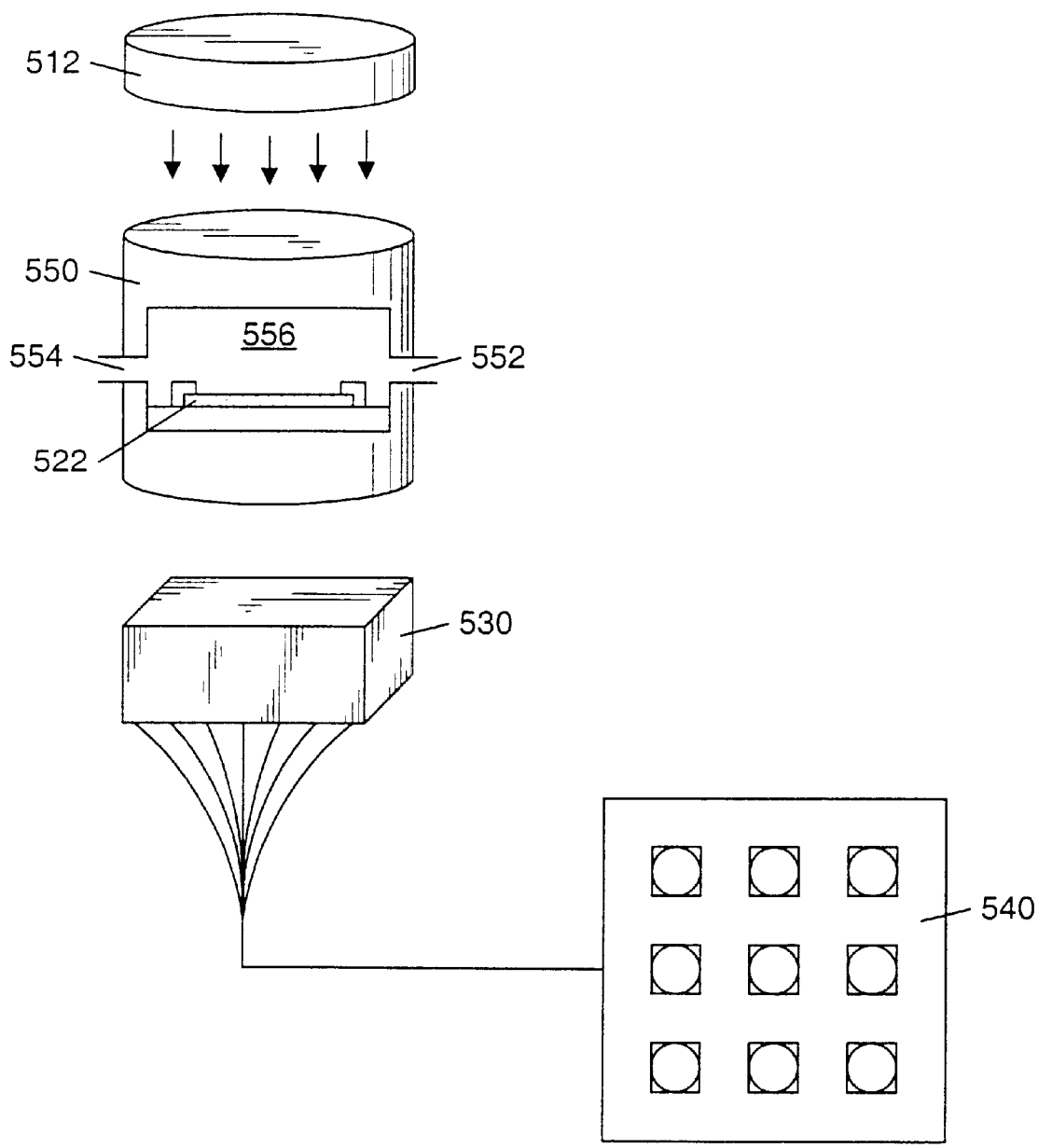
FIG. 17 depicts an analyte detection system which includes a sensor array disposed within a chamber.

Shown in FIG. 17 is an embodiment of a system for detecting analytes in a fluid. In one embodiment, the system includes a light source 512, a sensor array 522, a chamber 550 for supporting the sensor array and a detector 530. The sensor array 522 may include a supporting member which is configured to hold a variety of particles. In one embodiment, light originating from the light source 512 passes through the sensor array 522 and out through the bottom side of the sensor array. Light modulated by the particles may be detected by a proximally spaced detector 530. While depicted as being positioned below the sensor array, it should be understood that the detector may be positioned above the sensor array for reflectance measurements. Evaluation of the optical changes may be completed by visual inspection (e.g., by eye, or with the aid of a microscope) or by use of a microprocessor 540 coupled to the detector.

In this embodiment, the sensor array 522 is positioned within a chamber 550. The chamber 550, may be configured to allow a fluid stream to pass through the chamber such that the fluid stream interacts with the sensor array 522. The chamber may be constructed of glass (e.g., borosilicate glass or quartz) or a plastic material which is transparent to a portion of the light from the light source. If a plastic material is used, the plastic material should also be substantially unreactive toward the fluid. Examples of plastic materials which may be used to form the chamber include, but are not limited to, acrylic resins, polycarbonates, polyester resins, polyethylenes, polyimides, polyvinyl polymers (e.g., polyvinyl chloride, polyvinyl acetate, polyvinyl dichloride, polyvinyl fluoride, etc.), polystyrenes, polypropylenes, polytetrafluoroethylenes, and polyurethanes. An example of such a chamber is a Sykes-Moore chamber, which is commercially available from Bellco Glass, Inc., in New Jersey. Chamber 550, in one embodiment, includes a fluid inlet port 552 and a fluid outlet port 554. The fluid inlet 552 and outlet 554 ports are configured to allow a fluid stream to pass into the interior 556 of the chamber during use. The inlet and outlet ports may be configured to allow facile placement of a conduit for transferring the fluid to the chamber. In one embodiment, the ports may be hollow conduits. The hollow conduits may be configured to have an outer diameter which is substantially equal to the inner diameter of a tube for transferring the fluid to or away from the chamber. For example, if a plastic or rubber tube is used for the transfer of the fluid, the internal diameter of the plastic tube is substantially equal to the outer diameter of the inlet and outlet ports.

In another embodiment, the inlet and outlet ports may be Luer lock style connectors. Preferably, the inlet and outlet ports are female Luer lock connectors. The use of female Luer lock connectors will allow the fluid to be introduced via a syringe. Typically, syringes include a male Luer lock connector at the dispensing end of the syringe. For the introduction of liquid samples, the use of Luer lock connectors may allow samples to be transferred directly from a syringe to the chamber 550. Luer lock connectors may also allow plastic or rubber tubing to be connected to the chamber using Luer lock tubing connectors.

The chamber may be configured to allow the passage of a fluid sample to be substantially confined to the interior 556 of the chamber. By confining the fluid to a small interior volume, the amount of fluid required for an analysis may be minimized. The interior volume may be specifically modified for the desired application. For example, for the analysis of small volumes of fluid samples, the chamber may be designed to have a small interior chamber, thus reducing the amount of fluid needed to fill the chamber. For larger samples, a larger interior chamber may be used. Larger chambers may allow a faster throughput of the fluid during use.

Figure 18:
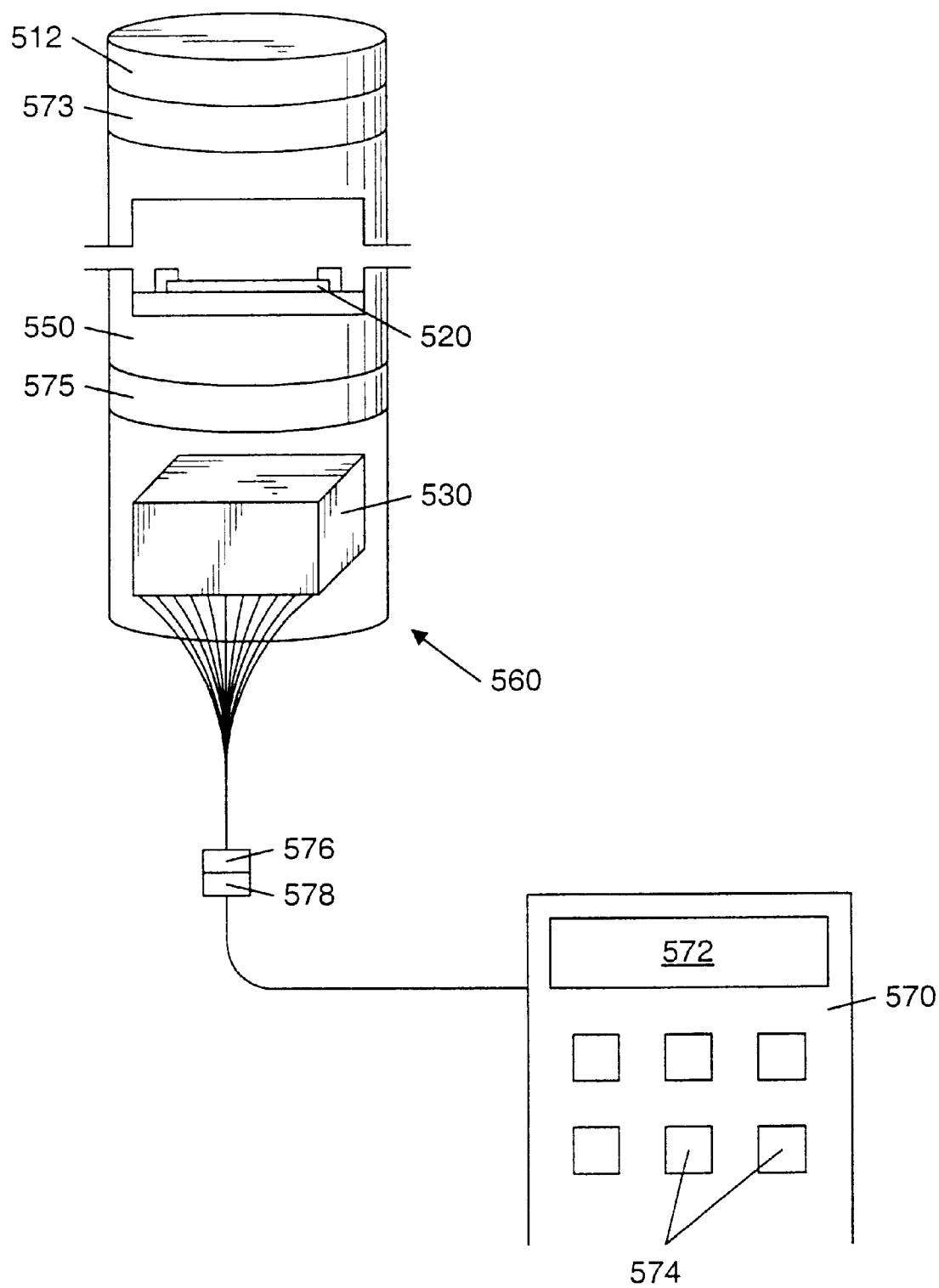
FIG. 18 depicts an integrated analyte detection system.

In another embodiment, depicted in FIG. 18, a system for detecting analytes in a fluid includes a light source 512, a sensor array 520, a chamber 550 for supporting the sensor array and a detector 530, all enclosed within a detection system enclosure 560. As described above, the sensor array 520 is preferably formed of a supporting member, which is configured to hold a variety of particles. Thus, in a single enclosure, all of the components of an analyte detection system are included.

The formation of an analyte detection system in a single enclosure may allow the formation of a portable detection system. For example, a small controller 570 may be coupled to the analyte detection system. The controller 570 may be configured to interact with the detector and display the results from the analysis. In one embodiment, the controller includes a display device 572 for displaying information to a user. The controller may also include input devices 574 (e.g., buttons) to allow the user to control the operation of the analyte detection system. For example, the controller may control the operation of the light source 512 and the operation of the detector 530.

The detection system enclosure 560 may be interchangeable with the controller. First and second coupling members 576 and 578 may be used to remove the detection system enclosure 560 from the controller 570. A second detection system enclosure may be readily coupled to the controller using first and second coupling members 576 and 578. In this manner, a variety of different types of analytes may be detecting using a variety of different detection system enclosures. Each of the detection system enclosures may include different sensor arrays mounted within their chambers. Instead of having to exchange the sensor array for different types of analysis, the entire detection system enclosure may be exchanged. This may prove advantageous when a variety of detection schemes is used. For example, a first detection system enclosure may be configured for white light applications. The first detection system enclosure may include a white light source, a sensor that includes particles that produce a visible light response in the presence of an analyte, and a detector sensitive to white light. A second detection system enclosure may be configured for fluorescent applications, including a fluorescent light source, a sensor array, which includes particles, which produce a fluorescent response on the presence of an analyte, and a fluorescent detector. The second detection system enclosure may also include other components necessary for producing a proper detection system. For example, the second detection system may also include a filter for preventing short wavelength excitation from producing "false" signals in the optical detection system during fluorescence measurements. A user need only select the proper detection system enclosure for the detection of the desired analyte. Since each detection system enclosure includes many of the required components, a user does not have to make light source selections, sensor array selections or detector arrangement selections to produce a viable detection system.

In another embodiment, the individual components of the system may be interchangeable. The system may include third and fourth coupling members 573 and 575 that allow the light source and the detector, respectively, to be removed from the chamber 550. This may allow a more modular design of the system. For example, an analysis may be first performed with a white light source to give data corresponding to an absorbance/reflectance analysis. After this analysis is performed, the light source may be changed to a ultraviolet light source to allow ultraviolet analysis of the particles. Since the particles have already been treated with the fluid, the analysis may be preformed without further treatment of the particles with a fluid. In this manner, a variety of tests may be performed using a single sensor array.

In one embodiment, the supporting member is made of any material capable of supporting the particles, while allowing the passage of the appropriate wavelength of light. The supporting member may also be made of a material substantially impervious to the fluid in which the analyte is present. A variety of materials may be used including plastics (e.g., photoresist materials, acrylic polymers, carbonate polymers, etc.), glass, silicon based materials (e.g., silicon, silicon dioxide, silicon nitride, etc.) and metals. In one embodiment, the supporting member includes a plurality of cavities. The cavities are preferably formed such that at least one particle is substantially contained within the cavity. Alternatively, a plurality of particles may be contained within a single cavity.

Figure 19:
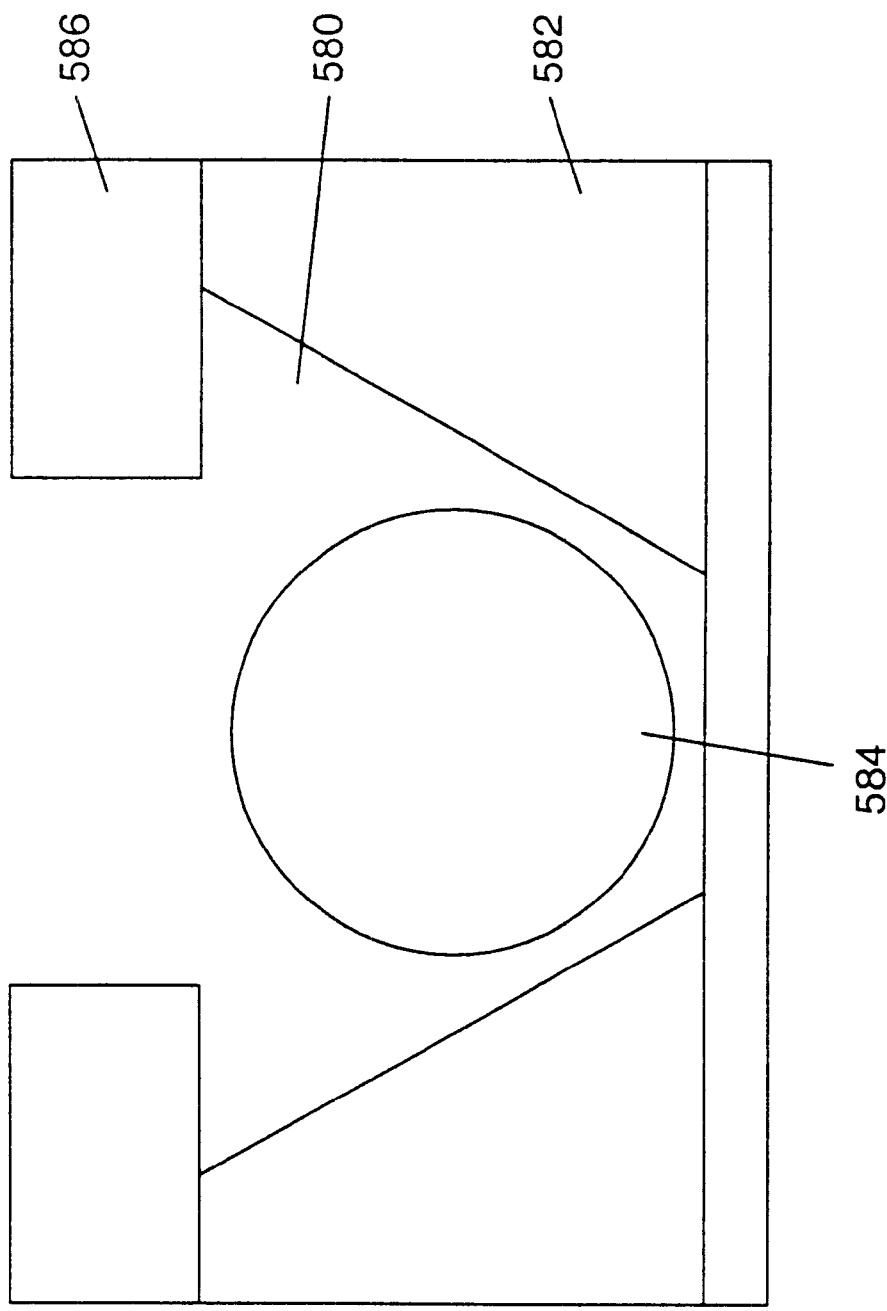
FIG. 19 depicts a cross-sectional view of a cavity covered by a mesh cover.
Figure 20:
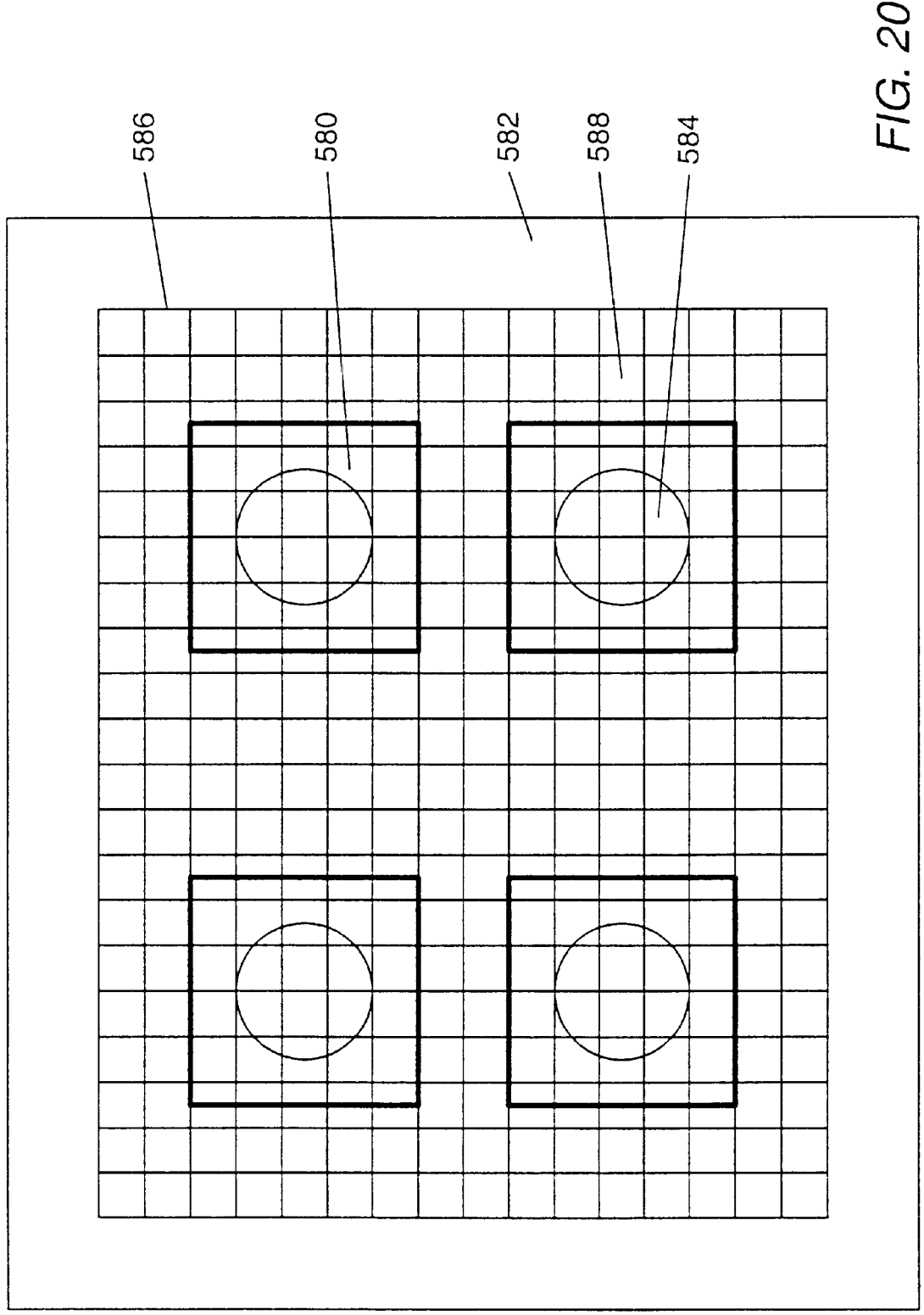
FIG. 20 depicts a top view of a cavity covered by a mesh cover.

In some embodiments, it will be necessary to pass liquids over the sensor array. The dynamic motion of liquids across the sensor array may lead to displacement of the particles from the cavities. In another embodiment, the particles are preferably held within cavities formed in a supporting member by the use of a transmission electron microscope ("TEM") grid. As depicted in FIG. 19, a cavity 580 is formed in a supporting member 582. After placement of a particle 584 within the cavity, a TEM grid 586 may be placed atop the supporting member 582 and secured into position. TEM grids and adhesives for securing TEM grids to a support are commercially available from Ted Pella, Inc., Redding, Calif. The TEM grid 586 may be made from a number of materials including, but not limited to, copper, nickel, gold, silver, aluminum, molybdenum, titanium, nylon, beryllium, carbon, and beryllium-copper. The mesh structure of the TEM grid may allow solution access as well as optical access to the particles that are placed in the cavities. FIG. 20 further depicts a top view of a sensor array with a TEM grid 586 formed upon the upper surface of the supporting member 582. The TEM grid 586 may be placed on the upper surface of the supporting member, trapping particles 584 within the cavities 580. As depicted, the openings 588 in the TEM grid 586 may be sized to hold the particles 584 within the cavities 580, while allowing fluid and optical access to cavities 580.

In another embodiment, a sensor array includes a supporting member configured to support the particles, while allowing the passage of the appropriate wavelength of light to the particle. The supporting member, in one embodiment, includes a plurality of cavities. The cavities may be formed such that at least one particle is substantially contained within the cavity. The supporting member may be configured to substantially inhibit the displacement of the particles from the cavities during use. The supporting member may also be configured to allow the passage of the fluid through cavities, e.g., the fluid may flow from the top surface of the supporting member, past the particle, and out the bottom surface of the supporting member. This may increase the contact time between the particle and the fluid.

Figure 21A:
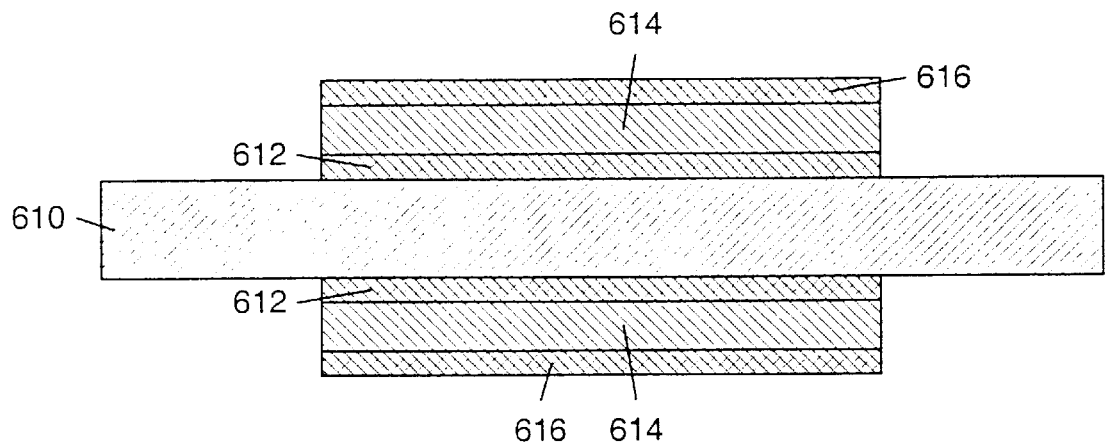
FIGS. 21A–G depict a cross-sectional view of a series of processing steps for the formation of a sensor array which includes a removable top and bottom cover.

FIGS. 21A–G depict a sequence of processing steps for the formation of a silicon based supporting member which includes a removable top cover and bottom cover. The removable top cover may be configured to allow fluids to pass through the top cover and into the cavity. The removable bottom cover may also be configured to allow the fluid to pass through the bottom cover and out of the cavity. As depicted in FIG. 21A, a series of layers may be deposited upon both sides of a silicon substrate 610. First removable layers 612 may be deposited upon the silicon substrate. The removable layers 612 may be silicon dioxide, silicon nitride, or photoresist material. In one embodiment, a layer of silicon dioxide is deposited upon both surfaces of the silicon substrate 610. Upon these removable layers, covers 614 may be formed. In one embodiment, covers 614 are formed from a material that differs from the material used to form the removable layers 612 and which is substantially transparent to the light source of a detection system. For example, if the removable layers 612 are formed from silicon dioxide, the cover may be formed from silicon nitride. Second removable layers 616 may be formed upon the covers 614. Second removable layers 616 may be formed from a material that differs from the material used to form the covers 614. Second removable layers 616 may be formed from a material similar to the material used to form the first removable layers 612. In one embodiment, first and second removable layers 612 and 616 are formed from silicon dioxide and covers 614 are formed from silicon nitride. The layers are patterned and etched using standard photolithographic techniques. In one embodiment, the remaining portions of the layers are substantially aligned in the position where the cavities are to be formed in the silicon substrate 610.

Figure 21B:
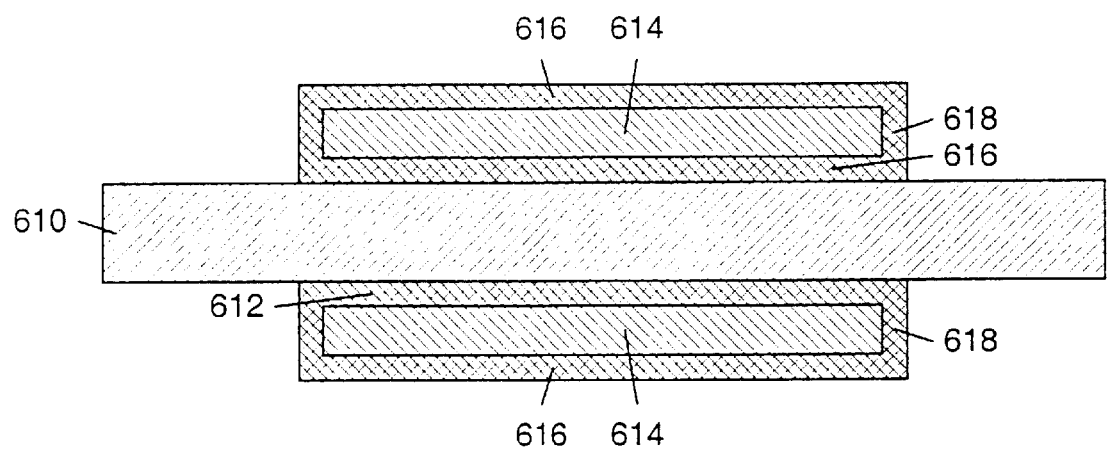
Figure 21C:
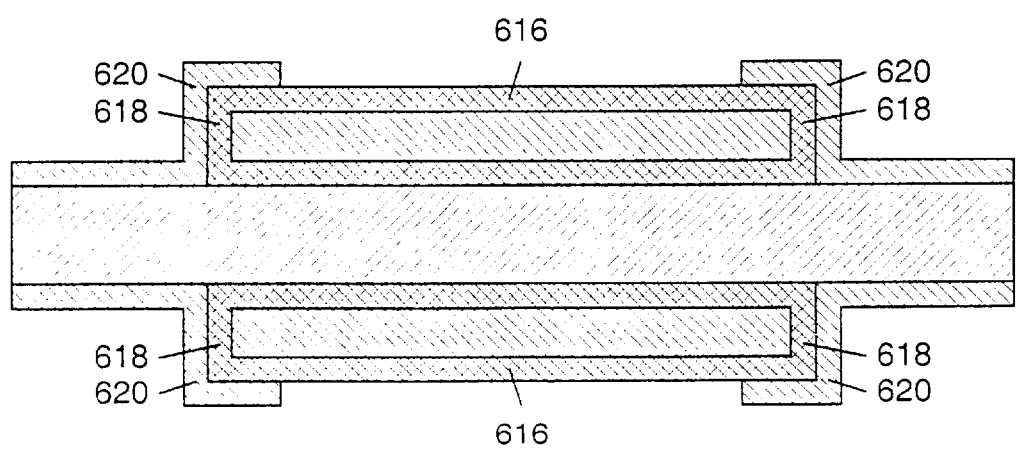

After the layers have been etched, spacer structures may be formed on the sidewalls of the first removable layers 612, the covers 614, and the second removable layers 616, as depicted in FIG. 21B. The spacer structures may be formed from the same material used to form the second removable layers 616. In one embodiment, depositing a spacer layer of the appropriate material and subjecting the material to an anisotropic etch may form the spacer structures. An anisotropic etch, such as a plasma etch, employs both physical and chemical removal mechanisms. Ions are typically bombarded at an angle substantially perpendicular to the semiconductor substrate upper surface. This causes substantially horizontal surfaces to be removed faster than substantially vertical surfaces. During this etching procedure the spacer layers are preferably removed such that the only regions of the spacer layers that remain may be those regions near substantially vertical surfaces, e.g., spacer structures 618.

Figure 23A:
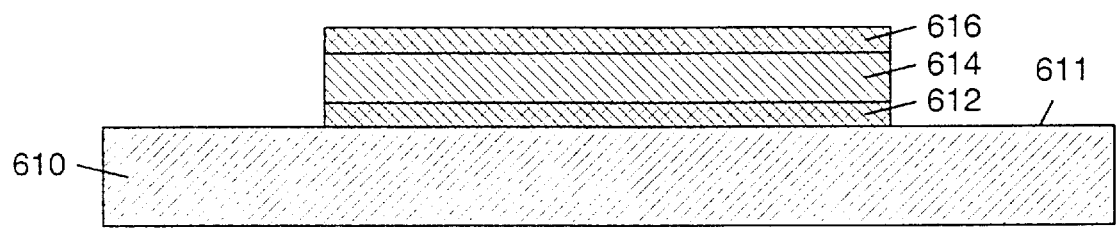
FIGS. 23A–G depict a cross-sectional view of a series of processing steps for the formation of a sensor array which includes a removable top.
Figure 23B:
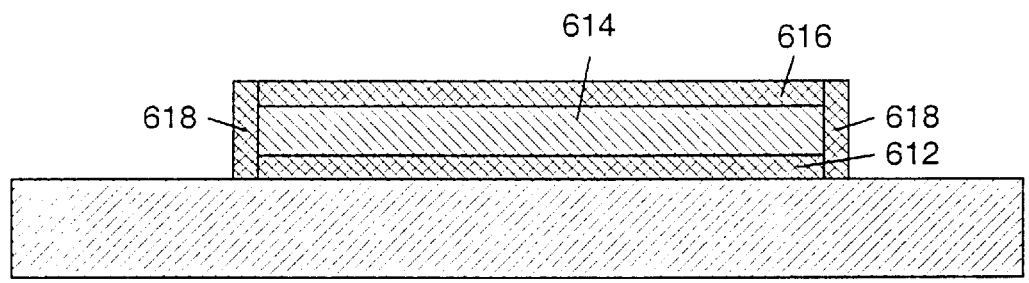
Figure 23C:
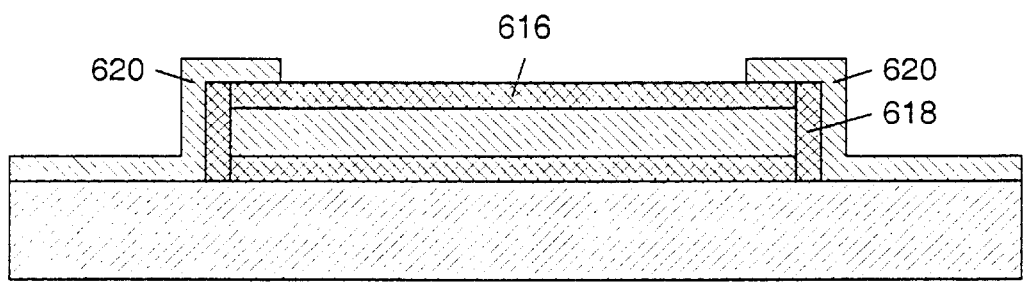

After formation of the spacer structures 618, cover support structures 620, depicted in FIG. 23C, may be formed upon the first removable layer 616 and the spacer structures 618. The cover support structure may be formed by initially depositing a support structure layer upon the second removable layer 616 and spacer structures 618. The support structure layer is then patterned and etched, using standard photolithography; to form the support structures 620. In one embodiment, the support structures 620 are formed from a material that differs from the removable layer materials. In one embodiment, the removable layers may be formed from silicon dioxide while the support structure and cover layer may be formed from silicon nitride.

Figure 21D:
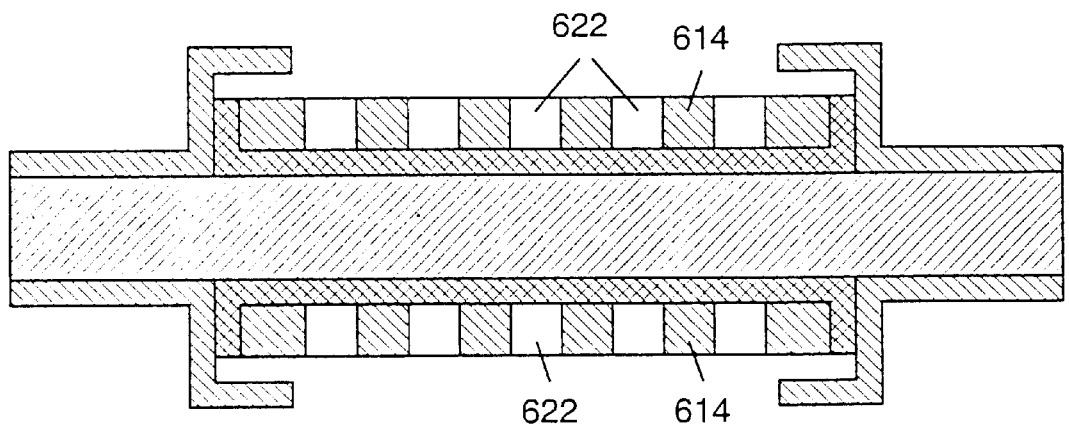

Turning to FIG. 21D, the second removable layers 616 and an upper portion of the spacer structures 618 are preferably removed using a wet etch process. Removal of the second removable layers leaves the top surface of the covers 614 exposed. This allows the covers to be patterned and etched such that openings 622 are formed extending through the covers. These openings 622 may be formed in the covers 614 to allow the passage of fluid through the cover layers. In one embodiment, the openings 622 are formed to allow fluid to pass through, while inhibiting displacement of the particles from the subsequently formed cavities.

Figure 21E:
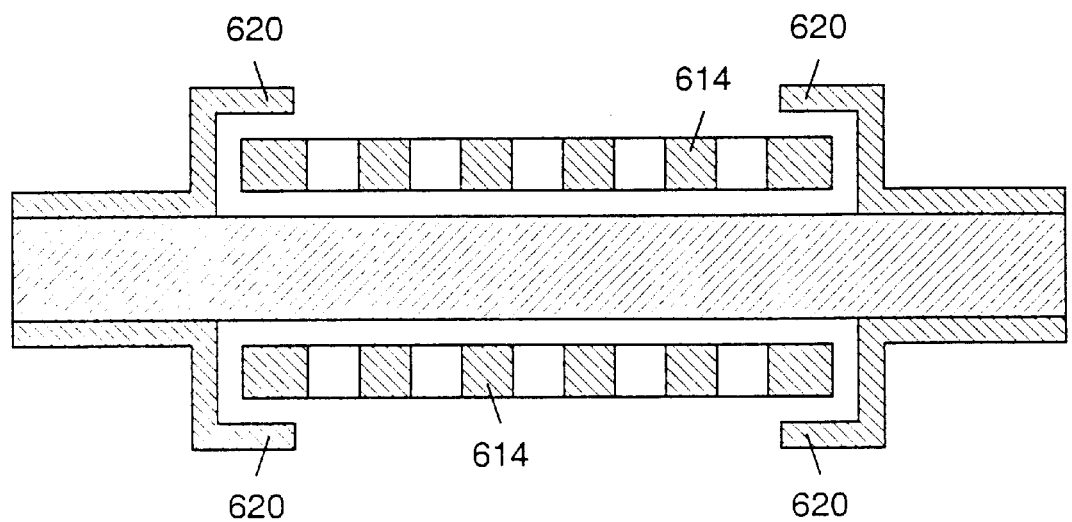

After the openings 622 have been formed, the remainder of the first removable layers 612 and the remainder of the spacer structures 618 may be removed using a wet etch. The removal of the removable layers and the spacer structures creates "floating" covers 614, as depicted in FIG. 21E. The covers 614 may be held in proximity to the silicon substrate 610 by the support structures 620. The covers 614 may now be removed by sliding the covers away from the support structures 620. In this manner removable covers 614 may be formed.

Figure 21F:
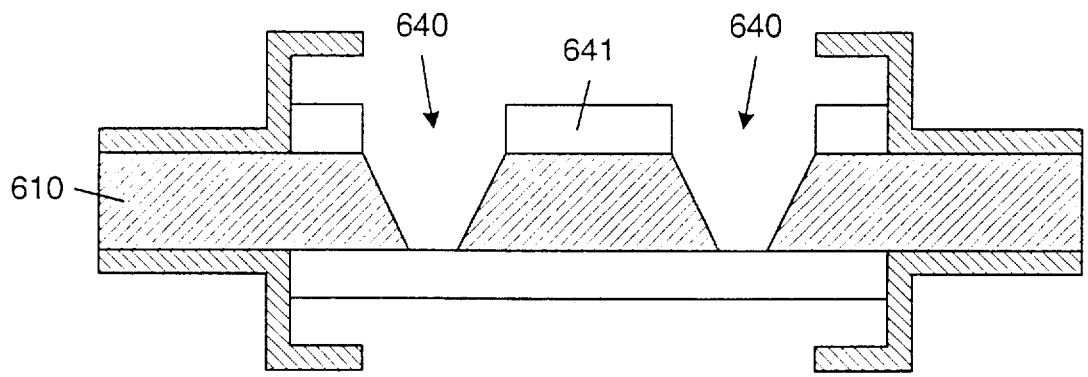

After the covers 614 are removed, cavities 640 may be formed in the silicon substrate 610, as depicted in FIG. 21F. The cavities 640 may be formed by, initially patterning and etching a photoresist material 641 to form a masking layer. After the photoresist material 641 is patterned, the cavities 640 may be etched into the silicon substrate 610 using a hydroxide etch, as described previously.

Figure 21G:
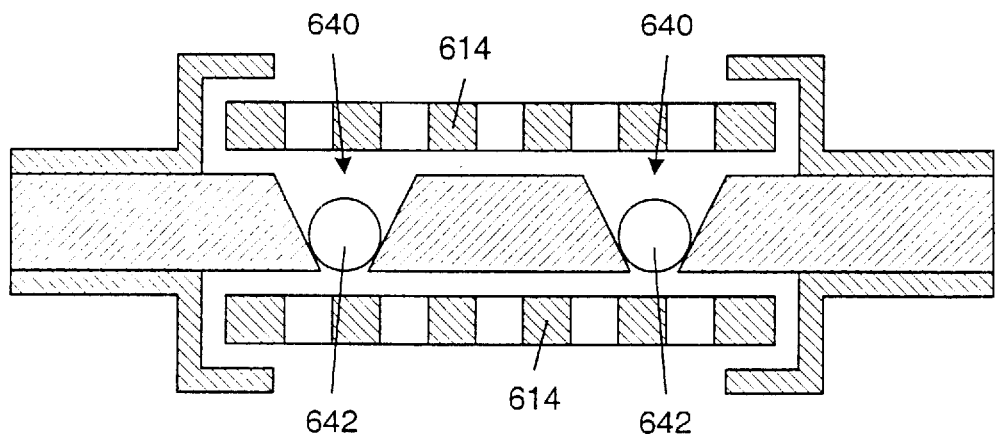

After the cavities 640 are formed, the photoresist material may be removed and particles 642 may be placed within the cavities, as depicted in FIG. 21G. The particles 642, may be inhibited from being displaced from the cavity 640 by placing covers 614 back onto the upper and lower faces of the silicon substrate 610.

Figure 22A:
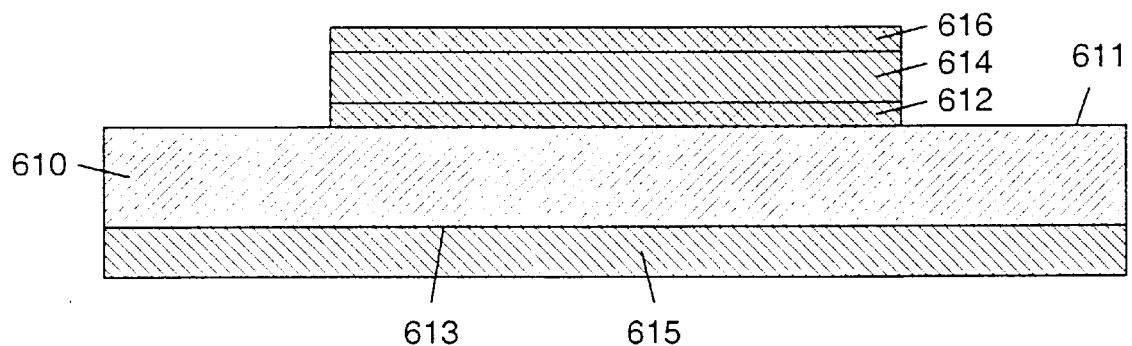
FIGS. 22A–G depict a cross-sectional view of a series of processing steps for the formation of a sensor array which includes a removable top and a stationary bottom cover.

In another embodiment, a sensor array may be formed using a supporting member, a removable cover, and a secured bottom layer. FIGS. 22A–G depict a series of processing steps for the formation of a silicon based supporting member which includes a removable top cover and a secured bottom layer. The removable top cover is preferably configured to allow fluids to pass through the top cover and into the cavity. As depicted in FIG. 22A, a series of layers may be deposited upon both sides of a silicon substrate 610. A first removable layer 612 may be deposited upon the upper face 611 of the silicon substrate 610. The removable layer 612 may be silicon dioxide, silicon nitride, or photoresist material. In one embodiment, a layer of silicon dioxide is deposited upon the silicon substrate 610. A cover 614 may be formed upon the removable layer 612 of the silicon substrate 610. In one embodiment, the cover 614 is formed from a material that differs from the material used to form the removable layer 612 and is substantially transparent to the light source of a detection system. For example, if the removable layer 612 is formed from silicon dioxide, the cover layer 614 may be formed from silicon nitride. In one embodiment, a bottom layer 615 is formed on the bottom surface 613 of the silicon substrate 610. In one embodiment, the bottom layer 615 is formed from a material that is substantially transparent to the light source of a detection system. A second removable layer 616 may be formed upon the cover 614. Second removable layer 616 may be formed from a material that differs from the material used to form the cover layer 614. Second removable layer 616 may be formed from a material similar to the material used to form the first removable layer 612. In one embodiment, first and second removable layers 612 and 616 are formed from silicon dioxide and cover 614 is formed from silicon nitride. The layers formed on the upper surface 611 of the silicon substrate may be patterned and etched using standard photolithographic techniques. In one embodiment, the remaining portions of the layers formed on the upper surface are substantially aligned in the position where the cavities are to be formed in the silicon substrate 610.

Figure 22B:
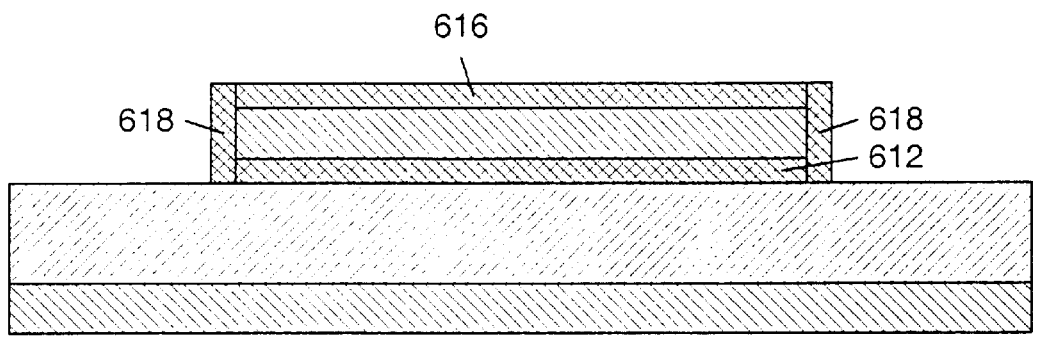

After the layers have been etched, spacer structures may be formed on the side walls of the first removable layer 612, the cover 614, and the second removable layer 616, as depicted in FIG. 22B. The spacer structures may be formed from the same material used to form the second removable layer 616. In one embodiment, the spacer structures may be formed by depositing a spacer layer of the appropriate material and subjecting the spacer layer to an anisotropic etch. During this etching procedure the spacer layer is preferably removed such that the only regions of the spacer layer which remain may be those regions near substantially vertical surfaces, e.g., spacer structures 618.

Figure 22C:
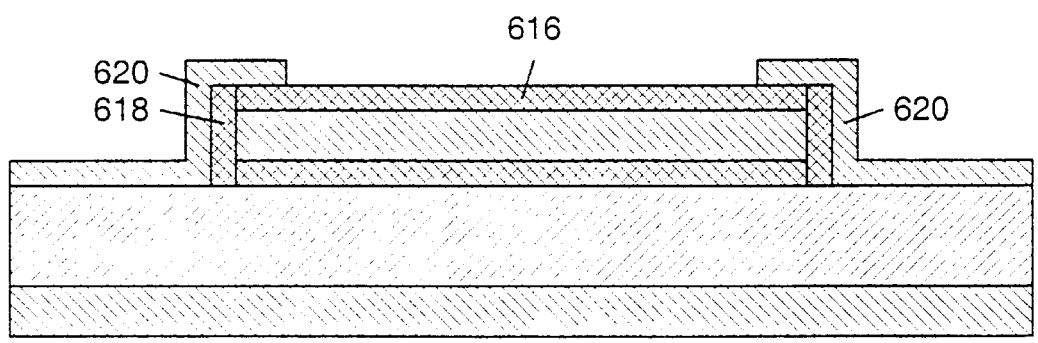

After formation of the spacer structures 618, cover support structures 620, depicted in FIG. 22C, may be formed upon the removable layer 616 and the spacer structures 618. The cover support structures 620 may be formed by depositing a support structure layer upon the second removable layer 616 and spacer structures 618. The support structure layer is then patterned and etched, using standard photolithography, to form the support structures 620. In one embodiment, the support structures are formed from a material that differs from the removable layer materials. In one embodiment, the removable layers may be formed from silicon dioxide while the support structures and cover may be formed from silicon nitride.

Figure 22D:
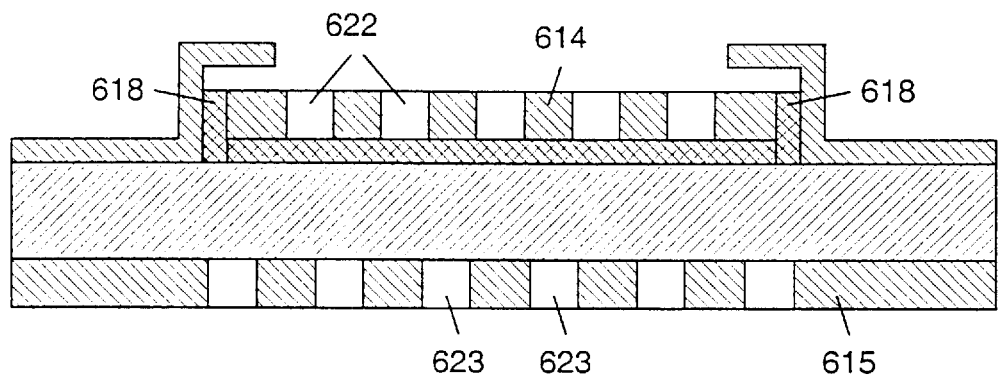

Turning to FIG. 22D, the second removable layer 616 and an upper portion of the spacer structures 618 may be removed using a wet etch process. Removal of the second removable layer leaves the top surface of the cover 614 exposed. This allows the cover 614 to be patterned and etched such that openings 622 are formed extending through the cover 614. These openings 622 may be formed in the cover 614 to allow the passage of fluid through the cover. In one embodiment, the openings 622 are formed to allow fluid to pass through, while inhibiting displacement of the particle from a cavity. The bottom layer 615 may also be similarly patterned and etched such that openings 623 may be formed extending thorough the bottom layer 615.

Figure 22E:
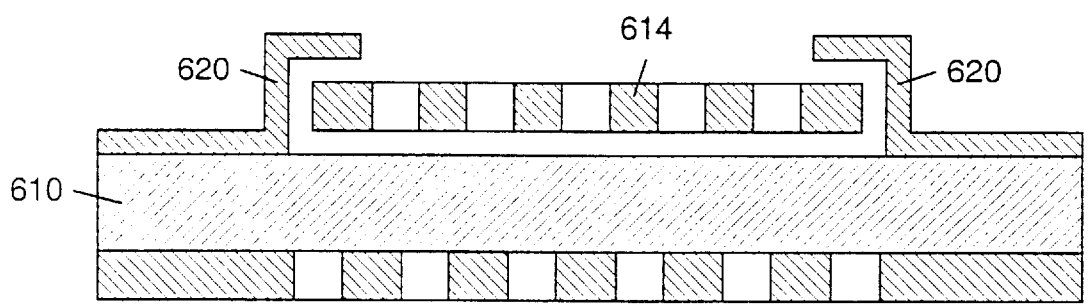
Figure 22F:
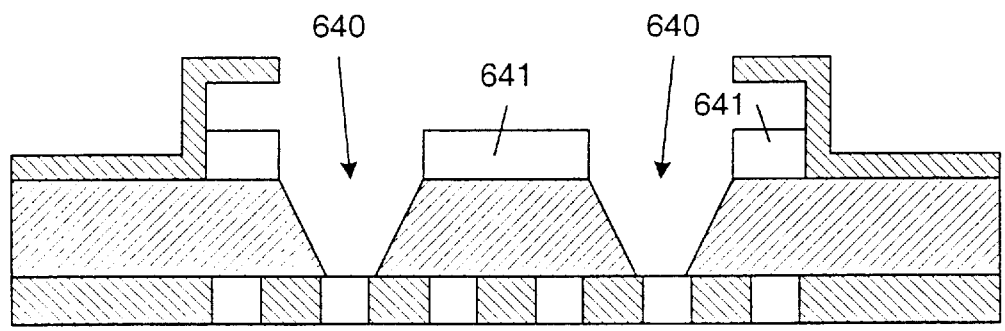

After the openings 622 and 623 are formed, the first removable layer 612 and the remainder of the spacer structures 618 may be removed using a wet etch. The removal of the removable layers and the spacer structures creates a "floating" cover 614, as depicted in FIG. 22E. The cover 614 may be held in proximity to the silicon substrate 610 by the support structures 620. The cover 614 may now be removed by sliding the cover 614 away from the support structures 620. In this manner a removable cover 614 may be formed.

Figure 23D:
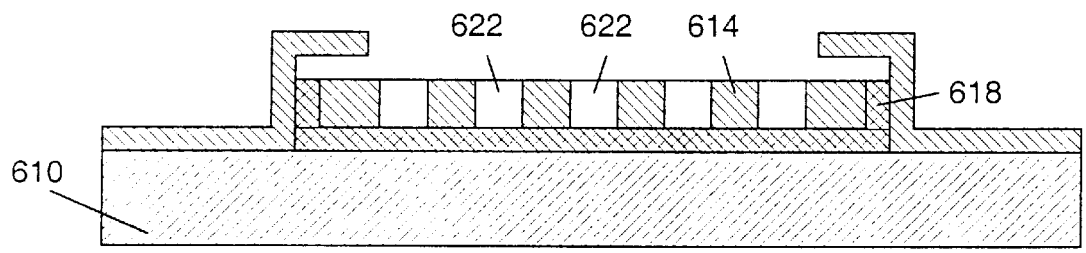
Figure 23E:
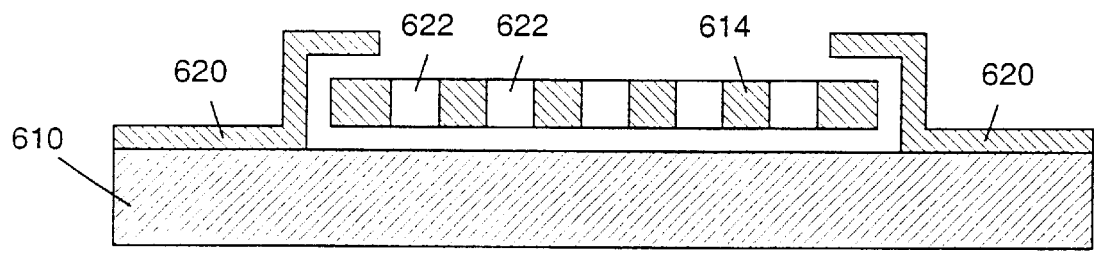
Figure 23F:
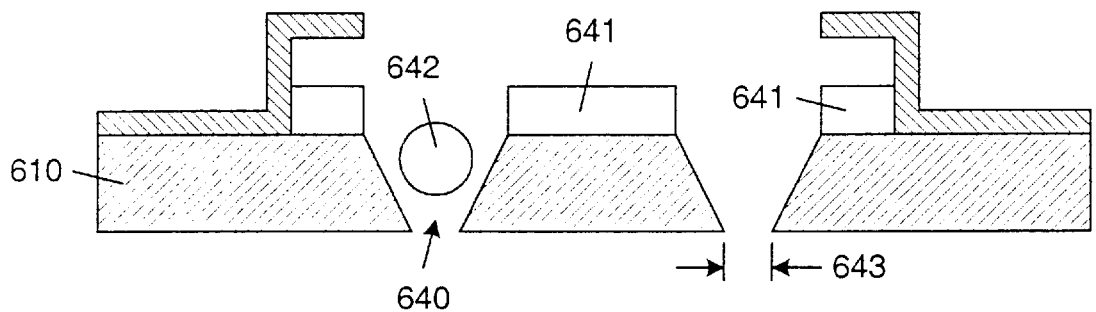

After the cover 614 is removed, cavities 640 may be formed in the silicon substrate 610, as depicted in FIG. 23F. The cavities 640 may be formed by initially depositing and patterning a photoresist material 641 upon the silicon support 610. After the photoresist material 641 is patterned, the cavities 640 may be etched into the silicon substrate 610 using a hydroxide etch, as described previously. The etching of the cavities may be accomplished such that a bottom width of the cavity 643 is less than a width of a particle 642. In one embodiment, the width of the bottom of the cavity may be controlled by varying the etch time. Typically, longer etching times result in a larger opening at the bottom of the cavity. By forming a cavity in this manner, a particle placed in the cavity may be too large to pass through the bottom of the cavity. Thus, a supporting member that does not include a bottom layer may be formed. An advantage of this process is that the processing steps may be reduced making production simpler.

Figure 22G:
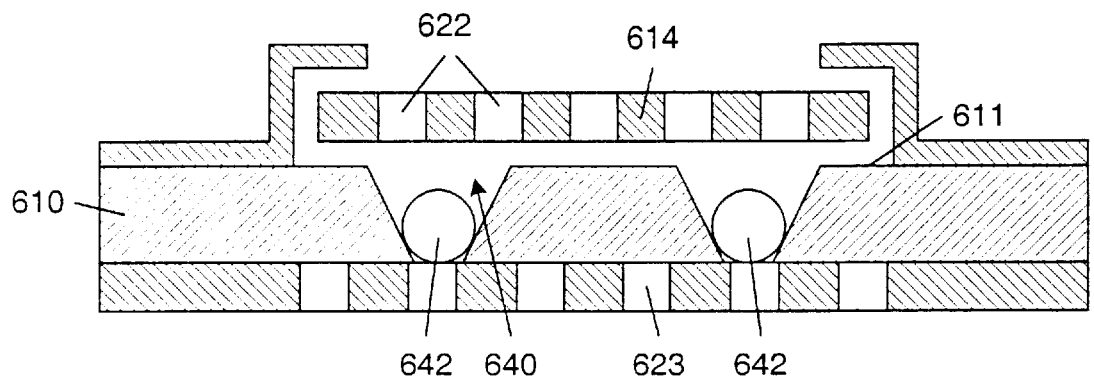

After the cavities 640 are formed, the photoresist material may be removed and particles 642 may be placed within the cavities, as depicted in FIG. 22G. The particles 642, may be inhibited from being displaced from the cavity 640 by placing cover 614 back onto the upper face 611 of the silicon substrate 610. The bottom layer 615 may also aid in inhibiting the particle 642 from being displaced from the cavity 640. Openings 622 in cover 614 and openings 623 in bottom layer 615 may allow fluid to pass through the cavity during use.

In another embodiment, a sensor array may be formed using a supporting member and a removable cover. FIGS. 23A–G depict a series of processing steps for the formation of a silicon based supporting member which includes a removable cover. The removable cover is preferably configured to allow fluids to pass through the cover and into the cavity. As depicted in FIG. 23A, a series of layers may be deposited upon the upper surface 611 of a silicon substrate 610. A first removable layer 612 may be deposited upon the upper face 611 of the silicon substrate 610. The removable layer 612 may be silicon dioxide, silicon nitride, or photoresist material. In one embodiment, a layer of silicon dioxide is deposited upon the silicon substrate 610. A cover 614 may be formed upon the removable layer 612. In one embodiment, the cover is formed from a material which differs from the material used to form the removable layer 612 and which is substantially transparent to the light source of a detection system. For example, if the removable layer 612 is formed from silicon dioxide, the cover 614 may be formed from silicon nitride. A second removable layer 616 may be formed upon the cover 614. Second removable layer 616 may be formed from a material that differs from the material used to form the cover 614. Second removable layer 616 may be formed from a material similar to the material used to form the first removable layer 612. In one embodiment, first and second removable layers 612 and 616 are formed from silicon dioxide and cover 614 is formed from silicon nitride. The layers formed on the upper surface 611 of the silicon substrate may be patterned and etched using standard photolithographic techniques. In one embodiment, the remaining portions of the layers formed on the upper surface are substantially aligned in the position where the cavities are to be formed in the silicon substrate 610.

After the layers have been etched, spacer structures 618 may be formed on the side walls of the first removable layer 612, the cover layer 614, and the second removable layer 616, as depicted in FIG. 23B. The spacer structures 618 may be formed from the same material used to form the second removable layer 616. In one embodiment, the spacers may be formed by depositing a spacer layer of the appropriate material upon the second removable layer and subjecting the material to an anisotropic etch. During this etching procedure the spacer layer is preferably removed such that the only regions of the spacer layer which remain may be those regions near substantially vertical surfaces, e.g., spacer structures 618.

After formation of the spacer structures 618, cover support structures 620, depicted in FIG. 23C, may be formed upon the removable layer 616 and the spacer structures 618. The cover support structure may be formed by initially depositing a support structure layer upon the second removable layer 616 and spacer structures 618. The support structure layer is then patterned and etched, using standard photolithography, to form the support structures 620. In one embodiment, the support structures 620 are formed from a material that differs from the removable layer materials. In one embodiment, the removable layers may be formed from silicon dioxide while the support structure and cover layer may be formed from silicon nitride.

Referring to FIG. 23C, the second removable layer 616 and an upper portion of the spacer structures 618 may be removed using a wet etch process. Removal of the second removable layer leaves the top surface of the cover 614 exposed as depicted in FIG. 23D. This allows the cover 614 to be patterned and etched such that openings 622 are formed extending through the cover 614. These openings 622 may be formed in the cover 614 to allow the passage of fluid through the cover 614.

After the openings 622 are formed, the remainder of the first removable layer 612 and the remainder of the spacer structures 618 may be removed using a wet etch. The removal of the removable layers and the spacer structures creates "floating" cover 614, as depicted in FIG. 23E. The cover 614 is preferably held in proximity to the silicon substrate 610 by the support structures 620. The cover 614 may now be removed by sliding the cover 614 away from the support structures 620. In this manner a removable cover 614 may be formed.

After the cover 614 is removed, cavities 640 may be formed in the silicon substrate 610, as depicted in FIG. 23F. The cavities 640 may be formed by initially depositing and patterning a photoresist material 641 upon the silicon support 610. After the photoresist material 614 is patterned, the cavities 640 may be etched into the silicon substrate 610 using a hydroxide etch, as described previously. The etching of the cavities may be accomplished such that a bottom width of the cavity 643 is less than a width of a particle 642. In one embodiment, the width of the bottom of the cavity may be controlled by varying the etch time. Typically, longer etching times result in a larger opening at the bottom of the cavity. By forming a cavity in this manner, a particle placed in the cavity may be too large to pass through the bottom of the cavity. Thus, a supporting member that does not include a bottom layer may be formed. An advantage of this process is that the processing steps may be reduced making production simpler.

Figure 23G:
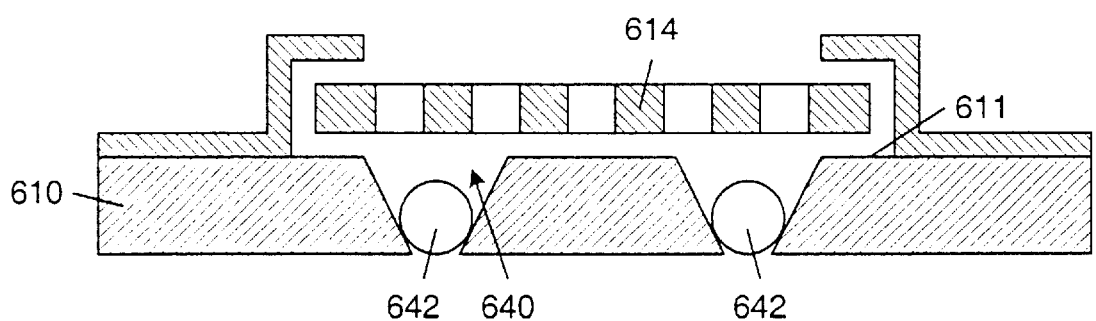

After the cavities 640 are formed, the photoresist material may be removed and particles 642 may be placed within the cavities, as depicted in FIG. 23G. The particles 642, may be inhibited from being displaced from the cavity 640 by placing cover 614 back onto the upper face 611 of the silicon substrate 610. The narrow bottom portion of the cavity may also aid in inhibiting the particle 642 from being displaced from the cavity 640.

Figure 24A:
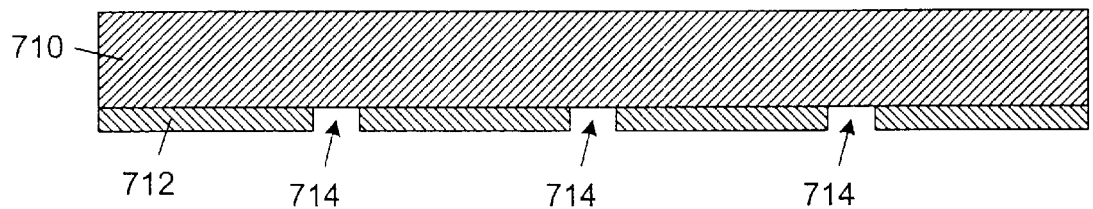
FIGS. 24A–D depict a cross-sectional view of a series of processing steps for the formation of a silicon based sensor array which includes a top and bottom cover with openings aligned with the cavity.

FIGS. 24A–D depict a sequence of processing steps for the formation of a silicon based supporting member which includes a top partial cover and a bottom partial cover. The top partial cover and bottom partial covers are in one embodiment configured to allow fluids to pass into the cavity and out through the bottom of the cavity. As depicted in FIG. 24A, a bottom layer 712 may be deposited onto the bottom surface of a silicon substrate 710. The bottom layer 712 may be silicon dioxide, silicon nitride, or photoresist material. In one embodiment, a layer of silicon nitride 712 is deposited upon the silicon substrate 710. In one embodiment, openings 714 are formed through the bottom layer as depicted in FIG. 24A. Openings 714, in one embodiment, are substantially aligned with the position of the cavities to be subsequently formed. The openings 714 may have a width that is substantially less than a width of a particle. Thus, a particle will be inhibited from passing through the openings 714.

Figure 24B:
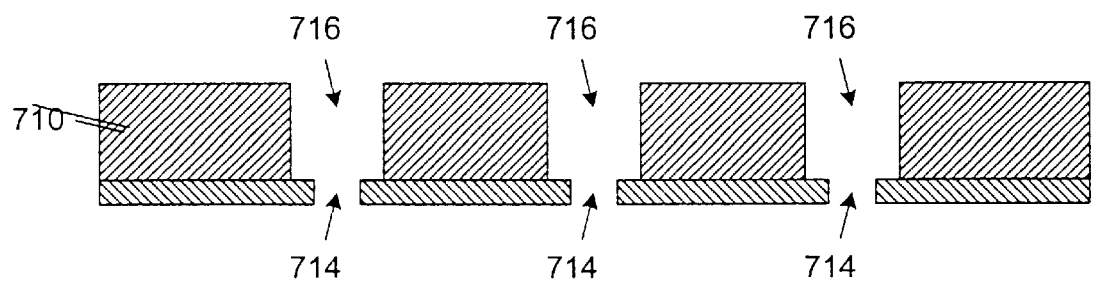

Cavities 716 may be formed in the silicon substrate 710, as depicted in FIG. 24B. The cavities 716 may be formed by initially depositing and patterning a photoresist layer upon the silicon substrate 710. After the photoresist material is patterned, cavities 716 may be etched into the silicon substrate 710 using a number of etching techniques, including wet and plasma etches. The width of the cavities 716 is preferably greater than the width of a particle, thus allowing a particle to be placed within each of the cavities. The cavities 716, in one embodiment, are preferably formed such that the cavities are substantially aligned over the openings 714 formed in the bottom layer.

Figure 24C:
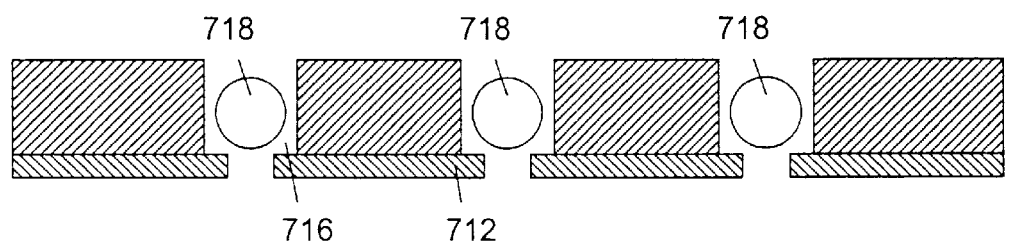

After the cavities have been formed, particles 718 may be inserted into the cavities 716, as depicted in FIG. 24C. The etched bottom layer 712 may serve as a support for the particles 718. Thus the particles 718 may be inhibited from being displaced from the cavities by the bottom layer 712. The openings 714 in the bottom layer 712 may allow fluid to pass through the bottom layer during use.

Figure 24D:
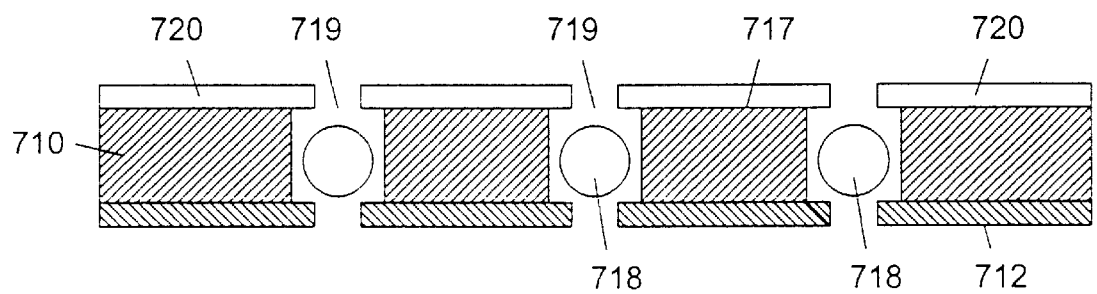

After the particles 718 are placed in the cavities, a top layer 720 may be placed upon the upper surface 717 of the silicon substrate as depicted in FIG. 24D. In one embodiment, the top layer 720 is formed from a material is substantially transparent to the light source of a detection system. The top layer may be formed from silicon nitride, silicon dioxide or photoresist material. In one embodiment, a sheet of photoresist material is used. After the top layer 720 is formed, openings 719 may be formed in the top layer to allow the passage of the fluid into the cavities. If the top layer 720 is composed of photoresist material, after depositing the photoresist material across the upper surface of the silicon substrate, the openings may be initially formed by exposing the photoresist material to the appropriate wavelength and pattern of light. If the top layer is compose of silicon dioxide or silicon nitride the top layer 720 may be developed by forming a photoresist layer upon the top layer, developing the photoresist, and using the photoresist to etch the underlying top layer.

Similar sensor arrays may be produced using materials other than silicon for the supporting member. For example, as depicted in FIGS. 25A–D, the supporting member may be composed of photoresist material. In one embodiment, sheets of photoresist film may be used to form the supporting member. Photoresist film sheets are commercially available from E. I. du Pont de Nemours and Company, Wilmington, Del. under the commercial name RISTON. The sheets come in a variety of sizes, the most common having a thickness ranging from about 1 mil. (25 $\mu$m) to about 2 mil. (50 $\mu$m).

Figure 25A:
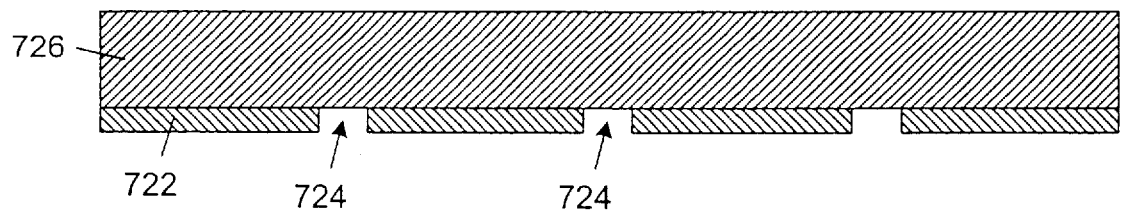
FIGS. 25A–D depict a cross-sectional view of a series of processing steps for the formation of a photoresist based sensor array which includes a top and bottom cover with openings aligned with the cavity.

In an embodiment, a first photoresist layer 722 is developed and etched such that openings 724 are formed as depicted in FIG. 25A. The openings may be formed proximate the location of the subsequently formed cavities. Preferably, the openings have a width that is substantially smaller than a width of the particle. The openings may inhibit displacement of the particle from a cavity. After the first photoresist layer 722 is patterned and etched, a main layer 726 is formed upon the bottom layer. The main layer 726 is preferably formed from a photoresist film that has a thickness substantially greater than a typical width of a particle. Thus, if the particles have a width of about 30 $\mu$m, a main layer may be composed of a 50 $\mu$m photoresist material. Alternatively, the photoresist layer may be composed of a multitude of photoresist layers placed upon each other until the desired thickness is achieved, as will be depicted in later embodiments.

Figure 25B:
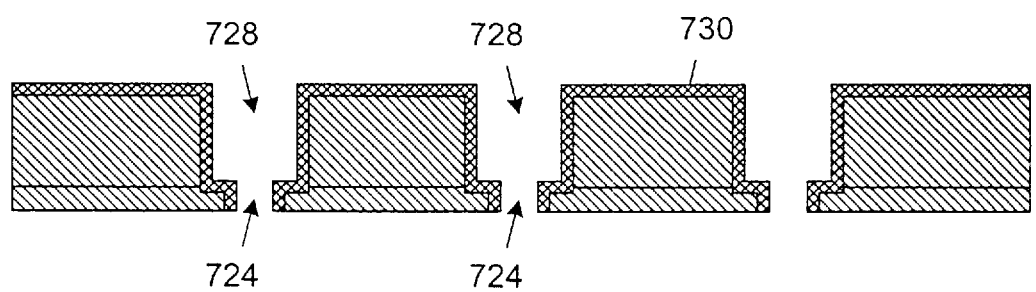

The main photoresist layer may be patterned and etched to form the cavities 728, as depicted in FIG. 25B. The cavities, in one embodiment, are substantially aligned above the previously formed openings 724. Cavities 728, in one embodiment, have a width which is greater than a width of a particle.

For many types of analysis, the photoresist material is substantially transparent to the light source used. Thus, as opposed to a silicon supporting member, the photoresist material used for the main supporting layer may be substantially transparent to the light used by the light source. In some circumstances, the transparent nature of the supporting member may allow light from the cavity to migrate, through the supporting member, into a second cavity. This leakage of light from one cavity to the next may lead to detection problems. For example, if a first particle in a first cavity produces a fluorescent signal in response to an analyte, this signal may be transmitted through the supporting member and detected in a proximate cavity. This may lead to inaccurate readings for the proximately spaced cavities, especially if a particularly strong signal is produced by the interaction of the particle with an analyte.

To reduce the occurrence of this "cross-talk", a substantially reflective layer 730 may be formed along the inner surface of the cavity. In one embodiment, the reflective layer 730 is composed of a metal layer which is formed on the upper surface of the main layer and the inner surface of the cavity. The metal layer may be deposited using chemical vapor deposition or other known techniques for depositing thin metal layers. The presence of a reflective layer may inhibit "cross-talk" between the cavities.

Figure 25C:
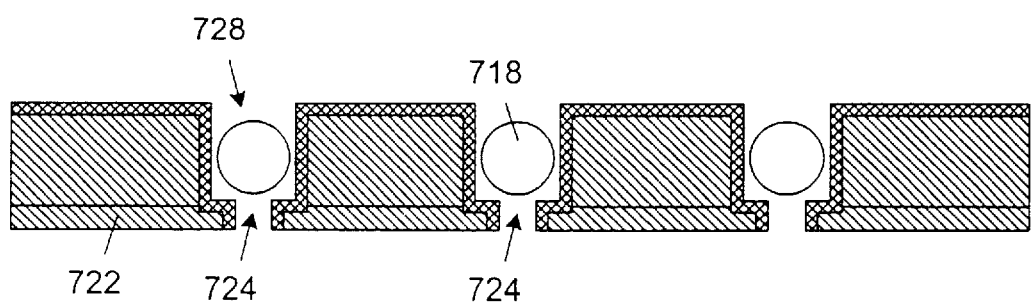

After the cavities 728 have been formed, particles 718 may be inserted into the cavities 728, as depicted in FIG. 25C. The first photoresist layer 722 may serve as a support for the particles 718. The particles may be inhibited from being displaced from the cavities by the first photoresist layer 722. The openings 724 in the first photoresist layer 722 may allow fluid to pass through the bottom layer during use.

Figure 25D:
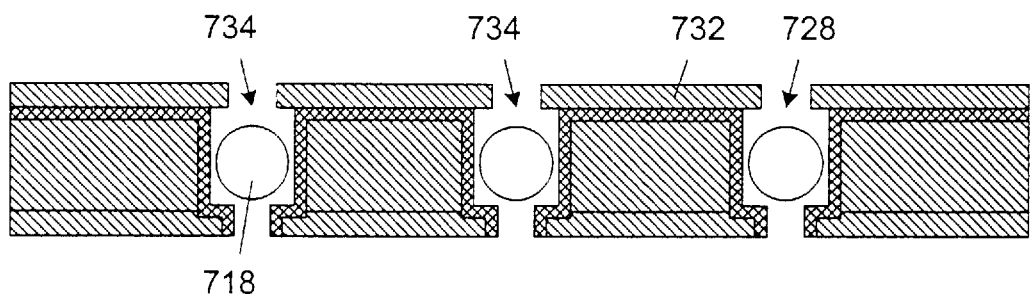

After the particles 718 are placed in the cavities 728, a top photoresist layer 732 may be placed upon the upper surface of the silicon substrate as depicted in FIG. 25D. After the cover layer is formed, openings 734 may be formed in the cover layer to allow the passage of the fluid into the cavities.

Figure 26A:
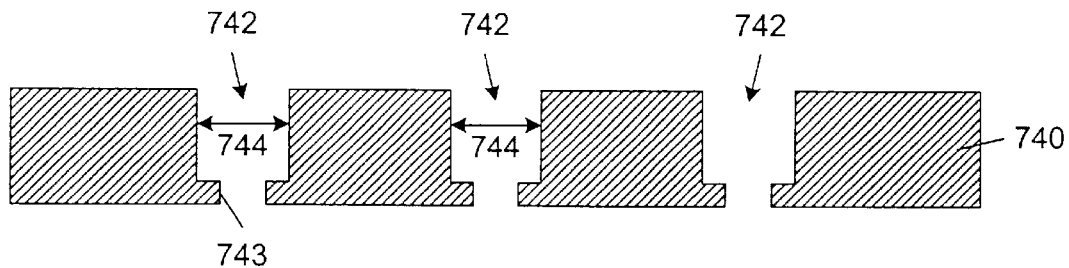
FIGS. 26A–E depict a cross-sectional view of a series of processing steps for the formation of a plastic based sensor array which includes a top and bottom cover with openings aligned with the cavity.
Figure 26B:
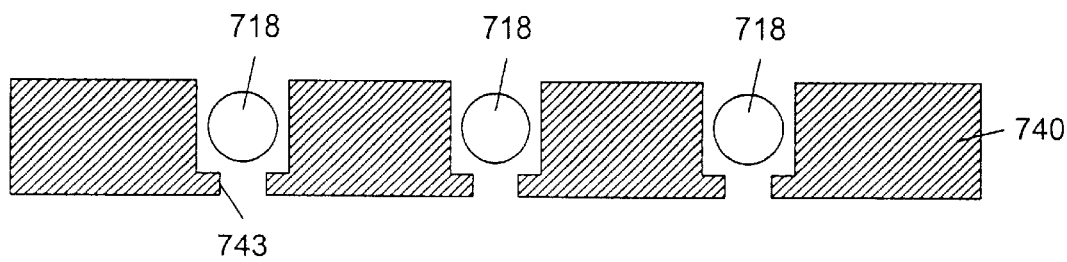
Figure 26C:
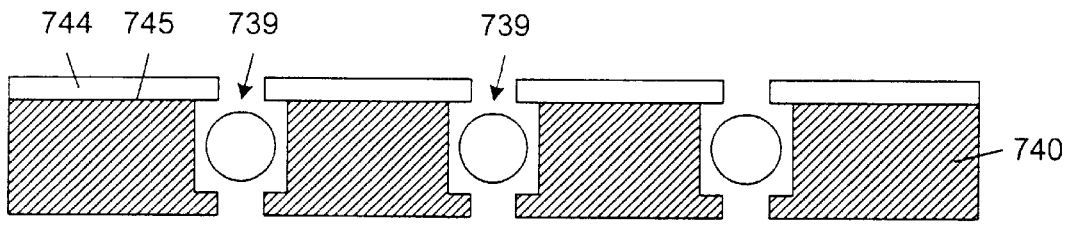
Figure 26D:
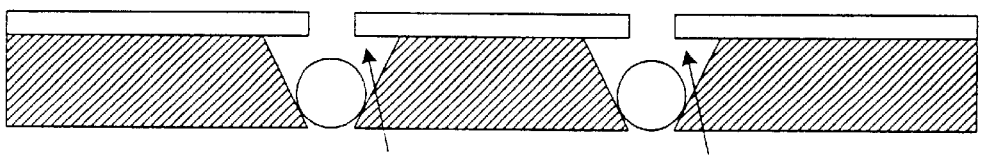

In another embodiment, the supporting member may be formed from a plastic substrate, as depicted in FIGS. 26A–E. In one embodiment, the plastic substrate is composed of a material, which is substantially resistant to the fluid, which includes the analyte. Examples of plastic materials which may be used to form the plastic substrate include, but are not limited to, acrylic resins, polycarbonates, polyester resins, polyethylenes, polyimides, polyvinyl polymers (e.g., polyvinyl chloride, polyvinyl acetate, polyvinyl dichloride, polyvinyl fluoride, etc.), polystyrenes, polypropylenes, polytetrafluoroethylenes, and polyurethanes. The plastic substrate may be substantially transparent or substantially opaque to the light produced by the light source. After obtaining a suitable plastic material 740, a series of cavities 742 may be formed in the plastic material. The cavities 742 may be formed by drilling (either mechanically or with a laser), transfer molding (e.g., forming the cavities when the plastic material is formed using appropriately shaped molds), or using a punching apparatus to punch cavities into the plastic material. In one embodiment, the cavities 742 are formed such that a lower portion 743 of the cavities is substantially narrower than an upper portion 744 of the cavities. The lower portion 743 of the cavities may have a width substantially less than a width of a particle. The lower portion 743 of the cavities 742 may inhibit the displacement of a particle from the cavity 742. While depicted as rectangular, with a narrower rectangular opening at the bottom, it should be understood that the cavity may be formed in a number of shapes including but not limited to pyramidal, triangular, trapezoidal, and oval shapes. An example of a pyramidal cavity, which is tapered such that the particle is inhibited from being displaced from the cavity, is depicted in FIG. 26D.

After the cavities 742 are formed, particles 718 may be inserted into the cavities 742, as depicted in FIG. 26B. The lower portion 743 of the cavities may serve as a support for the particles 718. The particles 718 may be inhibited from being displaced from the cavities 742 by the lower portion 743 of the cavity. After the particles are placed in the cavities 742, a cover 744 may be placed upon the upper surface 745 of the plastic substrate 740, as depicted in FIG. 26C. In one embodiment, the cover is formed from a film of photoresist material. After the cover 744 is placed on the plastic substrate 740, openings 739 may be formed in the cover layer to allow the passage of the fluid into the cavities.

Figure 26E:
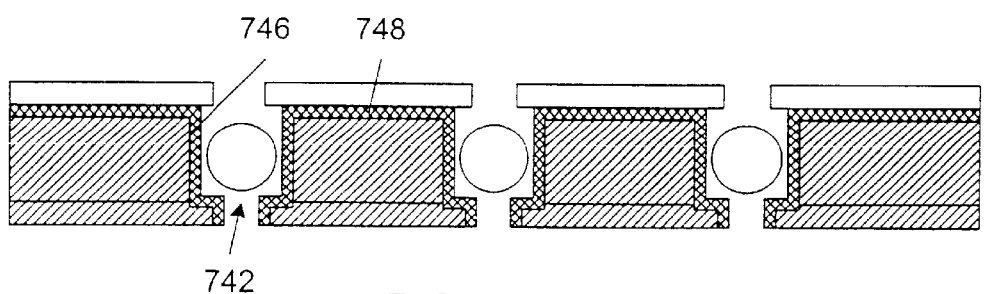

In some circumstances a substantially transparent plastic material may be used. As described above, the use of a transparent supporting member may lead to "cross-talk" between the cavities. To reduce the occurrence of this "cross-talk", a substantially reflective layer 748 may be formed on the inner surface 746 of the cavity, as depicted in FIG. 26E. In one embodiment, the reflective layer 748 is composed of a metal layer which is formed on the inner surface of the cavities 742. The metal layer may be deposited using chemical vapor deposition or other techniques for depositing thin metal layers. The presence of a reflective layer may inhibit cross-talk between the cavities.

Figure 27A:
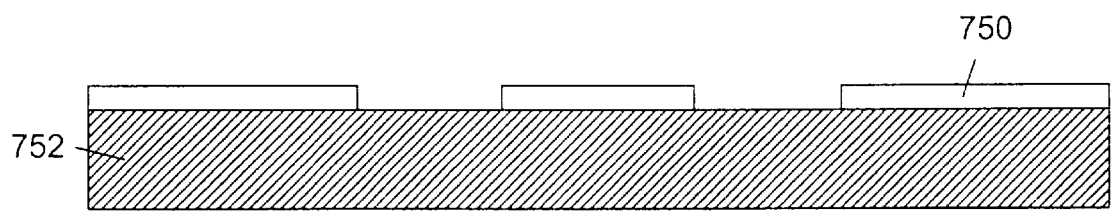
FIGS. 27A–D depict a cross-sectional view of a series of processing steps for the formation of a silicon based sensor array which includes a top cover with openings aligned with the cavity and a tapered cavity.

In another embodiment, a silicon based supporting member for a sensing particle may be formed without a bottom layer. In this embodiment, the cavity may be tapered to inhibit the passage of the particle from the cavity, through the bottom of the supporting member. FIGS. 27A–D, depicts the formation of a supporting member from a silicon substrate. In this embodiment, a photoresist layer 750 is formed upon an upper surface of silicon based supporting member 752, as depicted in FIG. 27A. The photoresist layer 750 may be patterned and developed such that the regions of the silicon substrate in which the cavities will be formed are exposed.

Figure 27B:
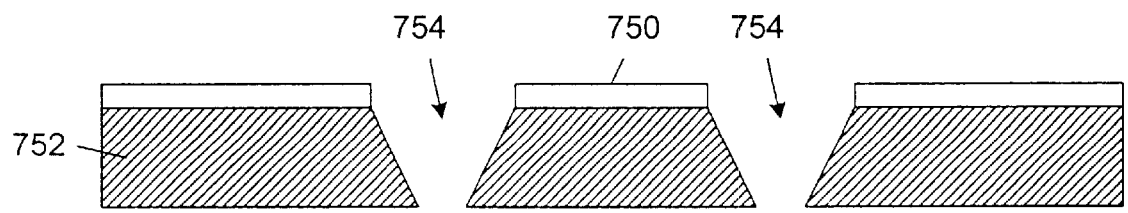
Figure 27C:
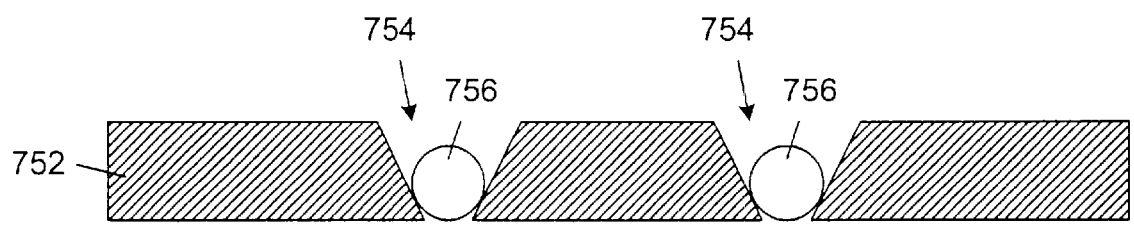
Figure 27D:
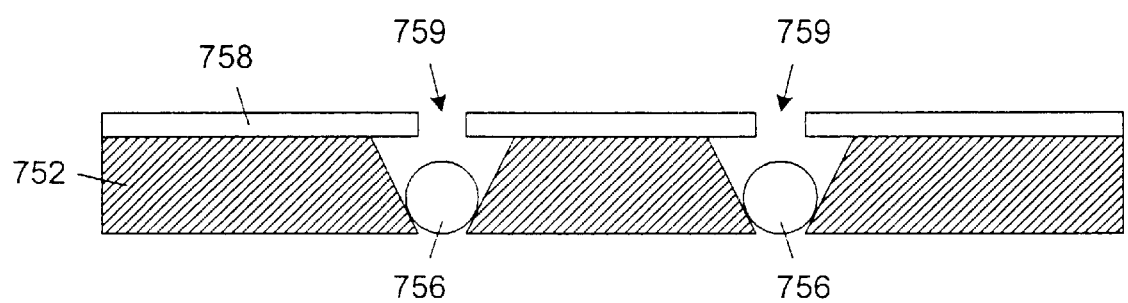

Cavities 754 may now be formed, as depicted in FIG. 27B, by subjecting the silicon substrate to an anisotropic etch. In one embodiment, a potassium hydroxide etch is used to produced tapered cavities. The etching may be controlled such that the width of the bottom of the cavities 754 is less than a width of the particle. After the cavities have been etched, a particle 756 may be inserted into the cavities 754 as depicted in FIG. 27C. The particle 756 may be inhibited from passing out of the cavities 754 by the narrower bottom portion of the cavities. After the particle is positioned within the cavities 754, a cover 758 may be formed upon the silicon based supporting member 752, as depicted in FIG. 27D. The cover may be formed of any material substantially transparent to the light produced by the light source used for analysis. Openings 759 may be formed in the cover 758 to allow the fluid to pass into the cavity from the top face of the silicon based supporting member 752. The openings 759 in the cover and the opening at the bottom of the cavities 754 together may allow fluid to pass through the cavity during use.

Figure 28A:
FIGS. 28A–E depict a cross-sectional view of a series of processing steps for the formation of a photoresist based sensor array which includes a top cover with openings aligned with the cavity and a tapered cavity.
Figure 28B:
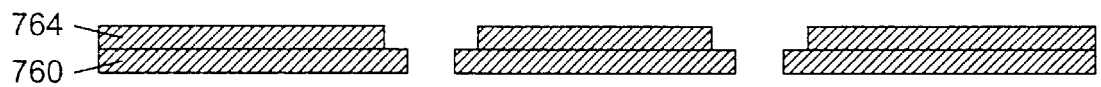

In another embodiment, a supporting member for a sensing particle may be formed from a plurality of layers of a photoresist material. In this embodiment, the cavity may be tapered to inhibit the passage of the particle from the cavity, through the bottom of the supporting member. FIGS. 28A–E depict the formation of a supporting member from a plurality of photoresist layers. In an embodiment, a first photoresist layer 760 is developed and etched to form a series of openings 762 which are positioned at the bottom of subsequently formed cavities, as depicted in FIG. 28A. As depicted in FIG. 28B, a second layer of photoresist material 764 may be formed upon the first photoresist layer 760. The second photoresist layer may be developed and etched to form openings substantially aligned with the openings of the first photoresist layer 760. The openings formed in the second photoresist layer 764, in one embodiment, are substantially larger than the layers formed in the first photoresist layer 760. In this manner, a tapered cavity may be formed while using multiple photoresist layers.

Figure 28C:
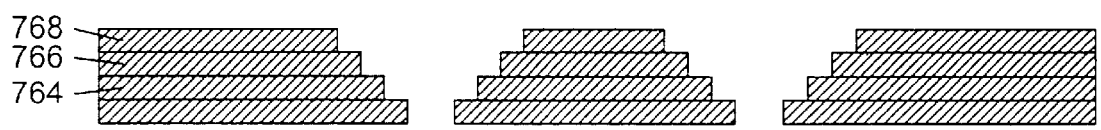

As depicted in FIG. 28C, additional layers of photoresist material 766 and 768 may be formed upon the second photoresist layer 764. The openings of the additional photoresist layers 766 and 768 may be progressively larger as each layer is added to the stack. In this manner, a tapered cavity may be formed. Additional layers of photoresist material may be added until the desired thickness of the supporting member is obtained. The thickness of the supporting member, in one embodiment, is greater than a width of a particle. For example, if a layer of photoresist material has a thickness of about 25 μm and a particle has a width of about 100 μm, a supporting member may be formed from four or more layers of photoresist material. While depicted as pyramidal, the cavity may be formed in a number of different shapes, including but not limited to, rectangular, circular, oval, triangular, and trapezoidal. Any of these shapes may be obtained by appropriate patterning and etching of the photoresist layers as they are formed.

Figure 28D:
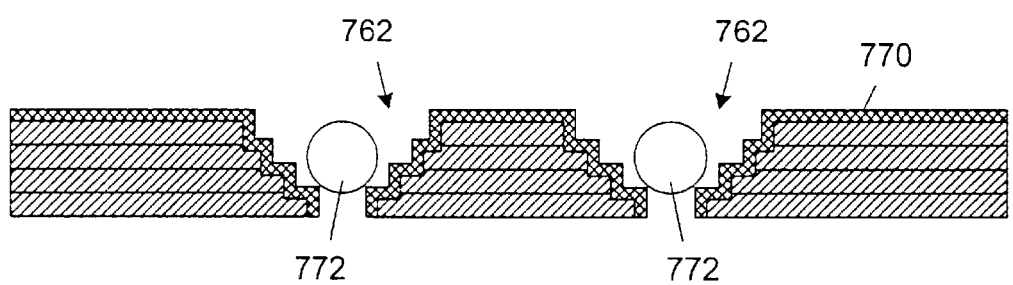

In some instances, the photoresist material may be substantially transparent to the light produced by the light source. As described above, the use of a transparent supporting member may lead to "cross-talk" between the cavities. To reduce the occurrence of this "cross-talk", a substantially reflective layer 770 may be formed along the inner surface of the cavities 762, as depicted in FIG. 28D. In one embodiment, the reflective layer is composed of a metal layer which is formed on the inner surface of the cavities 762. The metal layer may be deposited using chemical vapor deposition or other techniques for depositing thin metal layers. The presence of a reflective layer may inhibit "cross-talk" between the cavities.

Figure 28E:
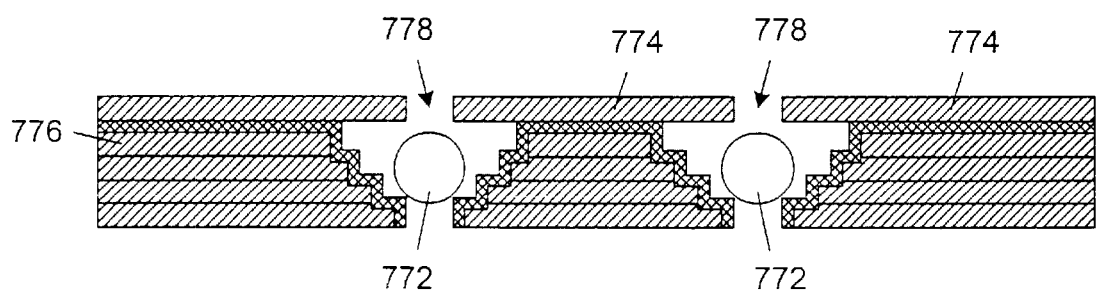

After the cavities 762 are formed, particles 772 may be inserted into the cavities 762, as depicted in FIG. 28D. The narrow portions of the cavities 762 may serve as a support for the particles 772. The particles 772 may be inhibited from being displaced from the cavities 762 by the lower portion of the cavities. After the particles 772 are placed in the cavities 762, a cover 774 may be placed upon the upper surface of the top layer 776 of the supporting member, as depicted in FIG. 28E. In one embodiment, the cover 774 is also formed from a film of photoresist material. After the cover layer is formed, openings 778 may be formed in the cover 774 to allow the passage of the fluid into the cavities.

Figure 29A:
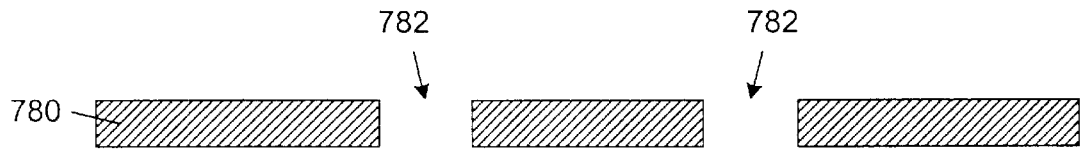
FIGS. 29A–E depict a cross-sectional view of a series of processing steps for the formation of a photoresist based sensor array which includes a top cover with openings aligned with the cavity and a bottom cover.
Figure 29B:
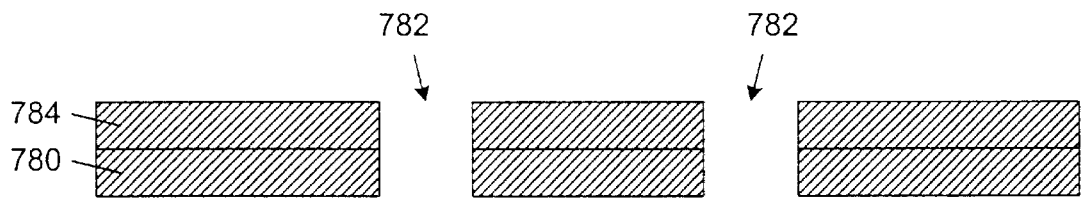

In another embodiment, a supporting member for a sensing particle may be formed from photoresist material which includes a particle support layer. FIGS. 29A–E depict the formation of a supporting member from a series of photoresist layers. In an embodiment, a first photoresist layer 780 is developed and etched to form a series of openings 782 which may become part of subsequently formed cavities. In another embodiment, a cavity having the appropriate depth may be formed by forming multiple layers of a photoresist material, as described previously. As depicted in FIG. 29B, a second photoresist layer 784 may be formed upon the first photoresist layer 780. The second photoresist layer 784 may be patterned to form openings substantially aligned with the openings of the first photoresist layer 782. The openings formed in the second photoresist layer 784 may be substantially equal in size to the previously formed openings. Alternatively, the openings may be variable in size to form different shaped cavities.

Figure 29C:
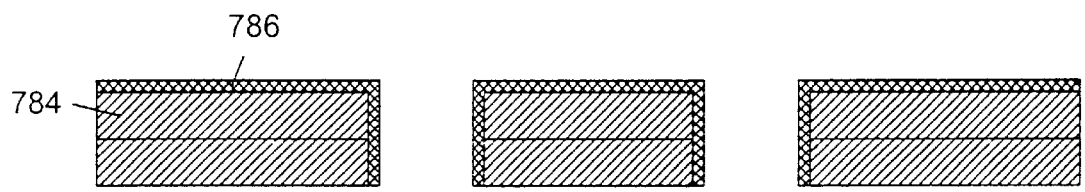

For reasons described above, a substantially reflective layer 786 may be formed along the inner surface of the cavities 782 and the upper surface of the second photoresist layer 784, as depicted in FIG. 29C. In one embodiment, the reflective layer is composed of a metal layer. The metal layer may be deposited using chemical vapor deposition or other techniques for depositing thin metal layers. The presence of a reflective layer may inhibit "cross-talk" between the cavities.

Figure 29D:
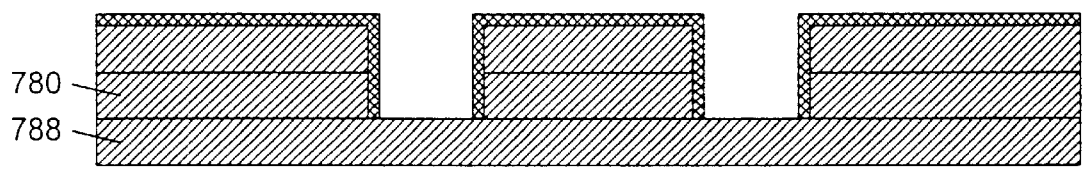

After the metal layer is deposited, a particle support layer 788 may be formed on the bottom surface of the first photoresist layer 780, as depicted in FIG. 29D. The particle support layer 788 may be formed from photoresist material, silicon dioxide, silicon nitride, glass or a substantially transparent plastic material. The particle support layer 788 may serve as a support for the particles placed in the cavities 782. The particle support layer, in one embodiment, is formed from a material that is substantially transparent to the light produced by the light source.

Figure 29E:
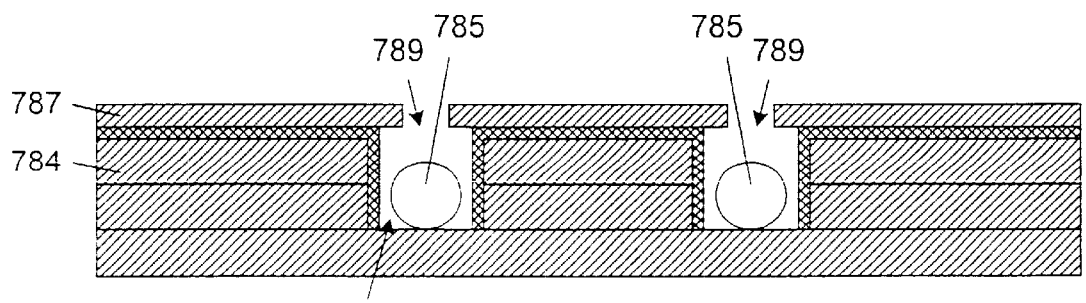

After the particle supporting layer 788 is formed, particles 785 may be inserted into the cavities 782, as depicted in FIG. 29E. The particle support layer 788 may serve as a support for the particles. Thus the particles 785 may be inhibited from being displaced from the cavities by the particle support layer 788. After the particles 785 are placed in the cavities 782, a cover 787 may be placed upon the upper surface of the second photoresist layer 784, as depicted in FIG. 29E. In one embodiment, the cover is also formed from a film of photoresist material. After the cover is formed, openings 789 may be formed in the cover 787 to allow the passage of the fluid into the cavities. In this embodiment, the fluid is inhibited from flowing through the supporting member. Instead, the fluid may flow into and out of the cavities via the openings 789 formed in the cover 787.

Figure 30A:
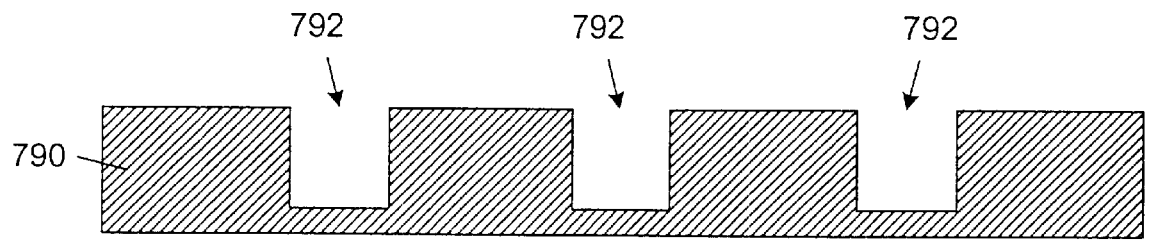
FIGS. 30A–D depict a cross-sectional view of a series of processing steps for the formation of a plastic based sensor array which includes a top cover with openings aligned with the cavity and a bottom cover.
Figure 30B:
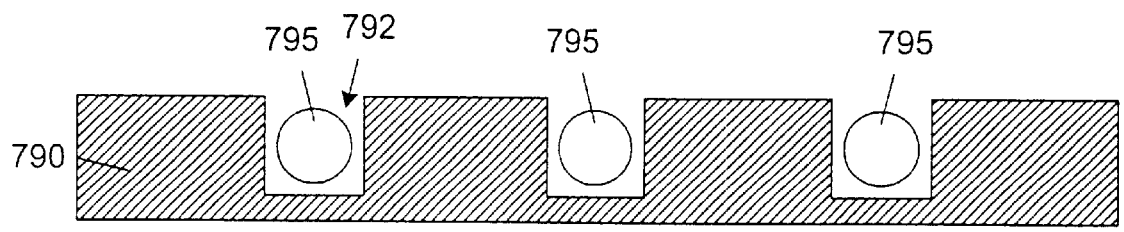
Figure 30C:
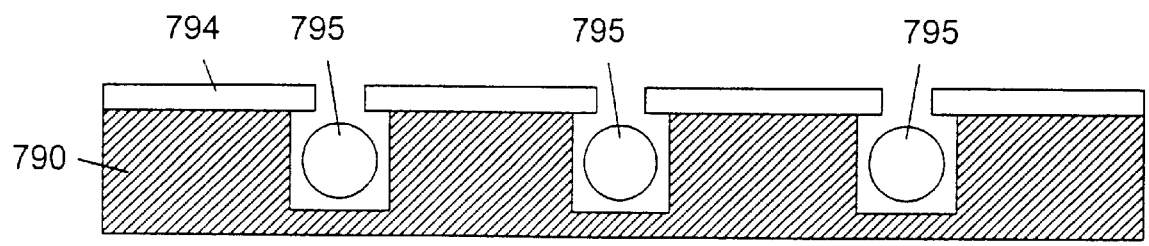
Figure 30D:
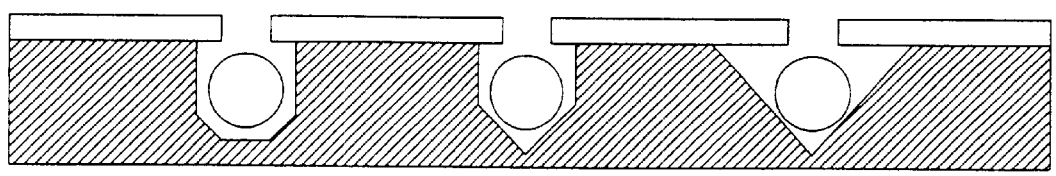

A similar supporting member may be formed from a plastic material, as depicted in FIGS. 30A–D. The plastic material may be substantially resistant to the fluid which includes the analyte. The plastic material may be substantially transparent or substantially opaque to the light produced by the light source. After obtaining a suitable plastic substrate 790, a series of cavities 792 may be formed in the plastic substrate 790. The cavities may be formed by drilling (either mechanically or with a laser), transfer molding (e.g., forming the cavities when the plastic substrate is formed using appropriately shaped molds), or using a punching machine to form the cavities. In one embodiment, the cavities extend through a portion of the plastic substrate, terminating proximate the bottom of the plastic substrate, without passing through the plastic substrate. After the cavities 792 are formed, particles 795 may be inserted into the cavities 792, as depicted in FIG. 30B. The bottom of the cavity may serve as a support for the particles 795. After the particles are placed in the cavities, a cover 794 may be placed upon the upper surface of the plastic substrate 790, as depicted in FIG. 30C. In one embodiment, the cover may be formed from a film of photoresist material. After the cover 794 is formed, openings 796 may be formed in the cover to allow the passage of the fluid into the cavities. While depicted as rectangular, is should be understood that the cavities may be formed in a variety of different shapes, including triangular, pyramidal, pentagonal, polygonal, oval, or circular. It should also be understood that cavities having a variety of different shapes may be formed into the same plastic substrate, as depicted in FIG. 30D.

Figure 31:
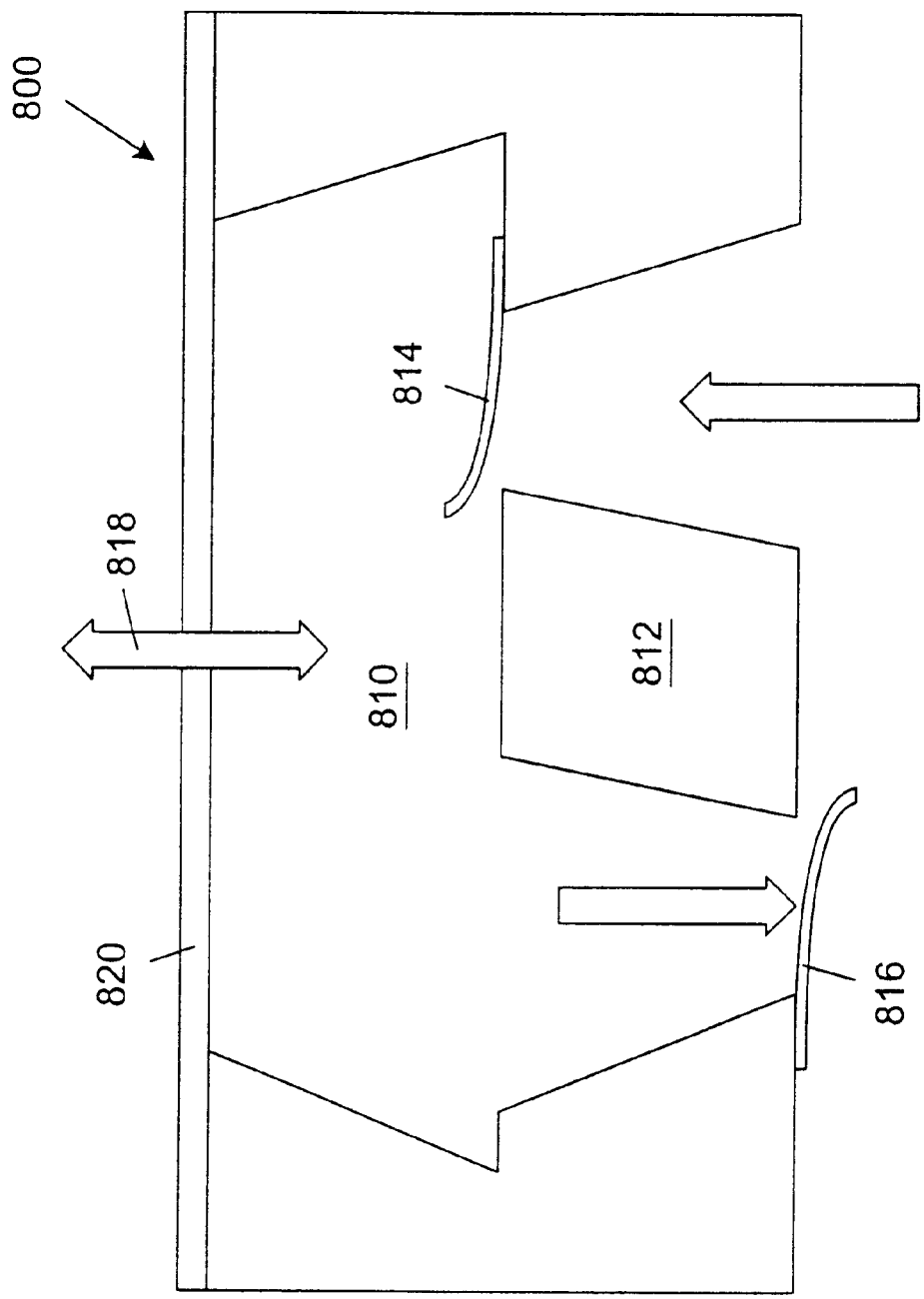
FIG. 31 depicts a cross-sectional view of a schematic of a micropump.

In one embodiment, a series of channels may be formed in the supporting member interconnecting some of the cavities, as depicted in FIG. 3. Pumps and valves may also be incorporated into the supporting member to aid passage of the fluid through the cavities. A schematic figure of a diaphragm pump 800 is depicted in FIG. 31. Diaphragm pumps, in general, include a cavity 810, a flexible diaphragm 812, an inlet valve 814, and an outlet valve 816. The flexible diaphragm 812, during use, is deflected as shown by arrows 818 to create a pumping force. As the diaphragm is deflected toward the cavity 810 it may cause the inlet valve 814 to close, the outlet valve 816 to open and any liquid which is in the cavity 810 will be forced toward the outlet 816. As the diaphragm moves away form the cavity 810, the outlet valve 816 maybe pulled to a closed position, and the inlet valve 814 may be opened, allowing additional fluid to enter the cavity 810. In this manner a pump may be used to pump fluid through the cavities. It should be understood that the pump depicted in FIG. 31 is a generalized version of a diaphragm based pump. Actual diaphragm pumps may have different shapes or may have inlet and outlet valves which are separate from the pumping device.

In one embodiment, the diaphragm 810 may be made from a piezoelectric material. This material will contract or expand when an appropriate voltage is applied to the diaphragm. Pumps using a piezoelectric diaphragms are described in U.S. Pat. Nos. 4,344,743, 4,938,742, 5,611,676, 5,705,018, and 5,759,015, all of which are incorporated herein by reference. In other embodiments, the diaphragm may be activated using a pneumatic system. In these systems, an air system may be coupled to the diaphragm such that changes in air density about the diaphragm, induced by the pneumatic system, may cause the diaphragm to move toward and away from the cavity. A pneumatically controlled pump is described in U.S. Pat. No. 5,499,909 which is incorporated herein by reference. The diaphragm may also be controlled using a heat activated material. The diaphragm may be formed from a temperature sensitive material. In one embodiment, the diaphragm may be formed from a material which is configured to expand and contract in response to temperature changes. A pump system which relies on temperature activated diaphragm is described in U.S. Pat. No. 5,288,214 which is incorporated herein by reference.

Figure 32:
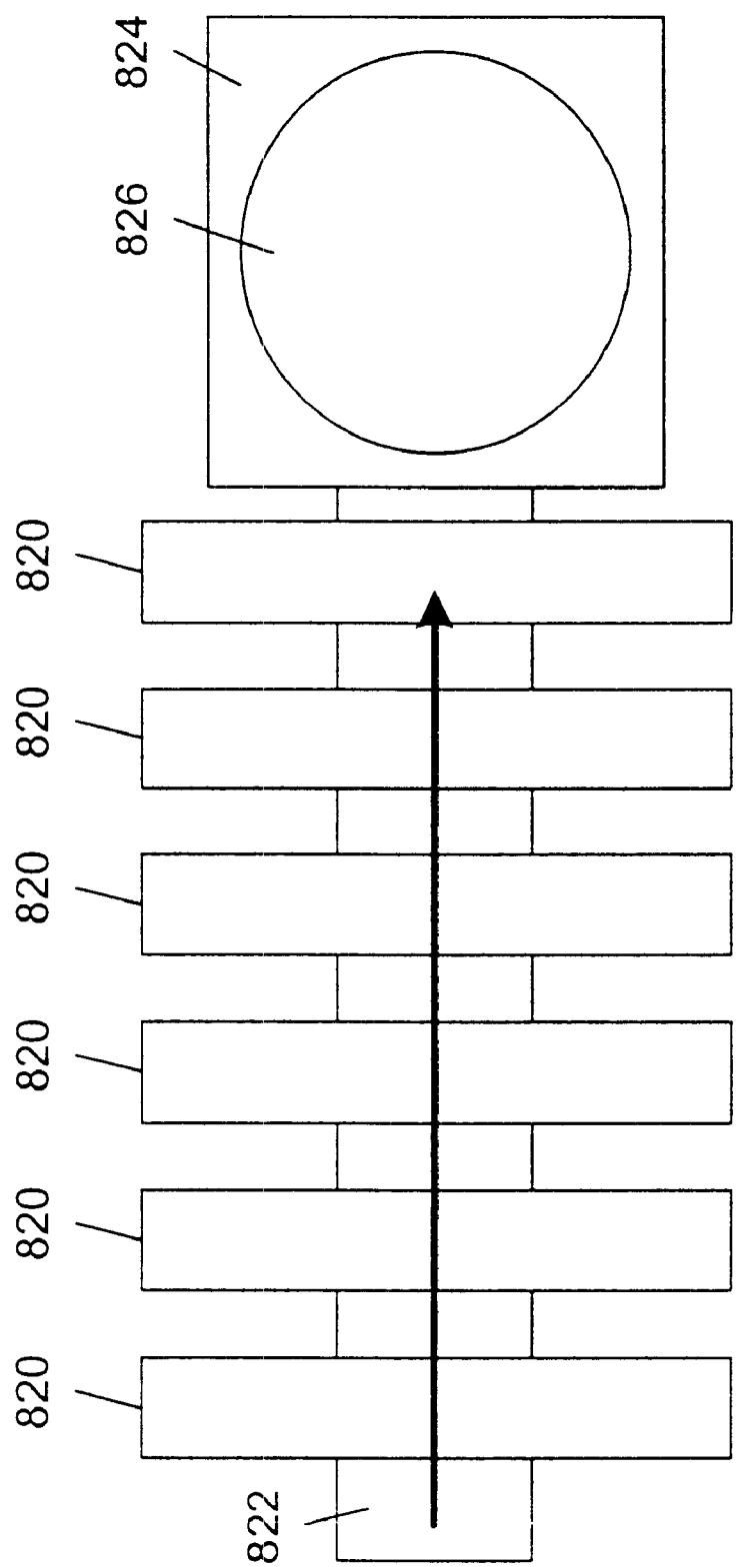
FIG. 32 depicts a top view of an electrohydrodynamic pump.

In another embodiment, an electrode pump system may be used. FIG. 32 depicts a typical electrode based system. A series of electrodes 820 may be arranged along a channel 822 which may lead to a cavity 824 which includes a particle 826. By varying the voltage in the electrodes 820 a current flow may be induced in the fluid within the channel 822. Examples of electrode based systems include, but are not limited to, electroosmosis systems, electrohydrodynamic systems, and combinations of electroosmosis and electrohydrodynamic systems.

Electrohydrodynamic pumping of fluids is known and may be applied to small capillary channels. In an electrohydrodynamic system electrodes are typically placed in contact with the fluid when a voltage is applied. The applied voltage may cause a transfer in charge either by transfer or removal of an electron to or from the fluid. This electron transfer typically induces liquid flow in the direction from the charging electrode to the oppositely charged electrode. Electrohydrodynamic pumps may be used for pumping fluids such as organic solvents.

Electroosmosis, is a process which involves applying a voltage to a fluid in a small space, such as a capillary channel, to cause the fluid to flow. The surfaces of many solids, including quartz, glass and the like, become variously charged, negatively or positively, in. the presence of ionic materials, such as for example salts, acids or bases. The charged surfaces will attract oppositely charged (positive or negative) counterions in aqueous solutions. The application of a voltage to such a solution results in a migration of the counterions to the oppositely charged electrode, and moves the bulk of the fluid as well. The volume flow rate is proportional to the current, and the volume flow generated in the fluid is also proportional to the applied voltage. An electroosmosis pump system is described in U.S. Pat. No. 4,908,112 which is incorporated herein by reference.

In another embodiment, a combination of electroosmosis pumps and electrohydrodynamic pumps may be used. Wire electrodes may be inserted into the walls of a channel at preselected intervals to form alternating electroosmosis and electrohydrodynamic devices. Because electroosmosis and electrohydrodynamic pumps are both present, a plurality of different solutions, both polar and non-polar, may be pump along a single channel. Alternatively, a plurality of different solutions may be passed along a plurality of different channels connected to a cavity. A system which includes a combination of electroosmosis pumps and electrohydrodynamic pumps is described in U.S. Pat. No. 5,632,876 which is incorporated herein by reference.

Figure 33:
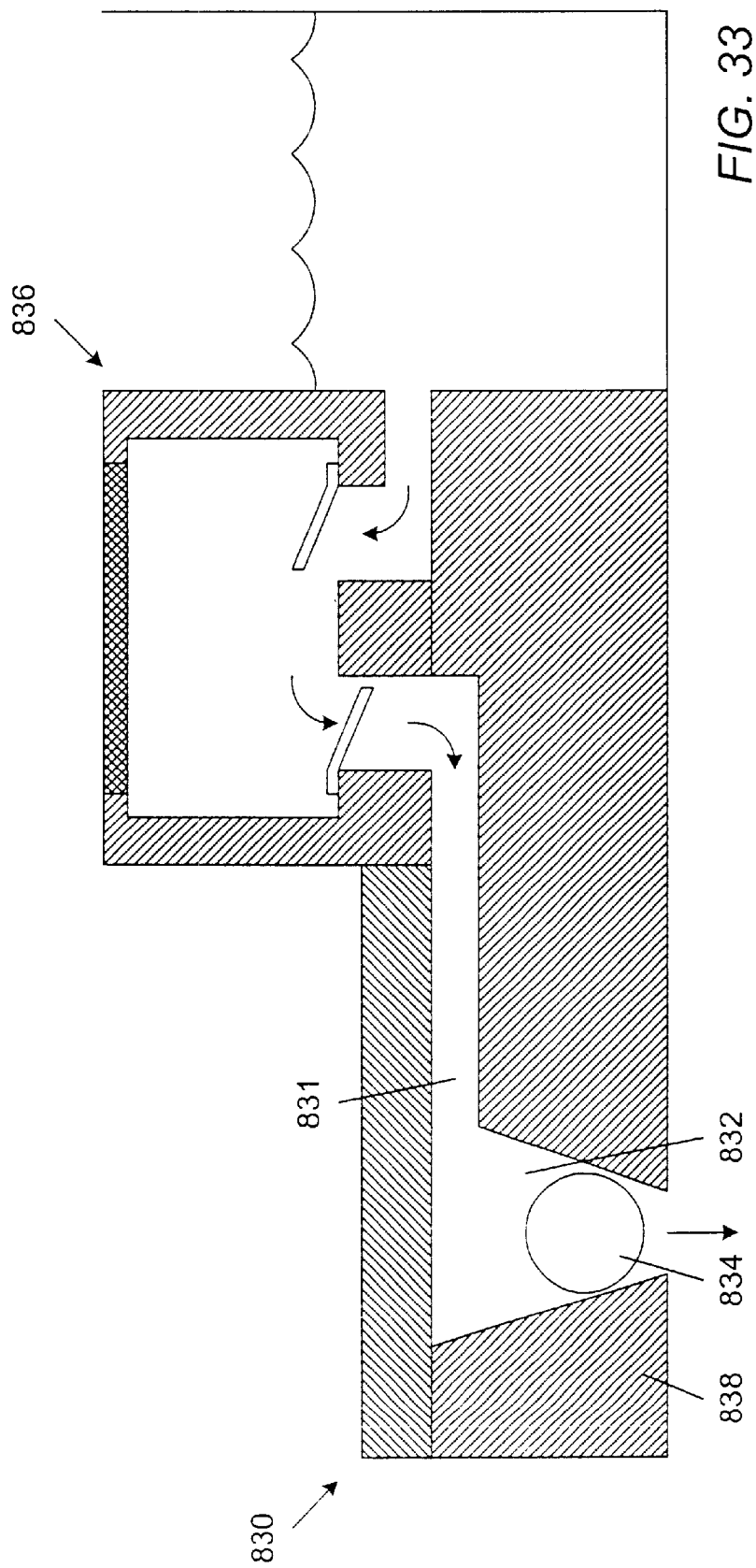
FIG. 33 depicts a cross-sectional view of a sensor array which includes a micropump.

In an embodiment, a pump may be incorporated into a sensor array system, as depicted in FIG. 33. A sensor array 830 includes at least one cavity 832 in which a particle 834 may be placed. The cavity 832 may be configured to allow fluid to pass through the cavity during use. A pump 836 may be incorporated onto a portion of the supporting member 838. A channel 831 may be formed in the supporting member 838 coupling the pump 836 to the cavity 832. The channel 831 may be configured to allow the fluid to pass from the pump 836 to the cavity 832. The pump 836 may be positioned away from the cavity 832 to allow light to be directed through the cavity during use. The supporting member 838 and the pump 836 may be formed from a silicon substrate, a plastic material, or photoresist material. The pump 836 may be configured to pump fluid to the cavity via the channel, as depicted by the arrows in FIG. 33. When the fluid reaches the cavity 832, the fluid may flow past the particle 834 and out through the bottom of the cavity. An advantage of using pumps is that better flow through the channels may be achieved. Typically, the channels and cavities may have a small volume. The small volume of the cavity and channel tends to inhibit flow of the fluid through the cavity. By incorporating a pump, the flow of fluid to the cavity and through the cavity may be increased, allowing more rapid testing of the fluid sample. While a diaphragm based pump system is depicted in FIG. 33, it should be understood that electrode based pumping systems might also be incorporated into the sensor array to produce fluid flows.

Figure 34:
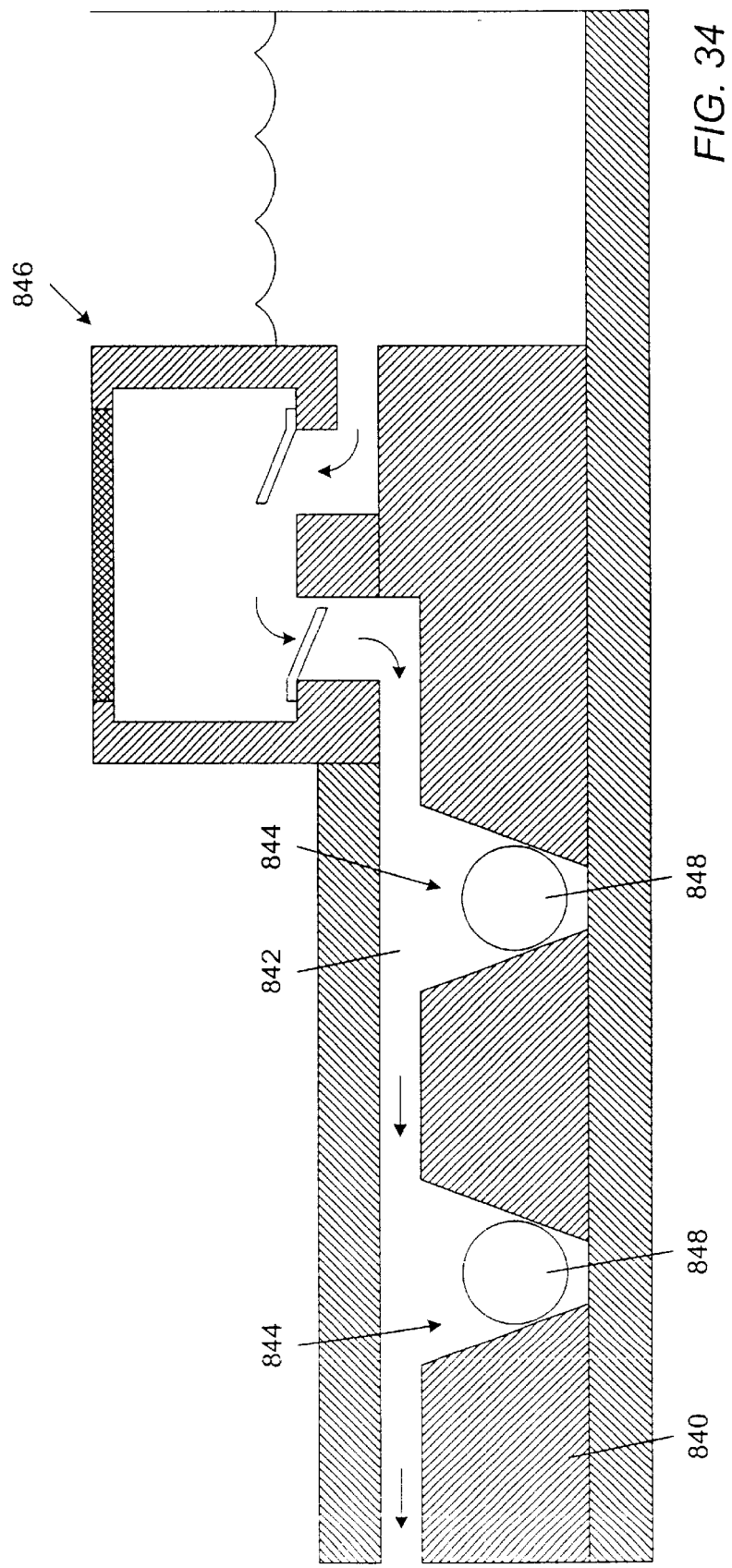
FIG. 34 depicts a cross-sectional view of a sensor array which includes a micropump and channels which are coupled to the cavities.

In another embodiment, a pump may be coupled to a supporting member for analyzing analytes in a fluid stream, as depicted in FIG. 34. A channel 842 may couple a pump 846 to multiple cavities 844 formed in a supporting member 840. The cavities 842 may include sensing particles 848. The pump may be configured to create a flow of the fluid through the channel 842 to the cavities 848. In one embodiment, the cavities may inhibit the flow of the fluid through the cavities 844. The fluid may flow into the cavities 844 and past the particle 848 to create a flow of fluid through the sensor array system. In this manner, a single pump may be used to pass the fluid to multiple cavities. While a diaphragm pump system is depicted in FIG. 34, it should be understood that electrode pumping systems might also be incorporated into the supporting member to create similar fluid flows.

Figure 35:
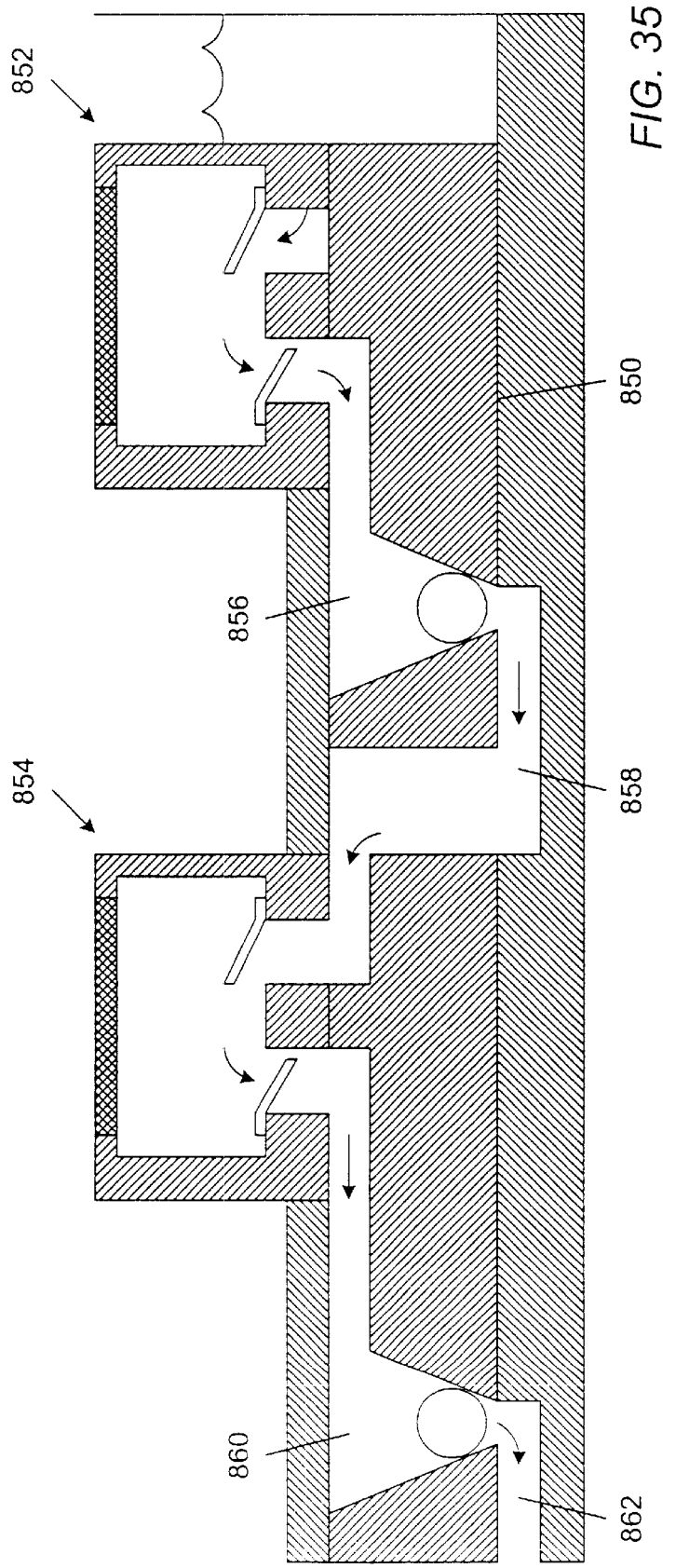
FIG. 35 depicts a cross-sectional view of a sensor array which includes multiple micropumps each micropump being coupled to a cavity.

In another embodiment, multiple pumps may be coupled to a supporting member of a sensor array system. In one embodiment, the pumps may be coupled in series with each other to pump fluid to each of the cavities. As depicted in FIG. 35, a first pump 852 and a second pump 854 may be coupled to a supporting member 850. The first pump 852 may be coupled to a first cavity 856. The first pump may be configured to transfer fluid to the first cavity 856 during use. The cavity 856 may be configured to allow the fluid to pass through the cavity to a first cavity outlet channel 858. A second pump 854 may also be coupled to the supporting member 850. The second pump 854 may be coupled to a second cavity 860 and the first cavity outlet channel 858. The second pump 854 may be configured to transfer fluid from the first cavity outlet channel 858 to the second cavity 860. The pumps may be synchronized such that a steady flow of fluid through the cavities is obtained. Additional pumps may be coupled to the second cavity outlet channel 862 such that the fluid may be pumped to additional cavities. In one embodiment, each of the cavities in the supporting member is coupled to a pump configured to pump the fluid stream to the cavity.

Figure 36:
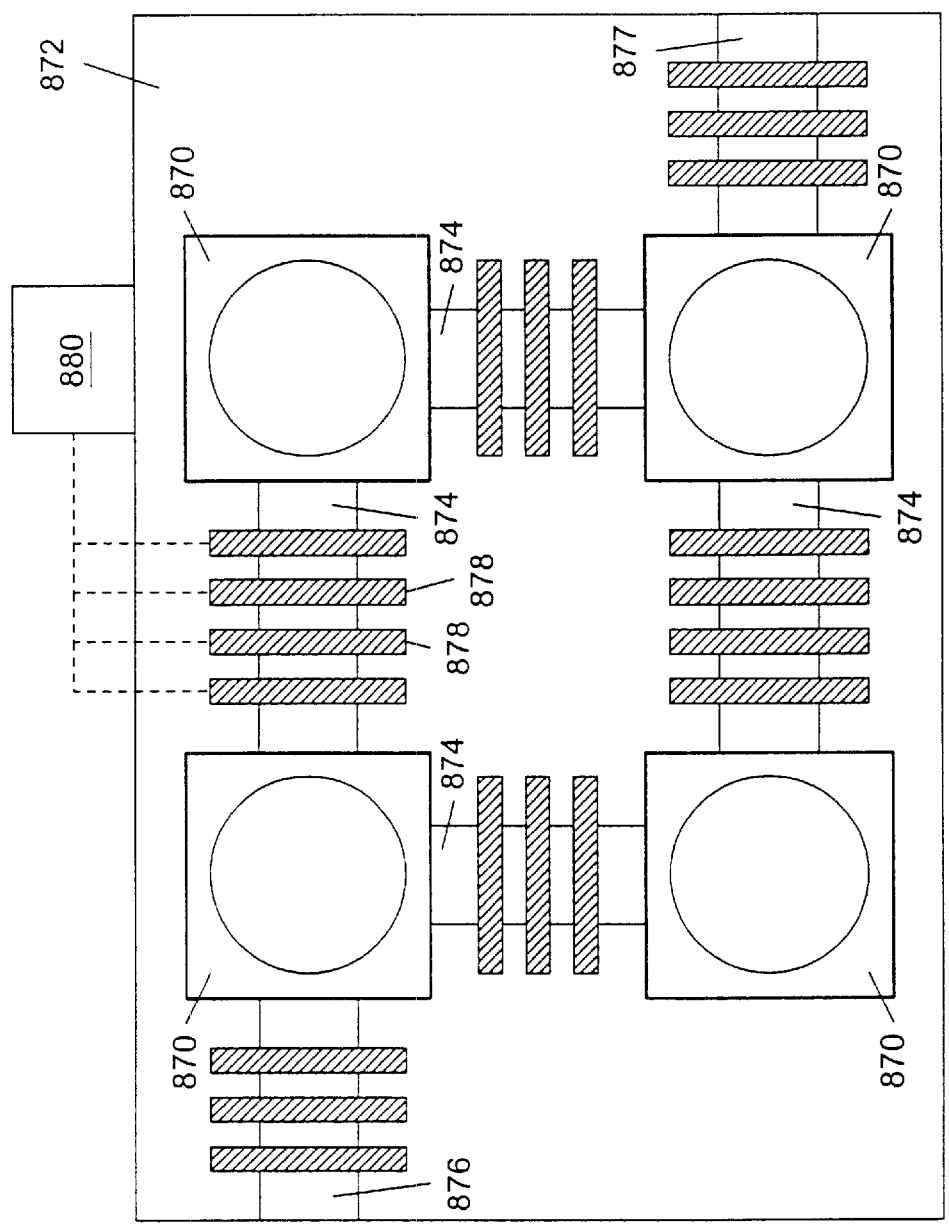
FIG. 36 depicts a top view of a sensor array which includes multiple electrohydrodynamic pumps.

In another embodiment, multiple electrode based pumps may be incorporated herein into the sensor array system. The pumps may be formed along the channels which couple the cavities. As depicted in FIG. 36, a plurality of cavities 870 may be formed in a supporting member 872 of a sensor array. Channels 874 may also be formed in the supporting member 872 interconnecting the cavities 870 with each other. An inlet channel 876 and an outlet channel 877, which allow the fluid to pass into and out of the sensor array, respectively, may also be formed. A series of electrodes 878 may be positioned over the channels 874, 876, and 877. The electrodes may be used to form an electroosmosis pumping system or an electrohydrodynamic pumping system. The electrodes may be coupled to a controller 880 which may apply the appropriate voltage to the appropriate electrodes to produce a flow of the fluid through the channels. The pumps may be synchronized such that a steady flow of fluid through the cavities is obtained. The electrodes may be positioned between the cavities such that the electrodes do not significantly interfere with the application of light to the cavities.

Figure 37:
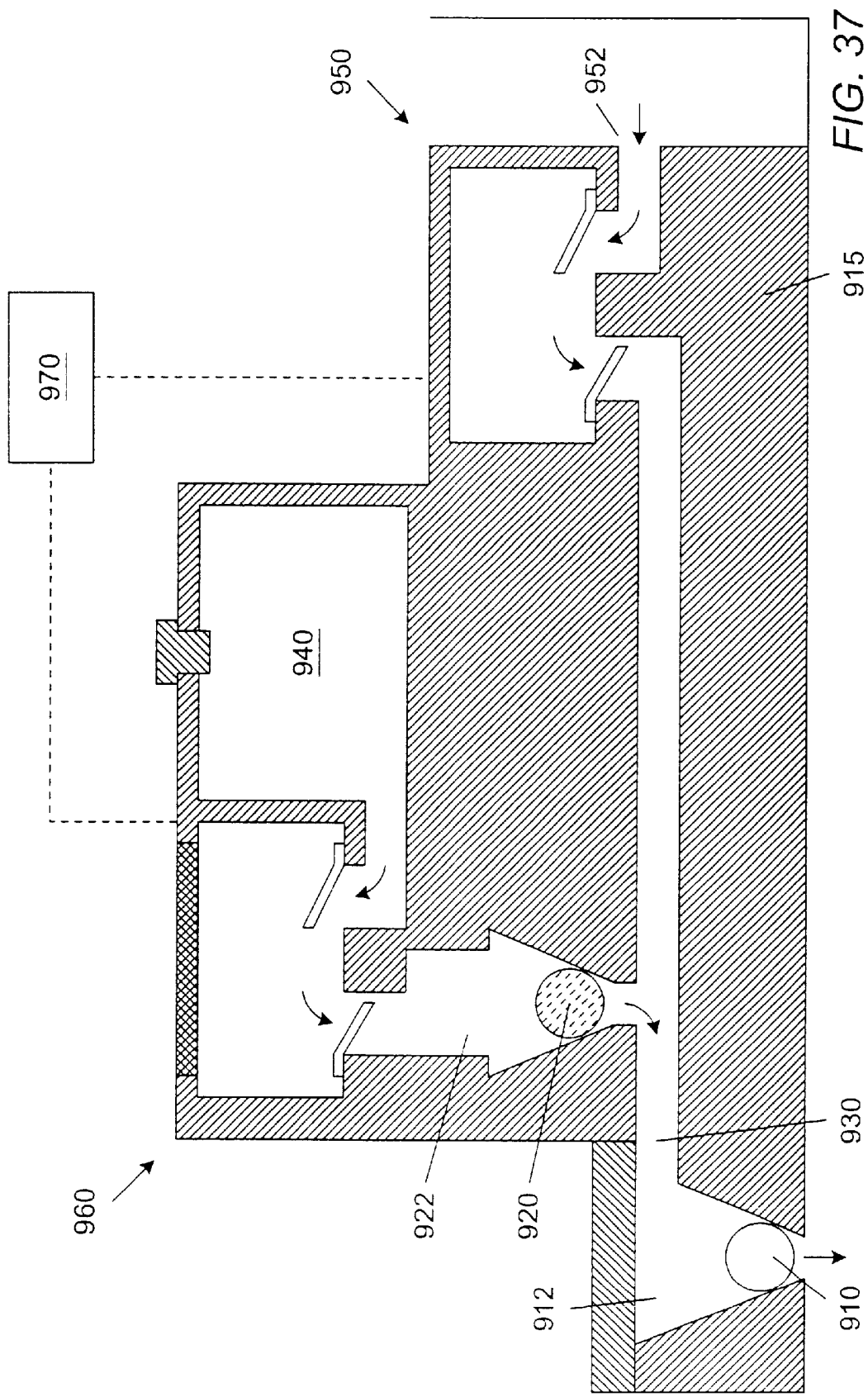
FIG. 37 depicts a cross-sectional view of a sensor array which includes a system for delivering a reagent from a reagent particle to a sensing cavity.

In some instances, it may be necessary to add a reagent to a particle before, during or after an analysis process. Reagents may include receptor molecules or indicator molecules. Typically, such reagents may be added by passing a fluid stream, which includes the reagent over the sensor array. In an embodiment, the reagent may be incorporated herein into the sensor array system, which includes two particles. In this embodiment, a sensor array system may include two particles 910 and 920 for each sensing position of the sensor array, as depicted in FIG. 37. The first particle 910 may be positioned in a first cavity 912. The second particle 920 may be positioned in a second cavity 922. In one embodiment, the second cavity is coupled to the first cavity via a channel 930. The second particle includes a reagent, which is at least partially removable from the second particle 920. The reagent may also be configured to modify the first particle 910, when the reagent is contacted with the first particle, such that the first particle will produce a signal when the first particle interacts with an analyte during use. The reagent may be added to the first cavity before, during or after a fluid analysis. The reagent is preferably coupled to the second particle 920. A portion of the reagent coupled to the second particle may be decoupled from the particle by passing a decoupling solution past the second particle. The decoupling solution may include a decoupling agent, which will cause at least a portion of the reagent to be at released by the particle. A reservoir 940 may be formed on the sensor array to hold the decoupling solution.

A first pump 950 and a second pump 960 may also be coupled to the supporting member 915. The first pump 950 may be configured to pump fluid from a fluid inlet 952 to the first cavity 912 via channel 930. The fluid inlet 952 is the location where the fluid, which includes the analyte, is introduced into the sensor array system. A second pump 950 may be coupled to the reservoir 940 and the second cavity 922. The second pump 960 may be used to transfer the decoupling solution from the reservoir to the second cavity 922. The decoupling solution may pass through the second cavity 922 and into first cavity 912. Thus, as the reagent is removed the second particle it may be transferred to the first cavity912, where the reagent may interact with the first particle 910. The reservoir may be refilled by removing the reservoir outlet 942, and adding additional fluid to the reservoir 940. While diaphragm based pump systems are depicted in FIG. 37, it should be understood that electrode based pumping systems may also be incorporated herein into the sensor array to produce fluid flows.

The use of such a system is described by way of example. In some instances it may be desirable to add a reagent to the first particle prior to passing the fluid which includes the analyte to the first particle. The reagent may be coupled to the second particle and placed in the sensor array prior to use, typically during construction of the array. A decoupling solution may be added to the reservoir before use. A controller 970 may also be coupled to the system to allow automatic operation of the pumps. The controller 970 may be configured to initiate the analysis sequence by activating the second pump 960, causing the decoupling solution to flow from the reservoir 940 to the second cavity 922. As the fluid passes through the second cavity 922, the decoupling solution may cause at least some of the reagent molecules to be released from the second particle 920. The decoupling solution may be passed out of the second cavity 922 and into the first cavity 912. As the solution passes through the first cavity, some of the reagent molecules may be captured by the first particle 910. After a sufficient number of molecules have been captured by the first particle 910, flow of fluid thorough the second cavity 922 may be stopped. During this initialization of the system, the flow of fluid through the first pump may be inhibited.

After the system is initialized, the second pump may be stopped and the fluid may be introduced to the first cavity. The first pump may be used to transfer the fluid to the first cavity. The second pump may remain off, thus inhibiting flow of fluid from the reservoir to the first cavity. It should be understood that the reagent solution may be added to the first cavity while the fluid is added to the first cavity. In this embodiment, both the first and second pumps may be operated substantially simultaneously.

Alternatively, the reagent may be added after an analysis. In some instances, a particle may interact with an analyte such that a change in the receptors attached to the first particle occurs. This change may not, however produce a detectable signal. The reagent attached to the second bead may be used to produce a detectable signal when it interacts with the first particle, if a specific analyte is present. In this embodiment, the fluid is introduced into the cavity first. After the analyte has been given time to react with the particle, the reagent may be added to the first cavity. The interaction of the reagent with the particle may produce a detectable signal. For example, an indicator reagent may react with a particle which has been exposed to an analyte to produce a color change on the particle. Particle which have not been exposed to the analyte may remain unchanged or show a different color change.

As shown in FIG. 1, a system for detecting analytes in a fluid may include a light source 110, a sensor array 120 and a detector 130. The sensor array 120 is preferably formed of a supporting member which is configured to hold a variety of particles 124 in an ordered array. A high sensitivity CCD array may be used to measure changes in optical characteristics which occur upon binding of the biological/chemical agents. Data acquisition and handling is preferably performed with existing CCD technology. As described above, colorimetric analysis may be performed using a white light source and a color CCD detector. However, color CCD detectors are typically more expensive than gray scale CCD detectors.

In one embodiment, a gray scale CCD detector may be used to detect colorimetric changes. In one embodiment, a gray scale detector may be disposed below a sensor array to measure the intensity of light being transmitted through the sensor array. A series of lights (e.g., light emitting diodes) may be arranged above the sensor array. In one embodiment, groups of three LED lights may be arranged above each of the cavities of the array. Each of these groups of LED lights may include a red, blue and a green light. Each of the lights may be operated individually such that one of the lights may be on while the other two lights are off. In order to provide color information while using a gray scale detector, each of the lights is sequentially turned on and the gray scale detector is used to measure the intensity of the light passing through the sensor array. After information from each of the lights is collected, the information may be processed to derive the absorption changes of the particle.

In one embodiment, the data collected by the gray scale detector may be recorded using 8 bits of data. Thus, the data will appear as a value between 0 and 255. The color of each chemical sensitive element may be represented as a red, blue and green value. For example, a blank particle (i.e., a particle which does not include a receptor) will typically appear white. When each of the LED lights (red, blue and green) are operated the CCD detector will record a value corresponding to the amount of light transmitted through the cavity. The intensity of the light may be compared to a blank particle, to determine the absorbance of a particle with respect to the LED light which is used. Thus, the red, green and blue components may be recorded individually without the use of a color CCD detector. In one embodiment, it is found that a blank particle exhibits an absorbance of about 253 when illuminated with a red LED, a value of about 250 when illuminated by a green LED, and a value of about 222 when illuminated with a blue LED. This signifies that a blank particle does not significantly absorb red, green or blue light. When a particle with a receptor is scanned, the particle may exhibit a color change, due to absorbance by the receptor. For example, it was found that when a particle which includes a 5-carboxyfluorescein receptor is subjected to white light, the particle shows a strong absorbance of blue light. When a red LED is used to illuminate the particle, the gray scale CCD detector may detect a value of about 254. When the green LED is used, the gray scale detector may detect a value of about 218. When a blue LED light is used, a gray scale detector may detect a value of about 57. The decrease in transmittance of blue light is believed to be due to the absorbance of blue light by the 5-carboxyfluorescein. In this manner the color changes of a particle may be quantitatively characterized using a gray scale detector.

As described above, after the cavities are formed in the supporting member, a particle may be positioned at the bottom of a cavity using a micromanipulator. This allows the location of a particular particle to be precisely controlled during the production of the array. The use of a micromanipulator may, however, be impractical for production of sensor array systems. An alternate method of placing the particles into the cavities may involve the use of a silk screen like process. A series of masking materials may be placed on the upper surface of the sensor array prior to filling the cavities. The masking materials may be composed of glass, metal or plastic materials. A collection of particles may be placed upon the upper surface of the masking materials and the particles may be moved across the surface. When a cavity is encountered, a particle may drop into the cavity if the cavity is unmasked. Thus particles of known composition are placed in only the unmasked regions. After the unmasked cavities are filled, the masking pattern may be altered and a second type of particles may be spread across the surface. Preferably, the masking material will mask the cavities that have already been filled with particle. The masking material may also mask other non-filled cavities. This technique may be repeated until all of the cavities are filled. After filling the cavities, a cover may be placed on the support member, as described above, to inhibit the displacement and mixing of the particles. An advantage of such a process is that it may be more amenable to industrial production of supporting members.

2. Further System Improvements

One challenge in a chemical sensor system is keeping dead volume to a minimum. This is especially problematic when an interface to the outside world is required (e.g., a tubing connection). In many cases the "dead volume" associated with the delivery of the sample to the reaction site in a "lab-on-a-chip" may far exceed the actual amount of reagent required for the reaction. Filtration is also frequently necessary to prevent small flow channels in the sensor arrays from plugging. Here the filter can be made an integral part of the sensor package.

Figure 38:
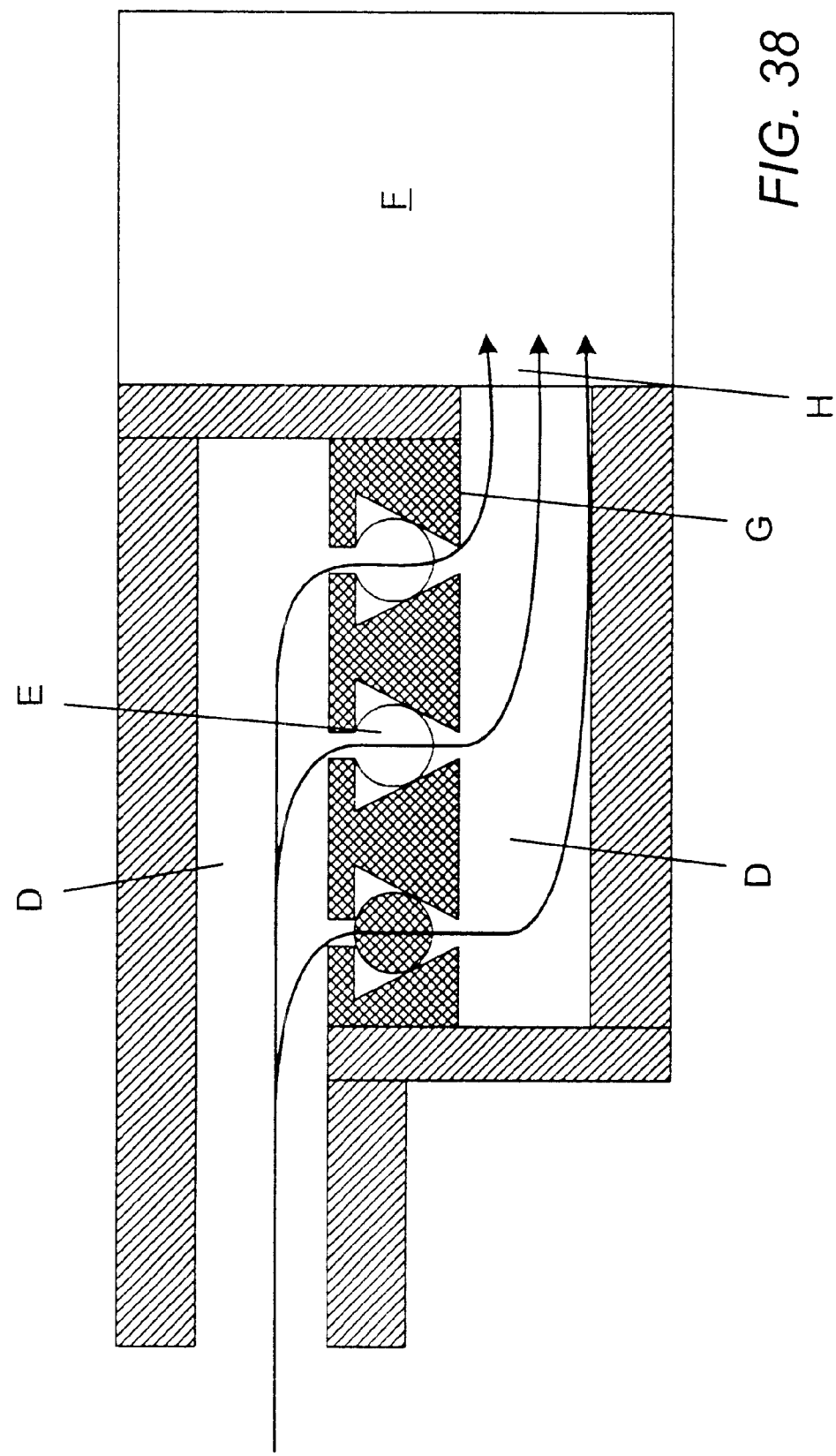
FIG. 38 depicts a cross-sectional view of a sensor array which includes a vacuum chamber.

In an embodiment, a system for detecting an analyte in a fluid includes a conduit coupled to a sensor array and a vacuum chamber coupled to the conduit. FIG. 38 depicts a system in which a fluid stream (E) passes through a conduit (D), onto a sensor array (G), and into a vacuum apparatus (F). The vacuum apparatus (F) may be coupled to the conduit (D) downstream from the sensor array (G). A vacuum apparatus is herein defined to be any system capable of creating or maintaining a volume at a pressure below atmospheric. Examples of vacuum apparatus include vacuum chambers. Vacuum chamber, in one embodiment, may be sealed tubes from which a portion of the air has been evacuated, creating a vacuum within the tube. A commonly used example of such a sealed tube is a "vacutainer" system commercially available from Becton Dickinson. Alternatively, a vacuum chamber which is sealed by a movable piston may also be used to generate a vacuum. For example, a syringe may be coupled to the conduit. Movement of the piston (i.e., the plunger) away from the chamber will create a partial vacuum within the chamber. Alternatively, the vacuum apparatus may be a vacuum pump or vacuum line. Vacuum pumps may include direct drive pumps, oil pumps, aspirator pumps or micropumps.

Figure 39:
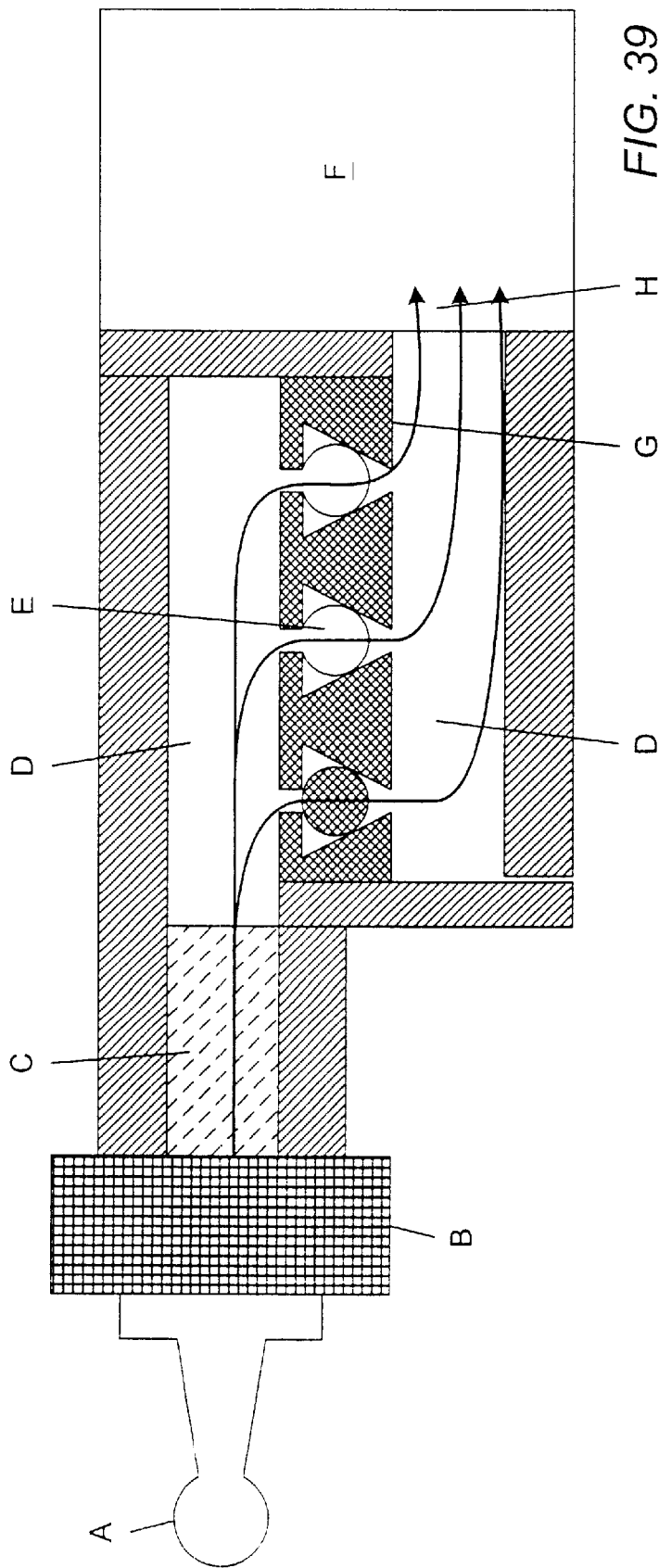
FIG. 39 depicts a cross-sectional view of a sensor array which includes a vacuum chamber, a filter, and a reagent reservoir.
Figure 41A:
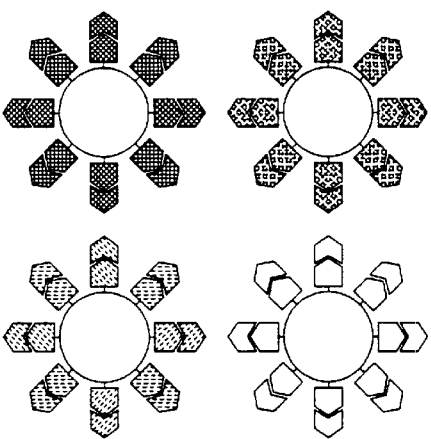
FIG. 41 depicts general scheme for the detection of antibodies which uses a sensor array composed of four individual beads.
Figure 41B:
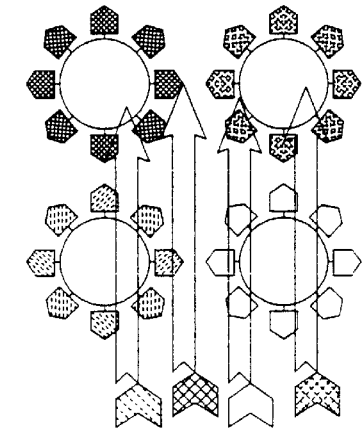
Figure 41C:
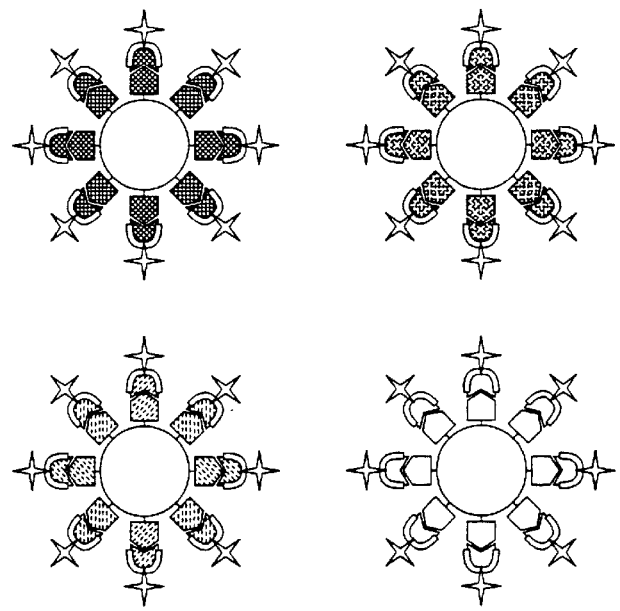
Figure 41D:
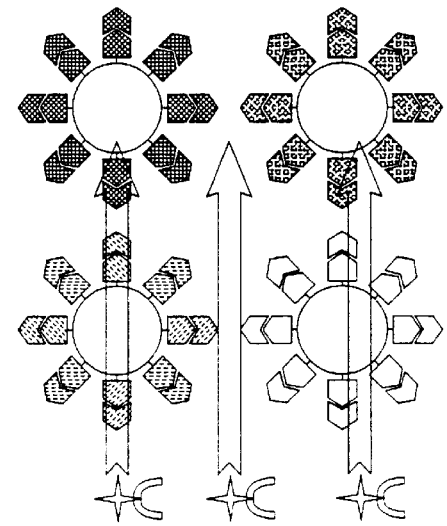

As opposed to previously described methods, in which a pump as used to force a fluid stream through a sensor array, the use of a vacuum apparatus allows the fluid to be pulled through the sensor array. Referring to FIG. 39, the vacuum apparatus (F) is coupled to downstream from a sensor array (G). When coupled to the conduit (D), the vacuum apparatus may exert a suction force on the fluid stream (E), forcing a portion of the stream to pass over, and in some instances, through the sensor array. In some embodiments, the fluid may continue to pass through the conduit, after passing the sensor array, and into the vacuum apparatus. In an embodiment where the vacuum apparatus is a pre-evacuated tube, the fluid flow will continue until the air within the tube is at a pressure substantially equivalent to the atmospheric pressure. The vacuum apparatus may include a penetrable wall (H). The penetrable wall forms a seal inhibiting air from entering the vacuum apparatus. When the wall is broken or punctured, air from outside of the system will begin to enter the vacuum apparatus. In one embodiment, the conduit includes a penetrating member, (e.g., a syringe needle), which allows the penetrable wall to be pierced. Piercing the penetrable wall causes air and fluid inside the conduit to be pulled through the conduit into the vacuum apparatus until the pressure between the vacuum apparatus and the conduit is equalized.

The sensor array system may also include a filter (B) coupled to the conduit (D) as depicted in FIG. 39. The filter (B) may be positioned along the conduit, upstream from the sensor array. Filter (B) may be a porous filter which includes a membrane for removing components from the fluid stream. In one embodiment, the filter may include a membrane for removal of particulates above a minimum size. The size of the particulates removed will depend on the porosity of the membrane as is known in the art. Alternatively, the filter may be configured to remove unwanted components of a fluid stream. For example, if the fluid stream is a blood sample, the filter may be configured to remove red and white blood cells from the stream, while leaving in the blood stream blood plasma and other components therein.

The sensor array may also include a reagent delivery reservoir (C). The reagent delivery system is preferably coupled to the conduit upstream from the sensor array. The reagent delivery reservoir may be formed from a porous material which includes a reagent of interest. As the fluid passes through this reservoir, a portion of the reagent within the regent delivery reservoir passes into the fluid stream. The fluid reservoir may include a porous polymer or filter paper on which the reagent is stored. Examples of reagents which may be stored within the reagent delivery reservoir include, but are not limited to, visualization agents (e.g., dye or fluorophores), co-factors, buffers, acids, bases, oxidants, and reductants.

The sensor array may also include a fluid sampling device (A) coupled to the conduit (D). The fluid sampling device is configured to transfer a fluid sample from outside the sensor array to the conduit. A number of fluid sampling devices may be used including, but not limited to a syringe needle, a tubing connector, a capillary tube, a micropuncture device, or a syringe adapter.

The sensor array may also include a micropump or a microvalve system, coupled to the conduit to further aid in the transfer of fluid through the conduit. Micropumps and valves have been previously described. In one embodiment, a micro-valve or micropump may be used to keep a fluid sample or a reagent solution separated from the sensor array. Typically, these microvalves and micropumps include a thin flexible diaphragm. The diaphragm may be moved to an open position, in one embodiment, by applying a vacuum to the outside of the diaphragm. In this way, a vacuum apparatus coupled to the sensor array may be used to open a remote microvalve or pump.

In another embodiment, a microvalve may be used to control the application of a vacuum to the system. For example, a microvalve may be positioned adjacent to the vacuum apparatus. The activation of the microvalve may allow the vacuum apparatus to communicate with the conduit or sensor array. The microvalve may be remotely activated at controlled times and for controlled intervals.

In one embodiment, a sensor array system, such as depicted in FIG. 39, may be used for analysis of blood samples. A micropuncture device (A) is used to extract a small amount of blood from the patient, e.g., through a finger prick. The blood may be drawn through a porous filter that serves to remove the undesirable particulate matter. For the analysis of antibodies or antigens in whole blood, the filtering agent may be chosen to remove both the white and red blood cells, while leaving in the fluid stream blood plasma and all of the components therein. Methods of filtering blood cells from whole blood are taught, for example, in U.S. Pat. Nos. 5,914,042; 5,876,605, and 5,211,850 which are incorporated by reference. The filtered blood may also be passed through a reagent delivery reservoir that may consist of a porous layer that is impregnated with the reagent(s) of interest. In many cases, a visualization agent will be included in this layer so that the presence of the analytes of interest in the chip can be resolved. The treated fluid may be passed above the electronic tongue chip through a capillary layer, down through the various sensing particles and through the chip onto the bottom capillary layer. After exiting the central region, the excess fluid flows into the vacuum apparatus. This excess fluid may serve as a source of sample for future measurements should more detailed analyses be warranted. A "hard copy" of the sample is thus created to back up the electronic data recorded for the specimen.

Other examples of testing procedures for bodily fluids are described in the following U.S. Pat. Nos. 4,596,657, 4,189,382, 4,115,277, 3,954,623, 4,753,776, 4,623,461, 4,069,017, 5,053,197, 5,503,985, 3,696,932, 3,701,433, 4,036,946, 5,858,804, 4,050,898, 4,477,575, 4,810,378, 5,147,606, 4,246,107, and 4,997,577 all of which are incorporated by reference.

This generally described sampling method may also be used for either antibody or antigen testing of bodily fluids. A general scheme for the testing of antibodies is depicted in FIG. 40. FIG. 40A depicts a polymer bead having a protein coating that can be recognized in a specific manner by a complimentary antibody. Three antibodies (within the dashed rectangle) are shown to be present in a fluid phase that bathes the polymer bead. Turning to FIG. 40B, the complimentary antibody binds to the bead while the other two antibodies remain in the fluid phase. A large increase in the complimentary antibody concentration is noted at this bead. In FIG. 40C a visualization agent such as protein A (within the dashed rectangle) is added to the fluid phase. The visualization agent is chosen because it possesses either a strong absorbance property or it exhibits fluorescence characteristics that can be used to identify the species of interest via optical measurements. Protein A is an example of a reagent that associates with the common region of most antibodies. Chemical derivatization of the visualization agent with dyes, quantum particles or fluorophores is used to evoke the desired optical characteristics. After binding to the bead-localized antibodies, as depicted in FIG. 40D, the visualization agent reveals the presence of the complimentary antibodies at the specific polymer bead sites.

FIG. 41 depicts another general scheme for the detection of antibodies which uses a sensor array composed of four individual beads. Each of the four beads is coated with a different antigen (i.e. a protein coating). As depicted in FIG. 41A, the beads are washed with a fluid sample which includes four antibodies. Each of the four antibodies binds to its complimentary antigen coating, as depicted in FIG. 41B. A visualization agent may be introduced into the chamber, as depicted in FIG. 41C. The visualization agent, in one embodiment, may bind to the antibodies, as depicted in FIG. 41D. The presence of the labeled antibodies is assayed by optical means (absorbance, reflectance, fluorescence). Because the location of the antigen coatings is known ahead of time, the chemical/biochemical composition of the fluid phase can be determined from the pattern of optical signals recorded at each site.

In an alternative methodology, not depicted, the antibodies in the sample may be exposed to the visualization agent prior to their introduction into the chip array. This may render the visualization step depicted in 41C unnecessary.

Figure 42:
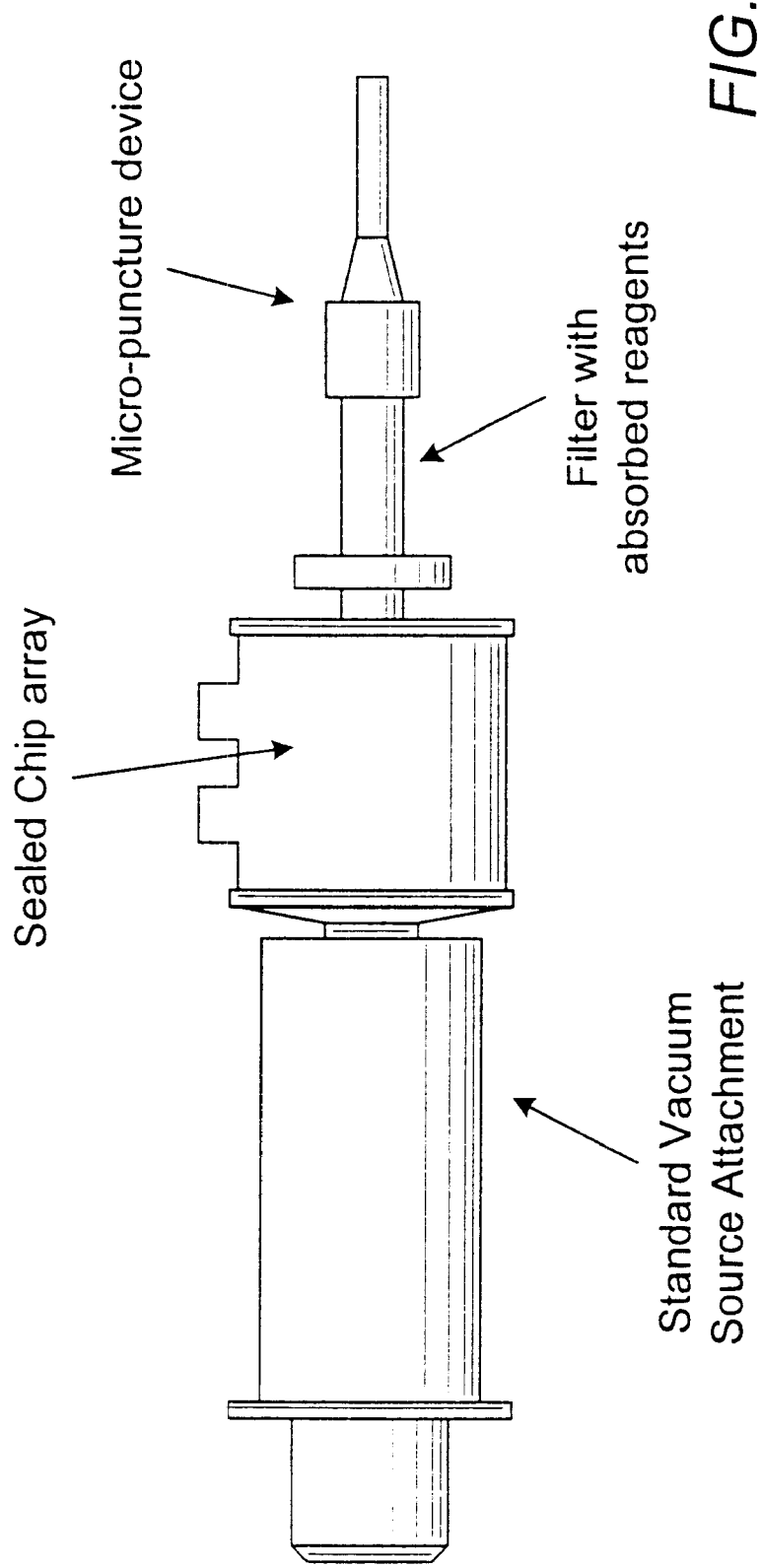
FIG. 42 depicts a sensor array which includes a vacuum chamber, a sensor array chamber, and a sampling device.

FIG. 42 depicts a system for detecting an analyte in a fluid stream. The system includes a vacuum apparatus, a chamber in which a sensor array may be disposed, and an inlet system for introducing the sample into the chamber. In this embodiment, the inlet system is depicted as a micropuncture device. The chamber holding the sensor array may be a Sikes-Moore chamber, as previously described. The vacuum apparatus is a standard "vacutainer" type vacuum tube. The micro puncture device includes a Luer-lock attachment which can receive a syringe needle. Between the micro-puncture device and the chamber a syringe filter may be placed to filter the sample as the sample enters the chamber. Alternatively, a reagent may be placed within the filter. The reagent may be carried into the chamber via the fluid as the fluid passes through the filter.

Figure 43:
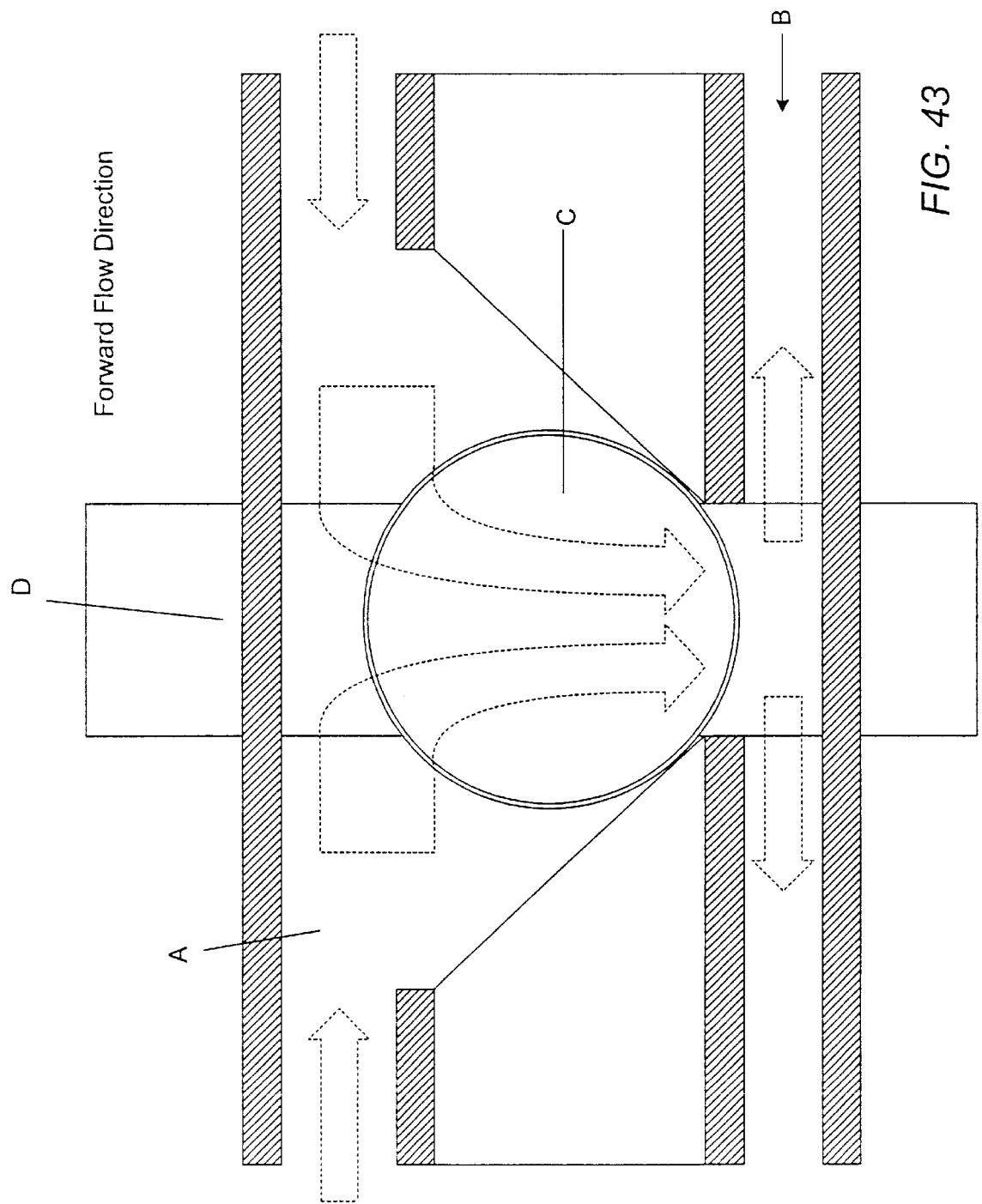
FIG. 43 depicts a flow path of a fluid stream through a sensor array from the top toward the bottom of the sensor array.

As has been previously described, a sensor array may be configured to allow the fluid sample to pass through the sensor array during use. The fluid delivery to the sensor array may be accomplished by having the fluid enter the top of the chip through the shown capillary (A), as depicted in FIG. 43. The fluid flow traverses the chip and exits from the bottom capillary (B). Between the top and bottom capillaries, the fluid is passed by the bead (C). Here the fluid containing analytes have an opportunity to encounter the receptor sites. The presence of such analytes may be identified using optical means. The light pathway is shown here (D). In the forward flow direction, the beads are typically forced towards the bottom of the pit. Under these circumstances, the bead placement is ideal for optical measurements.

Figure 44:
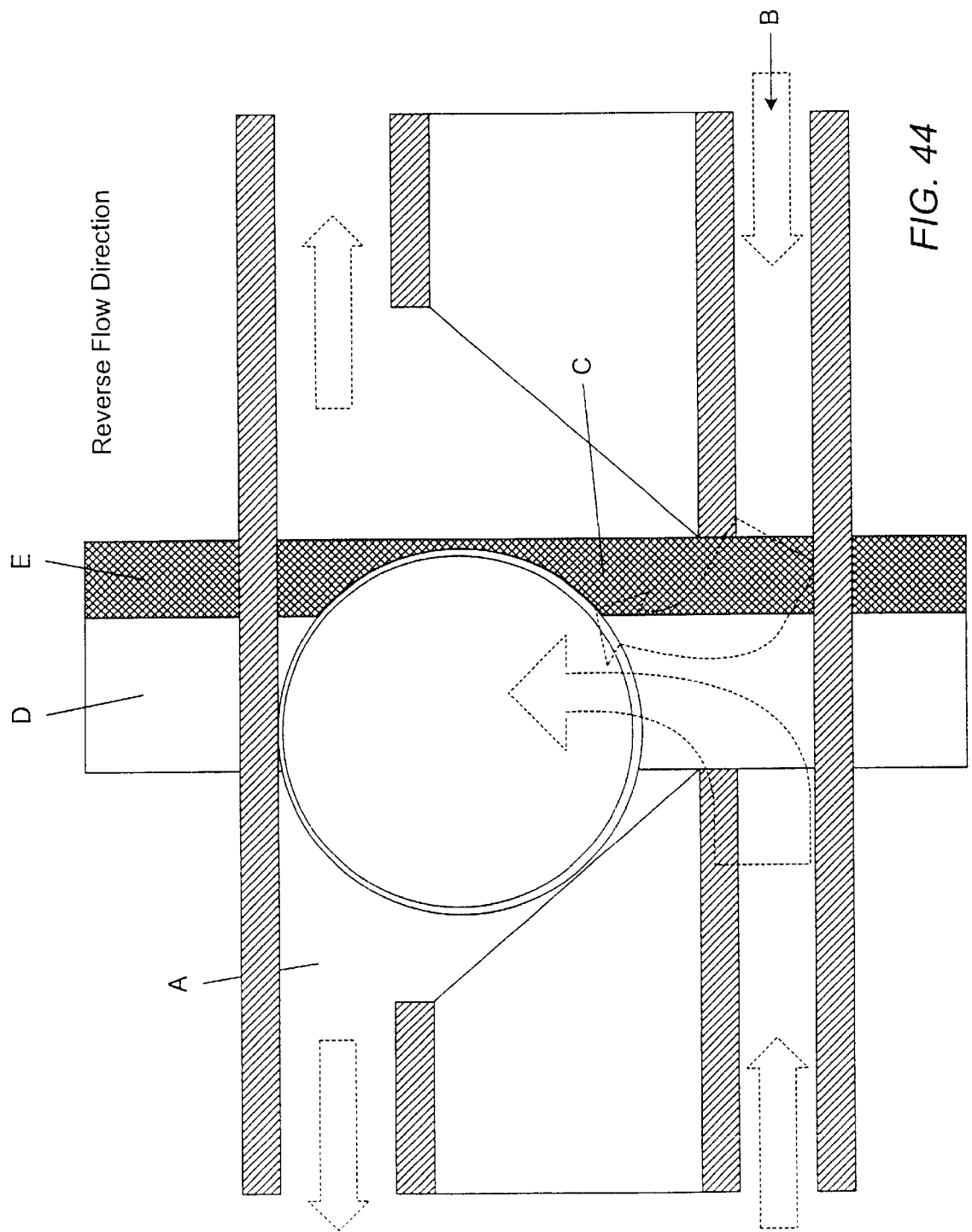
FIG. 44 depicts a flow path of a fluid stream through a sensor array from the bottom toward the top of the sensor array.

In another embodiment, the fluid flow may go from the bottom of the sensor array toward the top of the sensor array, as depicted in FIG. 44. The fluid exits from the top of the chip through the shown capillary (A). The fluid flow traverses the chip and enters from the bottom capillary (B). Between the top and bottom capillaries, the fluid can avoid the bead somewhat by taking an indirect pathway (C). The presence of analytes is identified using optical means as before. The light pathway is shown as (D). Unfortunately, only a portion of the light passes through the bead. In the reverse flow direction, the beads can be dislodged away from the analysis beam by the upward pressure of the fluid, as shown in FIG. 44. Under these circumstances, some of the light may traverse the chip and enter the detector (not shown) without passing through the sensor bead (Path E).

In any microfluidic chemical sensing system there may be a need to "store" the chemically sensitive elements in an "inert" environment. Typically, the particles may be at least partially surrounded by an inert fluid such as an inert, non reactive gas, a non-reactive solvent, or a liquid buffer solution. Alternatively, the particles may be maintained under a vacuum. Before exposure of the particles to the analyte, the inert environment may need to be removed to allow proper testing of the sample. In one embodiment, a system may include a fluid transfer system for the removal of an inert fluid prior to the introduction of the sample with minimum dead volume.

In one embodiment, a pumping system may be used to pull the inert fluid through from one side (by any pumping action, such as that provided by a vacuum downstream from the array). The inert fluid may be efficiently removed while the beads remain within the sensor array. Additionally, the analyte sample may be drawn toward the sensor array as the inert fluid is removed from the sensor array. A pocket of air may separate the analyte. sample from the inert fluid as the sample move through the conduit. Alternatively, the sample may be pumped from "upstream" using a micropump. Note that a vacuum downstream can produce a maximum of one atmosphere of head pressure, while an upstream pump could in principle produce an arbitrarily high head pressure. This can effect the fluid transport rates through the system, but for small volume microfluidic systems, even with low flow coefficients, one atmosphere of head pressure should provide acceptable transfer rates for many applications.

In another embodiment, the vacuum apparatus may be formed directly into a micromachined array. The vacuum apparatus may be configured to transmit fluid to and from a single cavity or a plurality of cavities. In one embodiment, a separate vacuum apparatus may be coupled to each of the cavities.

3. Chemical Improvements

The development of smart sensors capable of discrimination of different analytes, toxins, and bacteria has become increasingly important for environmental, health and safety, remote sensing, military, and chemical processing applications. Although many sensors capable of high sensitivity and high selectivity detection have been fashioned for single analyte detection, only in a few selected cases have array sensors been prepared which display multi-analyte detection capabilities. The obvious advantages of such array systems are their utility for the analysis of multiple analytes and their ability to be "trained" to respond to new stimuli. Such on site adaptive analysis capabilities afforded by the array structures makes their utilization promising for a variety of future applications.

Single and multiple analyte sensors both typically rely on changes in optical signals. These sensors typically make use of an indicator that undergoes a perturbation upon analyte binding. The indicator may be a chromophore or a fluorophore. A fluorophore is a molecule that absorbs light at a characteristic wavelength and then re-emits the light most typically at a characteristically different wavelength. Fluorophores include, but are not limited to rhodamine and rhodamine derivatives, fluorescein and fluorescein derivatives, coumarins and chelators with the lanthanide ion series. The emission spectra, absorption spectra and chemical composition of many fluorophores may be found, e.g., in the "Handbook of Fluorescent Probes and Research Chemicals", R. P. Haugland, ed. which is incorporated herein by reference. A chromophore is a molecule which absorbs light at a characteristic wavelength, but does not re-emit light.

As previously described, the receptor itself may incorporate the indicator. The binding of the analyte to the receptor may directly lead to a modulation of the properties of the indicator. Such an approach typically requires a covalent attachment or strong non-covalent binding of the indicator onto or as part of the receptor, leading to additional covalent architecture. Each and every receptor may need a designed signaling protocol that is typically unique to that receptor. General protocols for designing in a signal modulation that is versatile and general for most any receptor would be desirable.

In one embodiment, a general method for the creation of optical signal modulations for most any receptor that is coupled to an immobilized matrix has been developed. Immobilized matrices include, but are not limited to, resins, beads, and polymer surfaces. By immobilization of the receptor to the matrix, the receptor is held within a structure that can be chemically modified, allowing one to tune and to create an environment around the receptor that is sensitive to analyte binding. Coupling of the indicator to an immobilization matrix may make it sensitive to microenvironment changes which foster signal modulation of the indicator upon analyte binding. Further, by coupling the indicator to an immobilization matrix, the matrix itself becomes the signaling unit, not requiring a specific new signaling protocol for each and every receptor immobilized on the matrix.

In an embodiment, a receptor for a particular analyte or class of analytes may be designed and created with the chemical handles appropriate for immobilization on and/or in the matrix. A number of such receptors have been described above. The receptors can be, but are not limited to, antibodies, aptamers, organic receptors, combinatorial libraries, enzymes, and imprinted polymers.

Signaling indicator molecules may be created or purchased which have appropriate chemical handles for immobilization on and/or in the immobilization matrix. The indicators may possess chromophores or fluorophores that are sensitive to their microenvironment. This chromophore or fluorophore may be sensitive to microenvironment changes that include, but are not limited to, a sensitivity to local pH, solvatophobic or solvatophilic properties, ionic strength, dielectric, ion pairing, and/or hydrogen bonding. Common indicators, dyes, quantum particles, and semiconductor particles, are all examples of possible probe molecules. The probe molecules may have epitopes similar to the analyte, so that a strong or weak association of the probe molecules with the receptor may occur. Alternatively, the probe molecules may be sensitive to a change in their microenvironment that results from one of the affects listed in item above.

Binding of the analyte may do one of the following things, resulting in a signal modulation: 1) displace a probe molecule from the binding site of the receptor, 2) alter the local pH, 3) change the local dielectric properties, 4) alter the features of the solvent, 5) change the fluorescence quantum yield of individual dyes, 6) alter the rate/efficiency of fluorescence resonance energy transfer (FRET) between donor-acceptor fluorophore pairs, or 7) change the hydrogen bonding or ion pairing near the probe.

In an alternative embodiment, two or more indicators may be attached to the matrix. Binding between the receptor and analyte causes a change in the communication between the indicators, again via either displacement of one or more indicators, or changes in the microenvironment around one or more indicators. The communication between the indicators may be, but is not limited to, fluorescence resonance energy transfer, quenching phenomenon, and/or direct binding.

In an embodiment, a particle for detecting an analyte may be composed of a polymeric resin. A receptor and an indicator may be coupled to the polymeric resin. The indicator and the receptor may be positioned on the polymeric resin such that the indicator produces a signal in when the analyte interacts with the receptor. The signal may be a change in absorbance (for chromophoric indicators) or a change in fluorescence (for fluorophoric indicators).

A variety of receptors may be used, in one embodiment, the receptor may be a polynucleotide, a peptide, an oligosaccharide, an enzyme, a peptide mimetic, or a synthetic receptor.

In one embodiment, the receptor may be a polynucleotide coupled to a polymeric resin. For the detection of analytes, the polynucleotide may be a double stranded deoxyribonucleic acid, single stranded deoxyribonucleic acid, or a ribonucleic acid. Methods for synthesizing and/or attaching a polynucleotide to a polymeric resin are described, for example, in U.S. Pat. No. 5,843,655 which is incorporated herein by reference. "Polynucleotides" are herein defined as chains of nucleotides. The nucleotides are linked to each other by phosphodiester bonds. "Deoxyribonucleic acid" is composed of deoxyribonucleotide residues, while "Ribonucleic acid" is composed of ribonucleotide residues.

In another embodiment, the receptor may be a peptide coupled to a polymeric resin. "Peptides" are herein defined as chains of amino acids whose α-carbons are linked through peptide bonds formed by a condensation reaction between the a carboxyl group of one amino acid and the amino group of another amino acid. Peptides is intended to include proteins. Methods for synthesizing and/or attaching a protein or peptides to a polymeric resin are described, for example, in U.S. Pat. Nos. 5,235,028 and 5,182,366 which is incorporated herein by reference.

Alternatively, peptide mimetics may be used as the receptor. Peptides and proteins are sequences of amide linked amino acid building blocks. A variety of peptide mimetics may be formed by replacing or modifying the amide bond. In one embodiment, the amide bond may be replaced by alkene bonds. In another embodiment, the amide may be replaced by a sulphonamide bond. In another embodiment the amino acid sidechain may be placed on the nitrogen atom, such compounds are commonly known as peptoids. Peptides may also be formed from non-natural D-stereoisomers of amino acids. Methods for synthesizing and/or attaching a peptide mimetic to a polymeric resin is described, for example, in U.S. Pat. No. 5,965,695 which is incorporated herein by reference.

In another embodiment, the receptor may include an oligosaccharide coupled to a polymeric resin. An "oligosaccharide" is an oligomer composed of two or more monosaccharides, typically joined together via ether linkages. Methods for synthesizing and/or attaching oligosaccharides to a polymeric resin are described, for example, in U.S. Pat. Nos. 5,278,303 and 5,616,698 which are incorporated herein by reference.

In another embodiment, polynucleotides, peptides and/or oligosaccharides may be coupled to base unit to form a receptor. In one embodiment, the base unit may have the general structure:

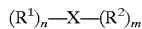

wherein X comprises carbocyclic systems or $C_1$–$C_{10}$ alkanes, n is an integer of at least 1, m is an integer of at least 1; and wherein each of $R^1$ independently represents —$(CH_2)_y$— $NR^3$—$C(NR^4)$—$NR^5$, —$(CH_2)_y$—$NR^6R^7$, —$(CH_2)_y$— $NH$—$Y$, —$(CH_2)_y$—$O$—$Z$;

where y is an integer of at least 1;

where $R^3$, $R^4$, and $R^5$ independently represent hydrogen, alkyl, aryl, alkyl carbonyl of 1 to 10 carbon atoms, or alkoxy carbonyl of 1 to 10 carbon atoms, or $R^4$ and $R^5$ together represent a cycloalkyl group;

where $R^6$ represents hydrogen, alkyl, aryl, alkyl carbonyl of 1 to 10 carbon atoms, or alkoxy carbonyl of 1 to 10 carbon atoms;

where $R^7$ represents alkyl, aryl, alkyl carbonyl of 1 to 10 carbon atoms, or alkoxy carbonyl of 1 to 10 carbon atoms;

where $R^6$ and $R^7$ together represent a cycloalkyl group;

where Y is a peptide, or hydrogen and where Z is a polynucleotide, an oligosaccharide or hydrogen; and wherein each of $R^2$ independently represents hydrogen, alkyl, alkenyl, alkynyl, phenyl, phenylalkyl, arylalkyl, aryl, or together with another $R^2$ group represent a carbocyclic ring. The use of a base unit such as described above may aid in the placement and orientation of the side groups to create a more effective receptor.

The receptor and indicators may be coupled to the polymeric resin by a linker group. A variety of linker groups may be used. The term "linker", as used herein, refers to a molecule that may be used to link a receptor to an indicator; a receptor to a polymeric resin or another linker, or an indicator to a polymeric resin or another linker. A linker is a hetero or homobifunctional molecule that includes two reactive sites capable of forming a covalent linkage with a receptor, indicator, other linker or polymeric resin. Suitable linkers are well known to those of skill in the art and include, but are not limited to, straight or branched-chain carbon linkers, heterocyclic carbon linkers, or peptide linkers. Particularly preferred linkers are capable of forming covalent bonds to amino groups, carboxyl groups, or sulfhydryl groups or hydroxyl groups. Amino-binding linkers include reactive groups such as carboxyl groups, isocyanates, isothiocyanates, esters, haloalkyls, and the like. Carboxyl-binding linkers are capable of forming include reactive groups such as various amines, hydroxyls and the like. Sulfhydryl-binding linkers include reactive groups such as sulfhydryl groups, acrylates, isothiocyanates, isocyanates and the like. Hydroxyl binding groups include reactive groups such as carboxyl groups, isocyanates, isothiocyanates, esters, haloalkyls, and the like. The use of some such linkers is described in U.S. Pat. No. 6,037,137 which is incorporated herein by reference.

A number of combinations for the. coupling of an indicator and a receptor to a polymeric resin have been devised. These combinations are schematically depicted in FIG. 55. In one embodiment, depicted in FIG. 55A, a receptor (R) may be coupled to a polymeric resin. The receptor may be directly formed on the polymeric resin, or be coupled to the polymeric resin via a linker. An indicator (I) may also be coupled to the polymeric resin. The indicator may be directly coupled to the polymeric resin or coupled to the polymeric resin by a linker. In some embodiments, the linker coupling the indicator to the polymeric resin is of sufficient length to allow the indicator to interact with the receptor in the absence of an analyte.

Figure 55A:
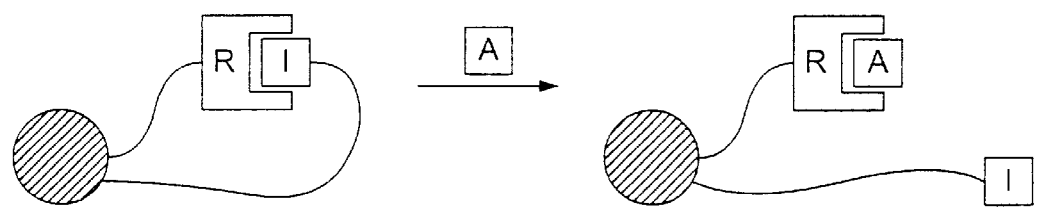
FIGS. 55A–I depict various sensing protocols for receptor-indicator-polymeric resin particles.
Figure 55B:
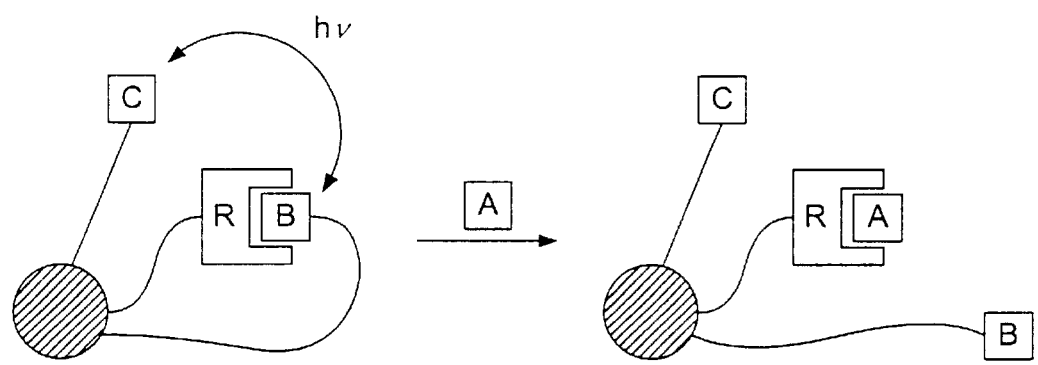

In another embodiment, depicted in FIG. 55B, a receptor (R) may be coupled to a polymeric resin. The receptor may be directly formed on the polymeric resin, or be coupled to the polymeric resin via a linker. An indicator (B) may also be coupled to the polymeric resin. The indicator may be directly coupled to the polymeric resin or coupled to the polymeric resin by a linker. In some embodiments, the linker coupling the indicator to the polymeric resin is of sufficient length to allow the indicator to interact with the receptor in the absence of an analyte (A). An additional indicator (C) may also be coupled to the polymeric resin. The additional indicator may be directly coupled to the polymeric resin or coupled to the polymeric resin by a linker. In some embodiments, the additional indicator is coupled to the polymeric resin, such that the additional indicator is proximate the receptor during use.

Figure 55C:
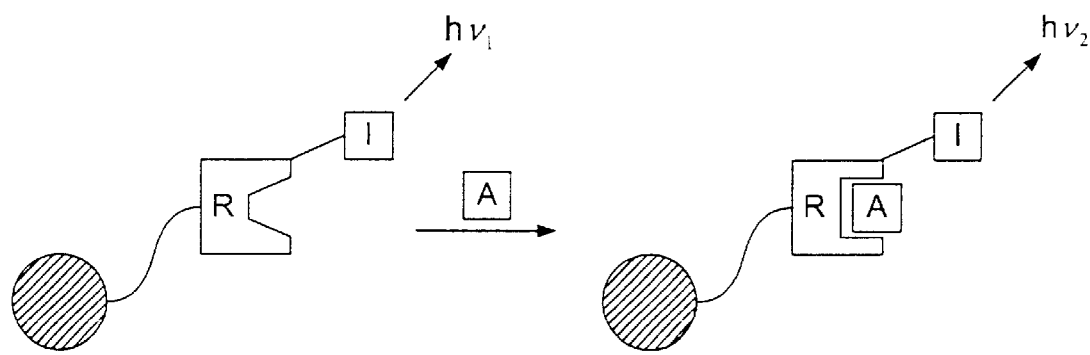

In another embodiment, depicted in FIG. 55C, a receptor (R) may be coupled to a polymeric resin. The receptor may be directly formed on the polymeric resin, or be coupled to the polymeric resin via a linker. An indicator (I) may be coupled to the receptor. The indicator may be directly coupled to the receptor or coupled to the receptor by a linker. In some embodiments, the linker coupling the indicator to the polymeric resin is of sufficient length to allow the indicator to interact with the receptor in the absence of an analyte (A), as depicted in FIG. 55E.

Figure 55D:
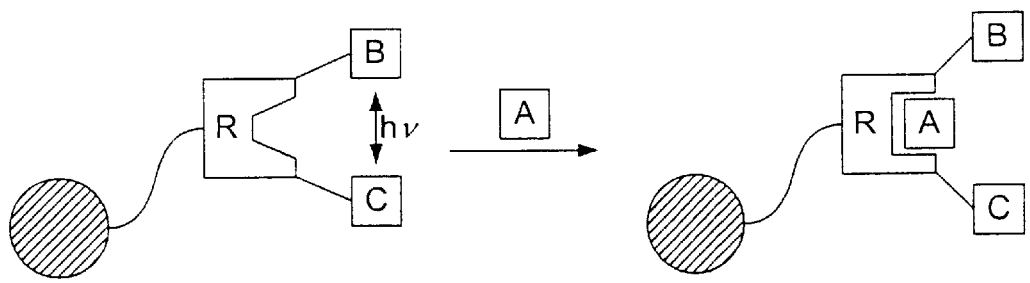
Figure 55E:
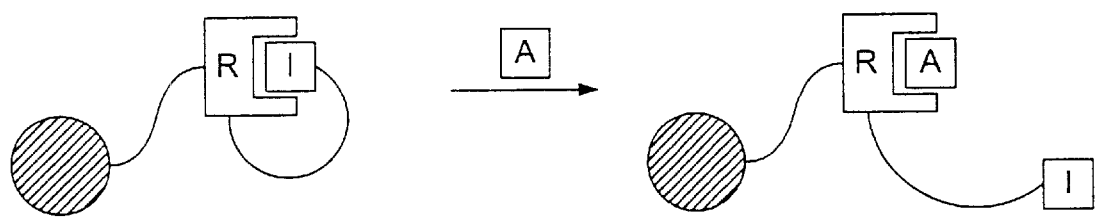
Figure 55F:
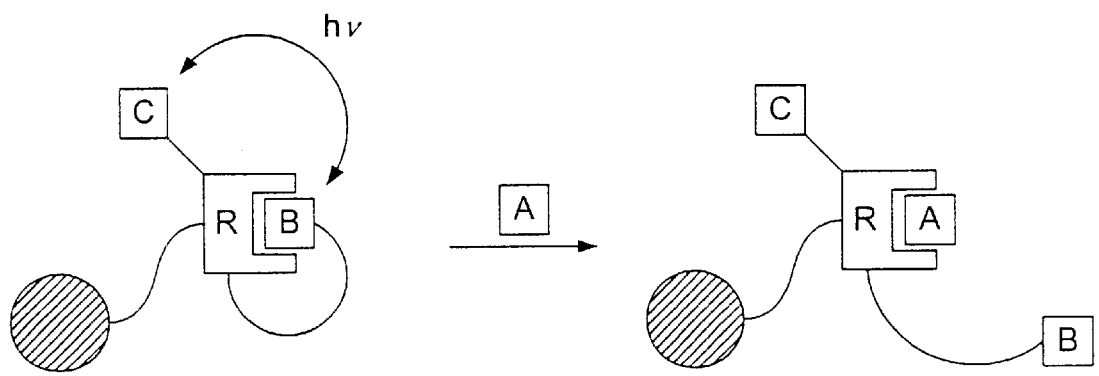

In another embodiment, depicted in FIG. 55D, a receptor (R) may be coupled to a polymeric resin. The receptor may be directly formed on the polymeric resin, or be coupled to the polymeric resin via a linker. An indicator (B) may be coupled to the receptor. The indicator may be directly coupled to the receptor or coupled to the receptor by a linker. An additional indicator (C) may also be coupled to the receptor. The additional indicator may be directly coupled to the receptor or coupled to the receptor by a linker. In some embodiments, the linker coupling the indicator (B) to the polymeric resin is of sufficient length to allow the indicator to interact with the receptor in the absence of an analyte (A), as depicted in FIG. 55F.

Figure 55G:
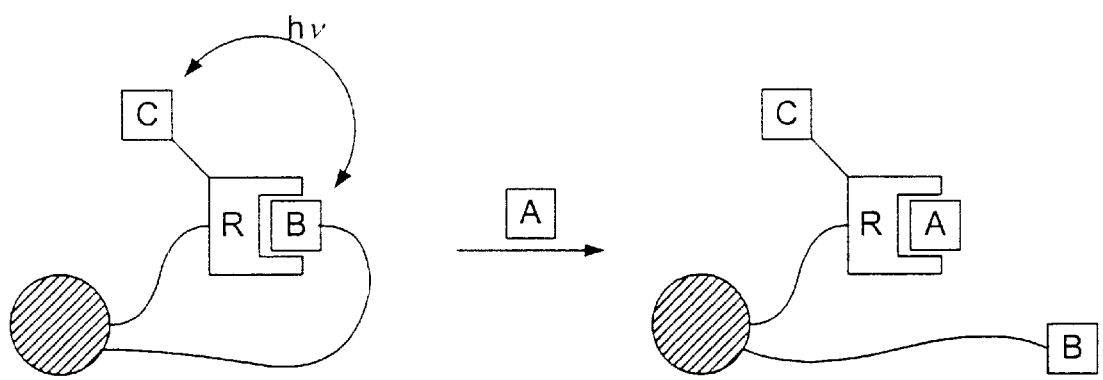

In another embodiment, depicted in FIG. 55G, a receptor (R) may be coupled to a polymeric resin. The receptor may be directly formed on the polymeric resin, or be coupled to the polymeric resin via a linker. An indicator (B) may be coupled to the polymeric resin. The indicator may be directly coupled to the polymeric resin or coupled to the polymeric resin by a linker. In some embodiments, the linker coupling the indicator to the polymeric resin is of sufficient length to allow the indicator to interact with the receptor in the absence of an analyte (A). An additional indicator (C) may also be coupled to the receptor. The additional indicator may be directly coupled to the receptor or coupled to the receptor by a linker.

Figure 55H:
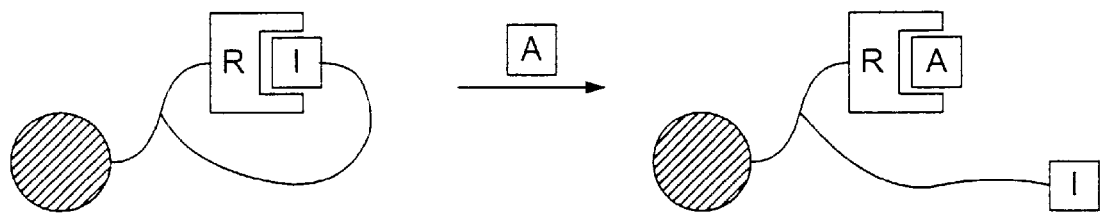

In another embodiment, depicted in FIG. 55H, a receptor (R) may be coupled to a polymeric resin by a first linker. An indicator (I) may be coupled to the first linker. The indicator may be directly coupled to the first linker or coupled to the first linker by a second linker. In some embodiments, the second linker coupling the indicator to the polymeric resin is of sufficient length to allow the indicator to interact with the receptor in the absence of an analyte (A).

Figure 55I:
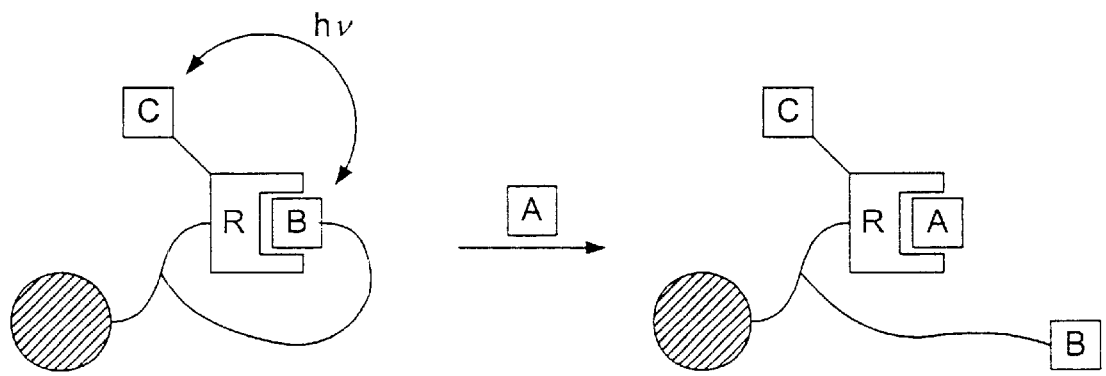

In another embodiment, depicted in FIG. 55I, a receptor (R) may be coupled to a polymeric resin by a first linker. An indicator (B) may be coupled to the first linker. The indicator may be directly coupled to the first linker or coupled to the first linker by a second linker. In some embodiments, the second linker coupling the indicator to the first linker is of sufficient length to allow the indicator to interact with the receptor in the absence of an analyte (A). An additional indicator (C) may be coupled to the receptor. The additional indicator may be directly coupled to the receptor or coupled to the receptor by a linker.

These various combinations of receptors, indicators, linkers and polymeric resins may be used in a variety of different signalling protocols. Analyte-receptor interactions may be transduced into signals through one of several mechanisms. In one approach, the receptor site may be preloaded with an indicator, which can be displaced in a competition with analyte ligand. In this case, the resultant signal is observed as a decrease in a signal produced by the indicator. This indicator may be a fluorophore or a chromophore. In the case of a fluorophore indicator, the presence of an analyte may be determined by a decrease in the fluorescence of the particle. In the case of a chromophore indicator, the presence of an analyte may be determined by a decrease in the absorbance of the particle.

A second approach that has the potential to provide better sensitivity and response kinetics is the use of an indicator as a monomer in the combinatorial sequences (such as either structure shown in FIG. 14), and to select for receptors in which the indicator functions in the binding of ligand. Hydrogen bonding or ionic substituents on the indicator involved in analyte binding may have the capacity to change the electron density and/or rigidity of the indicator, thereby changing observable spectroscopic properties such as fluorescence quantum yield, maximum excitation wavelength, maximum emission wavelength, and/or absorbance. This approach may not require the dissociation of a preloaded fluorescent ligand (limited in response time by $k_{off}$), and may modulate the signal from essentially zero without analyte to large levels in the presence of analyte.

In one embodiment, the microenvironment at the surface and interior of the resin beads may be conveniently monitored using spectroscopy when simple pH sensitive dyes or solvachromic dyes are imbedded in the beads. As a guest binds, the local pH and dielectric constants of the beads change, and the dyes respond in a predictable fashion. The binding of large analytes with high charge and hydrophobic surfaces, such as DNA, proteins, and steroids, should induce large changes in local microenvironment, thus leading to large and reproducible spectral changes. This means that most any receptor can be attached to a resin bead that already has a dye attached, and that the bead becomes a sensor for the particular analyte.

In one embodiment, a receptor that may be covalently coupled to an indicator. The binding of the analyte may perturb the local microenvironment around the receptor leading to a modulation of the absorbance or fluorescence properties of the sensor.

In one embodiment, receptors may be used immediately in a sensing mode simply by attaching the receptors to a bead that is already derivatized with a dye sensitive to its microenvironment. This is offers an advantage over other signalling methods because the signaling protocol becomes routine and does not have to be engineered; only the receptors need to be engineered. The ability to use several different dyes with the same receptor, and the ability to have more than one dye on each bead allows flexibility in the design of a sensing particle.

Changes in the local pH, local dielectric, or ionic strength, near a fluorophore may result in a signal. A high positive charge in a microenvironment leads to an increased pH since hydronium migrates away from the positive region. Conversely, local negative charge decreases the microenvironment pH. Both changes result in a difference in the protonation state of pH sensitive indicators present in that microenvironment. Many common chromophores and fluorophores are pH sensitive. The interior of the bead may be acting much like the interior of a cell, where the indicators should be sensitive to local pH.

The third optical transduction scheme involves fluorescence energy transfer. In this approach, two fluorescent monomers for signaling may be mixed into a combinatorial split synthesis. Examples of these monomers are depicted in FIG. 14. Compound 470 (a derivative of fluorescein) contains a common colorimetric/fluorescent probe that may be mixed into the oligomers as the reagent that will send out a modulated signal upon analyte binding. The modulation may be due to resonance energy transfer to monomer 475 (a derivative of rhodamine). When an analyte binds to the receptor, structural changes in the receptor will alter the distance between the monomers (schematically depicted in FIG. 8, 320 corresponds to monomer 470 and 330 corresponds to monomer 475). It is well known that excitation of fluorescein may result in emission from rhodamine when these molecules are oriented correctly. The efficiency of resonance energy transfer from fluorescein to rhodamine will depend strongly upon the presence of analyte binding; thus measurement of rhodamine fluorescence intensity (at a substantially longer wavelength than fluorescein fluorescence) will serve as a indicator of analyte binding. To greatly improve the likelihood of a modulatory fluorescein-rhodamine interaction, multiple rhodamine tags can be attached at different sites along a combinatorial chain without substantially increasing background rhodamine fluorescence (only rhodamine very close to fluorescein will yield appreciable signal). In one embodiment, depicted in FIG. 8, when no ligand is present, short wavelength excitation light (blue light) excites the fluorophore 320, which fluoresces (green light). After binding of analyte ligand to the receptor, a structural change in the receptor molecule brings fluorophore 320 and fluorophore 330 in proximity, allowing excited-state fluorophore 320 to transfer its energy to fluorophore 330. This process, fluorescence resonance energy transfer, is extremely sensitive to small changes in the distance between dye molecules (e.g., efficiency ~[distance]$^{-6}$).

In another embodiment, photoinduced electron transfer (PET) may be used to analyze the local microenvironment around the receptor. The methods generally includes a fluorescent dye and a fluorescence quencher. A fluorescence quencher is a molecule that absorbs the emitted radiation from a fluorescent molecule. The fluorescent dye, in its excited state, will typically absorbs light at a characteristic wavelength and then re-emit the light at a characteristically different wavelength. The emitted light, however, may be reduced by electron transfer with the fluorescent quncher, which results in quenching of the fluorescence. Therefore, if the presence of an analyte perturbs the quenching properties of the fluorescence quencher, a modulation of the fluorescent dye may be observed.

The above described signalling methods may be incorporated into a variety of receptor-indicator-polymeric resin systems. Turning to FIG. 55A, an indicator (I) and receptor (R) may be coupled to a polymeric resin. In the absence of an analyte, the indicator may produce a signal in accordance with the local microenvironment. The signal may be an absorbance at a specific wavelength or a fluorescence. When the receptor interacts with an analyte, the local microenvironment may be altered such that the produced signal is altered. In one embodiment, depicted in FIG. 55A, the indicator may partially bind to the receptor in the absence of an analyte. When the analyte is present the indicator may be displaced from the receptor by the analyte. The local microenvironment for the indicator therefore changes from an environment where the indicator is binding with the receptor, to an environment where the indicator is no longer bound to the receptor. Such a change in environment may induce a change in the absorbance or fluorescence of the indicator.

In another embodiment, depicted in Turning to FIG. 55C, an indicator (I) may be coupled to a receptor (R). The receptor may be coupled to a polymeric resin. In the absence of an analyte, the indicator may produce a signal in accordance with the local microenvironment. The signal may be an absorbance at a specific wavelength or a fluorescence. When the receptor interacts with an analyte, the local microenvironment may be altered such that the produced signal is altered. In contrast to the case depicted in FIG. 55A, the change in local microenvironment may be due to a conformation change of the receptor due to the biding of the analyte. Such a change in environment may induce a change in the absorbance or fluorescence of the indicator.

In another embodiment, depicted in FIG. 55E, an indicator (I) may be coupled to a receptor by a linker. The linker may have a sufficient length to allow the indicator to bind to the receptor in the absence of an analyte. The receptor (R) may be coupled to a polymeric resin. In the absence of an analyte, the indicator may produce a signal in accordance with the local microenvironment. As depicted in FIG. 55E, the indicator may partially bind to the receptor in the absence of an analyte. When the analyte is present the indicator may be displaced from the receptor by the analyte. The local microenvironment for the indicator therefore changes from an environment where the indicator is binding with the receptor, to an environment where the indicator is no longer bound to the receptor. Such a change in environment may induce a change in the absorbance or fluorescence of the indicator.

In another embodiment, depicted in FIG. 55H, a receptor (R) may be coupled to a polymeric resin by a first linker. An indicator may be coupled to the first linker. In the absence of an analyte, the indicator may produce a signal in accordance with the local microenvironment. The signal may be an absorbance at a specific wavelength or a fluorescence. When the receptor interacts with an analyte, the local microenvironment may be altered such that the produced signal is altered. In one embodiment, as depicted in FIG. 55H, the indicator may partially bind to the receptor in the absence of an analyte. When the analyte is present the indicator may be displaced from the receptor by the analyte. The local microenvironment for the indicator therefore changes from an environment where the indicator is binding with the receptor, to an environment where the indicator is no longer bound to the receptor. Such a change in environment may induce a change in the absorbance or fluorescence of the indicator.

In another embodiment, the use of fluorescence resonance energy transfer or photoinduced electron transfer may be used to detect the presence of an analyte. Both of these methodologies involve the use of two fluorescent molecules. Turning to FIG. 55B, a first fluorescent indicator (B) may be coupled to receptor (R). Receptor (R) may be coupled to a polymeric resin. A second fluorescent indicator (C) may also be coupled to the polymeric resin. In the absence of an analyte, the first and second fluorescent indicators may be positioned such that fluorescence energy transfer may occur. In one embodiment, excitation of the first fluorescent indicator may result in emission from the second fluorescent indicator when these molecules are oriented correctly. Alternatively, either the first or second fluorescent indicator may be a fluorescence quencher. When the two indicators are properly aligned, the excitation of the fluorescent indicators may result in very little emission due to quenching of the emitted light by the fluorescence quencher. In both cases, the receptor and indicators may be positioned such that fluorescent energy transfer may occur in the absence of an analyte. When the analyte is presence the orientation of the two indicators may be altered such that the fluorescence energy transfer between the two indicators is altered. In one embodiment, the presence of an analyte may cause the indicators to move further apart. This has an effect of reducing the fluorescent energy transfer. If the two indicators interact to produce an emission signal in the absence of an analyte, the presence of the analyte may cause a decrease in the emission signal. Alternatively, if one the indicators is a fluorescence quencher, the presence of an analyte may disrupt the quenching and the fluorescent emission from the other indicator may increase. It should be understood that these effects will reverse if the presence of an analyte causes the indicators to move closer to each other.

In another embodiment, depicted in FIG. 55D, a first fluorescent indicator (B) may be coupled to receptor (R). A second fluorescent indicator (C) may also be coupled to the receptor. Receptor (R) may be coupled to a polymeric resin. In the absence of an analyte, the first and second fluorescent indicators may be positioned such that fluorescence energy transfer may occur. In one embodiment, excitation of the first fluorescent indicator may result in emission from the second fluorescent indicator when these molecules are oriented correctly. Alternatively, either the first or second fluorescent indicator may be a fluorescence quencher. When the two indicators are properly aligned, the excitation of the fluorescent indicators may result in very little emission due to quenching of the emitted light by the fluorescence quencher. In both cases, the receptor and indicators may be positioned such that fluorescent energy transfer may occur in the absence of an analyte. When the analyte is presence the orientation of the two indicators may be altered such that the fluorescence energy transfer between the two indicators is altered. In one embodiment, depicted in FIG. 55D, the presence of an analyte may cause the indicators to move further apart. This has an effect of reducing the fluorescent energy transfer. If the two indicators interact to produce an emission signal in the absence of an analyte, the presence of the analyte may cause a decrease in the emission signal. Alternatively, if one the indicators is a fluorescence quencher, the presence of an analyte may disrupt the quenching and the fluorescent emission from the other indicator may increase. It should be understood that these effects will reverse if the presence of an analyte causes the indicators to move closer to each other.

In a similar embodiment to FIG. 55D, the first fluorescent indicator (B) and second fluorescent indicator (C) may be both coupled to receptor (R), as depicted in FIG. 55F. Receptor (R) may be coupled to a polymeric resin. First fluorescent indicator (B) may be coupled to receptor (R) by a linker group. The linker group may allow the first indicator to bind the receptor, as depicted in FIG. 55F. In the absence of an analyte, the first and second fluorescent indicators may be positioned such that fluorescence energy transfer may occur. When the analyte is presence, the first indicator may be displaced from the receptor, causing the fluorescence energy transfer between the two indicators to be altered.

In another embodiment, depicted in FIG. 55G, a first fluorescent indicator (B) may be coupled to a polymeric resin. Receptor (R) may also be coupled to a polymeric resin. A second fluorescent indicator (C) may be coupled to the receptor (R). In the absence of an analyte, the first and second fluorescent indicators may be positioned such that fluorescence energy transfer may occur. In one embodiment, excitation of the first fluorescent indicator may result in emission from the second fluorescent indicator when these molecules are oriented correctly. Alternatively, either the first or second fluorescent indicator may be a fluorescence quencher. When the two indicators are properly aligned, the excitation of the fluorescent indicators may result in very little emission due to quenching of the emitted light by the fluorescence quencher. In both cases, the receptor and indicators may be positioned such that fluorescent energy transfer may occur in the absence of an analyte. When the analyte is presence the orientation of the two indicators may be altered such that the fluorescence energy transfer between the two indicators is altered. In one embodiment, the presence of an analyte may cause the indicators to move further apart. This has an effect of reducing the fluorescent energy transfer. If the two indicators interact to produce an emission signal in the absence of an analyte, the presence of the analyte may cause a decrease in the emission signal. Alternatively, if one the indicators is a fluorescence quencher, the presence of an analyte may disrupt the quenching and the fluorescent emission from the other indicator may increase. It should be understood that these effects will reverse if the presence of an analyte causes the indicators to move closer to each other.

In another embodiment, depicted in FIG. 55I, a receptor (R) may be coupled to a polymeric resin by a first linker. A first fluorescent indicator (B) may be coupled to the first linker. A second fluorescent indicator (C) may be coupled to the receptor (R). In the absence of an analyte, the first and second fluorescent indicators may be positioned such that fluorescence energy transfer may occur. In one embodiment, excitation of the first fluorescent indicator may result in emission from the second fluorescent indicator when these molecules are oriented correctly. Alternatively, either the first or second fluorescent indicator may be a fluorescence quencher. When the two indicators are properly aligned, the excitation of the fluorescent indicators may result in very little emission due to quenching of the emitted light by the fluorescence quencher. In both cases, the receptor and indicators may be positioned such that fluorescent energy transfer may occur in the absence of an analyte. When the analyte is presence the orientation of the two indicators may be altered such that the fluorescence energy transfer between the two indicators is altered. In one embodiment, the presence of an analyte may cause the indicators to move further apart. This has an effect of reducing the fluorescent energy transfer. If the two indicators interact to produce an emission signal in the absence of an analyte, the presence of the analyte may cause a decrease in the emission signal. Alternatively, if one the indicators is a fluorescence quencher, the presence of an analyte may disrupt the quenching and the fluorescent emission from the other indicator may increase. It should be understood that these effects will reverse if the presence of an analyte causes the indicators to move closer to each other.

In one embodiment, polystyrene/polyethylene glycol resin beads may be used as a polymeric resin since they are highly water permeable, and give fast response times to penetration by analytes. The beads may be obtained in sizes ranging from 5 microns to 250 microns. Analysis with a confocal microscope reveals that these beads are segregated into polystyrene and polyethylene glycol microdomains, at about a 1 to 1 ratio. Using the volume of the beads and the reported loading of 300 pmol/bead, we can calculate an average distance of 35 Å between terminal sites. This distance is well within the Forester radii for the fluorescent dyes that we are proposing to use in our fluorescence resonance energy transfer ("FRET") based signaling approaches. This distance is also reasonable for communication between binding events and microenvironment changes around the fluorophores.

The derivatization of the beads with our receptors and with the indicators may be accomplished by coupling carboxylic acids and amines using EDC and HOBT. Typically, the efficiency of couplings are greater that 90% using quantitative ninhydrin tests. (See Niikura, K.; Metzger, A.; and Anslyn, E. V. "A Sensing Ensemble with Selectivity for Iositol Trisphosphate", *J. Am. Chem. Soc.* 1998, 120, 0000, which is incorporated herein by reference). The level of derivatization of the beads is sufficient to allow the loading of a high enough level of indicators and receptors to yield successful assays. However, an even higher level of loading may be advantageous since it would increase the multivalency effect for binding analytes within the interior of the beads. We may increase the loading level two fold and ensure that two amines are close in proximity by attaching an equivalent of lysine to the beads (see FIG. 45D). The amines may be kept in proximity so that binding of an analyte to the receptor will influence the environment of a proximal indicator.

Even though a completely random attachment of indicator and a receptor lead to an effective sensing particle, it may be better to rationally place the indicator and receptor in proximity. In one embodiment, lysine that has different protecting groups on the two different amines may be used, allowing the sequential attachment of an indicator and a receptor. If needed, additional rounds of derivatization of the beads with lysine may increase the loading by powers of two, similar to the synthesis of the first few generations of dendrimers.

In contrast, too high a loading of fluorophores will lead to self-quenching, and the emission signals may actually decrease with higher loadings. If self quenching occurs for fluorophores on the commercially available beads, we may incrementally cap the terminal amines thereby giving incrementally lower loading of the indicators.

Moreover, there should be an optimum ratio of receptors to indicators. The optimum ratio is defined as the ratio of indicator to receptor to give the highest response level. Too few indicators compared to receptors may lead to little change in spectroscopy since there will be many receptors that are not in proximity to indicators. Too many indicators relative to receptors may also lead to little change in spectroscopy since many of the indicators will not be near receptors, and hence a large number of the indicators will not experience a change in microenvironment. Through iterative testing, the optimum ratio may be determined for any receptor indicator system.

This iterative sequence will be discussed in detail for a particle designed to signal the presence of an analyte in a fluid. The sequence begins with the synthesis of several beads with different loadings of the receptor. The loading of any receptor may be quantitated using the ninhydrin test. (The ninhydrin test is described in detail in Kaiser, E.; Colescott, R. L.; Bossinger, C. D.; Cook, P. I. "Color Test for Detection of Free Terminal Amino Groups in the Solid-Phase Synthesis of Peptides", *Anal. Biochem.* 1970, 34, 595–598 which is incorporated herein by reference). The number of free amines on the bead is measured prior to and after derivatization with the receptor, the difference of which gives the loading. Next, the beads undergo a similar analysis with varying levels of molecular probes. The indicator loading may be quantitated by taking the absorption spectra of the beads. In this manner, the absolute loading level and the ratio between the receptor and indicators may be adjusted. Creating calibration curves for the analyte using the different beads will allow the optimum ratios to be determined.

The indicator loading may be quantitated by taking the absorption spectra of a monolayer of the beads using our sandwich technique (See FIG. 46D). The sandwich technique involves measuring the spectroscopy of single monolayers of the beads. The beads may be sandwiched between two cover slips and gently rubbed together until a monolayer of the beads is formed. One cover slip is removed, and mesh with dimensions on the order of the beads is then place over the beads, and the cover slip replaced. This sandwich is then placed within a cuvette, and the absorbance or emission spectra are recorded. Alternatively, an sensor array system, as described above, may be used to analyze the interaction of the beads with the analyte.

Figure 47:
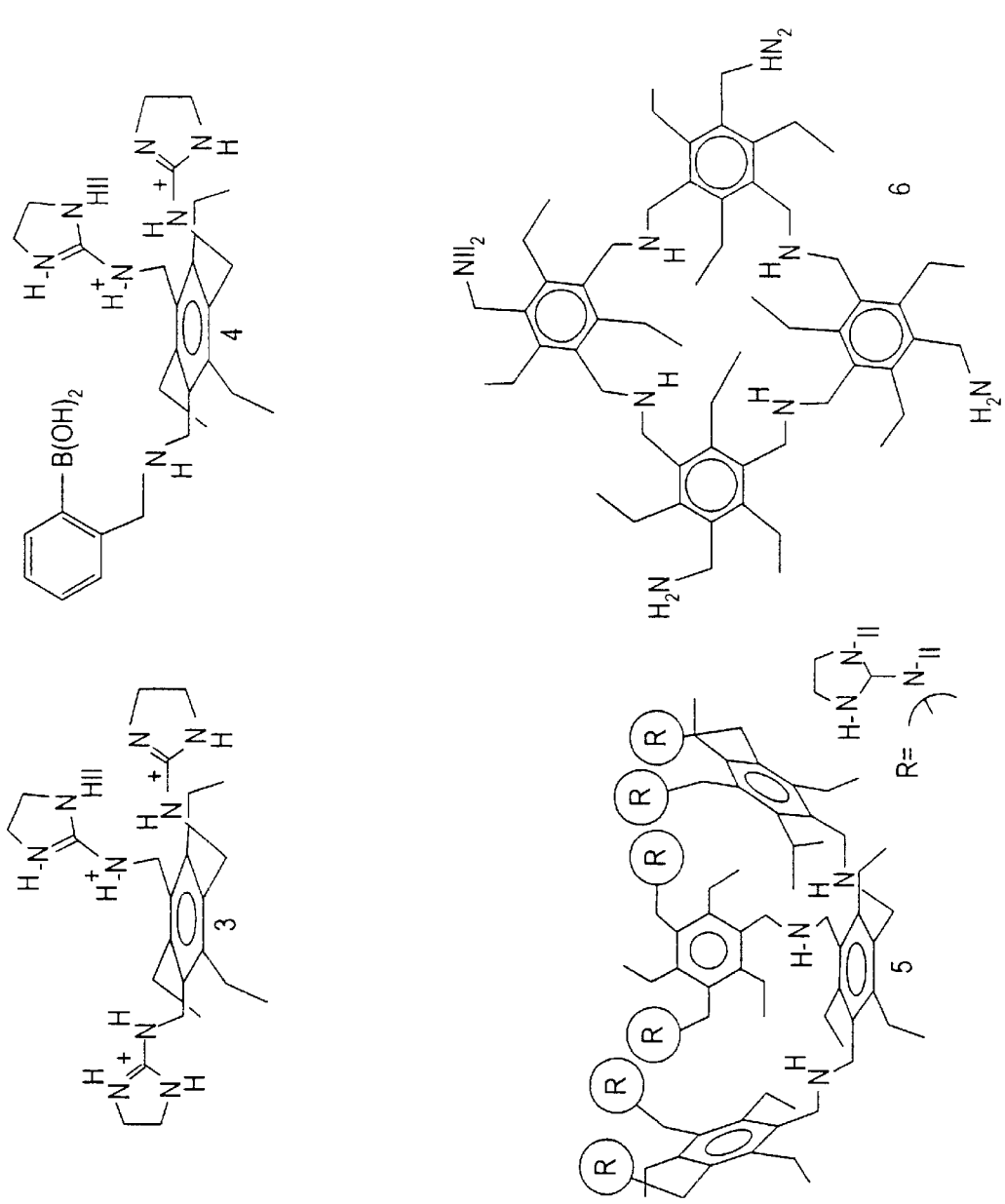
FIG. 47 depicts receptors 3–6.

A variety of receptors may be coupled to the polymeric beads. Many of these receptors have been previously described. Other receptors are shown in FIG. 47.

Figure 48:
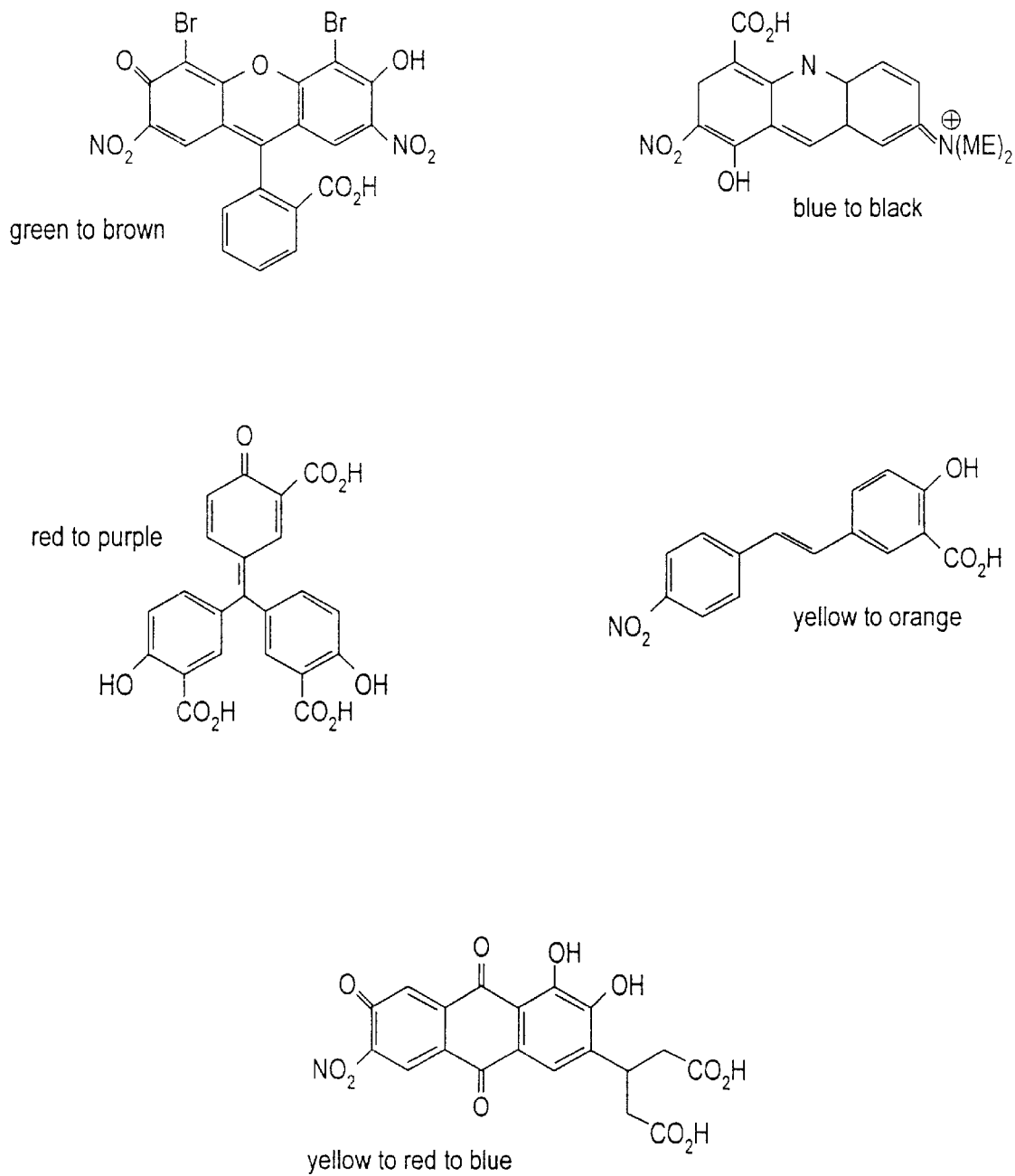
FIG. 48 depicts pH indicators which may be coupled to a particle.

As described generally above, an ensemble may be formed by a synthetic receptor and a probe molecule, either mixed together in solution or bound together on a resin bead. The modulation of the spectroscopic properties of the probe molecule results from perturbation of the microenvironment of the probe due to interaction of the receptor with the analyte; often a simple pH effect. The use of a probe molecule coupled to a common polymeric support may produce systems that give color changes upon analyte binding. A large number of dyes are commercially available, many of which may be attached to the bead via a simple EDC/HOBT coupling (FIG. 48 shows some examples of indicators). These indicators are sensitive to pH, and also respond to ionic strength and solvent properties. When contacted with an analyte, the receptor interacts with the analyte such that microenvironment of the polymeric resin may become significantly changed. This change in the microenvironment may induce a color change in the probe molecule. This may lead to an overall change in the appearance of the particle indicating the presence of the analyte.

Since many indicators are sensitive to pH and local ionic strength, index of refraction, and/or metal binding, lowering the local dielectric constant near the indicators may modulate the activity of the indicators such that they are more responsive. A high positive charge in a microenvironment leads to an increased pH since hydronium ions migrate away from the positive region. Conversely, local negative charge decreases the microenvironment pH. Both changes result in a difference on the protonation state of a pH sensitive indicator present in that microenvironment. The altering of the local dielectric environment may be produced by attaching molecules of differing dielectric constants to the bead proximate to the probe molecules. Examples of molecules which may be used to alter the local dielectric environment include, but are not limited to, planar aromatics, long chain fatty acids, and oligomeric tracts of phenylalanine, tyrosine, and tryptophan. Differing percentages of these compounds may be attached to the polymeric bead to alter the local dielectric constant.

Competition assays may also be used to produce a signal to indicate the presence of an analyte. The high specificity of antibodies makes them the current tools of choice for the sensing and quantitation of structurally complex molecules in a mixture of analytes. These assays rely on a competition approach in which the analyte is tagged and bound to the antibody. Addition of the untagged analyte results in a release of the tagged analytes and spectroscopic modulation is monitored. Surprisingly, although competition assays have been routinely used to determine binding constants with synthetic receptors, very little work has been done exploiting competition methods for the development of sensors based upon synthetic receptors. Yet, all the ways in which the microenvironment of the chromophore can be altered, as described above, may be amenable to the competition approach. Those that have been developed using synthetic receptors are mostly centered upon the use of cyclodextrins. (See e.g., Hamasaki, K.; Ikeda, H.; Nakamura, A.; Ueno, A.; Toda, F.; Suzuki, I.; Osa, T. "Fluorescent Sensors of Molecular Recognition. Modified Cyclodextrins Capable of Exhibiting Guest-Responsive Twisted Intramolecular Charge Transfer Fluorescence" *J. Am. Chem. Soc.* 1993, 115, 5035, and reference (5) therein, which are incorporated herein by reference) A series of parent and derivatized cyclodextrins have been combined with chromophores that are responsive to the hydrophobicity of their microenvironment to produce a sensor system. Displacement of the chromophores from the cyclodextrin cavity by binding of a guest leads to a diagnostic spectroscopy change.

This competitive approach has been used successfully, in one embodiment, for the detection of carbohydrates such as inositol-1,4,5-triphosphate ($IP_3$). In one embodiment, a synthetic receptor 5 may be paired with an optical signaling molecule 5-carboxyfluorescein, to quantitate $IP_3$ at nM concentrations. A competition assay employing an ensemble of 5-carboxyfluorescein and receptor 5 was used to measure binding constants. The addition of receptor 5 to 5-carboxyfluorescein resulted in a red shift of the absorption of 5-carboxyfluorescein. Monitoring the absorption at 502 nm, followed by analysis of the data using the Benesi-Hildebrand method, gave affinity constants of $2.2 \times 10^4$ $M^{-1}$ for 5-carboxyfluorescein binding to receptor 5. Addition of $IP_3$ to a solution of the complexes formed between 5 and 5-carboxyfluorescein resulted in displacement of 5-carboxyfluorescein and a subsequent blue shift.

In order to enhance the affinity of receptor 5 for $IP_3$, similar assays were repeated in methanol, and with 2% of the surfactant Triton-X. In methanol and the detergent solutions, 5-carboxyfluorescein prefers a cyclized form in which the 2-carboxylate has undergone an intramolecular conjugate addition to the quinoid structure. This form of 5-carboxyfluorescein is colorless and nonfluorescent. Upon addition of receptor 5 the yellow color reappears as does the fluorescence. The positive character of the receptor induces a ring opening to give the colored/fluorescent form of 5-carboxyfluorescein. Using the Benesi-Hildebrand method applied to absorption data a binding constant of $1.2 \times 10^5$ $M^{-1}$ was found for receptor 5 and 5-carboxyfluorescein. As anticipated based upon the differences in the spectroscopy of 5-carboxyfluorescein when it is bound to receptor 5 or free in solution, addition of $IP_3$ to a solution of receptor 5 and 5-carboxyfluorescein resulted in a decrease of absorbance and fluorescence due to release of 5-carboxyfluorescein into the methanol solution. Binding constants of $1.0 \times 10^8$ $M^{-1}$ and $1.2 \times 10^7$ for $IP_3$ and receptor 5 were found for methanol and the surfactant solution respectively.

Since fluorescence spectroscopy is a much more sensitive technique than UV/visible spectroscopy, and the use of methanol gave significantly stronger binding between receptor 5 and 5-carboxyfluorescein, as well as between receptor 5 and $IP_3$, the monitoring of fluorescence was found to be the method of choice for sensing nM concentrations of $IP_3$. We find that the addition of $IP_3$ to an ensemble of receptor 5 and 5-carboxyfluorescein in water may detect and quantitate $IP_3$ at a concentration as low as 1 mM. Importantly, in methanol a 10 nM $IP_3$ concentration was easily detected. A detection level in the nM range is appropriate for the development of an assay using methanol or surfactant as an eluent and capillary electrophoresis to sample and fractionate cellular components.

We have shown that receptor 5 binds $IP_3$ quite selectively over other similarly charged species present in cells. Polyanions with charges higher than $IP_3$, such as $IP_4$, $IP_5$, and oligonucleotides, however, are expected to bind with higher affinities. In order to fractionate the cellular components during signal transduction, and specifically monitor $IP_3$, a combination of a chemically sensitive particle and capillary electrophoresis (CE) may be used. As has been described above, a sensor array may include a well in which the particle is placed, along with a groove in which the capillary will reside. The capillary will terminate directly into the interior of the bead (See FIG. 49). Illumination from above and CCD analysis from below may be used to analyze the particle. Samples as small as 100 femtoliters may be introduced into an electrophoresis capillary for analysis. Using high sensitivity multiphoton-excited fluorescence as few as ~50,000 molecules of various precursors/metabolites of the neurotransmitter, serotonin may be detected. Cytosolic samples may be collected and fractionated in micron-diameter capillary electrophoresis channels. At the capillary outlet, components may migrate from the channel individually, and will be directed onto a bead that houses immobilized receptor 5 and the dyes appropriate for our various signaling strategies. Receptor binding of $IP_3$ or $IP_4$ will elicit modulations in the emission and/or absorption properties.

Dramatic spectroscopy changes accompany the chelation of metals to ligands that have chromophores. In fact, most colorimetric/fluorescent sensors for metals rely upon such a strategy. Binding of the metal to the inner sphere of the ligand leads to ligand/metal charge transfer bands in the absorbance spectra, and changes in the HOMO-LUMO gap that leads to fluorescence modulations.

In one embodiment, the binding of an analyte may be coupled with the binding of a metal to a chromophoric ligand, such that the metal may be used to trigger the response of the sensor for the analyte. The compound known as Indo-1 (see FIG. 50 for the structure and emission properties) is a highly fluorescent indicator that undergoes a large wavelength shift upon exposure to Ca(II). Further, compound 2 binds Ce(III) and the resulting complex is fluorescent. In one embodiment, the binding of Ca(II) or Ce(III) to these sensors may be altered by the addition of an analyte of interest. By altering the binding of these metals to a receptor a signal may be generated indicating the presence of the receptor.

Figure 45A:
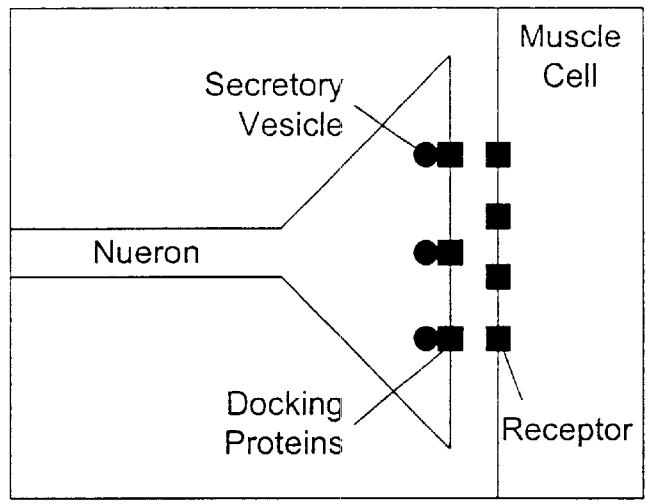
FIGS. 45A–C depict the disruption of neuromuscular communication by a toxin.
Figure 45B:
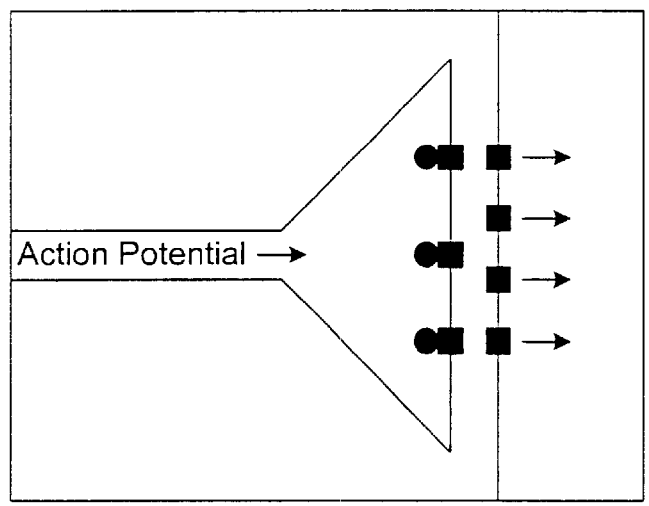
Figure 45C:
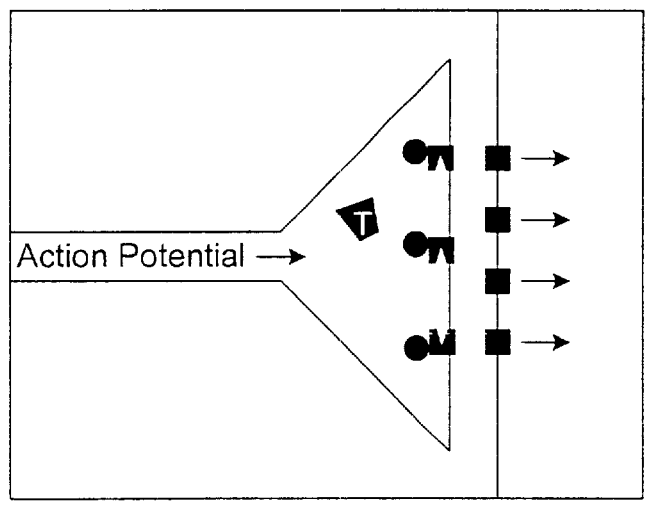
Figure 51:
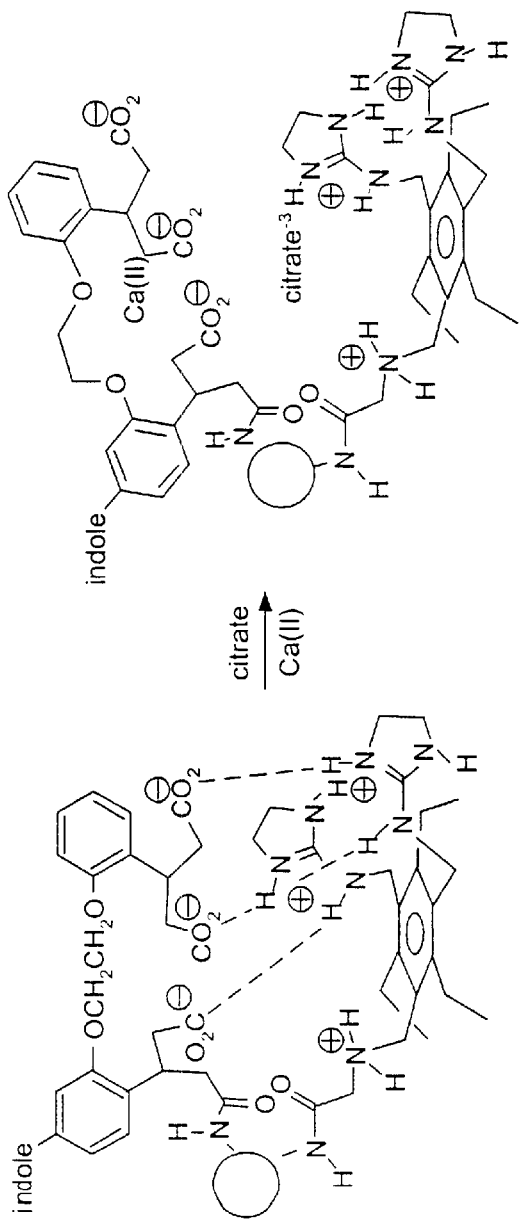
FIG. 51 depicts a scheme wherein binding of citrate to a receptor frees up the Indo-1 for Ca(II) binding.

In one embodiment, fluorescent indicators that have been used to monitor Ca(II) and Ce(III) levels in other applications may be applied to a polymeric supported system. Using the Ca(II) sensor Indo-1 as an example, the strategy is shown in FIG. 51. Indo-1 binds Ca(II) at nM concentrations (see FIG. 50). Attachment of Indo-1 and one of our guanidinium/amine based receptors 3–6 to a resin bead (derivatized with lysine as depicted in FIG. 45D) may lead to intramolecular interactions between the carboxylates of Indo-1 and the guanidiniums/ammoniums of a receptor. The coordination of the carboxylates of Indo-1 may result in a decreased affinity for Ca(1l). However, there should be cooperative binding of Ca(II) and our analytes. Once one of the anionic analytes is bound to its respective receptor, it will competitively displace the carboxylates of Indo-1 leading to increased Ca(II) binding, which in turn will result in a fluorescence modulation. Similarly, binding of Ca(II) to Indo-1 leaves the guanidiniums of the receptors free to bind citrate. The assays will likely be most sensitive at concentrations of the analytes and Ca(II) near their dissociation constants, where neither receptor is saturated and small changes in the extent of binding lead to large changes in fluorescence.

We also may switch the role of the metal and the ligand. Indo-1 is fluorescent with and without the Ca(II). However, compound 2 is not fluorescent until Ce(III) binds to it. Thus, a similar assay that relies upon a change of microenvironment in the interior of the bead depending upon the presence or absence of the analyte should perturb the binding of Ce(III) to compound 2. In this case, a repulsive interaction is predicted for the binding of Ce(III) when the positive charges of the guanidinium based receptors are not neutralized by binding to the anionic analytes.

In one embodiment, an indicator may be coupled to a bead and further may be bound to a receptor that is also coupled to the bead. Displacement of the indicator by an analyte will lead to signal modulation. Such a system may also take advantage of fluorescent resonance energy transfer to produce a signal in the presence of an analyte. Fluorescence resonance energy transfer is a technique that can be used to shift the wavelength of emission from one position to another in a fluorescence spectra. In this manner it creates a much more sensitive assay since one can monitor intensity at two wavelengths. The method involves the radiationless transfer of excitation energy from one fluorophore to another. The transfer occurs via coupling of the oscillating dipoles of the donor with the transition dipole of the acceptor. The efficiency of the transfer is described by equations first derived by Forester. They involve a distance factor (R), orientation factor (k), solvent index of refraction (N), and spectral overlap (J).

In order to incorporate fluorescence resonance energy transfer into a particle a receptor and two different indicators may be incorporated onto a polymeric bead. In the absence of an analyte the fluorescence resonance energy transfer may occur giving rise to a detectable signal. When an analyte interacts with a receptor, the spacing between the indicators may be altered. Altering this spacing may cause a change in the fluorescence resonance energy transfer, and thus, a change in the intensity or wavelength of the signal produced. The fluorescence resonance energy transfer efficiency is proportional to the distance (R) between the two indicators by $1/R^6$. Thus slight changes in the distance between the two indicators may induce significant changes in the fluorescence resonance energy transfer.

Figure 52:
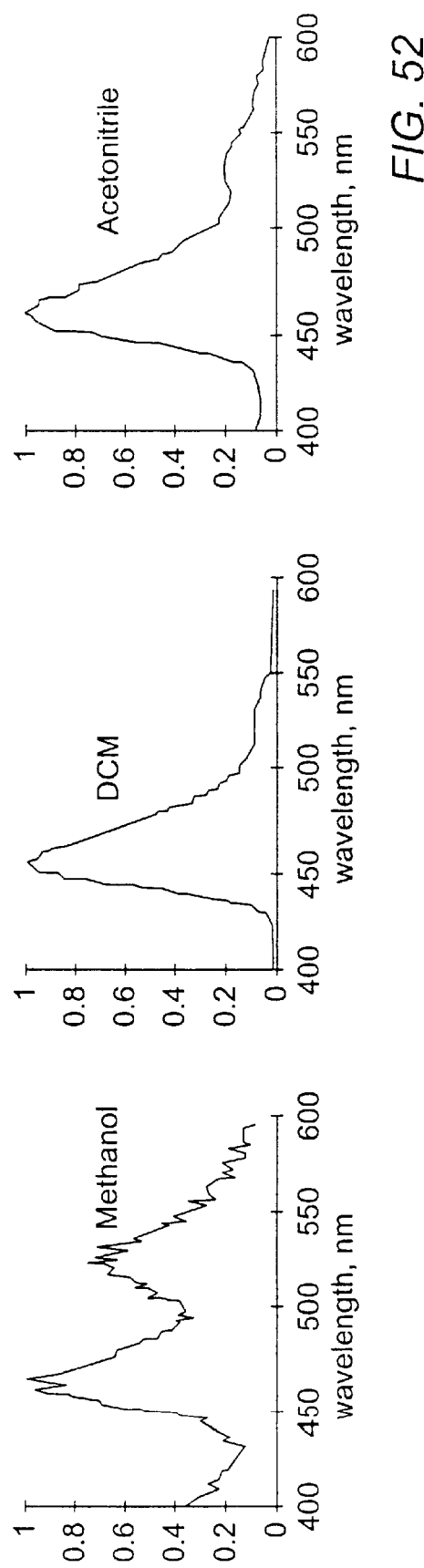
FIG. 52 depicts the change in FRET between coumarin and 5-carboxyfluorescein on resin beads as a function of the solvent.

In one embodiment, various levels of coumarin and fluorescein may be loaded onto resin beads so as to achieve gradiations in FRET levels from zero to 100%. FIG. 52 shows a 70/30 ratio of emission from 5-carboxyfluorescein and coumarin upon excitation of coumarin only in water. However, other solvents give dramatically different extents of FRET. This shows that the changes in the interior of the beads does lead to a spectroscopic response. This data also shows that differential association of the various solvents and 5-carboxyfluorescein on resin beads as a function of solvents. This behavior is evoked from the solvent association with the polymer itself, in the absence of purposefully added receptors. We may also add receptors which exhibit strong/selective association with strategic analytes. Such receptors may induce a modulation in the ratio of FRET upon analyte binding, within the microenvironment of the polystyrene/polyethylene glycol matrices.

In order to incorporate a wavelength shift into a fluorescence assays, receptors 3–6 may be coupled to the courmarin/5-carboxyfluorescein beads discussed above. When 5-carboxyfluorescein is bound to the various receptors and coumarin is excited, the emission will be primarily form coumarin since the fluorescein will be bound to the receptors. Upon displacement of the 5-carboxyfluorescein by the analytes, emission should shift more toward 5-carboxyfluorescein since it will be released to the bead environment which possesses coumarin. This will give us a wavelength shift in the fluorescence which is inherently more sensitive than the modulation of intensity at a signal wavelength.

There should be large changes in the distance between indicators (R) on the resin beads.

When the 5-carboxyfluorescein is bound, the donor/acceptor pair should be farther than when displacement takes place; the FRET efficiency scales as $1/R^6$. The coumarin may be coupled to the beads via a floppy linker, allowing it to adopt many conformations with respect to a bound 5-carboxyfluorescein. Hence, it is highly unlikely that the transition dipoles of the donor and acceptor will be rigorously orthogonal.

In one embodiment, a receptor for polycarboxylic acids and an appropriate probe molecule may be coupled to a polymeric resin to form a particle for the detection of polycarboxylic acid molecules. Receptors for polycarboxylic acids, as well as methods for their use in the detection of polycarboxylic acids, have been described in U.S. Pat. No. 6,045,579 which is incorporated herein by reference. This system involves, in one embodiment, the use of a receptor 3 which was found to be selective for the recognition of a tricarboxylic acid (e.g., citrate) in water over dicarboxylates, monocarboxylates, phosphates, sugars, and simple salts. The receptor includes guanidinium groups for hydrogen bonding and charge pairing with the tricarboxylic acid.

An assay for citrate has employed an ensemble of 5-carboxyfluorescein and 3. The binding between 3 and 5-carboxyfluorescein resulted in a lowering of the phenol $pK_a$ of 5-carboxyfluorescein, due to the positive microenvironment presented by 3. This shift in $pK_a$ (local pH) caused the phenol moiety to be in a higher state of protonation when 5-carboxyfluorescein was free in solution. The absorbance or fluorescence of 5-carboxyfluorescein decreases with higher protonation of the phenol. The intensity of absorbance increases with addition of host 3 to 5-carboxyfluorescein, and as predicted the intensity decreases upon addition of citrate to the ensemble of 3 and 5-carboxyfluorescein. The same effect was seen in the fluorescence spectrum ($\lambda$max=525 nm).

Figure 53:
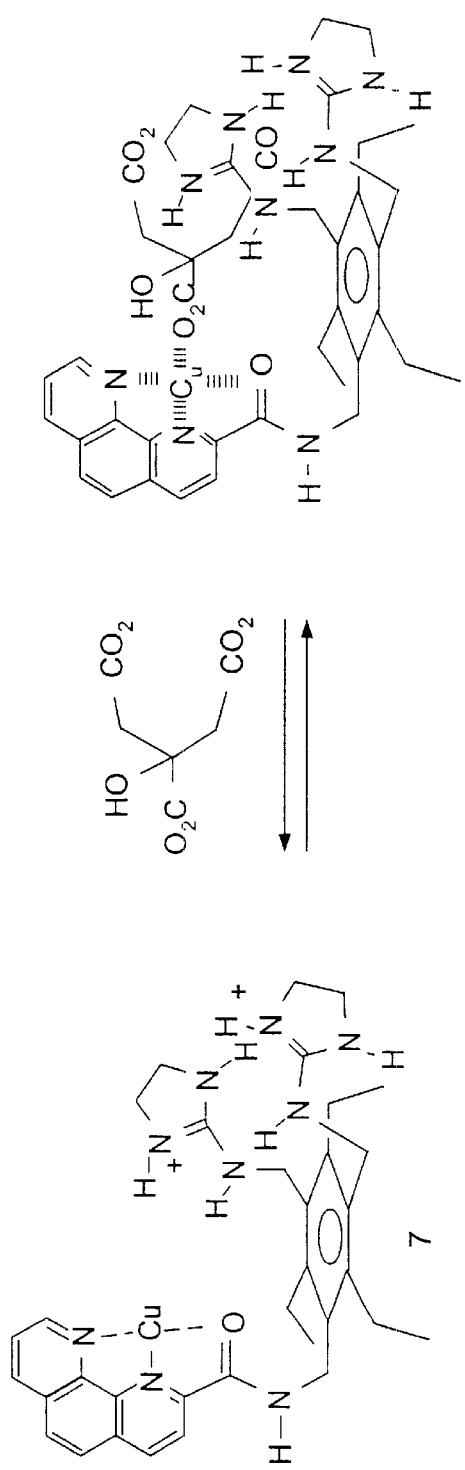
FIG. 53 depicts a scheme wherein a signal of apo-7 to citrate is triggered by Cu(II) binding.

In an embodiment, a metal may be used to trigger the response of a chromophore to the presence of an analyte. For example, compound 7 binds Cu(II) with a binding constant of $4.9 \times 10^5$ $M^{-1}$ (See FIG. 53). Addition of 1 eq. of Cu(II) increases the binding constant of citrate to compound 7 by a factor of at least 5. Importantly, the addition of citrate increases the binding of Cu(II) to the receptor by a factor of at least 10. Therefore the citrate and Cu(II) enhance each other's binding in a cooperative manner. Further, the emission spectra of compound 7 is quite sensitive to the addition of citrate when Cu(II) is present, but has no response to the addition of citrate in the absence of Cu(II). Thus the binding of a "trigger" may be perturbed with an analyte of interest, and the perturbation of the binding of the trigger may be used to spectroscopically monitor the binding of the analyte. The triggering of the sensing event by an added entity is similar to the requirement for enzymes in saliva to degrade food particulants into tastants recognizable by the receptors on mammalian taste buds.

Figure 54:
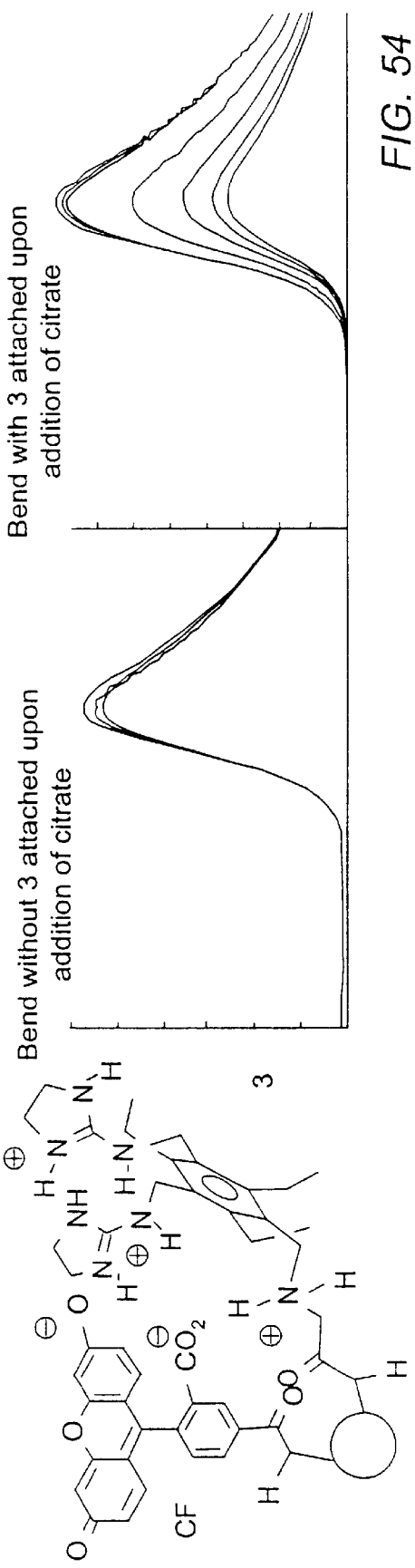
FIG. 54 depicts the response of receptor 3 and 5-carboxyfluoroscein on a resin bead to the addition of citrate.

In one embodiment, citrate receptor 3 may be immobilized on a polystyrene/polyethylene glycol bead, where on the same bead may also be attached a fluorescent probe molecule (FIG. 54). Solutions of citrate at different concentrations may be added to the beads, and the fluorescence spectra of the monolayer recorded. We find exactly the same fluorescence response toward citrate for the ensemble of receptor 3 and 5-carboxyfluorescein on the beads as in solution. Apparently, a similar microenvironment change to modulate the spectroscopy of 5-carboxyfluorescein occurs in the beads, although both 5-carboxyfluorescein and receptor 3 are just randomly placed throughout the bead.

Additional sensor system include sensors for tartrate and tetracyclin. Compound 4 binds tartrate in buffered water (pH 7.4) with a binding constant of approximately $10^5$ $M^{-1}$. The binding is slow on the NMR time scale, since we can observe both the bound and free receptor and tartrate. This binding is surprisingly strong for pure water. It must reflect good cooperativity between the host's boronic acid moiety and the two guanidinium groups for the recognition of the guest's vicinal diol and two carboxylates respectively. Compound 6 may act as a molecular receptor for tetracyclin. The compound has been synthesized, and by variable temperature NMR it has been found to be in a bowl conformation. Its binding properties with several indicators have been explored (most bind with affinities near $10^4$ $M^{-1}$). More importantly, the binding of tetracyclin has also been explored, and our preliminary results suggests that the binding constant in water is above $10^3$ $M^{-1}$.

Figure 56:
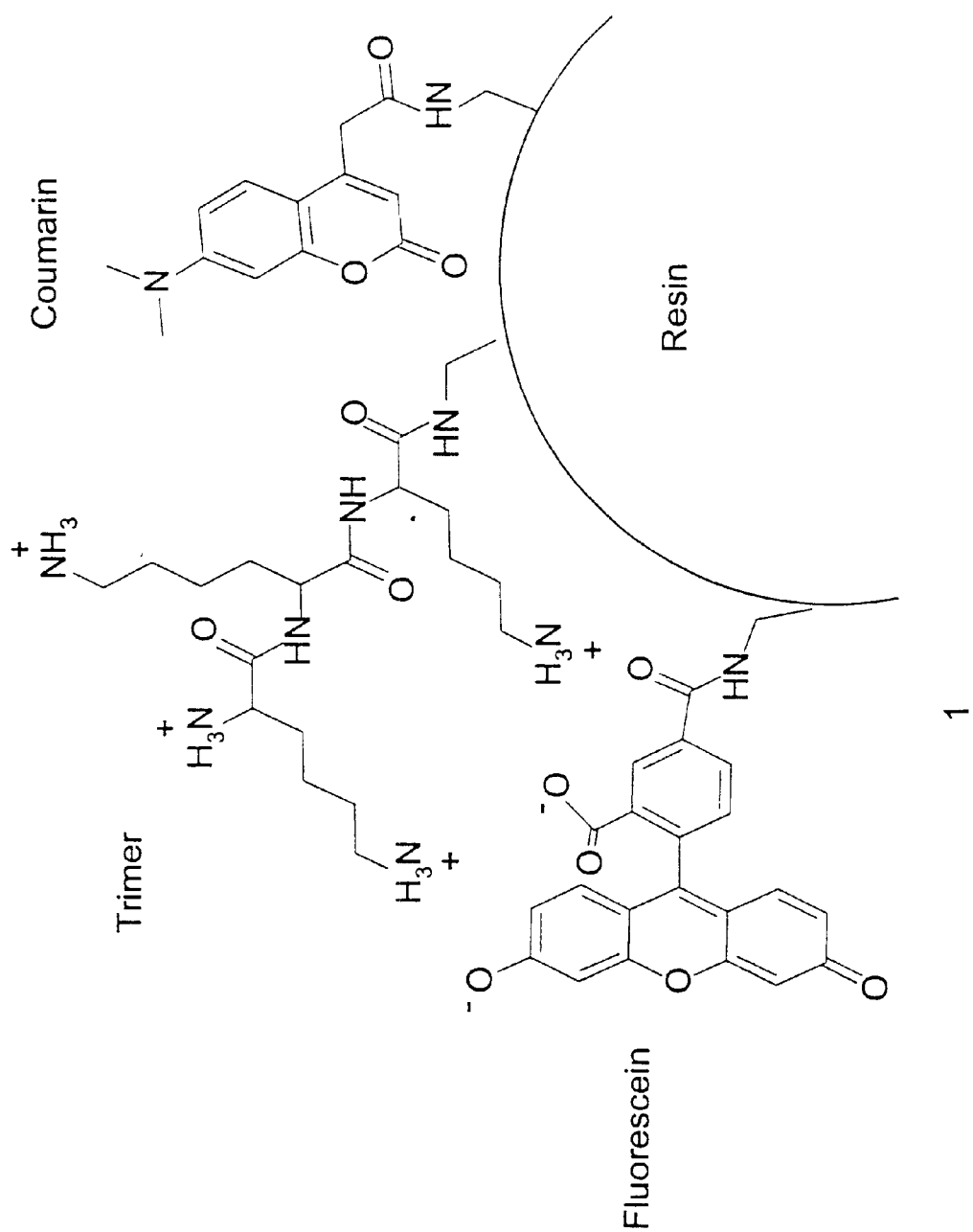
FIG. 56 depicts a peptide trimer receptor and a pair of fluorescent indicators coupled to a polymeric resin.

In another embodiment, a sensing particle may include an oligomer of amino acids with positively charged side chains such as the lysine trimer, depicted in FIG. 56, designed to act as the anion receptor, and an attached FRET pair for signaling. Sensing of different anions may be accomplished by optically monitoring intensity changes in the signal of the FRET pair as the analyte interacts with the oligomer.

Upon introduction of an anionic species to 1, the analyte may bind to the trimer, disturbing the trimer-fluorescein interaction, thereby, altering the fluorescein's ability to participate in the energy transfer mechanism. Using a monolayer of resin in a conventional fluorometer, the ratio of D:A emission for the FRET pair attached to TG-$NH_2$ resin is sensitive to different solvents as well as to the ionic strength of the solution. Epifluorescence studies may be performed to test the solvent dependence, ionic strength, and binding effects of different anions on the FRET TG-$NH_2$ resins. The images of the FRET TG-$NH_2$ resins within a sensor array, taken by a charged coupled device (CCD) may result in three output channels of red, green, and blue light intensities. The RGB light intensities will allow for comparison of the results obtained using a conventional fluorometer.

The signal transduction of 1 may be studied using a standard fluorometer and within the array platform using epifluorescence microscopy. The RGB analysis may be used to characterize the relative changes in emission of the FRET pair. Other resin-bound sensors may be synthesized by varying the amino acid subunits within the oligomers and the length of the peptide chains.

Figure 57:
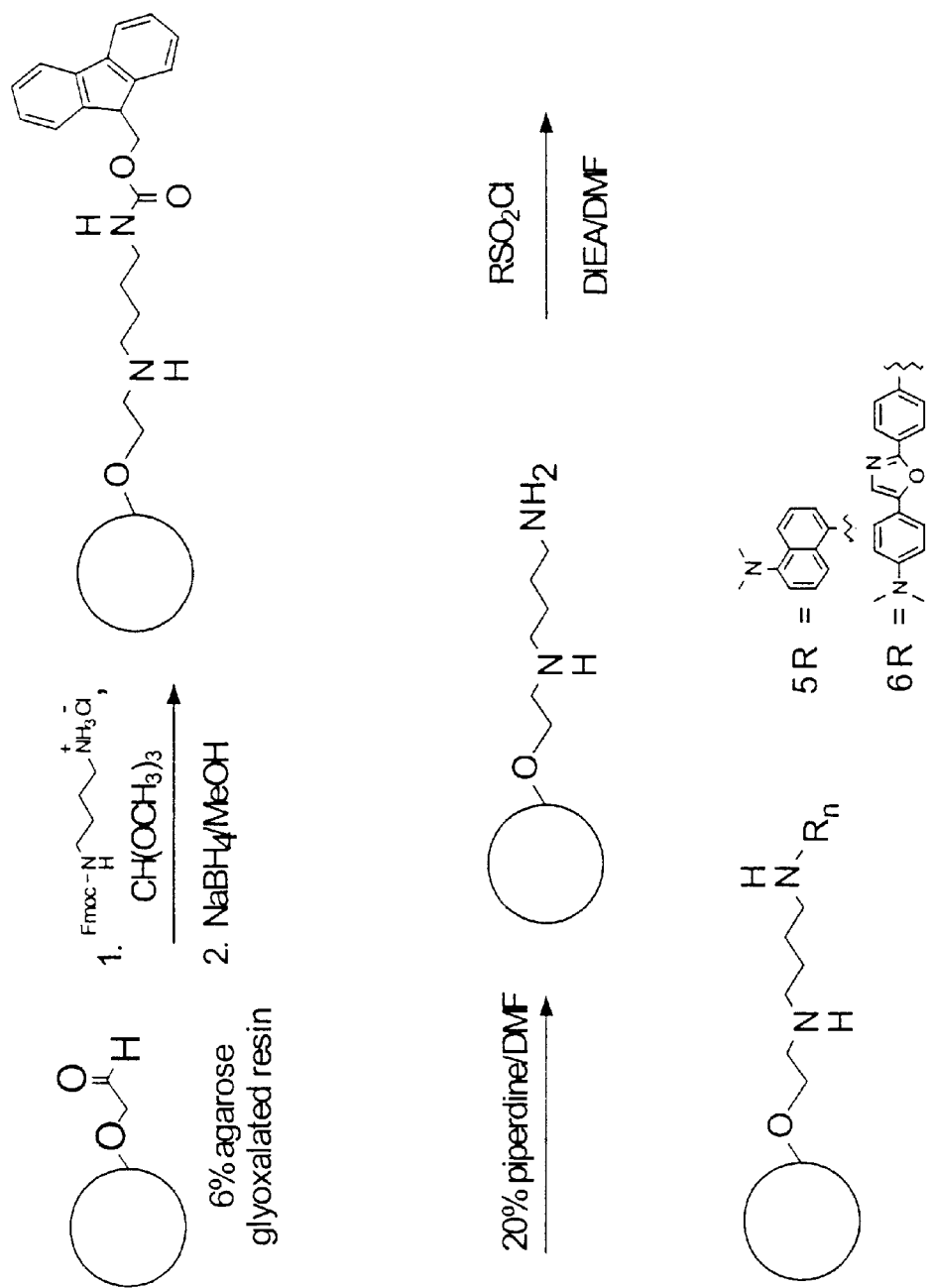
FIG. 57 depicts a synthetic scheme for anchoring dansyl and dapoxyl indicators to 6% agarose glyoxalated resin beads.

In another embodiment, solvatochromic dyes may be covalently linked to a receptor unit tethered to a resin bead that is capable of binding to small organic guests. In one example, dansyl and dapoxyl may act as sensitive probes of their microenvironment. When selecting a dye for use, characteristics such as high extinction coefficients, high fluorescence quantum yields, and large Stoke's shifts should be considered. Dapoxyl and dansyl were anchored to 6% agarose resin beads, in an effort to enhance the signaling response of these resin bound fluorophores in various solvent systems. Agarose beads are crosslinked galactose polymers that are more hydrophilic than the polystyrene-polyethylene glycol resins. The attachment of these solvatochromic dyes to the agarose resin beads is outlined in FIG. 57.

The dapoxyl labeled resin (6) was formed by reductively aminating glyoxalated agarose resin with mono (Fmoc)-butyldiamine hydrochloride salt using sodium borohydride as the reducing agent. The base labile protecting group, Fmoc, was removed from 3 with dilute base, and the solvatochromic dye was anchored to 4 through a reaction to form a sulfonamide bond resulting in 6. The tethering of dansyl to agarose resin was performed similarly.

Analysis of the agarose resins derivatized with dansyl and dapoxyl was attempted several times using a monolayer sample cell in a conventional fluorometer. However, satisfactory emission spectra of 5 and 6 in different solvent systems were not obtained due to the fragile nature of the agarose resin which placed restrictions on the manufacturing of the monolayer sample cell.

Significant signal enhancement of 5 and 6 was seen when the solvent system was changed from a 50 mM phosphate buffer (pH=7.0) to ethanol (EtOH), methanol (MeOH), and acetonitrile ($CH_3CN$). The emission of 6 increased three fold in EtOH and five fold in $CH_3CN$ when compared to the emission of 6 in a buffer. The agarose-dansyl resin, 5, demonstrated similar trends in response to different solvents; however, the intensities were smaller than for 6. For instance, the emission of 5 in EtOH for the red channel was 61% smaller in intensity units compared to 6 (2200 vs. 5800 arbitrary intensity units). This observation has been attributed to the lower quantum yield of fluorescence and the smaller extinction coefficient of dansyl to that of dapoxyl. From these initial studies, the average fluorescence intensity of the three beads of type 6 in EtOH across the red channel was 5800±300 arbitrary intensity counts with a percent standard deviation of 5.0%. Also, before changing to a new solvent, the agarose beads were flushed with the buffer for 5 minutes in order to return the agarose-dye resin to a "zero" point of reference. The background variance of the fluorescence intensity of 6 when exposed to each of the buffer washes between each solvent system was 5.0% and 4.0% in the red and green channels, respectively.

Figure 58:
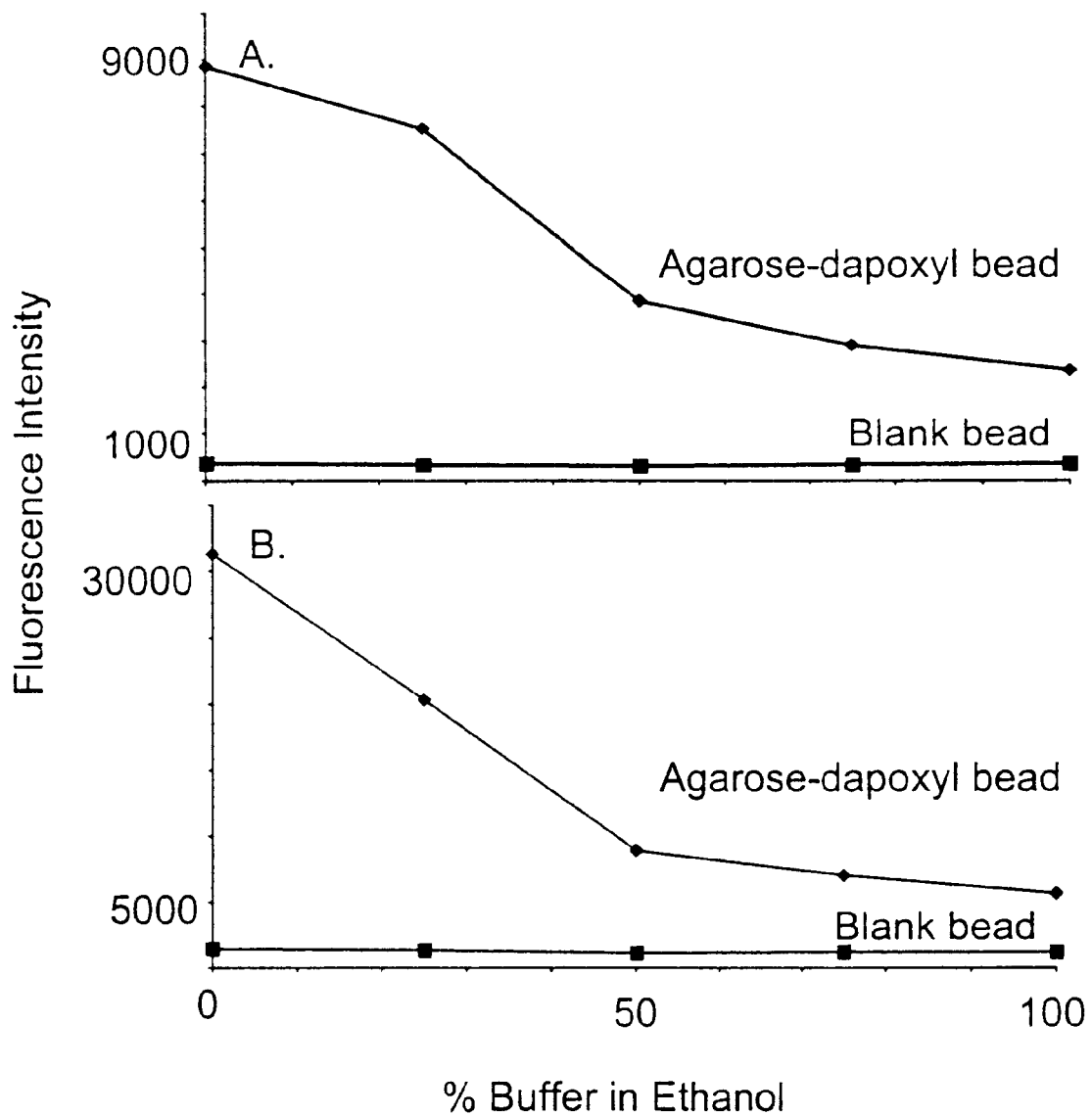
FIG. 58 depicts the RGB epifluorescence of 6 in EtOH with varying ratio buffer concentrations.

The response of 5 and 6 to varying ratios of two different solvents was also studied. As seen in FIG. 58, a detectable decrease in the emission of 6 is observed as the percent of the 50 mM phosphate buffer (pH=7) is increased in ethanol. The fluorescence intensity of 6 decreased by three fold from its original value in 100% EtOH to 100% buffer. There was an incremental decrease in the fluorescence emission intensities of 6 in both the red and green channels. Once again, 5 demonstrated similar trends in response to the varying ratios of mixed solvent systems; however, the intensities were smaller than 6.

Figure 59:
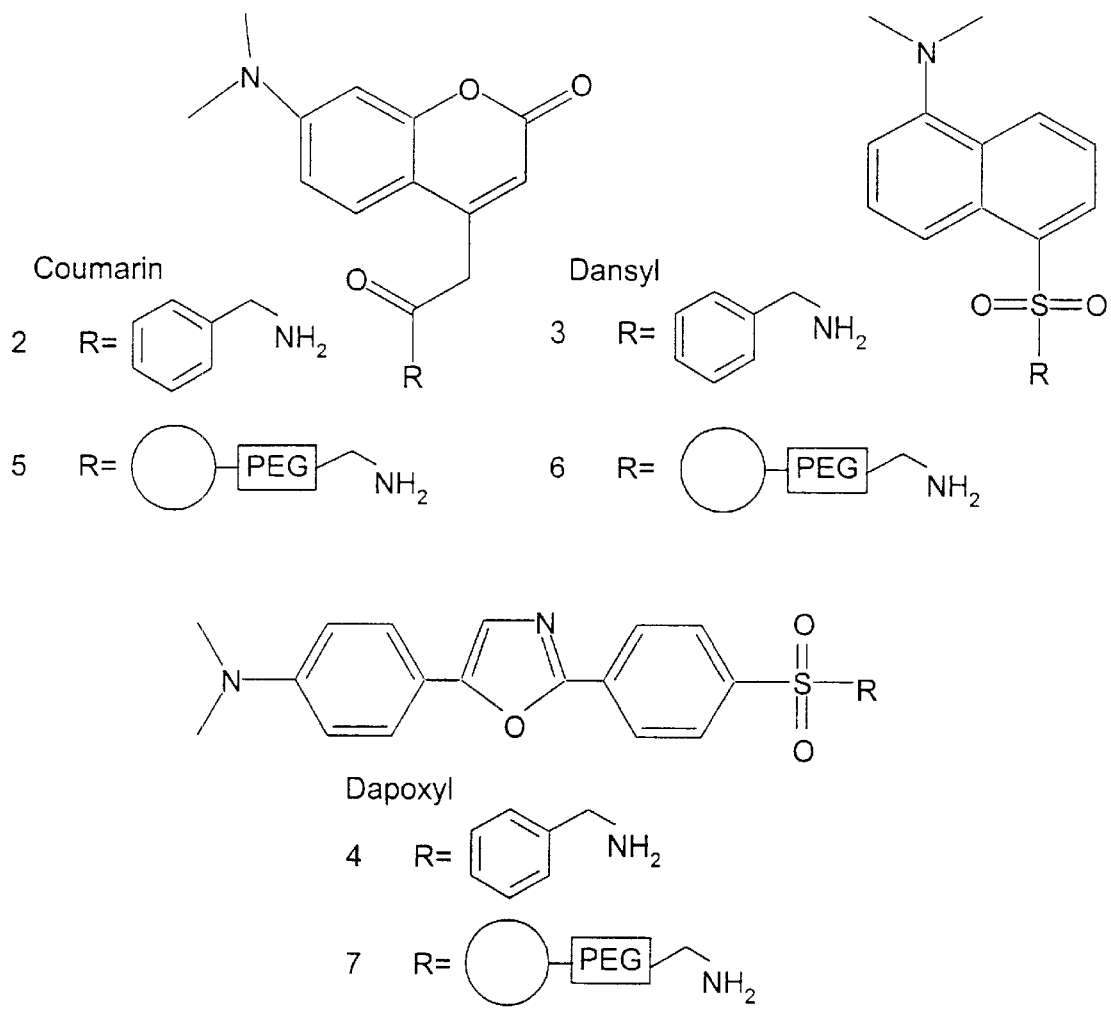
FIG. 59 depicts indicators and polymeric beads used for fluorescence studies.

In another example, each dye was derivatized with benzyl amine (2–4) for studies in solution phase and anchored to resin (5–7) for studies using the sandwich method and epi-fluorescence. The dyes and corresponding resins are depicted in FIG. 59.

Figure 60:
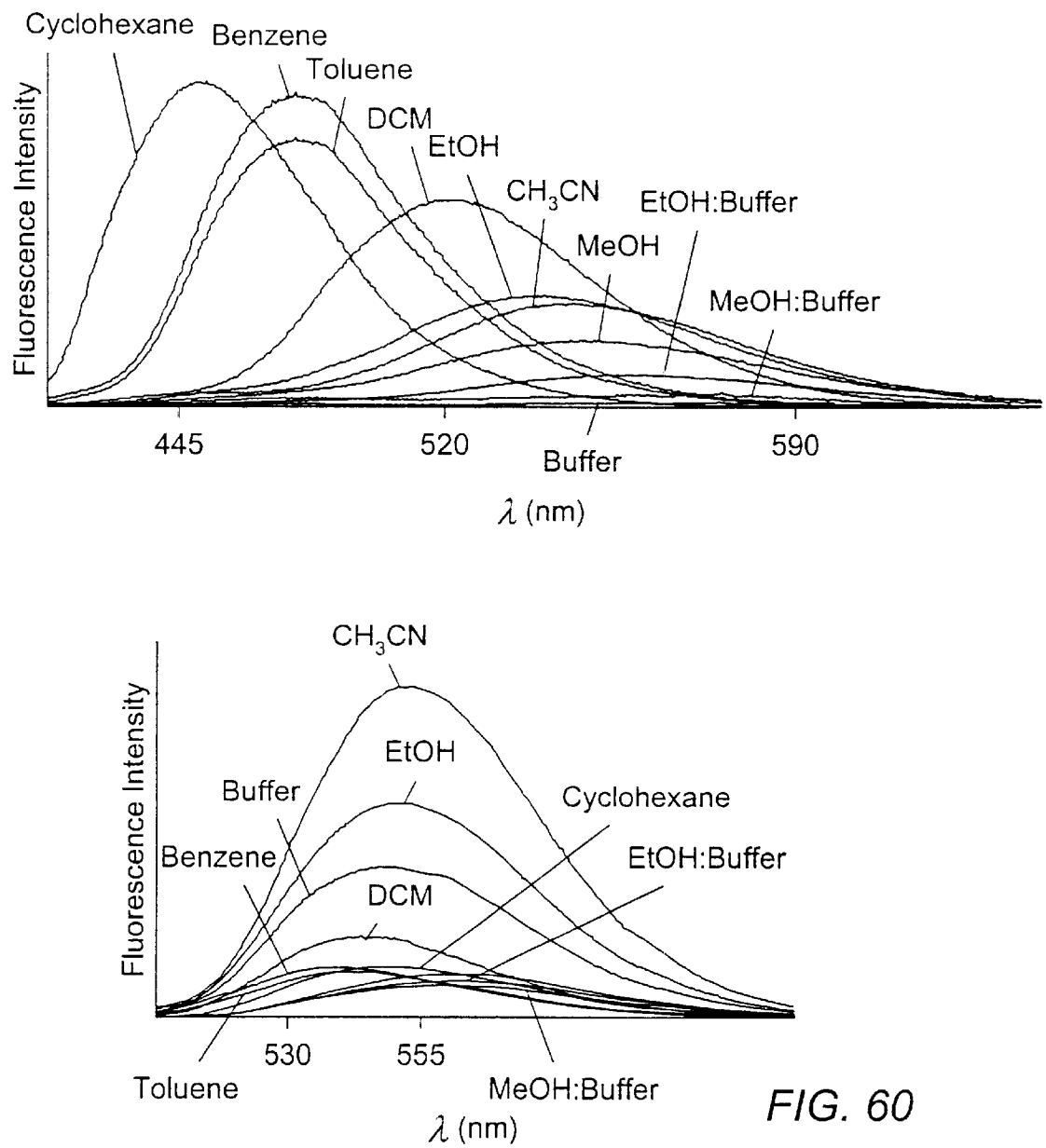
FIG. 60 depicts Emission spectra of derivatized dapoxyl dyes in various solvents.

Fluorescence studies have been performed for each dye in solution phase and attached to resin. FIG. 60 illustrates an example of the emission changes in 4 (part A.) and 7 (part B.) that result from exposure to different solvent systems. The quantum yield of 4 diminished in more polar protic media (i.e. ethanol); whereas, the quantum yield of 4 increased in more hydrophobic environments (i.e. cyclohexane). Also, the Stoke's shift of each probe changed significantly between nonpolar and polar media. For example, the Stoke's shift of 4 ($\lambda_{em}-\lambda_{abs}$) in 1:1 mixture of methanol and 1.0 M aqueous phosphate buffer was 221 nm, but the Stoke's shift of 4 was 80 nm in cyclohexane. 7 displayed similar trends, but the Stoke's shift from solvent to solvent was not as dramatic. The optical properties of 5–7 only varied slightly when compared to their homogeneous analogs.

Of the three fluorophores, the solvatochromic properties of coumarin were not as dramatic when compared to dansyl and dapoxyl. 6 and 7 displayed the largest Stoke's shifts. The emission wavelength for 5–7 red shifted when placed in more polar solvents. However, when 6 was placed in water, the Stoke's shift was the same as in when placed in cyclohexane as seen in FIG. 60. This trend was observed with each fluoresently labeled resin, and may be explained by the fact that these probes are hydrophobic and that they may actually reside within the hydrophobic core of the PEG-PS resin when submerged in water.

Figure 61:
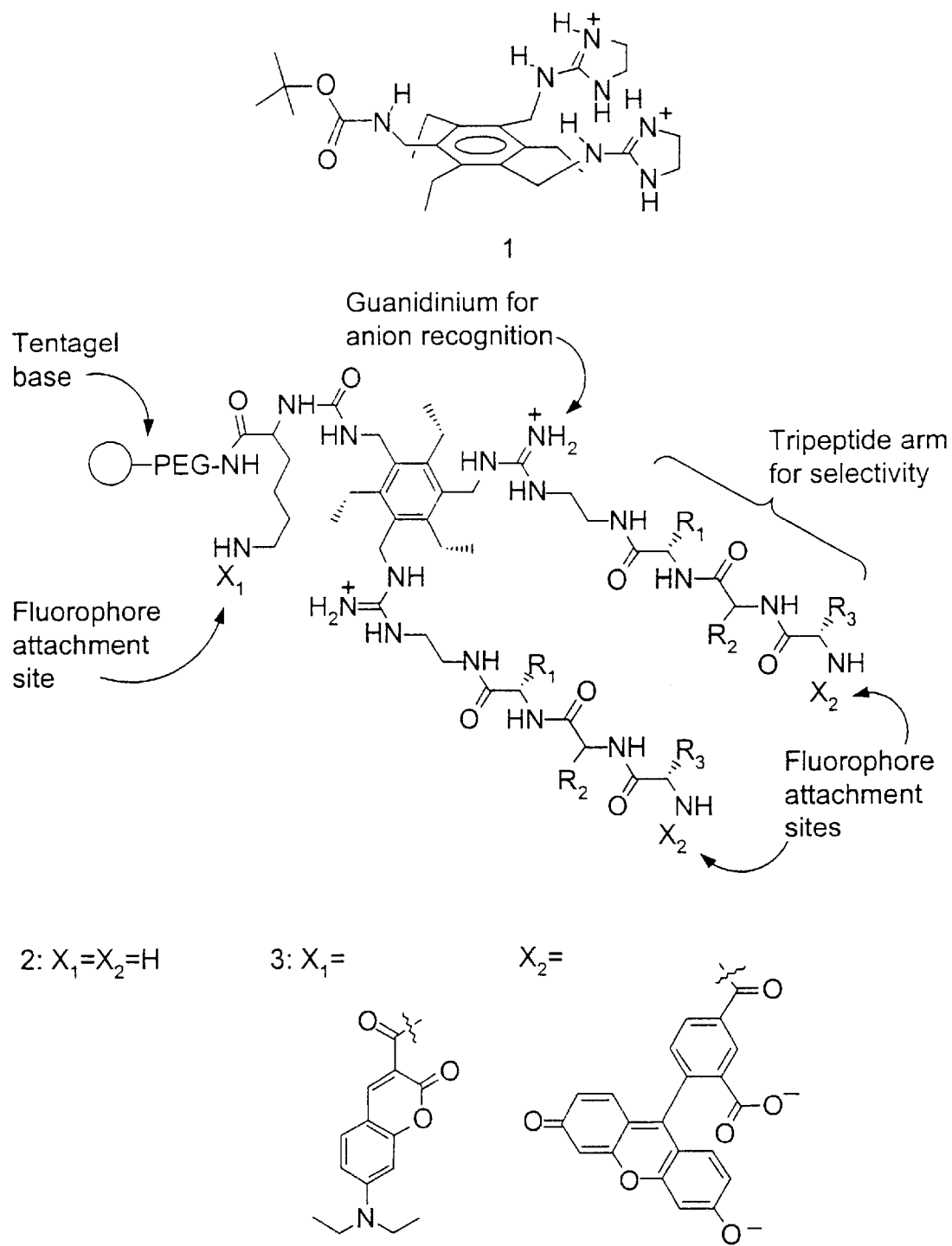
FIG. 61 depicts a general structure of a chemically sensitive particle that includes a receptor and multiple indicators coupled to a polymeric resin.

In another example a selective chemosensor for ATP was found. A bead with a polyethylene-glycol base was attached via guanidinium to two long polypeptide arms that were known to interact with the adenine group of ATP, as depicted in FIG. 61. The tripeptide arms contained two flourophore attachment sites for 5-carboxyfluorescein (fluorescein), and an attachment site for 7-diethylaminocoumarin-3-carboxylic acid (coumarin) located on the terminal end of the lysine that was attached to the core structure. The fluorophores act as receptors for the desired analyte. The fluorophores also act as indicators to signal changes in the environment before and after the addition of analytes.

Fluorescently labeled N-methylanthraniloyl-ATP were chosen to screen for ATP receptors. Sequences of amino acids were linked as tripeptides and equilibrated with a buffer. The resin was transferred to a microscope slide and illuminated with UV light. The results yielded 6 sequences with active beads that displayed fluorescent activity, and 3 sequences with inactive beads where there was no detectable fluorescent activity.

Three of the 6 active beads, and 1 of the 3 inactive beads were arbitrarily chosen to react with ATP (Sequences below in bold). When the fluorescein and coumarin were excited, there was no detectable difference in the FRET upon addition of ATP. This may be due to there being an average distance between the fluorophores within the beads, which does not significantly change upon binding ATP. However, all but one active bead (Thr-Val-Asp) exhibited a fluorescence modulation upon excitation of fluorescein. The lack of response from an active bead shows that screening against a derivatized analyte (MANT-ATP in this case) will not guarantee that the active beads are successful sensors when synthesized with attached fluorophores. Either this active bead binds the MANT protein of MANT-ATP or there is no significant microenvironment change around the fluorophores of the Thr-Val-Asp receptor upon binding ATP.

| Active Beads | Inactive Beads |
| --- | --- |
| His-Ala-Asp | His-Phe-Gly |
| Glu-Pro-Thr | Ser-Ala-Asp |
| Thr-Val-Asp | Trp-Asn-Glu |
| Met-Thr-His | |
| Asp-Ala-Asp | |
| Ser-Tyr-Ser | |

A large spectral response upon addition of ATP was observed with the Ser-Tyr-Ser sequence in the active bead. The increase in fluorescein emission is possibly due to a higher local pH around the fluorescein upon binding of ATP. Further studies were performed with the Ser-Tyr-Ser sequence and analytes, AMP, and GTP, which are structurally similar to ATP. This peptidic library member exhibited very high detection selectivity for ATP over these structurally similar potentially competing analytes. The lack of response to AMP suggests the necessity for triphosphates to bind strongly to the guanidinium entities of the receptor, while the lack of response to GTP indicates the specificity for nucleotide bases imparted by the tripeptide arms. The combination of serine and tyrosine suggests $\pi$-stacking between the phenol of tyr and adenine and hydrogen bonding interactions between the serine OH and/or the ribose or adenine. These studies have demonstrated that the union of a proven core with combinatorial methods, followed by the attachment of fluorophores, can create resin bound chemosensors with excellent selectivity.

As described above, a particle, in some embodiments, possesses both the ability to interact with the analyte of interest and to create a modulated signal. In one embodiment, the particle may include receptor molecules which undergo a chemical change in the presence of the analyte of interest. This chemical change may cause a modulation in the signal produced by the particle. Chemical changes may include chemical reactions between the analyte and the receptor. Receptors may include biopolymers or organic molecules. Such chemical reactions may include, but are not limited to, cleavage reactions, oxidations, reductions, addition reactions, substitution reactions, elimination reactions, and radical reactions.

In one embodiment, the mode of action of the analyte on specific biopolymers may be taken advantage of to produce an analyte detection system. As used herein biopolymers refers to natural and unnatural: peptides, proteins, polynucleotides, and oligosaccharides. In some instances, analytes, such as toxins and enzymes, will react with biopolymer such that cleavage of the biopolymer occurs. In one embodiment, this cleavage of the biopolymer may be used to produce a detectable signal. A particle may include a biopolymer and an indicator coupled to the biopolymer. In the presence of the analyte the biopolymer may be cleaved such that the portion of the biopolymer which includes the indicator may be cleaved from the particle. The signal produced from the indicator is then displaced from the particle. The signal of the bead will therefore change thus indicating the presence of a specific analyte.

Proteases represent a number of families of proteolytic enzymes that catalytically hydrolyze peptide bonds. Principal groups of proteases include metalloproteases, serine porteases, cysteine proteases and aspartic proteases. Proteases, in particular serine proteases, are involved in a number of physiological processes such as blood coagulation, fertilization, inflammation, hormone production, the immune response and fibrinolysis.

Numerous disease states are caused by and may be characterized by alterations in the activity of specific proteases and their inhibitors. For example emphysema, arthritis, thrombosis, cancer metastasis and some forms of hemophilia result from the lack of regulation of serine protease activities. In case of viral infection, the presence of viral proteases have been identified in infected cells. Such viral proteases include, for example, HIV protease associated with AIDS and NS3 protease associated with Hepatitis C. Proteases have also been implicated in cancer metastasis. For example, the increased presence of the protease urokinase has been correlated with an increased ability to metastasize in many cancers.

In one embodiment, the presence of a protease may be detected by the use of a biopolymer coupled to a polymeric resin. For the detection of proteases, the biopolymer may be a protein or peptide. Methods for synthesizing and/or attaching a protein or peptides to a polymeric resin are described, for example, in U.S. Pat. No. 5,235,028 which is incorporated herein by reference. "Proteins" and "peptides" are herein defined as chains of amino acids whose α-carbons are linked through peptide bonds formed by a condensation reaction between the a carboxyl group of one amino acid and the amino group of another amino acid. Peptides also include peptide mimetics such as amino acids joined by an ether as opposed to an amide bond.

The term "protease binding site" as used herein refers to an amino acid sequence that may be recognized and cleaved by a protease. The protease binding site contains a peptide bond that is hydrolyzed by the protease and the amino acid residues joined by this peptide bond are said to form the cleavage site. The protease binding site and conformation determining regions form a contiguous amino acid sequence. The protease binding site may be an amino acid sequence that is recognized and cleaved by a particular protease. It is well known that various proteases may cleave peptide bonds adjacent to particular amino acids. Thus, for example, trypsin cleaves peptide bonds following basic amino acids such as arginine and lysine and chymotrypsin cleaves peptide bonds following large hydrophobic amino acid residues such as tryptophan, phenylalanine, tyrosine and leucine. The serine protease elastase cleaves peptide bonds following small hydrophobic residues such as alanine. A particular protease, however, may not cleave every bond in a protein that has the correct adjacent amino acid. Rather, the proteases may be specific to particular amino acid sequences which serve as protease binding sites for each particular protease. Any amino acid sequence that comprises a protease binding site and may be recognized and cleaved by a protease is a suitable protease receptor. Known protease binding sites and peptide inhibitors of proteases posses amino acid sequences that are recognized by the specific protease they are cleaved by or that they inhibit. Thus known substrate and inhibitor sequences provide the basic sequences suitable for use as a protease receptor. A number of protease substrates and inhibitor sequences suitable for use as protease binding sites are described in U.S. Pat. No. 6,037,137 which is incorporated herein by reference. One of skill will appreciate that the protease substrates listed in U.S. Pat. No. 6,037,137 is not a complete list and that other protease substrates or inhibitor sequences may be used.

Proteases (e.g., botulinum and tetanus toxins) cleave peptide bonds at specific sequence sites on the proteins that "dock" neurotransmitter secretory vesicles to their cellular release sites (FIGS. 45A, 45B). When one or more of these proteins is degraded in this fashion, secretion is blocked and paralysis results (FIG. 45C). It is known that relatively low molecular weight peptides (~15–35 amino acids) based on the normal protein substrates of the botulinum toxins can be rapidly cleaved in solution by a toxin in a manner similar to the full-length protein. Such experiments have been described by Schmidt, J. J.; Stafford, R. G.; Bostian, K. A. "Type A botulinum neurotoxin proteolytic activity: development of competitive inhibitors and implications for substrate specificity at the $S_1$'binding subsite" *FEBS Lett*., 1998, 435, 61–64 and Shone, C. C.; Roberts, A. K. "Peptide substrate specificity and properties of the zinc-endopeptidase activity of botulinum type B neurotoxin" *Eur. J. Biochem*., 1994, 225, 263–270, both of which are incorporated herein by reference as if set forth herein. It has also been demonstrated that these peptide substrates can retain high levels of activity for both botulinum and tetanus toxins even when chemically modified by amino acid substitutions and fluorescence labeling (See also Soleihac, J.-M.; Cornille, F.; Martin, L.; Lenoir, C.; Foumie-Zaluski, M.-C.; Roques, B. P. "A sensitive and rapid fluorescence-based assay for determination of tetanus toxin peptidase activity" *Anal. Biochem*., 1996, 241, 120–127 and Adler, M.; Nicholson, J. D.; Hackley, B. E., Jr. "Efficacy of a novel metalloprotease inhibitor on botulinum neurotoxin B activity" *FEBS Lett*., 1998, 429, 234–238 both of which are incorporated herein by reference).

For newly discovered proteases, or proteases of which the protease recognition sequence is not known, a suitable amino acid sequence for use as the protease binding site may be determined experimentally. The synthesis of libraries of peptides and the use of these libraries to determine a protease binding sequence for a particular protease is described in U.S. Pat. No. 5,834,318 which is incorporated herein by reference. Generally, combinatorial libraries composed of between about 2 to about 20 amino acids may be synthesized. These libraries may be used to screen for an interaction with the protease. Analysis of the sequences that bind to the protease may be used to determine potential binding sequences for use as a receptor for the protease.

The interaction of the receptor with a protease may be indicated by an indicator molecule coupled to the receptor or the polymeric resin. In one embodiment, the indicator may be a chromophore or a fluorophore. A fluorophore is a molecule that absorbs light at a characteristic wavelength and then re-emits the light most typically at a characteristic different wavelength. Fluorophores include, but are not limited to rhodamine and rhodamine derivatives, fluorescein and fluorescein derivatives, coumarins and chelators with the lanthanide ion series. A chromophore is a molecule which absorbs light at a characteristic wavelength, but does not re-emit light.

In one embodiment, a peptide containing the cleavage sequence is immobilized through a covalent or strong non-covalent bond to an addressable site on a sensor array. In one embodiment, this may be accomplished by coupling the peptide to a polymeric resin, as described above. The polymeric resin may be positioned in a cavity of a sensor array, such as the sensor arrays described above. In some embodiments, different peptides containing different cleavage sequences for the various proteases may be immobilized at different array positions. A sample containing one or more proteases may be applied to the array, and peptide cleavage may occur at specific array addresses, depending on the presence of particular proteases. Alternatively, different peptides containing different cleavage sequences may be coupled to a single polymeric bead. In this manner, a single bead may be used to analyze multiple proteases.

A variety of signaling mechanisms for the above described cleavage reactions may be used. In an embodiment, a fluorescent dye and a fluorescence quencher may be coupled to the biopolymer on opposite sides of the cleavage site. The fluorescent dye and the fluorescence quencher may be positioned within the Forster energy transfer radius. The Forster energy transfer radius is defined as the maximum distance between two molecules in which at least a portion of the fluorescence energy emitted from one of the molecules is quenched by the other molecule. Forster energy transfer has been described above. Before cleavage, little or no fluorescence may be generated by virtue of the molecular quencher. After cleavage, the dye and quencher are no longer maintained in proximity of one another, and fluorescence may be detected (FIG. 62A). The use of fluorescence quenching is described in U.S. Pat. No. 6,037,137 which is incorporated herein by reference. Further examples of this energy transfer are described in the following papers, all of which are incorporated herein by reference: James, T. D.; Samandumara, K. R. A.; Iguchi, R.; Shinkai, S. *J. Am. Chem. Soc.* 1995, 117, 8982. Murukami, H.; Nagasaki, T.; Hamachi, I.; Shinkai, S. *Tetrahedron Lett.* 34, 6273. Shinkai, S.; Tsukagohsi, K.; Ishikawa, Y.; Kunitake, T. *J. Chem. Soc. Chem. Commun.* 1991, 1039. Kondo, K.; Shiomi, Y.; Saisho, M.; Harada, T.; Shinkai, S. *Tetrahedron.* 1992, 48, 8239. Shiomi, Y.; Kondo, K.; Saisho, M.; Harada, T.; Tsukagoshi, K.; Shinkai, S. *Supramol. Chem.* 1993, 2, 11. Shiomi, Y.; Saisho, M.; Tsukagoshi, K.; Shinkai, S. *J. Chem. Soc. Perkin Trans I* 1993, 2111. Deng, G.; James, T. D.; Shinkai, S. *J. Am. Chem. Soc.* 1994, 116, 4567. James, T. D.; Harada, T.; Shinkai, S. *J. Chem. Soc. Chem. Commun.* 1993, 857. James, T. D.; Murata, K.; Harada, T.; Ueda, K.; Shinkai, S. *Chem. Lett.* 1994, 273. Ludwig, R.; Harada, T.; Ueda, K.; James, T. D.; Shinkai, S. *J. Chem. Soc. Perkin Trans* 2. 1994, 4, 497. Sandanayake, K. R. A. S.; Shinkai, S. *J. Chem. Soc., Chem. Commun.* 1994, 1083. Nagasaki, T.; Shinmori, H.; Shinkai, S. *Tetrahedron Lett.* 1994, 2201. Murakami, H.; Nagasaki, T.; Hamachi, I.; Shinkai, S. *J. Chem. Soc. Perkin Trans* 2. 1994, 975. Nakashima, K.; Shinkai, S. *Chem. Lett.* 1994, 1267. Sandanayake, K. R. A. S.; Nakashima, K.; Shinkai, S. *J. Chem. Soc.* 1994, 1621. James, T. D.; Sandanayake, K. R. A. S.; Shinkai, S. *J. Chem. Soc., Chem. Commun.* 1994, 477. James, T. D.; Sandanayake, K. R. A. S.; Angew. Chem., Int. Ed. Eng. 1994, 33, 2207. James, T. D.; Sandanayake, K. R. A. S.; Shinkai, S. *Nature,* 1995, 374, 345.

The fluorophores may be linked to the peptide receptor by any of a number of means well known to those of skill in the art. In an embodiment, the fluorophore may be linked directly from a reactive site on the fluorophore to a reactive group on the peptide such as a terminal amino or carboxyl group, or to a reactive group on an amino acid side chain such as a sulfur, an amino, a hydroxyl, or a carboxyl moiety. Many fluorophores normally contain suitable reactive sites. Alternatively, the fluorophores may be derivatized to provide reactive sites for linkage to another molecule. Fluorophores derivatized with functional groups for coupling to a second molecule are commercially available from a variety of manufacturers. The derivatization may be by a simple substitution of a group on the fluorophore itself, or may be by conjugation to a linker. Various linkers are well known to those of skill in the art and are discussed below.

The fluorogenic protease indicators may be linked to a solid support directly through the fluorophores or through the peptide backbone comprising the indicator. In embodiments where the indicator is linked to the solid support through the peptide backbone, the peptide backbone may comprise an additional peptide spacer. The spacer may be present at either the amino or carboxyl terminus of the peptide backbone and may vary from about 1 to about 50 amino acids, preferably from 1 to about 20 and more preferably from 1 to about 10 amino acids in length. The amino acid composition of the peptide spacer is not critical as the spacer just serves to separate the active components of the molecule from the substrate thereby preventing undesired interactions. However, the amino acid composition of the spacer may be selected to provide amino acids (e.g. a cysteine or a lysine) having side chains to which a linker or the solid support itself, is easily coupled. Alternatively the linker or the solid support itself may be attached to the amino terminus of or the carboxyl terminus.

In an embodiment, the peptide spacer may be joined to the solid support by a linker. The term "linker", as used herein, refers to a molecule that may be used to link a peptide to another molecule, (e.g. a solid support, fluorophore, etc.). A linker is a hetero or homobifunctional molecule that provides a first reactive site capable of forming a covalent linkage with the peptide and a second reactive site capable of forming a covalent linkage with a reactive group on the solid support. Linkers as use din these embodiments are the same as the previously described linkers.

Figure 62A:
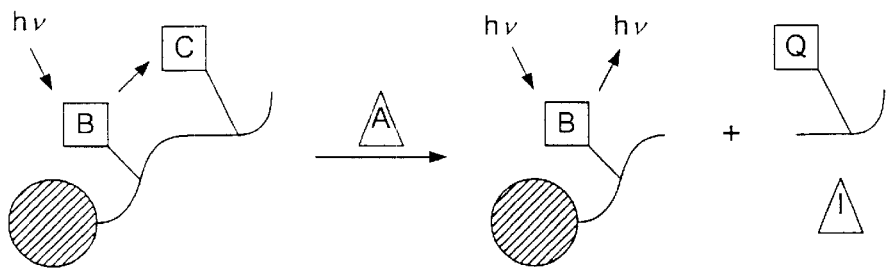
FIGS. 62A–D depict various sensing protocols for receptor-indicator-polymeric resin particles in which a cleavage reaction occurs.
Figure 62B:
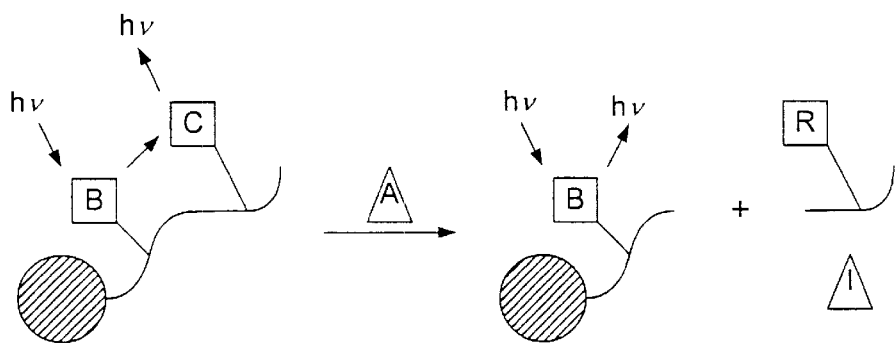

In an embodiment, a first fluorescent dye and a second fluorescent dye may be coupled to the biopolymer on opposite sides of the cleavage site. Before cleavage, a FRET (fluorescence resonance energy transfer) signal may be observed as a long wavelength emission. After cleavage, the change in the relative positions of the two dyes may cause a loss of the FRET signal and an increase in fluorescence from the shorter-wavelength dye (FIG. 62B). Examples of solution phase FRET have been described in Forster, Th. "Transfer Mechanisms of Electronic Excitation:, *Discuss. Faraday Soc.*, 1959, 27, 7; Khanna, P. L., Ullman, E. F. "4',5'-Dimethoxyl-6-carboxyfluorescein: A novel dipole-dipole coupled fluorescence energy transfer acceptor useful for fluorescence immunoassays", *Anal. Biochem.* 1980, 108, 156; and Morrison, L. E. "Time resolved Detection of Energy Transfer: Theory and Application to Immunoassays", *Anal. Biochem.* 1998, 174, 101, all of which are incorporated herein by reference.

Figure 62C:
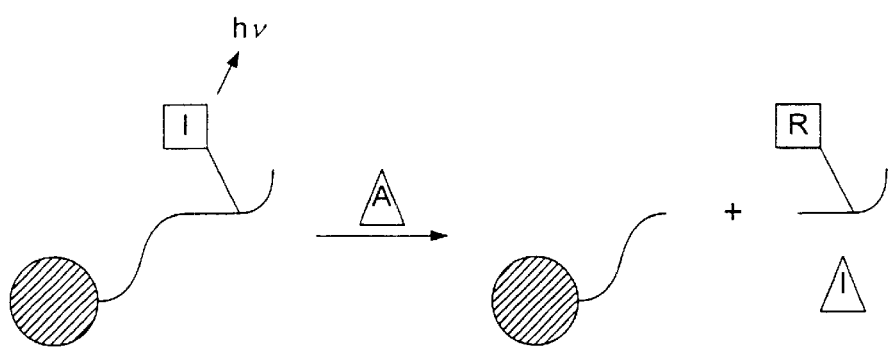

In another embodiment, a single fluorescent dye may be coupled to the peptide on the opposite side of the cleavage site to the polymeric resin. Before cleavage, the dye is fluorescent, but is spatially confined to the attachment site. After cleavage, the peptide fragment containing the dye may diffuse from the attachment site (e.g., to positions elsewhere in the cavity) where it may be measured with a spatially sensitive detection approach, such as confocal microscopy (FIG. 62C). Alternatively, the solution in the cavities may be flushed from the system. A reduction in the fluorescence of the particle would indicate the presence of the analyte (e.g., a protease).

In another embodiment, a single indicator (e.g., a chromophore or a fluorophore) may be coupled to the peptide receptor on the side of the cleavage site that remains on the polymeric resin or to the polymeric resin at a location proximate to the receptor. Before cleavage the indicator may produce a signal that reflects the microevironment determined by the interaction of the receptor with the indicator. Hydrogen bonding or ionic substituents on the indicator involved in analyte binding have the capacity to change the electron density and/or rigidity of the indicator, thereby changing observable spectroscopic properties such as fluorescence quantum yield, maximum excitation wavelength, or maximum emission wavelength for fluorophores or absorption spectra for chromophores. When the peptide receptor is cleaved, the local pH and dielectric constants of the beads change, and the indicator may respond in a predictable fashion. An advantage to this approach is that it does not require the dissociation of a preloaded fluorescent ligand (limited in response time by $k_{off}$). Furthermore, several different indicators may be used with the same receptor. Different beads may have the same receptors but different indicators, allowing for multiple testing for the presence of proteases. Alternatively, a single polymeric resin may include multiple dyes along with a single receptor. The interaction of each of these dyes with the receptor may be monitored to determine the presence of the analyte.

Nucleases represent a number of families of enzymes that catalytically hydrolyze the phosphodiester bonds of nucleic acids. Nucleases may be classified according to the nucleic acid that they are specific for. Ribonucleases ("RNases") are specific for ribonucleic acids while deoxyribonucleases ("DNases") are specific for deoxyribonucleic acids. Some enzymes will hydrolyze both ribonucleic acids and deoxyribonucleic acids. Nucleases may also be classified according to their point of attack upon the nucleic acid. Nucleases that attack the polymer at either the 3' terminus or the 5' terminus are known as exonucleases. Nucleases that attack the nucleic acid within the chain are called endonucleases.

Restriction enzymes recognize short polynucleotide sequences and cleave double-stranded nucleic acids at specific sites within or adjacent to these sequences. Approximately 3,000 restriction enzymes, recognizing over 230 different nucleic acid sequences, are known. They have been found mostly in bacteria, but have also been isolated from viruses, archaea and eukaryotes. Because many of these restriction enzymes are only found in a particular organism, nucleic acids may be used as a receptor to determine if a particular organism is present in a sample by analyzing for restriction enzymes. Restriction endonucleases specifically bind to nucleic acids only at a specific recognition sequence that varies among restriction endonucleases. Since restriction enzymes only cut nucleic acids in the vicinity of the recognition sequence, a receptor may be designed that includes the recognition sequence for the nuclease being investigated.

Most nucleases bind to and act on double stranded deoxyribonucleic acid ("DNA"). Restriction endonucleases are typically symmetrical dimers. Each monomeric unit binds to one strand of DNA and recognizes the first half the DNA recognition sequence. Each monomer also typically cuts one strand of DNA. Together, the dimer recognizes a palindromic DNA sequence and cuts both strands of DNA symmetrically about the central point in the palindromic sequence. Typically, each monomer of the restriction endonucleases needs at least two specific nucleotides that it recognizes, though in a few cases a restriction endonuclease monomer only needs to bind to one specific nucleotide and two others with less specificity. This means that restriction endonucleases may recognize a sequence of 4 nucleotides at a minimum, and generally recognize sequences that contain an even number of nucleotides (since the same sites are recognized by each monomer. Restriction endonucleases are known that recognize 4, 6, or 8 nucleotides, with only a few 8-cutters known. Some restriction endonucleases bind to recognition sequences that have an odd number of nucleotides (typically this is 5 or 7) with the central nucleotide specifically recognized or with some or strict specificity for a central base pair. The origin and sequence specificity of hundreds of restriction endonucleases are known and can be found from catalogs available from New England Biolabs, Boston, Mass.; Life Technologies, Rockville, Md.; Promega Scientific, Madison, Wis., Rouche Molecular Biochemicals, Indianapolis, Ind.

In one embodiment, the presence of a nuclease may be detected by the use of a polynucleotide coupled to a polymeric resin. For the detection of nucleases, the polynucleotide may be a double stranded deoxyribonucleic acid or a ribonucleic acid. Methods for synthesizing and/or attaching a polynucleotide to a polymeric resin are described, for example, in U.S. Pat. No. 5,843,655 which is incorporated herein by reference. "Polynucleotides" are herein defined as chains of nucleotides. The nucleotides are linked to each other by phosphodiester bonds. "Deoxyribonucleic acid" is composed of deoxyribonucleotide residues, while "Ribonucleic acid" is composed of ribonucleotide residues.

The term "nuclease binding site" as used herein refers to a polynucleotide sequence that may be recognized and cleaved by a nuclease. The nuclease binding site contains a phosphodiester bond that is cleaved by the nuclease and the polynucleotide residues joined by this phosphodiester bond are said to form the cleavage site.

For newly discovered nucleases, or nucleases of which the nuclease recognition sequence is not known, a suitable polynucleotide sequence for use as the nuclease binding site may be determined experimentally. Generally, combinatorial libraries of polynucleotides composed of between about 2 to about 20 nucleotides may be synthesized. The synthesis of such libraries is described, for example, in U.S. Pat. No. 5,843,655 which is incorporated herein by reference. These libraries may be used to screen for an interaction with the nuclease. Analysis of the sequences that bind to the nuclease may be used to determine potential binding sequences for use as a receptor for the nuclease.

The interaction of the receptor with a nuclease may be indicated by an indicator molecule coupled to the receptor or the polymeric resin. In one embodiment, the indicator may be a chromophore or a fluorophore.

In one embodiment, a polynucleotide containing the nuclease binding sequence is immobilized through a covalent or strong non-covalent bond to an addressable site on a sensor array. In one embodiment, this may be accomplished by coupling or synthesizing the polynucleotide on a polymeric resin, as described above. The polymeric resin may be positioned in a cavity of a sensor array, such as the sensor arrays described above. In some embodiments, different polynucleotides containing different cleavage sequences for the various nucleases may be immobilized at different array positions. A sample containing one or more nucleases may be applied to the array, and polynucleotide cleavage may occur at specific array addresses, depending on the presence of particular nucleases. Alternatively, different polynucleotides containing different cleavage sequences may be coupled to a single polymeric bead. In this manner, a single bead may be used to analyze multiple nucleases.

A variety of signaling mechanisms for the above described cleavage reactions may be used. In an embodiment, a fluorescent dye and a fluorescence quencher may be coupled to the polynucleotide on opposite sides of the cleavage site. The fluorescent dye and the fluorescence quencher may be positioned within the Forster energy transfer radius. Before cleavage, little or no fluorescence may be generated by virtue of the molecular quencher. After cleavage, the dye and quencher are no longer maintained in proximity of one another, and fluorescence may be detected (FIG. 62A).

The fluorophores may be linked to the polynucleotide receptor by any of a number of means well known to those of skill in the art. Examples of methods of attaching fluorophores and dyes to polynucleotides are described in U.S. Pat. Nos. 4,855,225; 5,188,934, and 5,366,860 all of which are incorporated herein by reference.

In another embodiment, a first fluorescent dye and a second fluorescent dye may be coupled to the polynucleotide receptor on opposite sides of the cleavage site. Before cleavage, a FRET (fluorescence resonance energy transfer) signal may be observed as a long wavelength emission. After cleavage, the change in the relative positions of the two dyes may cause a loss of the FRET signal and an increase in fluorescence from the shorter-wavelength dye (FIG. 62B).

In another embodiment, a single fluorescent dye may be coupled to the polynucleotide receptor on the opposite side of the cleavage site to the polymeric resin. Before cleavage, the dye is fluorescent, but is spatially confined to the attachment site. After cleavage, the nucleic acid fragment containing the dye may diffuse from the attachment site (e.g., to positions elsewhere in the cavity) where it may be measured with a spatially sensitive detection approach, such as confocal microscopy (FIG. 62C). Alternatively, the solution in the cavities may be flushed from the system. A reduction in the fluorescence of the particle would indicate the presence of the analyte (e.g., a nuclease).

Figure 62D:
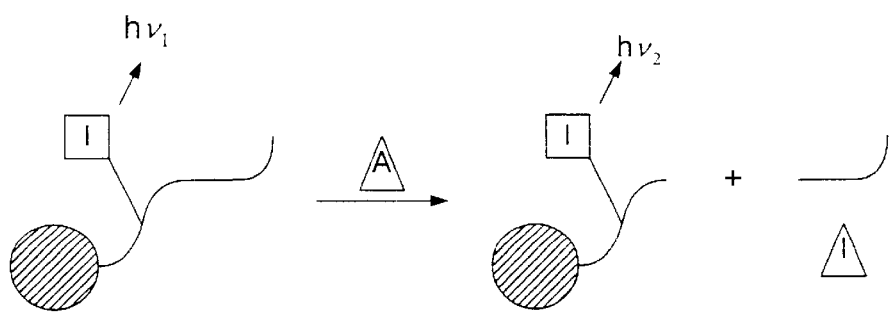

In another embodiment, depicted in FIG. 62D, a single indicator (e.g., a chromophore or a fluorophore) may be coupled to the polynucleotide receptor on the side of the cleavage site that remains on the polymeric resin or to the polymeric resin at a location proximate to the polynucleotide receptor. Before cleavage the indicator may produce a signal that reflects the microevironment determined by the interaction of the receptor with the indicator. Hydrogen bonding or ionic substituents on the indicator involved in analyte binding have the capacity to change the electron density and/or rigidity of the indicator, thereby changing observable spectroscopic properties such as fluorescence quantum yield, maximum excitation wavelength, or maximum emission wavelength for fluorophores or absorption spectra for chromophores. When the polynucleotide receptor is cleaved, the local pH and dielectric constants of the beads change, and the indicator may respond in a predictable fashion. An advantage to this approach is that it does not require the dissociation of a preloaded fluorescent ligand (limited in response time by $k_{off}$). Furthermore, several different indicators may be used with the same receptor. Different beads may have the same receptors but different indicators, allowing for multiple testing for the presence of nucleases. Alternatively, a single polymeric resin may include multiple dyes along with a single receptor. The interaction of each of these dyes with the receptor may be monitored to determine the presence of the analyte.

In another embodiment, polynucleotide receptors may be used to determine the presence of other types of analytes. It some instances, polynucleotide receptors will bind to small organic molecules. These small organic molecules may disrupt the action of nucleases upon the polynucleotide receptor. Typically, the small molecules will occupy the preferred binding site of the nuclease, inhibiting the action of the nuclease on the polynucleotide. Thus the presence of a small organic molecule, which is known to bind to a specific polynucleotide, may be detected by the observation of reduced nuclease activity at the specific polynucleotide. An analogous methodology may be applied to a peptide-protease reaction.

In another embodiment, oligosaccharides may also be used to determine the presence of analytes. In a system similar to those described above for peptides and polynucleotides, oligosaccharides may be coupled to a polymeric resin. In the presence of oligosaccharide cleaving agents (e.g., enzymes such as amylase, an enzyme that cleaves a long saccharide polymer and disaccharide cleaving enzymes such as invertase, β-galactosidase, and lactase, to name a few) the oligosaccharide may be cleaved. The cleavage of the oligosaccharide may be used to generate a signal. Methods for synthesizing and/or attaching oligosaccharides to a polymeric resin are described, for example, in U.S. Pat. Nos. 5,278,303 and 5,616,698 which are incorporated herein by reference.

In another embodiment, an analyte may cause a change to a biopolymer, but not necessarily cleavage of the biopolymer, when the analyte interacts with the biopolymer. The induced change may cause a detectable signal to be generated. Typically, the binding or association ability of an indicator molecule with a biopolymer is dependent upon the structure of the biopolymer. If the structure of the biopolymer is altered, the association of an indicator molecule may be significantly altered. Such a change may be accompanied by a change in the signal produced by the indicator. For biopolymers many different types of enzymes may induce a variety of structural changes to the biopolymer which may alter the binding site of an associated indicator molecule. Such changes may occur without cleavage of the biopolymer.

Alternatively, an indicator and a biopolymer may be coupled to a polymeric bead. The biopolymer may undergo a chemical reaction in the presence of an analyte. This chemical reaction may also induce a change in the chemical structure of the indicator. The change in the chemical structure of the indicator may lead to a detectable change in the optical properties of the particle, signaling the presence of the analyte.

In one example, NAD and glucose may be coupled to a polymeric bead. This system may be used to detect the presence of an carbohydrate modifying enzyme. For example, the system may be used to detect the presence of glucose dehydrogenase. In the presence of glucose dehydrogenase, glucose may be consumed, and in the process would convert the coupled NAD into NADH. NADH has both different UV absorbance and different fluorescence properties from NAD. These differences may be used to signal the presence of glucose dehydrogenase in a fluid sample. Many other types of enzymes may be detected in a similar manner.

Figure 63:
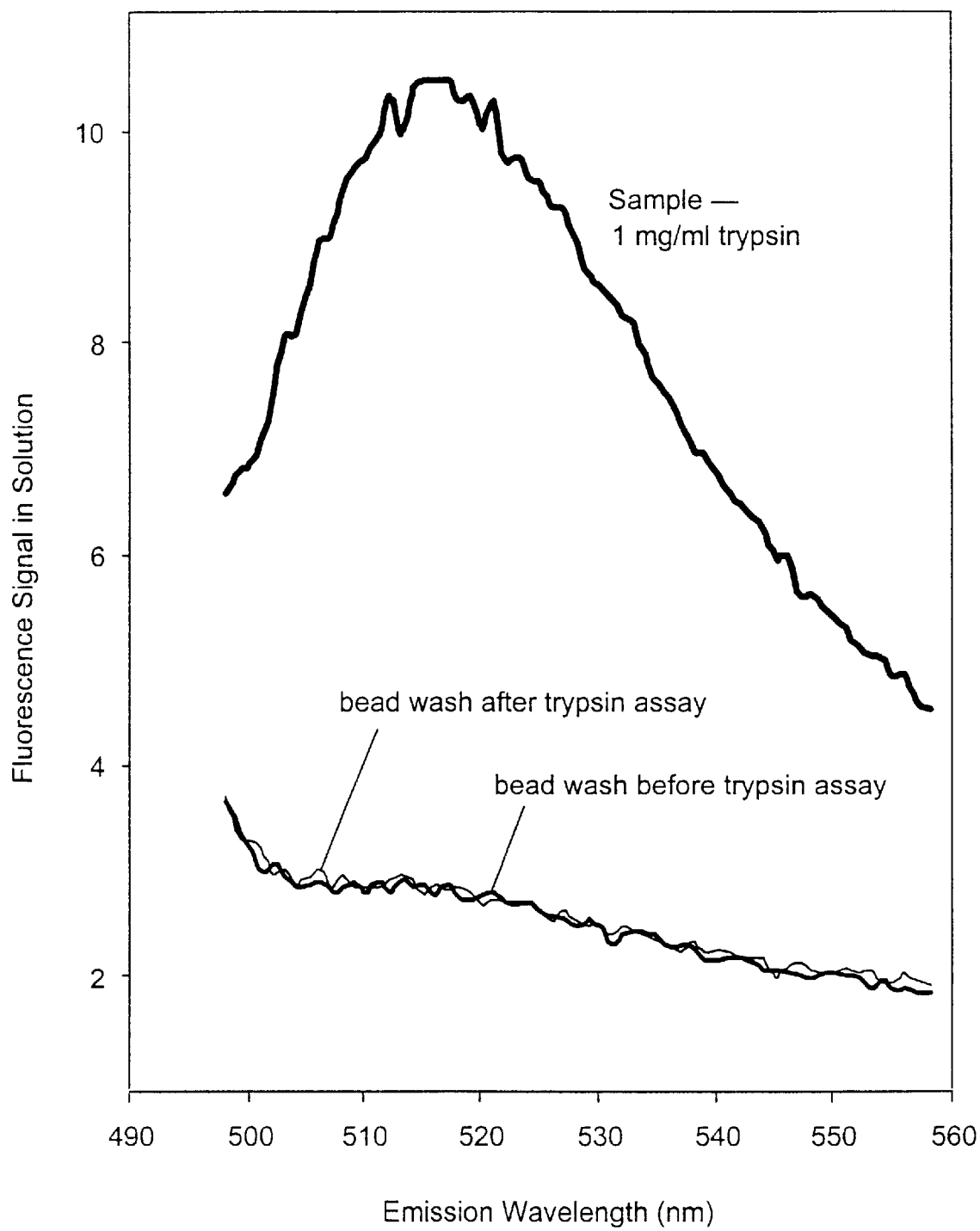
FIG. 63 depicts a plot of the fluorescence signal of a chemically sensitive particle in the presence of trypsin.

In an example, the protease trypsin was analyzed using an immobilized "sacrificial receptor" that is cleaved by trypsin, an event that results in modulation of a fluorescence signal. In an embodiment of a protease assay, a peptide that may be cleaved between two amino acids by the enzyme trypsin was immobilized. This immobilization was accomplished by first conjugating many streptavidin molecules to aldehyde-activated 6% agarose beads using a reductive amination procedure. A biotin chemical group attached to the amino-terminus of the peptide was strongly bound by the immobilized streptavidin molecules, thereby immobilizing the peptide chains. A fluorescein group was attached to the carboxyl-terminus of the peptide, thereby making the bead highly fluorescent. Importantly, the immobilized peptide contains a cleavage site recognized by trypsin between the biotin attachment site and the fluorescein, so that exposure of the bead to trypsin analyte causes release of fluorescent peptide fragments from the bead. This release may be visualized either as a decrease in the fluorescence at the bead, or by an increase in the fluorescence of the surrounding solution (see FIG. 63).

Transmitting Chemical Information Over a Computer Network

Herein we describe a system and method for the collection and transmission of chemical information over a computer network. The system, in some embodiments, includes an analyte detection device ("ADD") operable to detect one or more analytes or mixtures of analytes in a fluid containing one or more analytes, and computer hardware and software operable to send and receive data over a computer network to and from a client computer system.

Chemical information refers to any data representing the detection of a specific chemical or a combination of chemicals. These data may include, but are not limited to chemical identification, chemical proportions, or various other forms of information related to chemical detection. The information may be in the form of raw data, including binary or alphanumeric, formatted data, or reports. In some embodiments, chemical information relates to data collected from an analyte detection device. Such data includes data related to the color of the particles included on the analyte detection device. The chemical information collected from the analyte detection device may include raw data (e.g., a color, RBG data, intensity at a specific wavelength) etc. Alternatively the data may be analyzed by the analyte detection device to determine the analytes present. The chemical information may include the identities of the analytes detected in the fluid sample. The information may be encrypted for security purposes.

In one embodiment, the chemical information may be in Logical Observation Identifiers Names and Codes (LOINC) format. The LOINC format provides a standard set of universal names and codes for identifying individual laboratory results (e.g. hemoglobin, serum sodium concentration), clinical observations (e.g. discharge diagnosis, diastolic blood pressure) and diagnostic study observations, (e.g. PR-interval, cardiac echo left ventricular diameter, chest x-ray impression).

More specifically, chemical information may take the form of data collected by the analyte detection system. As described above, an analyte detection system may include a sensor array that includes a particle or particles. These particles may be configured to produce a detectable signal in response to the presence or absence of an analyte. The signal may be detected using a detector. The detector may detect the signal. The detector may also produce an output signal that contains information relating to the detected signal. The output signal may, in some embodiments be the chemical information.

In some embodiments, the detector may be a light detector and the signal produced by the particles may be modulated light. The detector may produce an output signal that is representative of the detected light modulation. The output signal may be representative of the wavelength of the light signal detected. Alternatively, the output signal may be representative of the strength of the light signal detected. In other embodiments, the output signal may include both wavelength and strength of signal information.

In some embodiments, use of a light source may not be necessary. The particles may rely on the use of chemiluminescence, thermoluminescence or piezoluminescence to provide a signal. In the presence of an analyte of interest, the particle may be activated such that the particles produce light. In the absence of an analyte, the particles may not exhibit produce minimal or no light. The chemical information may, therefore, be related to the detection or absence of a light produced by the particles, rather than modulated by the particles.

The detector output signal information may be analyzed by analysis software. The analysis software may be configured to convert the raw output data to chemical information that is representative of the analytes in the analyzed fluid system. The chemical information may be either the raw data before analysis by the computer software or the information generated by processing of the raw data.

The term "computer system" as used herein generally describes the hardware and software components that in combination allow the execution of computer programs. The computer programs may be implemented in software, hardware, or a combination of software and hardware. Computer system hardware generally includes a processor, memory media, and input/output (I/O) devices. As used herein, the term "processor" generally describes the logic circuitry that responds to and processes the basic instructions that operate a computer system. The term "memory medium" includes an installation medium, e.g., a CD-ROM, floppy disks; a volatile computer system memory such as DRAM, SRAM, EDO RAM, Rambus RAM, etc.; or a non-volatile memory such as optical storage or a magnetic medium, e.g., a hard drive. The term "memory" is used synonymously with "memory medium" herein. The memory medium may comprise other types of memory or combinations thereof. In addition, the memory medium may be located in a first computer in which the programs are executed, or may be located in a second computer that connects to the first computer over a network. In the latter instance, the second computer provides the program instructions to the first computer for execution. In addition, the computer system may take various forms, including a personal computer system, mainframe computer system, workstation, network appliance, Internet appliance, personal digital assistant (PDA), television system or other device. In general, the term "computer system" can be broadly defined to encompass any device having a processor that executes instructions from a memory medium.

The memory medium preferably stores a software program or programs for the reception, storage, analysis, and transmittal of information produced by an Analyte Detection Device (ADD). The software program(s) may be implemented in any of various ways, including procedure-based techniques, component-based techniques, and/or object-oriented techniques, among others. For example, the software program may be implemented using ActiveX controls, C++ objects, JavaBeans, Microsoft Foundation Classes (MFC), or other technologies or methodologies, as desired. A central processing unit (CPU), such as the host CPU, for executing code and data from the memory medium includes a means for creating and executing the software program or programs according to the methods, flowcharts, and/or block diagrams described below.

A computer system's software generally includes at least one operating system such as Windows NT, Windows 95, Windows 98, or Windows ME (all available from Microsoft Corporation); or Mac OS and Mac OS X Server (Apple Computer, Inc.), MacNFS (Thursby Software), PC MACLAN (Miramar Systems), or real time operating systems such as VXWorks (Wind River Systems, Inc.), QNX (QNX Software Systems, Ltd.), etc. The foregoing are all examples of specialized software programs that manage and provide services to other software programs on the computer system. Software may also include one or more programs to perform various tasks on the computer system and various forms of data to be used by the operating system or other programs on the computer system. Software may also be operable to perform the functions of an operating system (OS). The data may include but is not limited to databases, text files, and graphics files. A computer system's software generally is stored in non-volatile memory or on an installation medium. A program may be copied into a volatile memory when running on the computer system. Data may be read into volatile memory as the data is required by a program.

A server program may be defined as a computer program that, when executed, provides services to other computer programs executing in the same or other computer systems. The computer system on which a server program is executing may be referred to as a server, though it may contain a number of server and client programs. In the client/server model, a server program awaits and fulfills requests from client programs in the same or other computer systems. Examples of computer programs that may serve as servers include: Windows NT (Microsoft Corporation), Mac OS X Server (Apple Computer, Inc.), MacNFS (Thursby Software), PC MACLAN (Miramar Systems), etc.

A web server is a computer system which maintains a web site browsable by any of various web browser software programs. As used herein, the term 'web browser' refers to any software program operable to access web sites over a computer network.

An intranet is a network of networks that is contained within an enterprise. An intranet may include many interlinked local area networks (LANs) and may use data connections to connect LANs in a wide area network (WAN). An intranet may also include connections to the Internet. An intranet may use TCP/IP, HTTP, and other Internet protocols.

An extranet, or virtual private network, is a private network that uses Internet protocols and public telecommunication systems to securely share part of a business' information or operations with suppliers, vendors, partners, customers, or other businesses. An extranet may be viewed as part of a company's intranet that is extended to users outside the company. An extranet may require security and privacy. Companies may use an extranet to exchange large volumes of data, share product catalogs exclusively with customers, collaborate with other companies on joint development efforts, provide or access services provided by one company to a group of other companies, and to share news of common interest exclusively with partner companies.

Connection mechanisms included in a network may include copper lines, optical fiber, radio transmission, satellite relays, or any other device or mechanism operable to allow computer systems to communicate.

As used herein, ADD refers to any device or instrument operable to detect one or more specific analytes or mixtures of analytes in a fluid sample, wherein the fluid sample may be liquid, gaseous, solid, a suspension of a solid in a gas, or a suspension of a liquid in a gas. More particularly, an ADD includes a sensor array, light and detector as is described herein.

Figure 64:
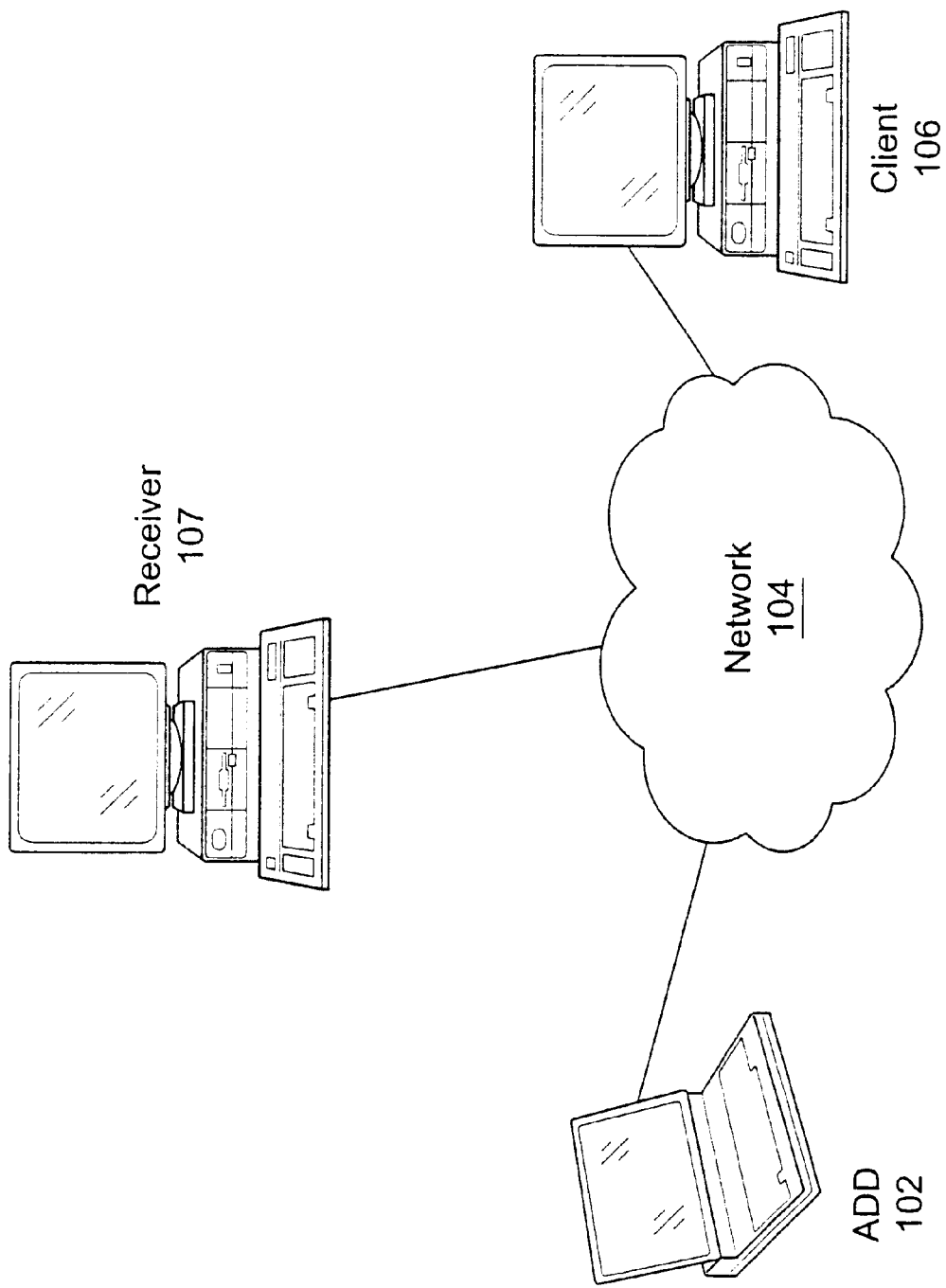
FIG. 64 depicts a block diagram illustrating a system for collecting and transmitting chemical information over a computer network.

As illustrated in FIG. 64, an ADD 102 is operable to analyze a fluid sample and detect one or more analytes in the sample, producing output data specifying the results of the detection process. ADD 102 may be operable to connect to a computer network 104, such as the Internet. As used herein, "computer network" may refer to any type of intranet or extranet network which connects computers and/or networks of computers together, thereby providing connectivity between various systems for communication there between, using various network communication protocols, such as TCP/IP, FTP, HTTP, HTTPS, etc. ADD 102 may execute software to communicate with other computer systems connected to network 104.

A client computer 106 may also be connected to network 104. The client system 106 may be a computer system, network appliance, Internet appliance, personal digital assistant (PDA) or other system. Client computer system 106 may execute software to communicate with ADD 102, thus facilitating transmission of chemical data from the ADD 102 to client computer system 106 and vice versa.

In one embodiment, the ADD may execute software operable to transmit chemical data via any of various communication protocols over the network to one or more recipient client computer systems and to receive responses from the recipient client computers. These protocols may include, but are not limited to, TCP/IP, FTP, HTTP, and HTTPS. As stated above, the chemical information may be encrypted for security purposes.

Figure 65:
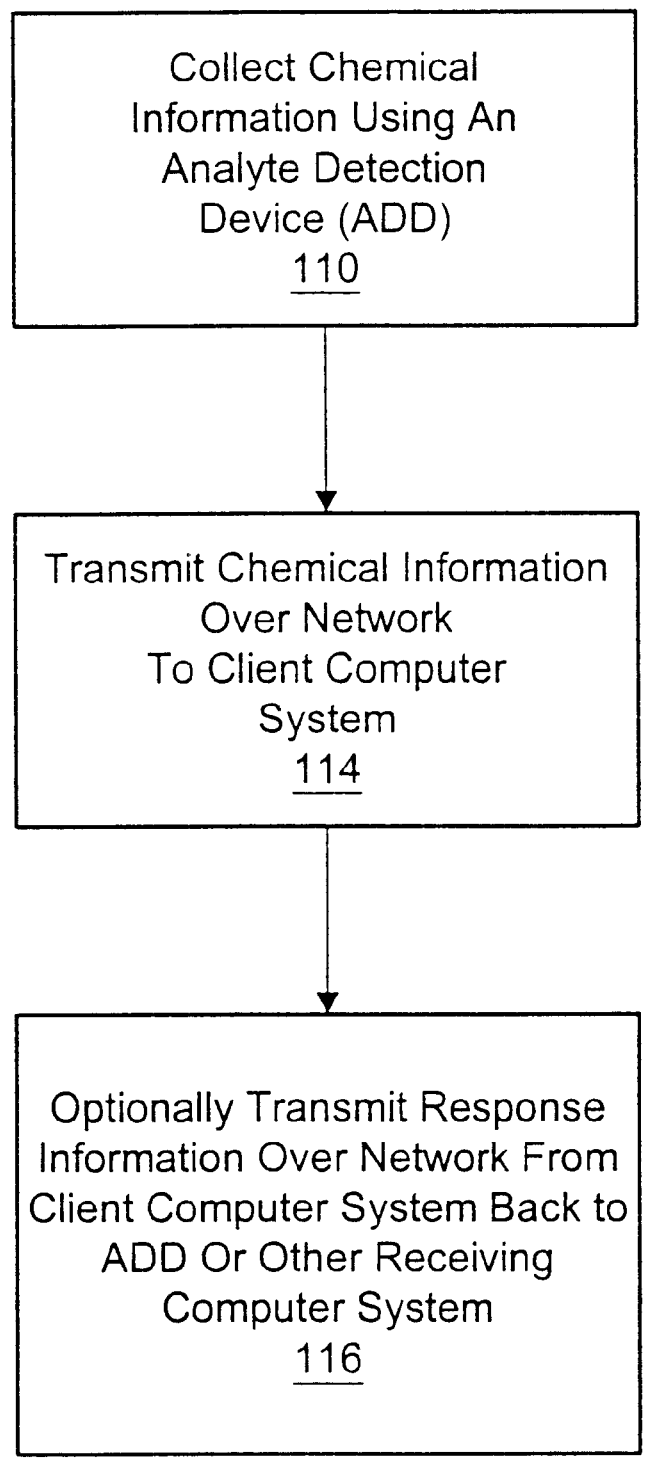
FIG. 65 depicts a flowchart of a method for collecting and transmitting chemical information over a computer network.

As FIG. 65 illustrates, in step 110 an ADD 102 may be used to analyze a chemical sample and detect one or more particular analytes or combinations of analytes, producing output data comprising the results of the detection process. As stated above, this information may be in a variety of forms and formats, including binary, alphanumeric, reports, etc. In one embodiment, the ADD is configured to detect optical signals produced by the reaction of the analyte with a sensor array of particles. The optical signals may be converted to output data representative of the optical signal.

In step 112 the chemical information may be transmitted over network 104 to one or more client computer systems 106 using any of a variety of network communication protocols as described herein.

In step 114 one or more client computer systems 106 may each optionally transmit a response back to ADD 102. The response may include, but is not limited to, a request for additional information, a confirmation of received data, or a transmittal of chemical information back to the ADD.

Some embodiments of the ADD include a light source, a sensor array, and a detector. The sensor array, in some embodiments, is formed of a supporting member which is configured to hold a variety of chemically sensitive particles (herein referred to as "particles") in an ordered array. The particles are, in some embodiments, elements which will create a detectable signal in the presence of an analyte. The particles may produce optical (e.g., absorbance or reflectance) or fluorescence/phosphorescent signals upon exposure to an analyte. Examples of particles include, but are not limited to, functionalized polymeric beads. The particles may include a receptor molecule coupled to a polymeric bead. The receptors, in some embodiments, are chosen for interacting with analytes. The interaction may take the form of a binding/association of the receptors with the analytes. The supporting member may be made of any material capable of supporting the particles, while allowing the passage of the appropriate wavelengths of light. The supporting member may include a plurality of cavities. The cavities may be formed such that at least one particle is substantially contained within the cavity. Upon contact of the beads with a fluid sample, a detectable optical signal may be generated by the receptor molecules' reactions with the one or more analytes in the sample.

Figure 66:
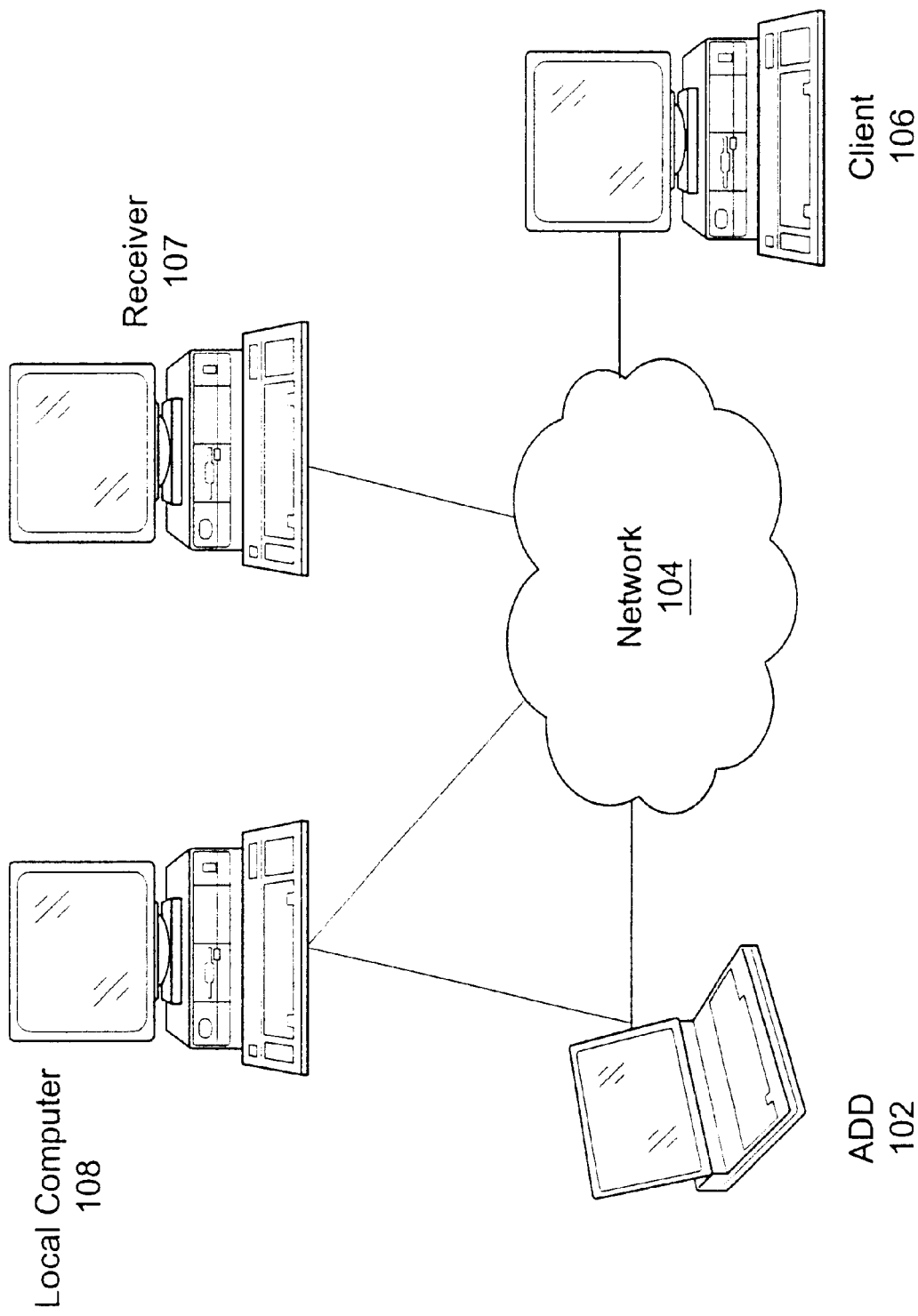
FIG. 66 depicts a block diagram illustrating a system for collecting and transmitting chemical information over a computer network.

In an alternate form of the invention, ADD 102 may be operable to upload chemical data directly to a local computer system 108, for example, by a communications link such as a serial data connection, wireless data link, modem, floppy drive, etc., as depicted in FIG. 66. Local computer system 108 may be connected to the computer network 104, as may be client computer system 106. The local computer system 108 may have software executable to transmit chemical information to the client computer system 106 and to receive response information back from the client computer system 106, and client computer system 106 may have software executable to receive chemical information and to transmit a response back to local computer system 108 or to one or more receiving computer systems 107.

Figure 67:
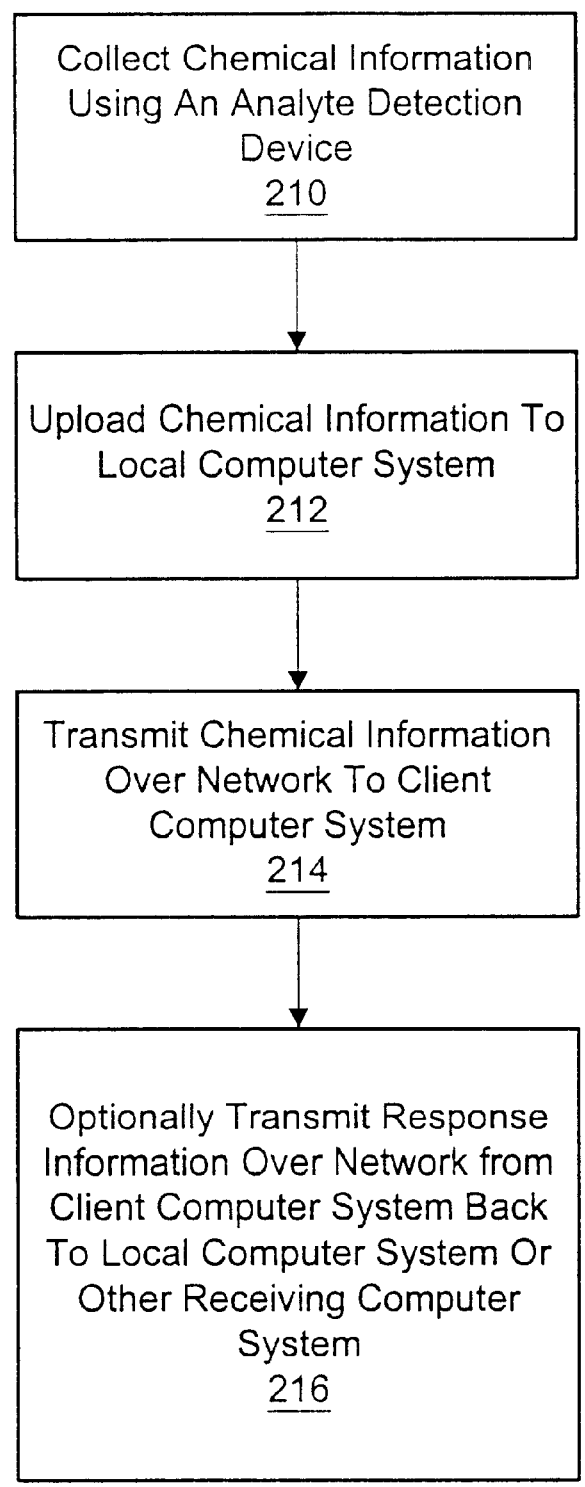
FIG. 67 depicts a flowchart of a method for collecting and transmitting chemical information over a computer network.

As FIG. 67 illustrates, in step 210 an ADD 102 may be used to analyze a chemical sample and detect one or more particular analytes or combinations of analytes, producing output data comprising the results of the detection process.

In step 212 chemical information may be uploaded to a local computer system 108, such as by a communication link as described above. Local computer system 108 is connected to the network 104 and may use a software program executable to transmit the chemical information over network 104.

As shown in step 214, the chemical information may be transmitted over network 104 to one or more client computer systems 106 using any of a variety of network communication protocols, such protocols being familiar to one skilled in the network communication art.

In step 216 client computer system 106 may optionally transmit a response back to local computer system 106 over network 104, or to one or more receiving computer systems 107.

Figure 68:
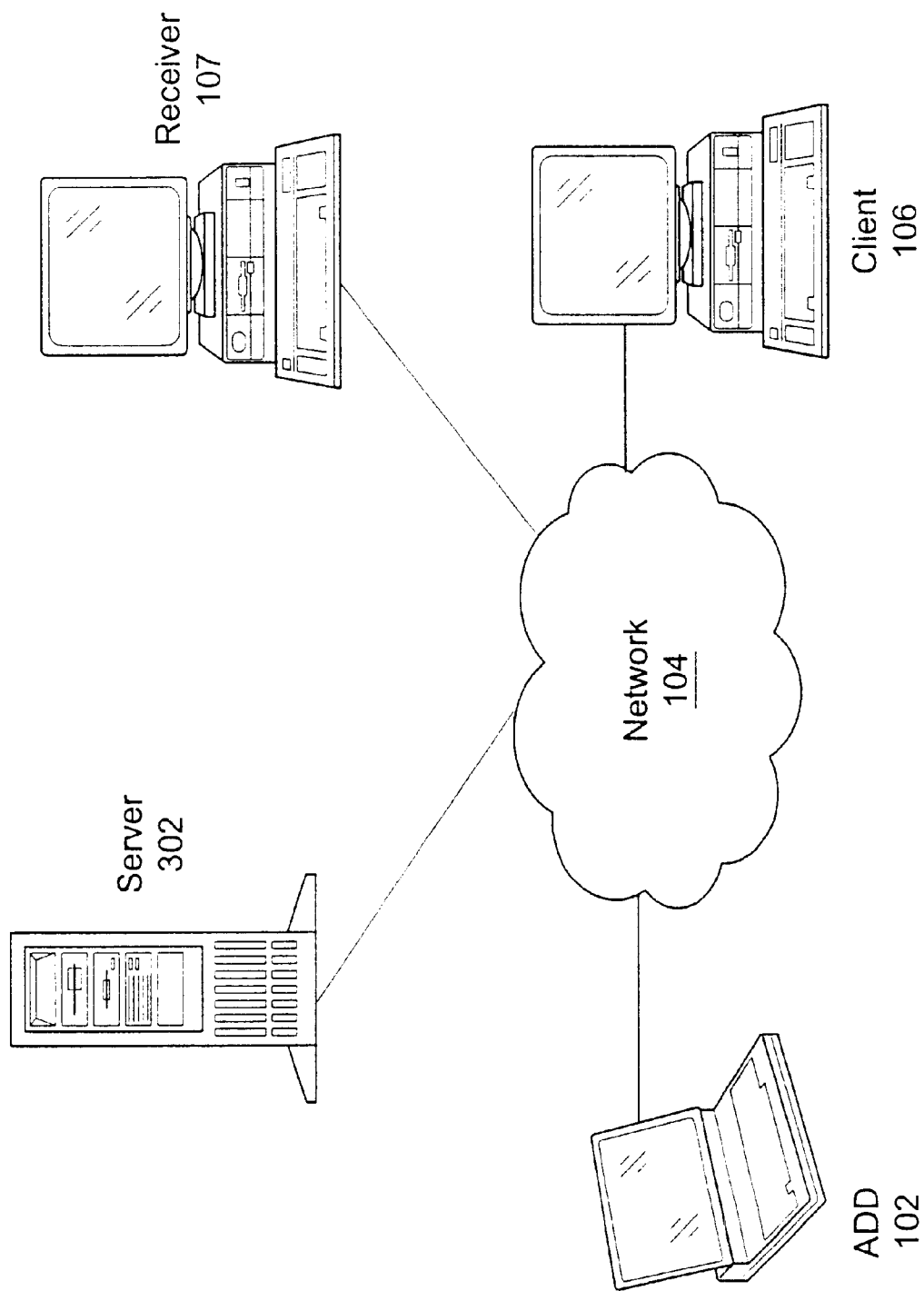
FIG. 68 depicts a block diagram illustrating a system for collecting and transmitting chemical information over a computer network.

As shown in FIG. 68, ADD 102 may connect to a server 302, either directly, as with a communication link, or remotely, via computer network 104. The server 302 is operable to receive and store the chemical information, and to make the chemical information available to client computer systems 106 also connected to network 104. The server 302 may be any of a variety of servers. For example, server 302 may be a web server, wherein the server is operable to maintain a web site, accessible by client computer systems 106 with browser software. The user of client computer system 106 may view and/or download the chemical information from server 302 using the browser software. As another example, the server may be an FTP server, in which case the user of client computer system 106 may be able to transfer the chemical information from server 302 to client computer system 106 using an FTP software program. As yet another example, server 302 may allow remote login to an account by client computer system 106, wherein the account has been established for use by the user of client computer system. The user of client computer system 106 may then view, edit, or transfer the chemical information as needed. Client computer system 106 may then optionally transmit a response back to server 302, which may then be accessed by the ADD. Client computer system 106 may also transmit the response information to one or more additional client computer systems 107. In all of these embodiments, security measures may be employed to protect the identity of the users, as well as the privacy and integrity of the information. Such security measures may include secure login, encryption, private communication lines, and other security measures.

Figure 69:
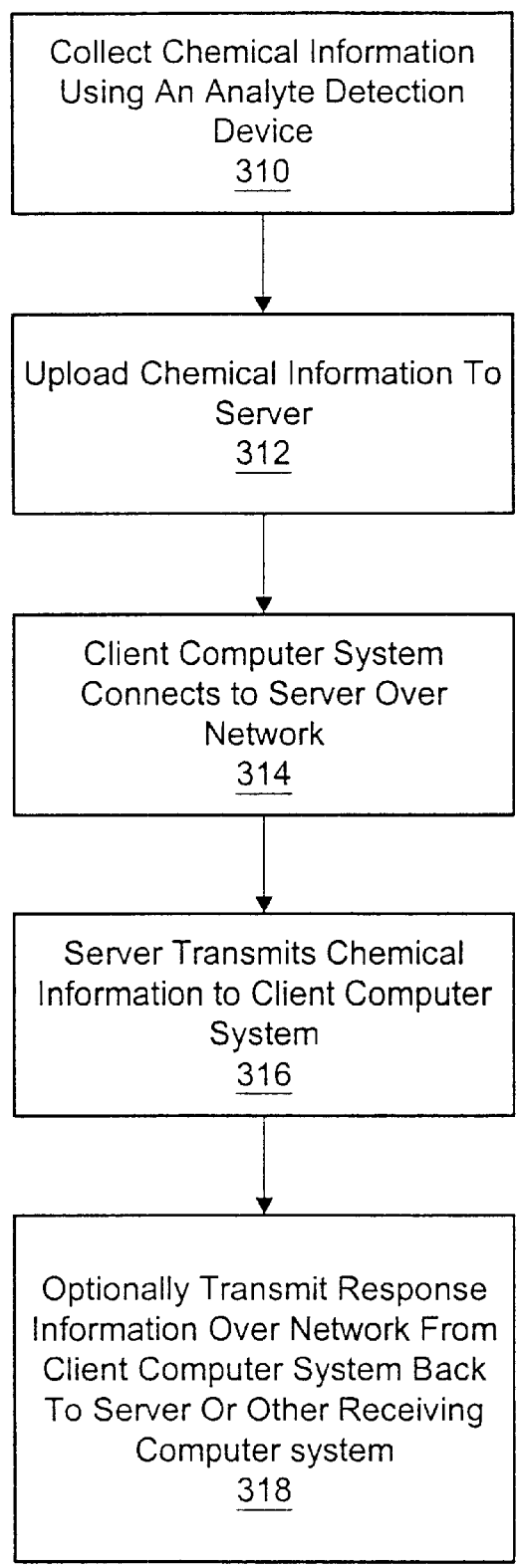
FIG. 69 depicts a flowchart of a method for collecting and transmitting chemical information over a computer network.

As FIG. 69 illustrates, in step 310 an ADD 102 may be used to analyze a chemical sample and detect one or more particular analytes or combinations of analytes, producing output data comprising the results of the detection process.

In step 312 the chemical information may be uploaded to a server 302, either directly, as by communication link, or via the computer network 104. There, the chemical information may be stored.

As described above, server 302 is connected to network 104, as is the client computer system 106. In step 314 client computer system 106 may connect to server 302 over network 104.

As shown in step 316, chemical information may be transmitted by server 302 over the network to client computer system 106 using any of a variety of network communication protocols, such as TCP/IP, FTP, HTTP, HTTPS, etc.

In step 318 client computer system 106 may optionally transmit response information back to server 302, which then may be accessed by ADD 102 to retrieve the response information, or to one or more additional client computer systems 107.

In one embodiment, server 302 is a web server operable to maintain a web site. When a client computer system accesses the web site of web server 120, web server 120 provides various data and information to the client browser on client system 106, possibly including a graphical user interface (GUI) that displays the information, descriptions of the information, and/or other information that might be useful to the users of the system.

In some embodiments, the ADD may include an electronic controller, as described herein. The electronic controller may allow the ADD to be operated by a client computer that is coupled to the electronic controller. The client computer may include software that provides the user information regarding the operation of the ADD. The client computer may allow the user of the client computer to issue commands that allow operation of the ADD from the electronic controller. The issued commands may be converted to control signals. The control signals may be received by the electronic controller. The electronic controller may operate components of the ADD in response to the received control signals.

The client computer may be coupled directly to the ADD. Alternatively, the client computer may be coupled to the ADD via a computer network. In this embodiment, an operator may be in a different location than the location of the ADD. By sending control signals over the computer network, the operator may remotely control the operation of the ADD. The ADD may also be configured to transmit the obtained chemical information back to the client computer via the computer network.

In another embodiment, the client computer may be coupled to the ADD via a server, as described before. The client computer may be configured to receive and/or transmit information to the ADD. In one embodiment, the ADD may be configured to receive control signals from the client computer via the server. The operation of the ADD may, therefore, be controlled via a client computer through a server. As discussed before the ADD may also transmit chemical information back to the client computer via the server.

In one embodiment, the ADD may be used to detect and identify one or more analytes in the blood serum of an animal or person in a remote location. The ADD may be configured with the appropriate detection components and software to detect the presence of any of a great number of different analytes. The serum sample may be processed by the ADD and the results, the chemical information, transmitted to a client computer system residing at a diagnosis center (e.g. a veterinary hospital or medical office). There a medical expert may receive the chemical information and interpret it to diagnose the probable cause and/or source of the detected analytes. The medical expert may use this information to make a diagnosis of the patients medical condition. Based on the diagnosed medical condition, the medical expert may also prescribe medication for the treatment of the medical condition. This information may be transmitted back to the ADD over a computer network or a server. The information may also be transmitted to other client computer systems that are linked using a computer network or a server. For example, the medical expert may transmit a prescription to the ADD and to a client computer system at a pharmacy, which may then fill the prescription.

In another example of the use of an embodiment of the invention, ADD 102 is used to detect pollutants in a water supply, e.g. a remote lake or stream. ADD 102 processes the water sample, and the resulting detection information is transmitted to the web server 302 at an Environmental Monitoring station. The pollution information may include both identification and concentrations of the chemicals detected. There, the information may be input into a software program which updates a map of area waterways with pollution information superimposed thereon. The updated map may be displayed on a web site for use by interested parties.

In another embodiment, the invention may be used for home drug metabolite tracking. Detection and measurement of blood and urine components by ADD 102 may be used to track the appearance and disappearance of various drug components after dosing. The user of ADD 102 may upload the test results to a client computer system 106 used by a health care professional. The upload may be accomplished either by transferring the information to a local computer system, then transmitting over network 104 to client computer system 106 of the health professional, or directly from ADD 102 to client system 106 over network 104 (e.g., through an internal modem similar to those used in PDAs or other hand-held computing devices). Results of the tests may be examined either by human or software, and recommendations made to either continue current drug protocol or to modify dosing to achieve a desired metabolite profile. These recommendations may then be transmitted back to the user of ADD 102, either via the local computer system, or directly, depending upon the ADD communication capabilities. Through this method, accurate determinations of doses needed to achieve effective treatment while avoiding dangerous over-medication may be possible. This offers a revolutionary change from current approaches, in which most or all people in a population are treated identically, regardless of ethnicity, gender, age, and medication with other drugs. Some studies indicate that effective and toxic dose levels can vary significantly for these different subgroups of patients. By providing a simple and fast means for frequent metabolite analysis and evaluation, network uploading of ADD detection results, and possible subsequent downloading of recommendations can open fundamentally new ways to treat patients.

According to another embodiment, the method and system may be used for home blood component analysis by a patient. Similar to drug metabolite tracking, the results of analyses for natural blood components (e.g., glucose, insulin, cholesterol (LDLs/MDLs), triglycerides, prostate-specific antigen, and other indicators of health state) may be uploaded to a client computer system 106 of a health care professional. Examination of test results could then be used for diagnosis, or at least early-warning screening for possible pathologies. Recommendations for action (e.g., drug use or scheduling of appointment) may then be transmitted back to the patient's ADD 102 or local computer system 106 or phoned to the patient. Again, the potential for simple, fast, and frequent measurements may provide safeguards for patients in certain risk groups (e.g., diabetes), who would otherwise need to make frequent trips to the lab or at the minimum would otherwise have to manually call in/email home test results—a far less reliable approach than automated uploading of the chemical information by the ADD following its analysis.

Another embodiment of the invention pertains to field-testing of environmental conditions. Automated sensing of environmental conditions, including the presence of natural chemicals, industrial wastes, and biological/chemical warfare agents is. possible using an embodiment of the invention. Uploading of test results via radio transmission may provide remote sensing capabilities, and may provide response capabilities through human or central computer directed action. Response instructions may then be downloaded either to the sensing site or to another strategic response position. Such a system may be useful, for example, in determining the presence of toxins in a public water supply, and the subsequent centralized-directed cessation of water flow from the supply pool.

In one embodiment, data may be collected from a remote location and the data transmitted to a third party at an alternate location. A sample may be provided to a replaceable sensor cartridge having multiple analyte sensors and being configured as part of the testing device. The sample may be from a subject (e.g. a patient) and provided to the replaceable sensor cartridge by an operator. Data regarding the sample, from the multiple analyte sensor, may be transmitted to a central data service. At the central data service, one or more tests may be performed on the electronic data using the central data service. After the tests have been performed, an electronic message may be transmitted to a third party, remote from the central data service. The information may include the results of one or more of the tests. In some embodiments, the tests may be selected by the third party. After the third party has received the results of the test the appropriate response (e.g. treatment in the case of medical diagnostics) may be selected.

A sensor array system may also be used for remote diagnostic screening. In one embodiment, a medical practitioner may prescribe a treatment to a patient during a visit. The medical practitioner may also wish to monitor the quantity of treatment for the patient. In one embodiment, the patient may provide a sample to a remote analyte testing device. The results produced by the analyte testing device may be transmitted to a central data service center. The central data service center may perform an analysis of the data and make recommendations to the patient to modify, maintain or cease the current treatment. The treatment may be in the form of medication, or an applied medical procedure. For medication treatments, the central data center may also note if any other medications are present. If so, the central data service center may advise the patient and/or practitioner of possible adverse drug interactions. Allergic reactions may also be detected and reported in this manner.

Office visits may also be scheduled using the sensor array system. Data collected from a patients sample may be sent from the sensor array system to a central data service. The electronic test data may be analyzed at the central data service. The results of the tests may be transmitted to a medical practitioner. The medical practitioner, upon review of the test results may schedule an appointment for the patient. The subject may be notified of the need for an office visit through the central data service. Alternatively, the medical practitioner may decide that an office visit is unnecessary, but wish to alter the treatment. The medical practitioner may, either directly or indirectly (through the central data service) inform the patient of the change of treatment.

Diagnostic Uses of the Sensor Array System

One of the largest markets for the health care industry is the diagnostic market. The worldwide market for diagnostic products is in the range of about $20 billion a year. Much of this market is driven by the current managed health care environment. The importance of diagnostics in the reduction of health care costs have created a need for early and less expensive diagnosis. Generally, an early and accurate diagnosis may lead to early prognosis, reduced unnecessary testing and significantly lower health costs. This is especially true for animal management. Animal diagnosis tends to be less accurate because of the types of testing being used. Instead of performing detailed diagnostic testing of animals, many animal care workers tend to prepare preventive mixtures which include a number of drugs for a variety of potential diseases that the animals may or may not have. These mixtures are expensive and may, in the case of antibiotics, promote antibiotic resistant pathogens.

The previously described sensor array system may be used for a wide variety of diagnostic testing for both animals and humans. As described before, the sensor array may include a variety of particles that are chemically sensitive to a variety of types of analytes. In one embodiment, the particles may be composed of polymeric beads. Attached to the polymeric beads may be at least one receptor. The receptors may be chosen based on their binding ability with the analyte of interest.

The sensor array may be adapted for use with a variety of bodily fluids. Blood and urine are the most commonly used bodily fluids for diagnostic testing. Other body fluids such as saliva, sweat, mucus, semen, and milk may also be analyzed using a sensor array. The analysis of most bodily fluids will, typically, require a filtration of the material prior to analysis. For example, cellular material and proteins may need to be removed from the bodily fluids. As previously described, the incorporation of filters onto the sensor array platform, may allow the use of a sensor array with blood samples. These filters may also work in a similar manner with other bodily fluids, especially urine. Alternatively, a filter may be attached to a sample input port of the sensor array system, allowing the filtration to take place as the sample is introduced into the sensor array.

In one embodiment, a sensor array may be customized for use as an immunoassay diagnostic tool. Immunoassays rely on the use of antibodies or antigens for the detection of a component of interest. In nature, antibodies are produced by immune cells in response to a foreign substance (generally known as the "antigen"). The antibodies produced by the immune cell in response to the antigen will typically bind only to the antigen that elicited the response. These antibodies may be collected and used as receptors that are specific for the antigen that was introduced into the organism.

In many common diagnostic tests, antibodies are used to generate an antigen specific response. Generally, the antibodies are produced by injecting an antigen into an animal (e.g., a mouse, chicken, rabbit, or goat) and allowing the animal to have an immune response to the antigen. Once an animal has begun producing antibodies to the antigen, the antibodies may be removed from the animal's bodily fluids, typically an animal's blood (the serum or plasma) or from the animal's milk. Techniques for producing an immune response to antigens in animals are well known.

Once removed from the animal, the antibody may be coupled to a polymeric bead. The antibody may then acts as a receptor for the antigen that was introduced into the animal. In this way, a variety of chemically specific receptors may be produced and used for the formation of a chemically sensitive particle. Once coupled to a particle a number of well known. techniques may be used for the determination of the presence of the antigen in a fluid sample. These techniques include radioimmunoassay (RIA) and enzyme immunoassays such as enzyme-linked immunosorbent assay (ELISA). ELISA testing protocols are particularly suited for theuse of a solid support such as polymeric beads. The ELISA test typically involves the adsorption of an antibody onto a solid support. The antigen is introduced and allowed to interact with the antibody. After the interaction is completed a chromogenic signal generating process is performed which creates an optically detectable signal if the antigen is present. Alternatively, the antigen may be bound to the solid support and a signal generated if the antibody is present. Immunoassay techniques have been previously described, and are also described in the following U.S. Pat. Nos. 3,843,696, 3,876,504, 3,709,868, 3,856,469, and 4,567,149 all of which are incorporated by reference.

In one embodiment, an immunoassay sensor array may be used for the diagnosis of bacterial infections in animals. Many animals suffer from a variety of bacterial, viral, parasitic, and/or fungal diseases that may be unmonitored or not specifically diagnosed by the animals caretakers. Bacterial infections may be particularly troublesome since bacterial infections tend to cause a number of different health problems, some of which effect the quality of products produced from the animals. It is desirable for the animal caretakers to diagnosis and treat such problems as quickly as possible. The testing of animals, especially animals such as chickens and cattle, may be difficult due to the large number of individual animals in the flock or herd. A diagnostic tool for animal testing should be easy to use, accurate, quick and inexpensive. Such a tool would allow better animal health management, especially for large collections of animals.

For example, mastitis is a common bacterial infection that occurs in the udders of cows. The presence of the mastitis causing bacteria in cows may render the milk produced by the cows unsuitable for sale. Once detected, the treatment will involve the use of a mixture antibiotics that also renders the milk unusable for a period of days. This can result in a tremendous financial loss for the owners of the cows, especially if the infection spreads to the other cows of the herd.

Current mastitis detection includes daily observation of the bulk tank somatic cell count. The bulk tank represent the bulk milk collected from many different cows from the herd. The somatic cell count is a measure of any inflammatory blood cells present in the milk of the cow, thus it is a measure of any inflammatory process that may have affected the udder of the cow. The somatic cell count offers a method of screening for potential problems in both the herd and the individual cows, but a confirmation test is necessary for a definitive diagnosis of mastitis. The confirmation tests typically involve culturing the milk and analyzing the milk for the particular strains of bacteria that cause mastitis. This process can take from 1 to 2 days to complete. Meanwhile, the communal use of milking machines may cause the infection to spread within the herd.

The sensor array system described herein may be used to improve the diagnostic procedures for testing milk samples for cows. In one embodiment, antibodies that are specific for the bacteria that cause mastitis may be bound to the receptors. Immunoassays for the detection of mastitis are described in U.S. Pat. No. 5,168,044 which is incorporated by reference. Using the testing protocols previously described, the sensor array system may be used to detect the presence of mastitis causing bacteria in any of the bodily fluids of a cow. The immunoassay is typically faster, (i.e., completed in hours instead of days) and may allow rapid sampling of individual members of the herd. In general, the immunoassays are much more accurate than cell culture methods, which tend to give false positive results.

Another advantage of using a sensor array system, is that multiple bacterial strains may be analyzed simultaneously. Cow milk, as well as other bodily fluids, may include other bacteria that may potentially cause health problems for the animal. For example, a variety of gram-positive bacteria such as staphylococcus and streptococcus and gram-negative bacteria such as coliforms (e.g., E. Coli), Proteus and Psuedomonas may also be present in the fluid sample. Typically, mastitis tests ignore these bacteria, or in some cases, may confuse the presence of these bacteria for the mastitis causing bacteria. In one embodiment, a sensor array may include multiple particles, each particle including a receptor that is specific for a particular bacterial strain. In a single test, all of the bacteria present in the animal may be detected. This is particularly important for determining the proper treatment of the animal. By identifying the strains of bacteria present in the animal's sample the appropriate antibiotics may be chosen for a treatment. This may help to avoid the proliferation of antibiotic resistant pathogens due to unnecessary use of antibiotics.

While described in detail for the detection of mastitis in cows, it should be understood that the above described method of detecting bacteria in bodily fluids may be applied to a variety of different bacteria found in both animals and/or humans. The sensor array would only need to be modified with respect to the type of antibodies (or antigen) that are used for the testing procedure.

Additionally, bacteria in soil and grain samples may also be detected using an immunoassay procedure. In the case of soils and grains, an extraction of these mediums with a suitable solvent may be required prior to analysis. For example, a grain sample may be soaked in water and the undissolved material filtered out before the water is analyzed. The analysis of the water may then take place using any of the procedures for fluid samples previously described and the presence of bacteria in the grain (or soil) may be determined.

In one embodiment, the sensor array is used to detect Mycobacterium tuberculosis, the causative agent of tuberculosis. Immunoassays for the detection of Mycobacterium tuberculosis are described in U.S. Pat. No. 5,631,130 which is incorporated by reference.

Many animals also suffer from a variety of parasitic diseases. Parasitic diseases may, occasionally, appear in humans as well. For example, one of the most prevalent parasitic disease found in dogs is heartworms. Heartworms are caused by the *D. immitis* parasite. The early detection of the presence of this parasite in a dog is important. If caught at an early stage, the parasite may be treated with the use of drugs before any permanent damage to the heart is caused. A number of tests may be used for the detection of a heartworm infection. Those that are most applicable for the sensor array system are based on immunoassays. One test, known as the indirect fluorescent antibody test is specific for antibodies produced by the dog against the heartworm microfilaria. Another test utilizes an ELISA based screening for detecting circulating worm antigen. Both of these immunoassay tests have a high degree of specificity for the detection of heartworms.

The previously described sensor array may be adapted for the detection of heartworms using either of these well know techniques. Additionally, other parasitic infections may be simultaneously analyzed for by the use of the additional particles which include receptors for other types of parasitic infections, including protozoan infections. Alternatively, a mixture of particles that are specific for either parasites or bacteria may be incorporated into a single sensor array unit. Since the analytes for bacteria and parasites tend to be found in the same bodily fluids (e.g., blood), the use of such a sensor array would allow the diagnosis of potential bacterial and parasitic diseases for an animal (or a human) to be simultaneously detected. While the above test has been described with respect to a dog, it should be understood that the testing procedure would be applicable to other animals and humans.

Another source of disease in humans and animals is from viral infections. For example, feline leukemia is a viral infection that, until recently, was the most common fatal disease of cats. The disease is primarily caused by the exposure of the cat to the feline leukemia virus (FeLV). The feline leukemia virus may be detected using immunoassay techniques. Three major tests have been used to determine the presence of FeLV. The blood ELISA test is the most accurate, and will detect the presence of FeLV at any stage of infection. FeLV antigen may be used as a receptor that binds FeLV. An older test is based on a indirect fluorescent antibody (IFA) test for antibodies that are produced against FeLV. A third test is a tears/saliva ELISA test. The IFA and tear/saliva ELISA tests are only accurate in the late stages of the disease. As described above, the attachment of the appropriate antibodies or antigens on the particle will allow any of these testing procedures to be performed using the sensor array system.

The HIV virus and the hepatitis C virus (togovirus and calicivirus) are examples of viruses that humans may be tested for. These viruses are most commonly detected using an ELISA testing method. The ELISA testing methods for HIV or hepatitis C look for antibodies in the bodily fluids of the person being tested. The most commonly analyzed bodily fluids used for these tests are blood and saliva. The attachment of the appropriate antigens on a particle will allow any of these testing procedures to be performed using the sensor array system. An advantage of the use of a sensor array for the detection of viruses in humans, is that many other pathogens may be simultaneously analyzed for. For example, viral infections from other viruses (e.g., hepatitis A, hepatitis B, human herpesvirus-8, cytomegalovirus, varicella zoster virus, etc.) and other pathogens (e.g., *Pneumocystis carinii, Toxoplasma gondii, Mycobacterium avium, Mycobacterium intracellulare, Treponema pallidum,* etc.) may be detected simultaneously with HIV and/or hepatitis C by the use of multiple particles with the appropriate antibodies or antigens. *Pneumocystis carinii, Toxoplasma gondii, Mycobacterium avium, Mycobacterium intracellulare,* cytomegalovirus, human herpesvirus-8, and varicella zoster virus are organisms that cause infections in immunocompromised patients. *Treponema pallidum* is the bacteria that causes syphilis. Immunoassays for the detection of *Pneumocystis carinii* are described in U.S. Pat. No. 4,925,800 which is incorporated by reference. Immunoassays for the detection of *Toxoplasma gondii,* cytomegalovirus, Herpes simplex virus, and *Treponema pallidum* are described in U.S. Pat. No. 4,294,817 which is incorporated by reference. Immunoassays for the detection of *Toxoplasma gondii* are also described in U.S. Pat. No. 5,965,590 which is incorporated by reference. Immunoassays for the detection of Hepatitis B use Hepatitis B surface antigen as a receptor.

It should be understood that parasitic, viral and bacterial infections may all be analyzed at substantially the same time using the sensor array system. The sensor array system may include all of the necessary reagents and indicators required for the visualization of each of these tests. In addition, the sensor array may be formed such that these reagents are compartmentalized. In this manner, the reagents required for a viral tests may be isolated from those used for a bacterial test. The sensor array may offer a complete pathogen analysis of an animal or persons bodily fluid with a single test.

The presence of fungus in grains may also be detected using a sensor array system. The fungus in grains may be removed using an extraction technique. The samples may be analyzed with a sensor array system which includes particles that are sensitive to the presence of a variety of fungi. In this was, the fungi present in a grain sample may be monitored.

Diagnostic tests have also been used for the detection of various organic molecules in humans and animals. These molecules may be detected by a variety of testing procedures, including, but not limited to, immunoassay techniques, enzyme binding techniques, and synthetic receptors.

The concentration of glucose in human blood is commonly measured for people with diabetes. The measurement of the blood glucose level may be performed more than 5 times a day for some individuals. Currently available home testing relies, primarily, on a blood test for the determination of the concentration of glucose. The determination of glucose is typically determined by the enzymatic decomposition of glucose. Some methods for the determination of glucose in blood are described in U.S. Pat. Nos. 3,964,974 and 5,563,042 which are incorporated by reference.

Cholesterol is also a common constituent of blood that is frequently monitored by people. As with glucose, a number of home testing kits have been developed that rely on the use of an enzyme based testing method for the determination of the amount of cholesterol in blood. A method for the determination of cholesterol in blood is described in U.S. Pat. No. 4,378,429 which is incorporated by reference.

The triglyceride level in blood is also commonly tested for because it is an indicator of obesity, diabetes, and heart disease. A system for assaying for triglycerides in bodily fluids is described in U.S. Pat. No. 4,245,041 which is incorporated by reference.

The concentration of homocysteine may be an important indicator of cardiovascular disease and various other diseases and disorders. Various tests have been constructed to measure the concentration of homocysteine in bodily fluids. A method for the determination of homocysteine in blood, plasma, and urine is described in U.S. Pat. No. 6,063,581 which is incorporated by reference.

Cholesterol, triglyceride, homocysteine, and glucose testing may be performed simultaneously using the sensor array system. Particles that are sensitive to either cholesterol, triglyceride, homocysteine, or glucose may be placed in the sensor array. Blood serum that is passed over the area may, therefore, be analyzed for glucose, triglyceride, and cholesterol. A key feature of a glucose, triglyceride, homocysteine, and/or cholesterol test is that the test should be able to reveal the concentration of these compounds in the persons blood. This may be accomplished using the sensor array by calibrating the reaction of the particles to cholesterol, triglyceride, or glucose. The intensity of the signal may be directly correlated to the concentration. In another embodiment, multiple particles may be used to detect, for example, glucose. Each of the particles may be configured to produce a signal when a specific amount of glucose is present. If the glucose present is below a predetermined concentration, the particle may not produce a detectable signal. By visually noting which of the particles are producing signals and which are not, a semi-quantitative measure of the concentration of glucose may be determined. A similar methodology may be used for cholesterol, triglyceride, homocysteine, or any testing system thereof (e.g., glucose/cholesterol/triglyceride/homocysteine, cholesterol/triglyceride, glucose/triglyceride, glucose/cholesterol, etc.).

Another use for the sensor array system is in hormone testing. The most common types of hormone testing in use today are fertility testing devices (e.g., pregnancy tests and ovulation tests). Both of these tests typically rely on either an immunoassay or enzyme assay methodology. Other hormones, such as progesterone for fertility monitoring or estrogen for hormone therapy treatments may also be monitored. Th sensor array may be used in hormone testing for specific hormones or for multiple hormones in a manner similar to that described for glucose/cholesterol testing.

Another practical use for the sensor array system is for therapeutic drug monitoring. Therapeutic drug monitoring is the measurement of the serum level of a drug and the coordination of this serum level with a serum therapeutic range. The serum therapeutic range is the concentration range where the drug has been shown to be efficacious without causing toxic effects in most people. Typically, therapeutic drug monitoring relies on the analysis of blood serum or plasma from a patient. In general, therapeutic drug monitoring relies on the use of immunoassays, similar to the ones described previously.

A general problem with monitoring of drug serum levels may occur when a patient is using more than one drug. In some instances, the drugs may produce a positive result in an immunoassay, especially if the drugs have a similar chemical structure. In some instances, the receptor (antibody or antigen) may be altered to prevent a particular interference. The use of a sensor array, however, may avoid this problem. Because a sensor array may include a variety of different particles, each of the particles may be customized for a particular drug. If multiple drugs are present in a patients serum, the presence of the drugs may be determined by observing which of the particles is activated. Even though some of the particles may be reactive to more than one of the drugs, other receptors may be more finely tuned to a specific drug. The pattern and intensity of the reactions of the particles with the drugs may be used to accurately assess the drugs present in the patient.

One area of therapeutic monitoring includes the monitoring of anticonvulsant drugs. Anticonvulsant drugs are usually measured by an immunoassay. Common anticonvulsant drugs that require monitoring include phenytoin (Dilantin®), carbamazepine (Tegretol®), valproic acid (Depakene®), primidone (Mysoline®), and phenobarbital. Since primidone is metabolized to phenobarbital, both drugs must be measured when the patient is taking primidone.

Another of therapeutic drug monitoring that a sensor array may be used for is the monitoring of Digoxin. Digoxin is a medicine that slows the heart and helps it pump more effectively. The bioavailability of different oral preparations of digoxin tends to be highly variable from patient to patient. Digoxin measurements may be made using an immunoassay. Some immunoassays for digoxin, however, have cross-reactivity with a hormone-like substance know as digoxin-like immunoreactive factor, or DLIF. Care must be taken to distinguish between digoxin and digitoxin, another cardiac glycoside. Digoxin assays generally have a low cross-reactivity with digitoxin, but digitoxin serum therapeutic levels may be 10 times those of digoxin. The use of a sensor array system that includes a variety of particles, some of which are more sensitive to DLIF or digitoxin, may allow a more accurate assessment of digoxin levels in a patient.

Theophylline is a bronchodilator with highly variable inter-individual pharmacokinetics. Serum levels must be monitored after achievement of steady-state concentrations to insure maximum therapeutic efficacy and prevent toxicity. Immunoassay is the most common method used for monitoring this drug.

Lithium compounds are used to treat bipolar depressive disorders. Serum lithium concentrations are measured by ion selective electrode technology. An ion selective electrode has a membrane which allows passage of the ion of interest but not other ions. A lithium electrode will respond to lithium concentrations but not to other small cations such as potassium. Several small analyzers which measure lithium using ion selective electrode technology are available. The use of particles that are sensitive to lithium ion concentrations, as have been described previously, may allow lithium ion measurements to be preformed without the use of lithium ion electrodes. Such systems will allow the analysis of multiple ions in the serum, unlike the electrode based systems which are specific for lithium ions.

The tricyclic antidepressant drugs include imipramine and its pharmacologically active metabolite desipramine; amitriptyline and its metabolite nortriptyline; and doxepin and its metabolite nordoxepin. Both the parent drugs and the metabolites are available as pharmaceuticals. These drugs are primarily used to treat bipolar depressive disorders. Imipramine may also be used to treat enuresis in children, and severe Attention Deficit Hyperactivity Disorder that is refractory to methylphenidate. Potential cardiotoxicity is the major reason to measure these drugs. Immunoassay methods are available for measuring imipramine and the other tricyclics. When measuring tricyclic antidepressants which have pharmacologically active metabolites, it is important to measure both the parent drug and the metabolite. A sensor array system is well suited for this type of analysis. Mixtures of receptors for parent drug and the metabolites may be incorporated into a single sensor array. In addition, a sensor array system may be used to detect a variety of tricyclic antidepressant drugs, allowing any of the drugs to be tested using a single test.

Screening patients for drugs of abuse in the urine may be indicated to help differentiate symptoms, or to insure that a patient is substance-free before undergoing medical procedures. Drug screening of pregnant women with a history of drug abuse may be useful as an educational tool and help guide treatment of the newborn. In addition, some employers require a drug screen as part of an employment or pre-employment physical. Nearly all workers in some occupations, such as law enforcement and transportation, are subject to periodic, random, and post-incident drug screening. The chemical sensor array may be used to detect a variety of drugs of abuse in a quick and easy manner. Typically, a variety of different tests must be used to test for each class of drug. By incorporating multiple particles into a single sensor array, some or all of the most commonly used drugs of abuse may be determined in a single step.

Urine screening tests for drugs of abuse detect general classes of compounds, such as amphetamines, barbiturates, benzodiazepines, or opiates. Drug screening also includes testing for cocaine, marijuana, and phencyclidine (PCP). The screening test for cocaine detects benzoyl ecgonine, the major metabolite of cocaine. The marijuana test detects D-9-tetrahydrocannabinol, a principle product of marijuana smoke. One problem of the screening test is that the test, in some instances, may not be able to distinguish between illicit drugs and prescription or over-the counter compounds of the same class. A patient taking codeine and another taking heroin would both have a positive screening test for opiates. Some over-the-counter medications can cause a positive drug screen in a person who has not taken any illegal or prescription drugs. For instance, over-the-counter sympathomimetic amines such as pseudoephedrine and phenylpropanolamine may cause a false-positive screen for amphetamines. Eating food containing poppyseeds may result in a positive urine screening test for opiates, since poppyseeds contain naturally-occurring opiates. However, confirmation testing will distinguish between positive opiate tests resulting from poppyseed ingestion and those resulting from heroin or other opiates, because different metabolic breakdown products are present. Monoacetylmorphine (also called 6-monoacetylmorphine or 6-MAM) is a heroin metabolite. The presence of this metabolite is conclusive evidence that heroin was ingested.

Most of these problems of false positive results may be avoided through the use of a sensor array. The sensor array may include a variety of particles, each specific for a particular drug. Some of the particles may be specific designed to interact with the drug of abuse, for example amphetamine. Other particles may be designed to interact with an over-the-counter drug such as pseudoephedrine. The use of a variety of particles may allow a more accurate or complicated analysis to be performed through the use of a pattern recognition system. Even though many of the drugs may react with one or more particles, the pattern and intensity of the signals produced by the particles in the sensor array may be used to determine the identity of the drugs present in the patient. The most commonly used test method for screening urine for drugs of abuse is immunoassay. A number of single use devices incorporating immunoassays and designed to be used outside of the traditional laboratory are currently available.

Hyperglycemia can be diagnosed only after ruling out spurious influences, especially drugs, including caffeine, corticosteroids, indomethacin, oral contraceptives, lithium, phenytoin, furosemide, thiazides, etc. Thus, a sensor array may be used to expedite diagnosis of hyperglycemia by determining the presence of drugs that may cause false positives.

In another embodiment, a sensor array may be used to asses the presence of toxins in a person or animal's system. In general, toxins may be any substance that could be ingested that would be detrimental to one's health. For animals, a few examples of toxins include lead, organic phosphates, chlorinated hydrocarbons, petroleum distillates, alkaloids (present in many types of poisonous plants), ethylene glycol, etc. People may ingest a variety of these compounds, along with a number of different types of drugs, either over-the counter, prescription, or illegal. In many instances the patient, either animal or human, may exhibit symptoms which indicate the presence of a poison, however, the diagnosis of the particular poison ingested by the person may be difficult. This may be particularly difficult for animals or children, since the owner may not know what the animal/child has eaten. For people, if the poisoning is severe, the person may be unconscious and unable to tell the physician the cause of the poisoning.

The use of a sensor array, may allow a medical expert to accurately and quickly assess the types of toxins present in a patient. A single sensor array may hold particles that are reactive to a wide variety of toxins. A single analysis of a sample of the patients bodily fluids (e.g., blood) may allow the medical expert to determine the identity of the poison. Once identified, the proper treatment may be used to help the patient.

A sensor array may also be used for soil testing. As with the grain testing, the testing of soil samples may require an extraction of the soil samples by a suitable solvent. For metals and other inorganic salts, the solvent used may be either water or dilute aqueous acid solutions. The soil may also be extracted with organic solvents to extract any organic compounds that are present in the soil sample. These solution containing the extractable material may then be analyzed using a sensor array. The sensor array may include particles that are specific for a variety of soil contaminates such as paints, lead, phosphates, pesticides, petroleum products, industrial fallout, heavy metals, etc. The use of a sensor array may allow one or more of these materials to be simultaneously analyzed in a soil sample.

EXAMPLES

In the below recited table are examples of analytes that have been detected using the sensor array system described herein. In the Receptor/Enzyme column are listed examples of receptors that may be used for the corresponding analyte. These receptors are covalently bound to a polymeric resin, using methods described herein.

| Analyte | Type | Receptor/Enzyme |
|---|---|---|
| Sodium, Potassium | Small Molecule (Electrolyte) | Crown ethers, cryptands, chromoionophores such as Chromolyte ® (from Bayer), Enzymes such as β-galactosidase, or other metalloenzymes. |
| Bicarbonate | Small Molecule (Electrolyte) | Enzymes such as Carbonic anhydrase |
| Calcium | Small Molecule (Electrolyte) | Complexometric dyes such as Arsenazo III, Xylenol Orange, Alizaren Complexone |
| Magnesium | Small Molecule (Electrolyte) | Complexometric dyes such as Calmagite, Magon |
| Chloride | Small Molecule (Electrolyte) | Enzymes and/or small molecule detectors such as Amylase, Phenyl mercury compounds, mercuric thiocynanates, diphenylcarbazones |
| Oxygen | Small Molecule (Metabolite) | Oxygen complexing molecules such as porphyins, synthetic hemeglobins, Ruthenium trisbipyridine |
| Carbon dioxide | Small Molecule (Metabolite) | Enzymes such as Carbonic anhydrase |
| pH | Small Molecule (Electrolyte) | PH indicator dyes such as Hydroxynitrophenylacetic acid, Congo Red, Brilliant Yellow, Carboxyphenolphthalein |
| Creatinine | Small Molecule (Metabolite) | Enzymes such as Creatinine deiminase or small molecule detectors such as picrate |
| Urea | Small Molecule (Metabolite) | Enzymes such as Urease |
| Glucose | Small Molecule (Metabolite) | Enzymes such as Glucose oxidase/Peroxidase |
| Hepatitis B | Virus | Antigen/antibody pairs such as Hepatitis B surface antigen |
| Feline Leukemia | Virus | Antigen/antibody pairs such as FeLV antigen |
| Cytokines | Small Molecule (Markers), | Small molecule markers and/or |
| Interleukin 1 Interleukin 2 Interleukin 4 Interleukin 6 Interleukin 10 Gamma Interferon Tumor Necrosis Factor (TNF) | Cellular signals | antigen/antibody pairs |

Nucleic Acid Identification Methodology

In one embodiment, the chemical sensor array may be used for the determination of the sequence of nucleic acids. Generally, a receptor may be attached to a polymeric bead to form a particle. The receptor may have a specificity for a predetermined sequence of a nucleic acid. Examples of receptors include deoxyribonucleic acids (DNA) natural or synthetic (e.g., oligomeric DNA), ribonucleic acids (RNA) natural or synthetic, and enzymes. A number of methods may be used to analyze a nucleic acid to determine its sequence. The methods, summarized below, maybe adapted for use in the previously described chemical sensor array to analyze a sample which includes a nucleic acid analyte.

In one embodiment, hybridization may be used to identify nucleic acids. This method relies on the purine-pyrimidine pairing properties of the nucleic acid complementary strands in the DNA-DNA, DNA-RNA and RNA-RNA duplexes. The two strands of DNA are paired by the establishment of hydrogen bonds between the adenine-thymine (A—T) bases and the guanine-cystosine (G—C) bases. Hydrogen bonds also form the adenine-uracil (A—U) base pairs in the DNA-RNA or RNA-RNA duplexes. Hybridization is highly sequence dependent. Sequences have the greatest affinity with each other where, for every purine in one sequence (nucleic acid) there exists a corresponding pyrimidine in the other nucleic acid and vice versa. The target fragment with the sequence of interest is hybridized, generally under highly stringent conditions that tolerate no mismatches. U.S. Pat. No. 6,013,440 to Lipshutz, et al. describes hybridization in further detail and is incorporated by reference as if fully set forth herein.

Despite the high specificity of hybridization, there may be some mismatched nucleic acid strands. There are several ways to prevent mismatched strands from causing false positives. Ribonuclease enzymes may be used to dispose of mismatched nucleic acid pairs forming a RNA/DNA or RNA/RNA hybrid duplex. There are many types of ribonuclease enzymes that may be used for this purpose, including RNase A, RNase T1 and RNase T2. Ribonuclease enzymes specifically digest single stranded RNA. When RNA is annealed to form double stranded RNA or an RNA/DNA duplex, it may no longer be digested with these enzymes. When a mismatch is present in the double stranded molecule, however, cleavage at the point of mismatch may occur. In one embodiment, a label may be attached to the RNA coupled to the particle. In the presence of a mismatch, cleavage may occur at the point of the mismatch. The cleavage may cause the labeled fragment to fall off the bead, causing a decrease in the signal detected from the bead. If the nucleic acid are perfectly complementary, then the fragment may remain uncleaved in the presence of the ribonuclease enzymes and the intensity of the signal produced by the particle may remain unchanged.

S1 Nuclease Cleavage may also be used to cleave mismatched pairs. S1 nuclease, an endonuclease specific for single-stranded nucleic acids, may recognize and cleave limited regions of mismatched base pairs in DNA:DNA or DNA:RNA duplexes. Normally, for S1 Nuclease to recognize and cleave a duplex a mismatch of at least about four consecutive base pairs is required. In a similar manner as described above, the cleavage of a labeled nucleic acid fragment may indicate the presence of a mismatched nucleic acid duplex.

T4 endonuclease VII (T4E7) and T7E1 are small proteins from bacteriophages that bind as homodimers and cleave aberrant DNA structures including Holliday Junctions. These molecules preferentially cleave mismatched duplexes. (Described in Youil R, Kemper B, Cotton RGH. Detection of 81 of 81 Known Mouse Beta-Globin Promoter Mutations With T4 Endonuclease-VII—The EMC Method. Genomics 1996;32:431–5, incorporated by reference as if fully set forth herein).

In another method, Chemical Cleavage of Mismatches (CCM) may be used. This technique relies upon the use of intercalation. Examples of intercalators include, but are not limited to, the chemicals hydroxylamine and osmium tetroxide to react with a mismatch in a DNA heteroduplex. Mismatched thymines are susceptible to modification by osmium tetroxide (or tetraethyl ammonium acetate and potassium permanganate) and mismatched cytosines can be modified by hydroxylamine. The modified bases are then cleaved by hot piperidine treatment. In a similar manner as described above, the cleavage of a labeled nucleic acid fragment may indicate the presence of a mismatched nucleic acid duplex.

In another embodiment, DNA-binding proteins may be used to identify nucleic acids. Most sequence-specific DNA-binding proteins bind to the DNA double helix by inserting an α-helix into the major groove (Pabo & Sauer 1992 Annu. Rev. Biochem. 61. 1053–1095; Harrison 1991 Nature (London) 353, 715–719; and Klug 1993 Gene 135, 83–92). U.S. Pat. No. 5,869,241 to Edwards, et al. describes in detail methods for identifying proteins having the ability to bind defined nucleic acid sequences and is incorporated by reference as if fully set forth herein. In an embodiment, the DNA-binding proteins may be attached to a polymeric particle. The DNA-binding proteins may interact with the polymeric particle to produce a signal using a variety of the previously described signaling protocols.

Mispair Recognition Proteins, e.g., MutS, may also be used to detect mismatched base pairs in double-stranded DNA. There are several methods by which Mispair Recognition Proteins can be used. Mispair Recognition Proteins may bind to a mismatched base pair. Modified forms of a mismatch recognition protein may cleave a heteroduplex in the vicinity of a mismatched pair. A mismatch repair system dependent reaction, e.g., MutHLS, may be used for mismatch-provoked cleavage at one or more GATC sites. A mismatch repair system may be used in the formation of a mismatch-provoked gap in heteroduplex DNA. Mismatch-containing nucleotides may be labeled with a nucleotide analog, e.g., a biotinylated nucleotide. Molecules containing a base pair mismatch may be removed through the binding of the mismatch to the components of the mismatch repair system or by the binding of a complex of a mismatch and components of a mismatch repair system to other cellular proteins. Molecules containing mismatches may also be removed through the incorporation of biotin into such a molecule and subsequent removal by binding to avidin. The use of Mispair Recognition Proteins is described in detail in U.S. Pat. No. 6,008,031 to Modrich, et al., which is incorporated by reference as if fully set forth herein. Hsu IC, Yang QP, Kahng MW, Xu JF. Detection of DNA point mutations with DNA mismatch repair enzymes. Carcinogenesis 1994;15:1657–62. 1, which is incorporated by reference as if fully set forth herein, describes the use of MutY in combination with thymine glycosylase for mismatch detection.

Yet another technique is Oligonucleotide Ligation Assay. In this method, the enzyme DNA ligase is used to join two oligonucleotides, annealed to a strand of DNA, that are exactly juxtaposed. A single base pair mismatch at the junction of the two oligonucleotides will prevent ligation. Ligation is scored by assaying for labels on the two oligonucleotides becoming present on a single molecule.

In another embodiment, an intercalating molecule may be used as a receptor. The combination of the intercalator with the polymeric bead may be used as a particle for a sensor array system. Intercalators typically react with duplex DNA by insertion into the duplex DNA. If the intercalator has a visible or ultraviolet absorbance or fluorescence, the wavelength or intensity of the intercalators signal may be altered when the intercalator is intercalated into duplex DNA. Examples of such intercalators include, but are not limited to, ethidium bromide, POTO, and Texas Red. Many intercalators exhibit some sequence selectivity. Thus, an intercalator bound to a polymeric resin may be used to analyzing DNA analytes for specific sequences. By using a variety of different intercalators in a single sensor array, the identity of the nucleic acid may be identified through a pattern recognition methodology.

The use of particles that are custom made for a variety of different nucleic acid testing schemes allows greater flexibility than the current commercially available nucleic acid devices. For example, the use of silicon chips in which the nucleic acid receptor is coupled directly to the chip may be less flexible since the size of the oligomeric receptor built onto the chip is limited to 25–30 base pairs. Methods for synthesizing oligomeric nucleic acids on a bead, however, may be used to couple oligomeric nucleic acids which include more than 100 base pairs.

Tests used to identify nucleic acids sometimes require that the amount of nucleic acid in the sample be increased. Techniques have been developed to amplify the chemical of interest. For example, it is possible to control which strand of a duplex nucleic acid is amplified by using unequal amounts of primer so that the primer for the undesired strand is effectively rate limiting during the amplification step. Methods of determining appropriate primer ratios and template sense are well known to those of skill in the art (see, e.g., PCR Protocols: a Guide to Methods and Applications, Innis et al., eds. Academic Press, Inc. N.Y. 1990).

Polymerase Chain Reaction (PCR) is a widely used technique which enables a scientist to amplify DNA and RNA sequences at a specific region of a genome by more than a millionfold, provided that at least part of its nucleotide sequence is already known. The portions on both sides of the region to be amplified are used to create two synthetic DNA oligonucleotides, one complementary to each strand of the DNA double helix, which serve as primers for a series of synthetic reactions which are catalyzed by a DNA polymerase enzyme. Effective amplification may require up to 30 to 40 repetitive cycles of template nucleic acid denaturation, primer annealing and extension of the annealed primers by the action of a thermostable polymerase. A more detailed description as well as applications of PCR are provided in U.S. Pat. Nos. 4,683,195; 4,683,202; and 4,965,188; Saiki et al., 1985, Science 230:1350–1354; Mullis et al., 1986, Cold Springs Harbor Symp. Quant. Biol. 51:263–273; Mullis and Faloona, 1987, Methods Enzymol. 155:335–350; PCR Technology-principles and applications for DNA amplification, 1989, (ed. H. A.Erlich) Stockton Press, New York; PCR Protocols: A guide to methods and applications, 1990, (ed. M. A. Innis et al.) Academic Press, San Diego; and PCR Strategies, 1995, (ed. M. A. Innis et al.) Academic Press, San Diego, Barany, 1991, PCR Methods and Applic. 1:5–16); Gap-LCR (PCT Patent Publication No. WO 90/01069); each of which is incorporated by reference as if fully set forth herein.

In Allele-Specific PCR (also called the amplification refractory mutation system or ARMS) the assay occurs within the PCR reaction itself. Sequence-specific PCR primers which differ from each other at their terminal 3' nucleotide are used to only amplify the normal allele in one reaction, and only the mutant allele in another reaction. When the 3' end of a specific primer is fully matched, amplification occurs. When the 3' end of a specific primer is mismatched, amplification fails to occur.

Other amplification techniques include Ligase Chain Reaction, described in Wu and Wallace, 1989, Genomics 4:560–569 and Barany, 1991, Proc. Natl. Acad. Sci. USA 88:189–193, incorporated by reference as if fully set forth herein; Strand Displacement Amplification; Nucleic Acid Sequence Base Amplification; Transcription Mediated Amplification; Repair Chain Reaction, described in European Patent Publication No. 439,182 A2), 3SR (Kwoh et al., 1989, Proc. Natl. Acad. Sci. USA 86:1173–1177; Guatelli et al., 1990, Proc. Natl. Acad. Sci. USA 87:1874–1878; PCT Patent Publication No. WO 92/0880Å), and NASBA (U.S. Pat. No. 5,130,238), incorporated by reference as if fully set forth herein; Self-sustained Sequence Replication; Strand Displacement Amplification, etc., described in Manak, DNA Probes, $2^{nd}$ Edition, p 255–291, Stockton Press (1993)), incorporated by reference as if fully set forth herein; and Non-Isotopic RNase Cleavage Assay, described in Goldrick M M, Kimball G R, Liu Q, Martin L A, Sommer S S, Tseng J Y H. Nirca(™)—A Rapid Robust Method For Screening For Unknown Point Mutations. Biotechniques 1996;21:106–12, incorporated by reference as if fully set forth herein. Non-Isotopic RNase Cleavage Assay amplifies RNA. RNase enzymes, e.g., RNase 1 and RNase T1, increase the sensitivity of the assay.

Manufacturing Methods for a Sensor Array

As described above, after the cavities are formed in the supporting member, a particle may be positioned at the bottom of a cavity using a micromanipulator. This allows the location of a particular particle to be precisely controlled during the production of the array. The use of a micromanipulator may, however, be impractical for mass-production of sensor arrays. A number of methods for inserting particles that may be amenable to an industrial application have been devised.

In one embodiment, the use of a micromanipulator may be automated. Particles may be "picked and placed" using a robotic automated assembly. The robotic assembly may include one or more dispenser heads. A dispenser head may be configured to pick up and hold a particle. Alternatively, a dispenser head may be configured to hold a plurality of particles and dispensing only a portion of the held particles. An advantage of using a dispense head is that individual particles or small groups of particles may be placed at precise locations on the sensor array. A variety of different types of dispense heads may be used.

Figure 70A:
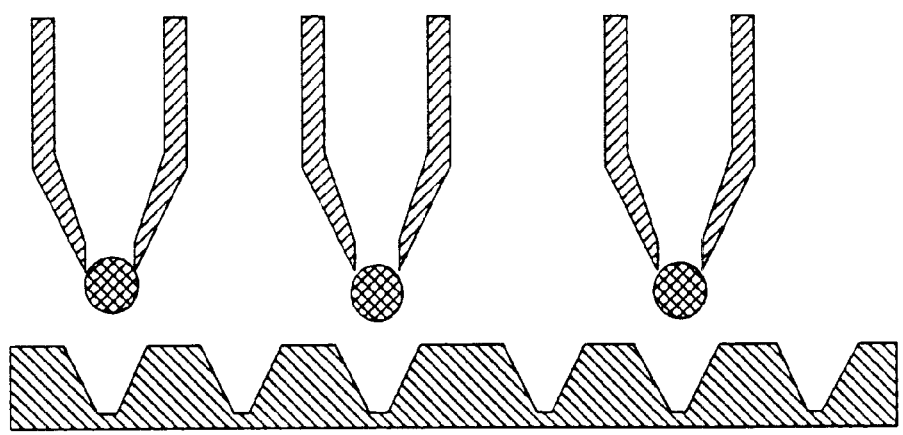
FIGS. 70A–B depict a method of inserting particles into a sensor array using a vacuum pickup dispenser head.
Figure 70B:
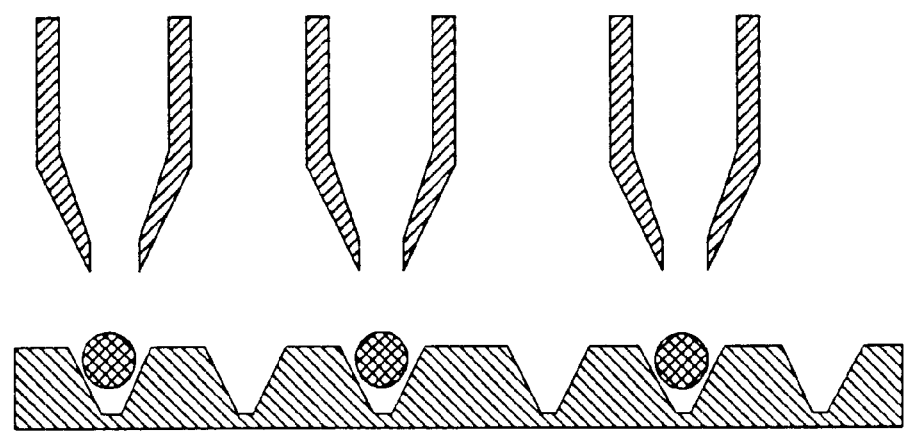

In one embodiment, a vacuum pick-up/dispense head may be used. The dispense head uses a vacuum system to pick up particles. The dispense head may be formed using small diameter tubing, with an inner diameter (ID) smaller than the particle outer diameter (OD). The dispense head may be coupled to a robotic control system via an arm. The robotic control system may be programmed to first move the dispense head to a storage location of the correct particle type, vacuum would be applied to the dispense head once it is "dipped" into the particle storage compartment, thus grasping one particle. The robotic control system would then move the arm such that the dispense head is in a position in close proximity to (or actual contact with) the appropriate location on the sensor array (See FIG. 70A). The dispense head vacuum would then be turned off (i.e., the vacuum would be removed), and if necessary a slight positive pressure could be applied to the dispense head. The particle would thus be dislodged from the dispense head onto the sensor array (See FIG. 70B).

The robotic control system may include a single dispense head or a plurality of dispense heads. The use of a plurality of dispense heads would allow multiple cavities of the sensor array to be filled during a single filing operation. In this manner the efficiency of filling the sensor array may be increased.

Another example of a robotic vacuum pick-up/dispense head is described in U.S. Pat. No. 6,151,973 to Geysen which is incorporated herein by reference.

Figure 71A:
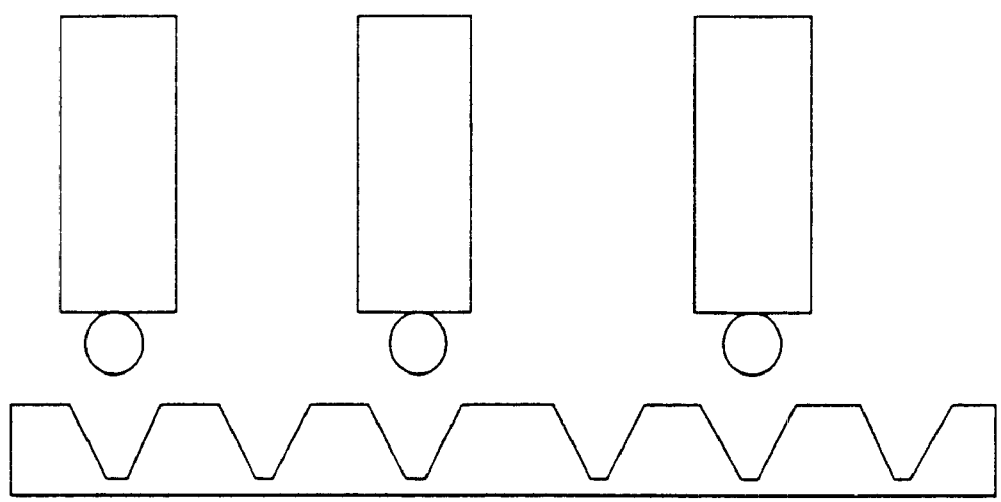
FIGS. 71A–B depict a method of inserting particles into a sensor array using a solid dispenser head.
Figure 71B:
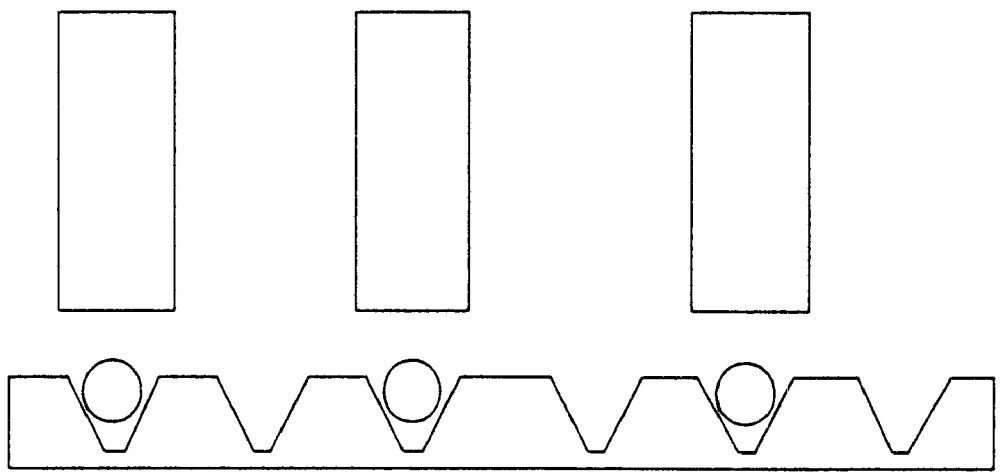

The dispense head could also be in the form of a "solid" pick-up wand. The solid dispense head may rely on natural attractive forces between a particle and the dispense head material to attach a particle to the dispense head. For example, when a particle is placed in close proximity to the dispense head, electrostatic interactions between the particle and the dispense head may cause the particle to "stick" to the dispense head. The dispense head may be placed at the appropriate location over a cavity of the sensor array (See FIG. 71A). When the particle is placed in close proximity to the sensor array, the attractive forces between the chip and particle, along with gravitational forces, may cause the particle to transfer from the dispense head to the sensor array (See FIG. 71B). For example, with PEG particles, a dispense head made of tungsten will cause the PEG particle to attach to the tungsten tip, but the particle may still be transferred to a silicon based sensor array when brought into close proximity of the sensor array. A single solid dispense head or a plurality of solid dispense heads may be used.

In another embodiment, the dispense head could also be formed from one or more "pipettes" with an inner diameter greater than the diameter of the particles. Particles may be delivered directly into the bore of the pipette using a pump/dispense system. Such a system is similar to precision adhesive dispense systems in current use. The particles may be suspended in a liquid (e.g., water), and controlled amounts of the liquid would be pumped through the head to deliver a particle to the appropriate location on the sensor array chip. Such a dispensing system may have difficulties delivering only one particle at a time. Any extra particles, however, may be removed form the sensor array after application. Additionally, by making an array of pipettes the rate of particle placement may be increased. Other advantages of this approach may include the ability to deliver the particles in an aqueous environment if the particle chemistry so requires, as well making the deliver of different particles to each head fast and efficient, since no "pick up" step is required.

The "pipette" system relies on the use of controlled amounts of liquid to transport the particle from a storage area to the tip of the dispense head. In one embodiment, blast of air may be used to force a portion of the liquid toward the dispense head tip. In another embodiment, the dispense head may be made using technology essentially identical to that used in "ink-jet" printer heads. These heads typically rely on bursts of heat to quickly heat the liquid, causing bubbles of the liquid to be forced to the tip of the dispense head.

Once the pick-up/dispense head has delivered a particle or collection of particles to the appropriate location on the sensor array it may be desirable to insure that a single particle be collected at exactly the correct position on the sensor array. This may be accomplished using a vacuum chuck-like effect, as illustrated in FIGS. 72A–72D.

Figure 72A:
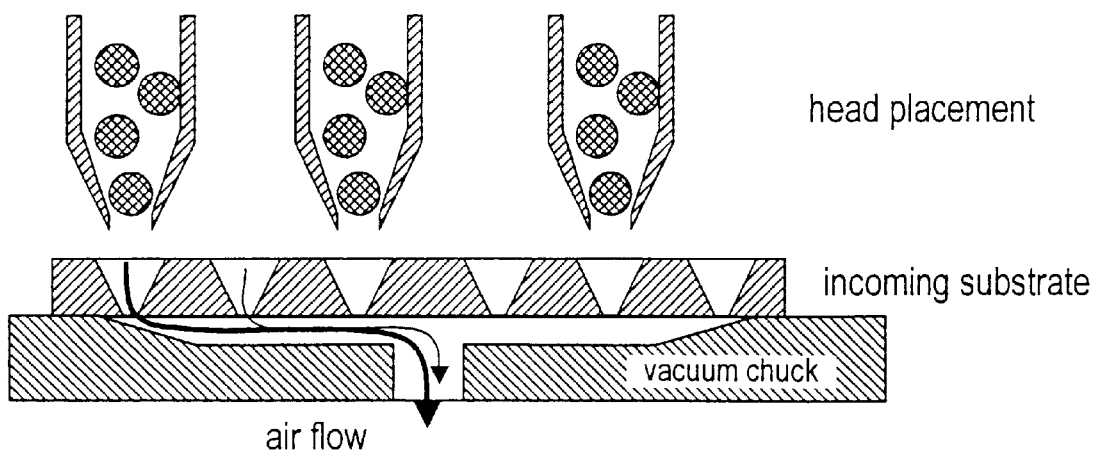
FIGS. 72A–D depict a method of inserting particles into a sensor array using a vacuum chuck.
Figure 72B:
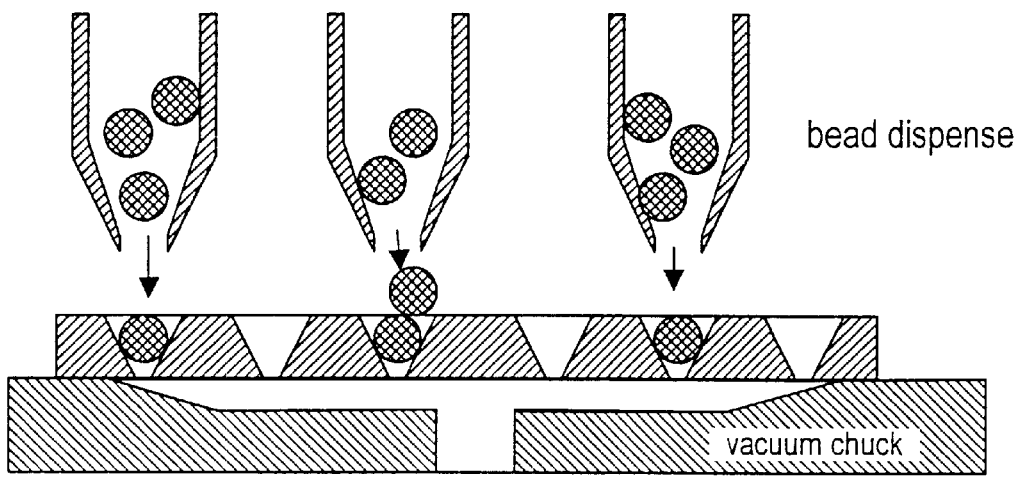
Figure 72C:
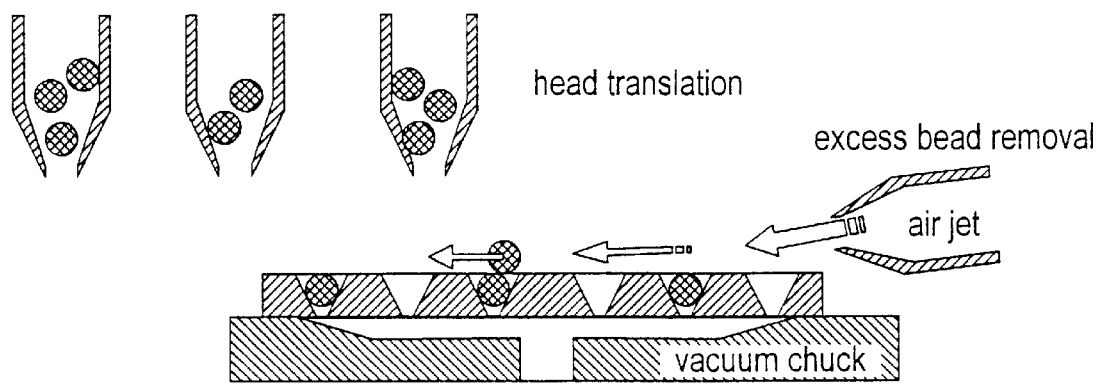
Figure 72D:
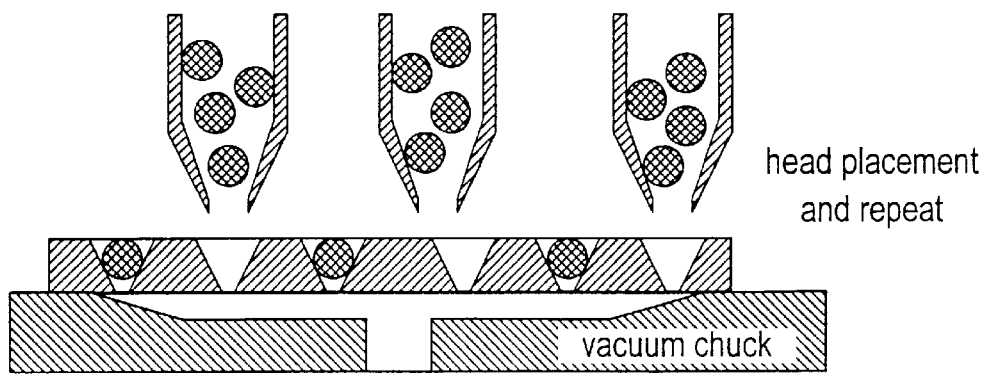

In one embodiment, the sensor array includes cavities used to locate and at least partially contain the particles. When placed on a main vacuum chuck, each individual cavity may also acts as a vacuum chuck. The sensor array, when placed on a vacuum chuck may allow air-flow through the cavities. FIG. 72A depicts a multi-tip dispense head that allows the simultaneous application of many particles. The head is aligned to the cavities in the sensor array using an appropriate mechanical alignment system. If a particle is simply brought into proximity with the cavity, the fluid (e.g., air, but could also be a liquid) flow through the cavity may draw the particle into its proper location and hold it there (as depicted in FIG. 72B). In some embodiments, the dispense head may delivered more than one particle to a given cavity. Only one of the dispensed particles, however, is fully held in place by the vacuum at any give cavity. After the dispense head is moved away from the sensor array, excess particles may be removed using a side-directed jet (air or some other fluid) as depicted in FIG. 72C. The desired particles are held in their storage pits by the pressure differential across pits produced by the vacuum chuck. The process may now be repeated. In FIG. 72D another pipette head is illustrated that dispenses a distinct set of particles from that dispensed by the first head. This may allow more rapid dispensing of a larger variety of particle types.

When the sensor array is placed on a vacuum chuck, the particles may be picked up with a vacuum dispense head. The particles may then be pulled off of the dispense tool when the vacuum of the dispense head is released. The applied vacuum from the vacuum chuck may keep the particles from in the cavities. After the particles have been dispensed, a cover may be disposed on the sensor array to keep the particles in place. The cover may be attached to the sensor array using a pressure sensitive adhesive. After the cover is placed onto the sensor array, the vacuum may be released and the sensor array removed from the vacuum chuck.

Passive Transport of Fluid Samples

For some chemical sensor array systems, fluids may be transported into and across the sensor array during use. In one embodiment, fluids my be transferred into arid through a sensor array using a system that relies on variations in the surface wetting characteristics of a channel. An advantage of such a system is that the system may be "passive" (i.e., no external power source or components). Upon the introduction of a sample, the samples may be drawn into the system and distributed to the particles. This is particularly advantageous for small portable sensor array systems.

In one embodiment, a chemical sensor array is composed of a number of superimposed layers. FIG. 73 depicts a side-sectional view of the sensor array system. A support layer 1010 (e.g., a glass layer) is used as the foundation for the system. A spacer layer 1020 is formed upon the support layer. The support layer may be formed of a relatively inert material using standard semiconductor lithographic techniques. In one embodiment, the support layer may be formed from photoresist (e.g., a dry film photoresist). Alternatively, silicon nitride or silicon dioxide may be used as the spacer layer. The spacer layer may be patterned such that the spacer layer supports an outer portion of an overlying sensor layer 1030. This etching of the spacer layer 1020 may form a channel 1022 under the cavities formed in the sensor layer 1030. This channel 1022, may allow fluids to pass through the cavities and out of the sensor array system.

The sensor layer 1030 includes a number of cavities 1036 for holding a particle 1038. The formation of cavities in a sensor layer has been described earlier. In one embodiment, the sensor layer is formed from silicon. The silicon sensor layer may be partially etched such that an inlet and channel may be formed in the silicon layer. As depicted in FIG. 73 the outer portion of the sensor layer may be thicker than the interior portions. The application of a cover layer 1050, may be accomplished by resting the cover layer on the elevated portions of the sensor layer. This creates a channel 1042 between the cover layer and the sensor layer.

The etched portion of the sensor layer may be divided into segments coupled by a channel. FIG. 74A depicts a top view of the sensor array system and FIG. 74B depicts a bottom view. The first segment 1041 acts as a well or reservoir for the introduction of fluid samples. The second segment 1045 may include a number of cavities, which include particles. The first segment may be coupled to the second segment by one or more channels 1043, formed in the sensor array. The channels allow the fluid to flow from the reservoir to the cavities. The cover layer 1050 may be positioned over the support layer 1010 to form a channel. Materials and methods for forming the cover layer have been described previously.

Referring back to FIG. 73, the conduction of a fluid through the channel may be accomplished using a combination of hydrophobic and hydrophilic surfaces. In one embodiment, a series of hydrophobic segments 1032 are applied to a surface of channels 1022 and 1042. A layer of a hydrophilic material 1034 may be placed on the opposite surface of the channel, with respect to the hydrophobic materials. When an aqueous fluid sample is introduced into the channel, the water is attracted toward the hydrophilic layer while being repelled by the hydrophobic layer. This attraction/repulsion creates a current within the channel. The hydrophilic surfaces may be composed of silicon or hexamethyldisilane. The hydrophobic surfaces may be composed of silicon dioxide, silicon nitride, silicon dinitride, siloxane, or silicon oxynitride. In addition, FIG. 73 depicts a bubble-trap 1035 that may consist of a wall in a hydrophobic region.

Referring back to FIG. 73, the conduction of a fluid through the channel may be accomplished using a combination of hydrophobic and hydrophilic surfaces. In one embodiment, a series of hydrophobic segments 1032 are applied to a surface of channels 1022 and 1042. A layer of a hydrophilic material 1034 may be placed on the opposite surface of the channel, with respect to the hydrophobic materials. When an aqueous fluid sample is introduced into the channel, the water is attracted toward the hydrophilic layer while being repelled by the hydrophobic layer. This attraction/repulsion creates a current within the channel. The hydrophilic surfaces may be composed of silicon or hexamethyldisilane. The hydrophobic surfaces may be composed of silicon dioxide, silicon nitride, silicon dinitride, siloxane, or silicon oxynitride.

The system depicted in FIG. 73 may cause a current to flow in a direction from the left side toward the right. Thus the fluid, introduced at inlet 1040, may flow through the channel 1042 in a direction toward the particles. After contacting the particles, the fluid may pass thorough the cavity and into the lower channel 1022. The hydrophilic and hydrophobic portions of the lower channel may induce a current that cause the fluid to flow toward the outlet of the sensor array system.

Figure 77:
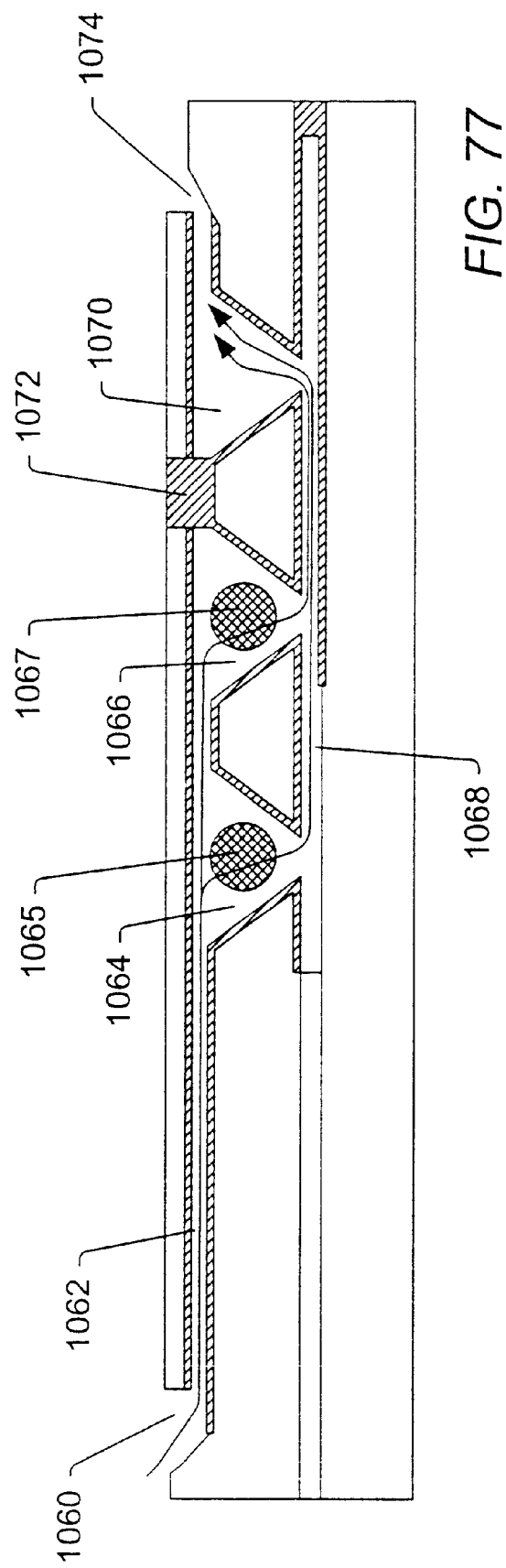
FIG. 77 depicts an alternate cross sectional view of a sensor array which includes a passive transport system.

Likewise, the system depicted in FIG. 77 may cause current to flow in a direction from the left side to toward the right. Alternatively, the fluid may exit through the top portion of the system through the cover. The fluid may be introduced at inlet 1060 and flow through channel 1062. Fluid may then flow through cavity 1064 past particle 1065. The fluid may also flow through cavity 1066 past particle 1067. The wall 1072 prevents the fluid from flowing past cavity 1066 in the in channel 1062. After flowing through the cavities, the fluid flows through channel 1068 and then up through cavity 1070. The hydrophilic and hydrophobic portions of the lower channel may induce a current that cause the fluid to flow toward the outlet 1074 of the sensor array system.

Figure 75D:
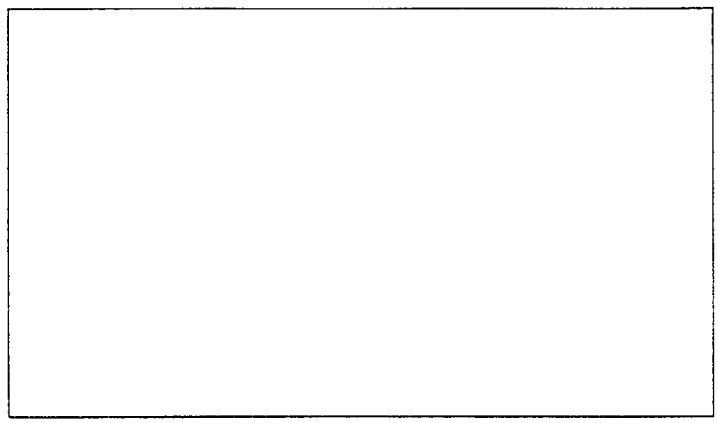
FIGS. 75A–D depict top views of the individual layers used to form a sensor array.

The sensor array may be formed from a plurality of layers. The layers may be assembled with dry film materials and ultraviolet curable epoxy. The support layer serves as a base for the system. The support layer may be formed of a variety of materials including, but not limited to glass, silicon nitride, silicon, silicon dioxide, plastic, and dry film photoresist. The support layer is depicted in FIG. 75D.

Figure 75C:
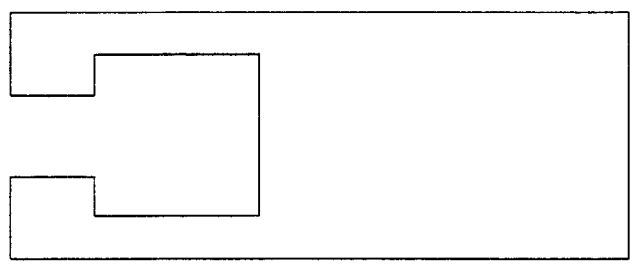

Onto the support layer is formed a spacer layer. The pattern for an embodiment of the spacer layer is depicted in FIG. 75C. The spacer layer maybe placed in the locations that will not be directly under the cavities. The spacer layer may allow a channel to be formed under the sensor array.

Figure 75B:
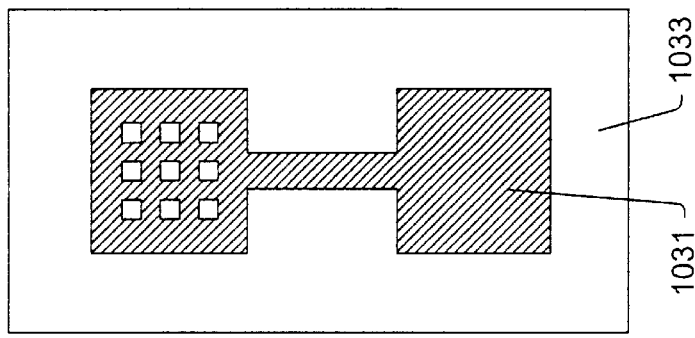

The sensor layer is formed upon the spacer layer. A pattern for the etching of the sensor layer is depicted in FIG. 75B. The shaded areas 1031 represent the portion of the sensor layer that is etched to a thickness that is less than the remaining portion of the sensor layer 1033. The sensor layer may be formed from a variety of materials, including silicon, plastic, and dry film photoresist, as has been described before. The sensor layer may be aligned with the support layer to allow a channel to be formed under the cavities. The channel may allow fluids to pass from the sensor array system.

Figure 75A:
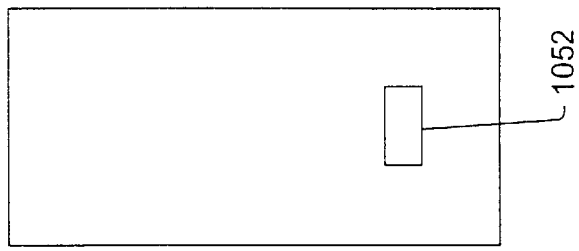

A cover layer is placed over the sensor layer. The etching of the cover layer may allow an upper channel 1042 to be formed between the sensor layer and the cover layer. The cover layer, in one embodiment, includes an opening 1052 that allows a fluid to be passed through the cover layer to the sensor layer. A pattern for the cover layer is depicted in FIG. 75A. The opening may be aligned with a reservoir section of the sensor layer.

Figure 76:
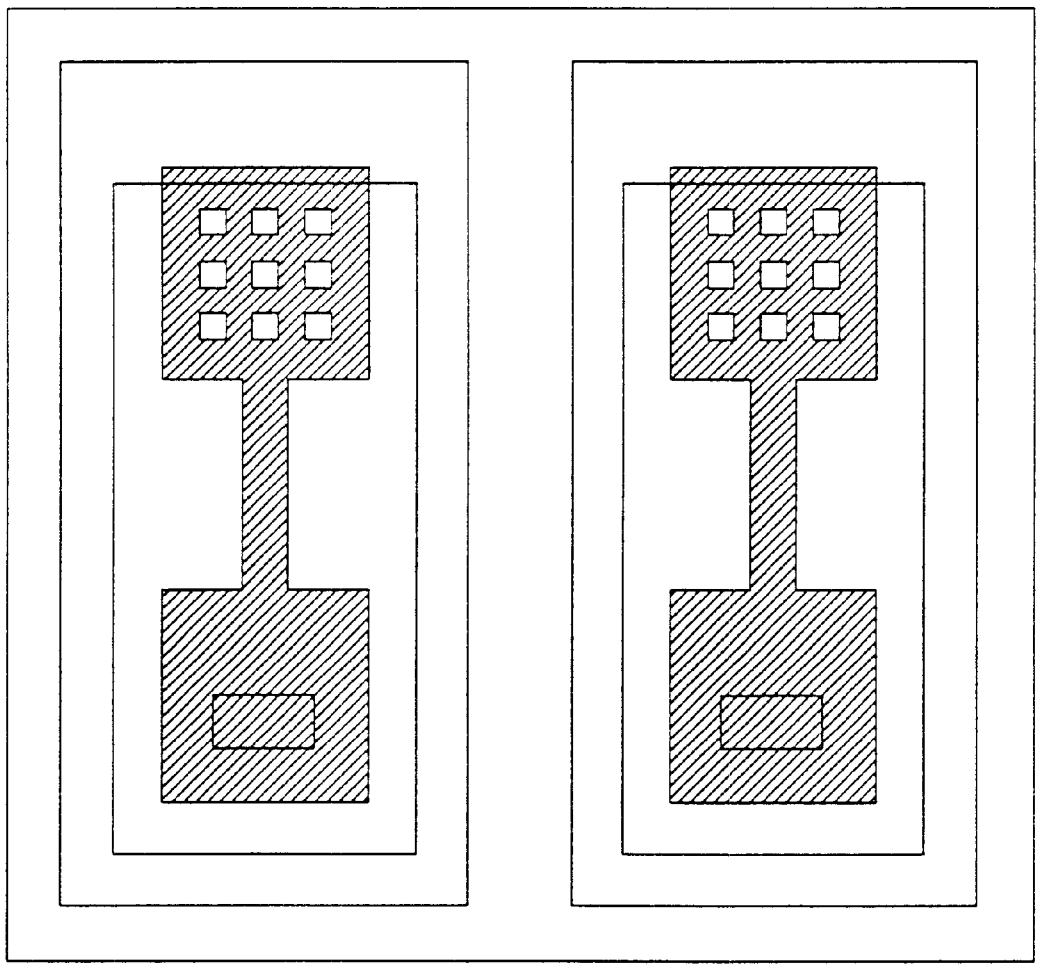
FIG. 76 depicts a top view of a sensor array which includes multiple suites of arrays.

In general, the use of a passive fluid transport system allows only a single use of the sensor array. Although the sensor array may have many chemical particles, and hence has multi-analyte capability, the surface wetting "pump" may only be used once. For many testing situations (e.g., medical testing) this is not a significant problem, since it is desirable to dispose of the sensing element after a single use. If multiple testing of samples is to be performed an "array of arrays" may be used, as depicted in FIG. 76. In this case, multiple sample introduction sites, each coupled to its own suite of sensor sites, may be fabricated. This setup may allow multiple uses of the sensor array (i.e., use one sensor suite for each test) or allow the simultaneous analysis of multiple samples.

Portable Sensor Array System

A sensor array system becomes most powerful when the associated instrumentation may be delivered and utilized at the application site. That is, rather than remotely collecting the samples and bringing them to a centrally based analysis site, it may be advantageous to be able to conduct the analysis at the testing location. Such a system may be use, for example, for point of care medicine, on site monitoring of process control applications, military intelligence gathering devices, environmental monitoring, and food safety testing.

Figure 78:
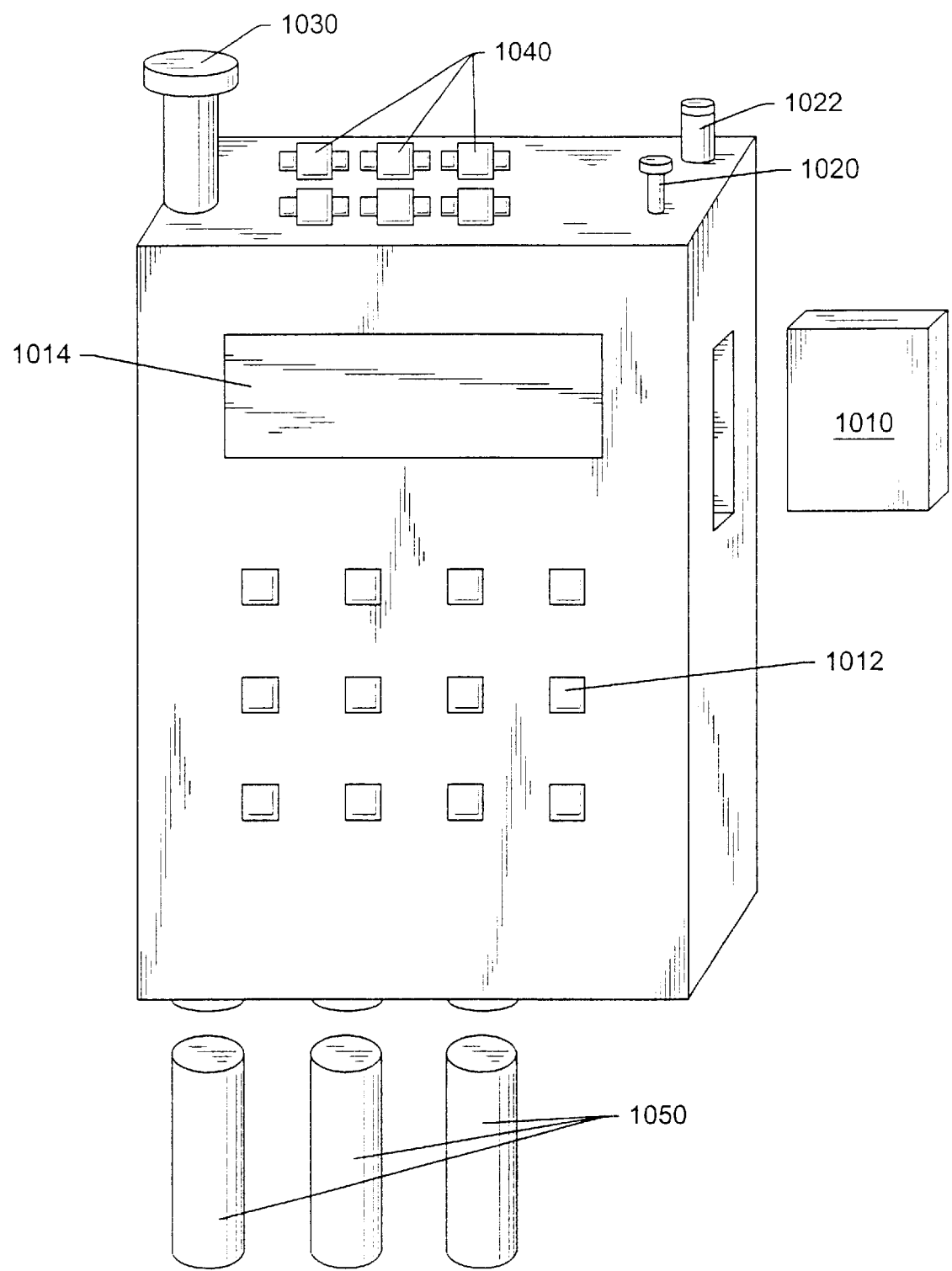
FIG. 78 depicts a portable sensor array system.

An embodiment of a portable sensor array system is depicted in FIG. 78. The portable sensor array system would, in one embodiment, have a size and weight that would allow the device to be easily carried by a person to a testing site. The portable sensor array system includes a light source, a sensor array, and a detector. The sensor array, in some embodiments, is formed of a supporting member which is configured to hold a variety of particles in an ordered array. The particles are, in some embodiments, elements which will create a detectable signal in the presence of an analyte. The particles may include a receptor molecule coupled to a polymeric bead. The receptors may be chosen for interacting with specific analytes. This interaction may take the form of a binding/association of the receptors with the analytes. The supporting member may be made of any material capable of supporting the particles. The supporting member may include a plurality of cavities. The cavities may be formed such that at least one particle is substantially contained within the cavity. The sensor array has been previously described in greater detail.

The portable sensor array system may be used for a variety of different testing. The flexibility of the sensor array system, with respect to the types of testing, may be achieved through the use of a sensor array cartridge. Turning to FIG. 78, a sensor array cartridge 1010 may be inserted into the portable sensor array system 1000 prior to testing. The type of sensor array cartridge used will depend on the type of testing to be performed. Each cartridge will include a sensor array which includes a plurality of chemically sensitive particles, each of the particles including receptors specific for the desired task. For example, a sensor array cartridge for use in medical testing for diabetes may include a number of particles that are sensitive to sugars. A sensor array for use in water testing, however, would include different particles, for example, particles specific for pH and/or metal ions.

The sensor array cartridge may be held in place in a manner analogous to a floppy disk of a computer. The sensor array cartridge may be inserted until it snaps into a holder disposed within the portable sensor system. The holder may inhibit the cartridge from falling out from the portable sensor system and place the sensor in an appropriate position to receive the fluid samples. The holder may also align the sensor array cartridge with the light source and the detector. A release mechanism may be incorporated into the holder that allows the cartridge to be released and ejected from the holder. Alternatively, the portable sensor array system may incorporate a mechanical system for automatically receiving and ejecting the cartridge in a manner analogous to a CD-ROM type system.

The analysis of simple analyte species like acids/bases, salts, metals, anions, hydrocarbon fuels, solvents may be repeated using highly reversible receptors. Chemical testing of these species may be repeatedly accomplished with the same sensor array cartridge. In some cases, the cartridge may require a flush with a cleaning solution to remove the traces from a previous test. Thus, replacement of cartridges for environmental usage may be required on an occasional basis (e.g., daily, weekly, or monthly) depending on the analyte and the frequency of testing Alternatively, the sensor array may include highly specific receptors. Such receptors are particularly useful for medical testing, and testing for chemical and biological warfare agents. Once a positive signal is recorded with these sensor arrays, the sensor array cartridge may need to be replaced immediately. The use of a sensor array cartridge makes this replacement easy.

Fluid samples may be introduced into the system at ports 1020 and 1022 at the top of the unit. Two ports are shown, although more ports may be present. One 1022 may be for the introduction of liquids found in the environment and some bodily fluids (e.g., water, saliva, urine, etc.). The other port 1020 may be used for the delivery of human whole blood samples. The delivery of blood may be accomplished by the use of a pinprick to pierce the skin and a capillary tube to collect the blood sample. The port may be configured to accept either capillary tubes or syringes that include blood samples.

For the collection of environmental samples, a syringe 1030 may be used to collect the samples and transfer the samples to the input ports. The portable sensor array system may include a holder that allows the syringe to be coupled to the side of the portable sensor array system. One of the ports 1020 may include a standard luer lock adapter (either male or female) to allow samples collected by syringe to be directly introduced into the portable sensor array system from the syringe.

The input ports may also be used to introduce samples in a continuous manner. The introduction of samples in a continuous manner may be used, e.g., to evaluate water streams. An external pump may be used to introduce samples into the portable sensor array system in a continuous manner. Alternatively, internal pumps disposed within the portable sensor array system may be activated to pull a continuous stream of the fluid sample into the portable sensor array system. The ports are also configured to allow the introduction of gaseous samples.

In some cases it may be necessary to filter a sample prior to its introduction into the portable sensor array system. For example, environmental samples may be filtered to remove solid particles prior to their introduction into the portable sensor array system. Commercially available nucleopore filters 1040 anchored at the top of the unit may be used for this purpose. In one embodiment, filters 1040 may have luer lock connections (either male or female) on both sides allowing them to be connected directly to an input port and a syringe.

In one embodiment, all of the necessary fluids required for the chemical/biochemical analyses are contained within the portable sensor array system. The fluids may be stored in one or more cartridges 1050. The cartridges 1050 may be removable from the portable sensor array system. Thus, when a cartridge 1050 is emptied of fluid, the cartridge may be replaced by a new cartridge or removed and refilled with fluid. The cartridges 1050 may also be removed and replaced with cartridges filled with different fluids when the sensor array cartridge is changed. Thus, the fluids may be customized for the specific tests being run. Fluid cartridges may be removable or may be formed as an integral part of the reader.

The fluid cartridges 1050 may include a variety of fluids for the analysis of samples. In one embodiment, each cartridge may include up to about 5 mL of fluid and be used for about 100 tests before being depleted. One or more of the cartridges 1050 may include a cleaning solution. The cleaning solution may be used to wash and/or recharge the sensor array prior to a new test. In one embodiment, the cleaning solution may be a buffer solution. Another cartridge 1050 may include visualization agents. Visualization agents may be used to create a detectable signal from the particles of the sensor array after the particles interact with the fluid sample. In one embodiment, visualization agents include dyes (visible or fluorescent) or molecules coupled to a dye, which interact with the particles to create a detectable signal. In an embodiment, a cartridge 1050 may be a vacuum reservoir. The vacuum reservoir may be used to draw fluids into the sensor array cartridge. The vacuum cartridge would act in an analogous manner to the vacutainer cartridges described previously. In another embodiment, a fluid cartridge may be used to collect fluid samples after they pass through the sensor array. The collected fluid samples may be disposed of in an appropriate manner after the testing is completed.

In one embodiment, an alpha-numeric display screen 1014 may be used to provide information relevant to the chemistry/biochemistry of the environment or blood samples. Also included within the portable sensor array system is a data communication system. Such systems include data communication equipment for the transfer of numerical data, video data, and sound data. Transfer may be accomplished using either data or analog standards. The data may be transmitted using any transmission medium such as electrical wire, infrared, RF and/or fiber optic. In one embodiment, the data transfer system may include a wireless link (not shown) that may be used to transfer the digital chemistry/biochemistry data to a closely positioned communications package. In another embodiment, the data transfer system may include a floppy disk drive for recording the data and allowing the data to be transferred to a computer system. In another embodiment, the data transfer system may include a serial or parallel port connection hardware to allow transfer of data to a computer system.

The portable sensor array system may also include a global positioning system ("GPS"). The GPS may be used to track the area that a sample is collected from. After collecting sample data, the data may be fed to a server, which compiles the data along with GPS information. Subsequent analysis of this information may be used to generate a chemical/biochemical profile of an area. For example, tests of standing water sources in a large area may be used to determine the environmental distribution of pesticides or industrial pollutants.

Other devices may also be included in the portable sensor array that are specific for other applications. For example, for medical monitoring devices including but not limited to EKG monitors, blood pressure devices, pulse monitors, and temperature monitors.

The detection system may be implemented in a number of different ways such that all of the detection components fit within the casing of the portable sensor array system. For the optical detection/imaging device, either CMOS or CCD focal plane arrays may be used. The CMOS detector offers some advantages in terms of lower cost and power consumption, while the CCD detector offers the highest possible sensitivity. Depending on the illumination system (see below), either mono-chrome or color detectors may be used. A one-to-one transfer lens may be employed to project the image of the bead sensor array onto the focal plane of the detector. All fluidic components may be sealed away from contact with any optical or electronic components. Sealing the fluids away from the detectors avoids complications that may arise from contamination or corrosion in systems that require direct exposure of electronic components to the fluids under test. Other detectors such as photodiodes, cameras, integrated detectors, photoelectric cells, interferometers, and photomultiplier tubes may be used.

The illumination system for colorimetric detection may be constructed in several manners. When using a monochrome focal plane array, a multi-color, but "discrete-wavelength-in-time" illumination system may be used. The simplest implementation may include several LED's (light emitting diodes) each operating at a different wavelength. Red, green, yellow, and blue wavelength LEDs are now commercially available for this purpose. By switching from one LED to the next, and collecting an image associated with each, colorimetric data may be collected.

It is also possible to use a color focal plane detector array. A color focal plane detector may allow the determination of colorimetric information after signal acquisition using image processing methods. In this case, a "white light" illuminator is used as the light source. "White light" LEDs may be used as the light source for a color focal plane detector. White light LEDs use a blue LED coated with a phosphor to produce a broad band optical source. The emission spectrum of such devices may be suitable for colorimetric data acquisition. A plurality of LEDs may be used. Alternatively a single LED may be used.

Other light sources that may be useful include electroluminescent sources, fluorescent light sources, incandescent light sources, laser lights sources, laser diodes, arc lamps, and discharge lamps. The system may also be configured to use external light source (both natural and unnatural) for illumination.

A lens may be positioned in front of the light source to allow the illumination area of the light source to be expanded. The lens may also allow the intensity of light reaching the sensor array to be controlled. For example the illumination of the sensor array may be made more uniform by the use of a lens. In one example, a single LED light may be used to illuminate the sensor array. Examples of lenses that may be used in conjunction with an LED include Diffusing plate PN K43-717 Lens JML, PN61874 from Edmund scientific.

In addition to calorimetric signaling, chemical sensitizers may be used that produce a fluorescent response. The detection system may still be either monochrome (for the case where the specific fluorescence spectrum is not of interest, just the presence of a fluorescence signal) or color-based (that would allow analysis of the actual fluorescence spectrum). An appropriate excitation notch filter (in one embodiment, a long wavelength pass filter) may be placed in front of the detector array. The use of a fluorescent detection system may require an ultraviolet light source. Short wavelength LEDs (blue to near UV), may be used as the illumination system for a fluorescent based detection system.

In some embodiments, use of a light source may not be necessary. The particles may rely on the use of chemiluminescence, thermoluminescence or piezoluminescence to provide a signal. In the presence of an analyte of interest, the particle may be activated such that the paticles produce light. In the absence of an analyte, the particles may not exhibit produce minimal or no light.

The portable sensor array system may also include an electronic controller which controls the operation of the portable sensor array system. The electronic controller may also be capable of analyzing the data and determining the identity of the analytes present in a sample. While the electronic controller is described herein for use with the portable sensor array system, it should be understood that the electronic controller may be used with an of the previously described embodiments of an analyte detection system.

The controller may be configured to control the various operations of the portable sensor array. Some of the operations that may be controlled or measured by the controller include: (i) determining the type of sensor array present in the portable sensor array system; (ii) determining the type of light required for the analysis based on the sensor array; (iii) determining the type of fluids required for the analysis, based on the sensor array present; (iv) collecting the data produced during the analysis of the fluid sample; (v) analyzing the data produced during the analysis of the fluid sample; (vi) producing a list of the components present in the inputted fluid sample (vii) monitoring sampling conditions (e.g., temperature, time, density of fluid, turbidity analysis, lipemia, bilirubinemia, etc).

Additionally, the controller may provide system diagnostics and information to the operator of the apparatus. The controller may notify the user when routine maintenance is due or when a system error is detected. The controller may also manage an interlock system for safety and energy conservation purposes. For example, the controller may prevent the lamps from operating when the sensor array cartridge is not present.

The controller may also be configured to interact with the operator. The controller preferably includes an input device 1012 and a display screen 1014. A number of operations controlled by the controller, as described above, may be dependent on the input of the operator. The controller may prepare a sequence of instructions based on the type of analysis to be performed. The controller may send messages to the output screen to let the used know when to introduce samples for the test and when the analysis is complete. The controller may display the results of any analysis performed on the collected data on the output screen.

Many of the testing parameters may be dependent upon the type of sensor array used and the type of sample being collected. The controller will, in some embodiments, require the identity of the sensor array and test being performed in order to set up the appropriate analysis conditions. Information concerning the sample and the sensor array may be collected in a number of manners. In one embodiment, the sample and sensor array data may be directly inputted by the user to the controller. Alternatively, the portable sensor array may include a reading device which determines the type of sensor cartridge being used once the cartridge is inserted. In one embodiment, the reading device may be a bar code reader which is configured to read a bar code placed on the sensor array. In this manner the controller can determine the identity of the sensor array without any input from the user. In another embodiment, the reading device may be mechanical in nature. Protrusions or indentation formed on the surface of the sensor array cartridge may act as a code for a mechanical reading device. The information collected by the mechanical reading device may be used to identify the sensor array cartridge. Other devices may be used to accomplish the same function as the bar code reader. These devices include, but are not limited to, smartcard readers and RFID systems.

The controller may also accept information from the user regarding the type of test being performed. The controller may compare the type of test being performed with the type of sensor array present in the portable sensor array system. If an inappropriate sensor array cartridge is present, an error message may be displayed and the portable sensor array system may be disabled until the proper cartridge is inserted. In this manner, incorrect testing resulting from the use of the wrong sensor cartridge may be avoided.

The controller may also monitor the sensor array cartridge and determine if the sensor array cartridge is functioning properly. The controller may run a quick analysis of the sensor array to determine if the sensor array has been used and if any analytes are still present on the sensor array. If analytes are detected, the controller may initiate a cleaning sequence, where a cleaning solution is passed over the sensor array until no more analytes are detected. Alternatively, the controller may signal the user to replace the cartridge before testing is initiated.

Figure 79A:
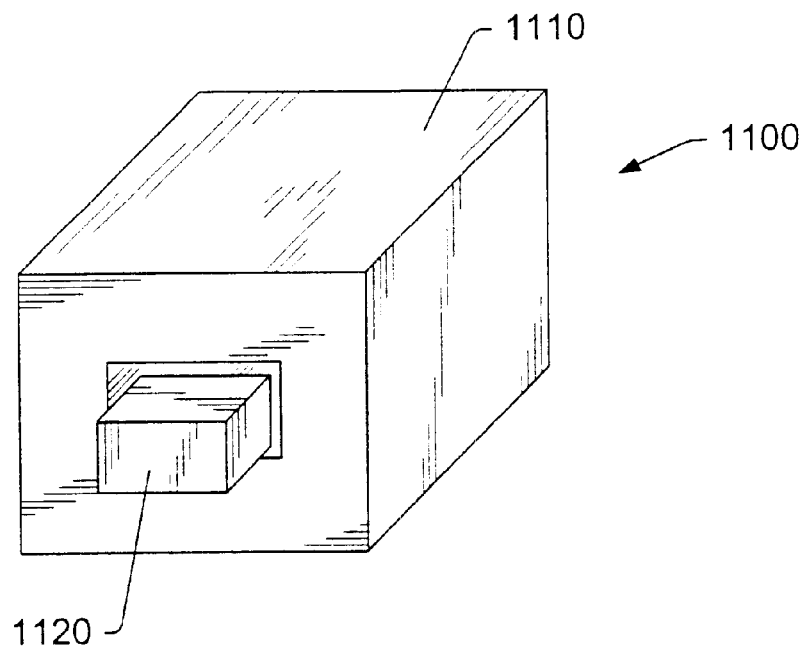
FIGS. 79A–B depict views of an alternate portable sensor array.
Figure 79B:
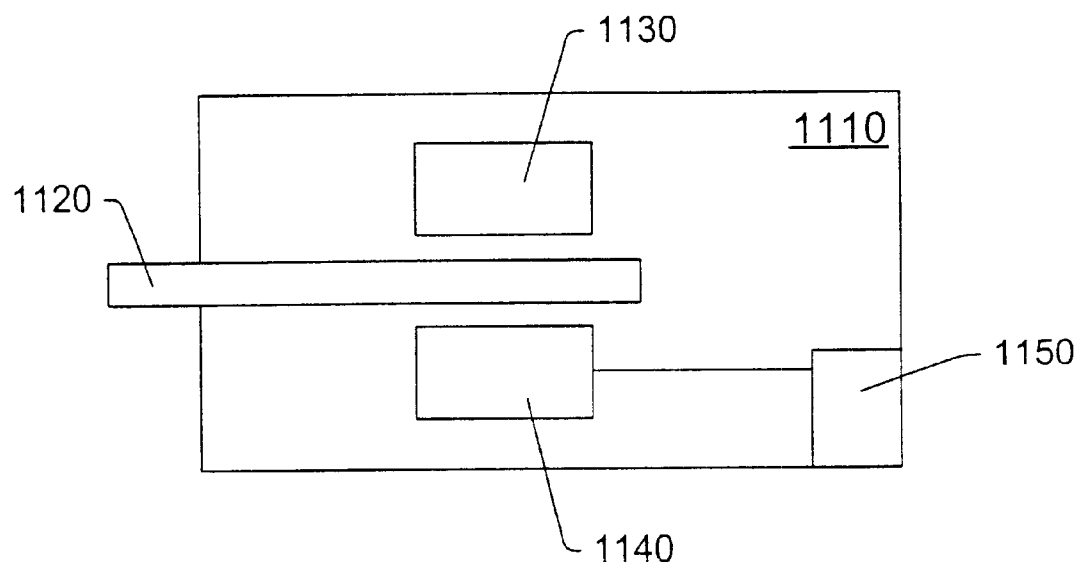

Another embodiment of a portable sensor array system is depicted in FIGS. 79A and 79B. The portable sensor array 1100 includes a body 1110 that holds the various components used with the sensor array system. A sensor array, such as the sensor arrays described herein, may be placed in cartridge 1120. Cartridge 1120 may support the sensor array and allow the proper positioning if the sensor array within the portable sensor system.

A schematic cross-sectional view of the body of the portable sensor array system is depicted in FIG. 79B. The cartridge 1120, in which the sensor array is disposed, extends into the body 1110. Within the body, a light source 1130 and a detector 1140 are positioned proximate to the cartridge 1120. When the cartridge 1120 is inserted into the reader, the cartridge may be held, by the body 1110, at a position proximate to the location of the sensor array within the cartridge. The light source 1130 and detectors 140 may be used analyze samples disposed within the cartridge. An electronic controller 1150 may be coupled to detector. The electronic controller 1150 may be configured to receive data collected by the portable sensor array system. The electronic controller may also be used to transmit data collected to a computer.

Figure 80:
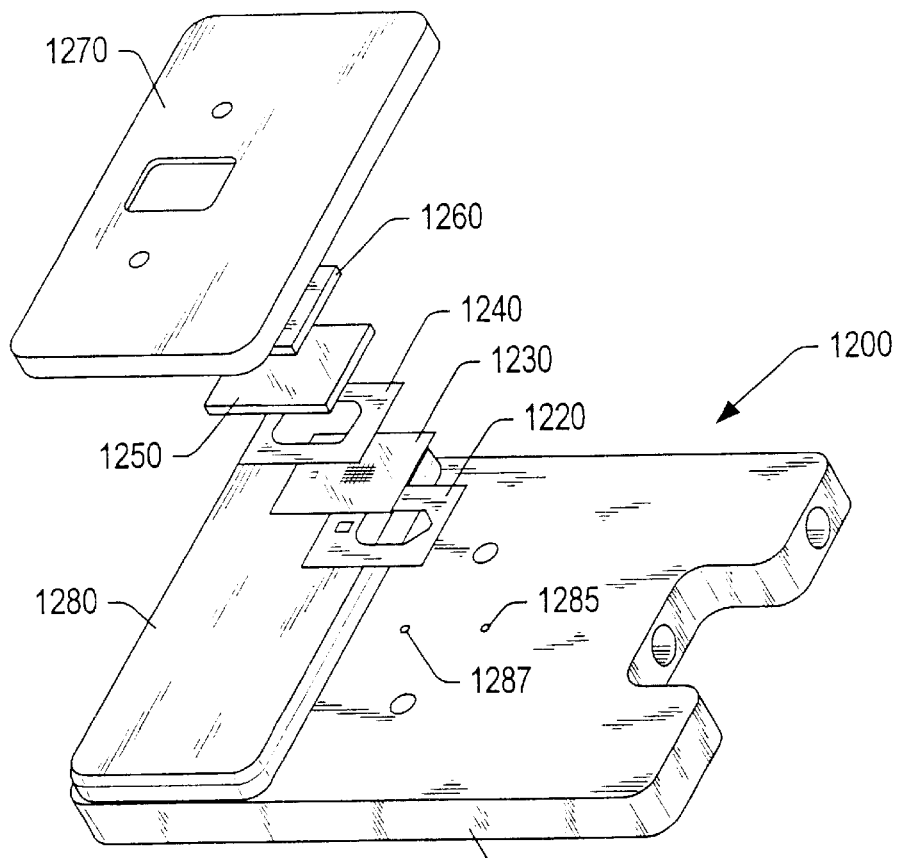
FIG. 80 depicts an exploded view of a cartridge for use in a portable sensor array.

An embodiment of a cartridge for use in a sensor array system is depicted in FIG. 80. The cartridge includes carrier body 1210, which is formed of a material that is substantially transparent to a wavelength of light used by the detector. In one embodiment, plastic materials may be used. Examples of plastic materials that may be used include polycarbonates and polyacrylates. In one embodiment, the body may be formed from Cyrolon AR2 Abrasion Resistant polycarbonate sheet at thicknesses of 0.118 inches and 0.236 inches. A sensor array gasket 1220 may be placed on the carrier body 1210. The sensor array gasket 1220 may help reduce or inhibit the amount of fluids leaking from the sensor array. Leaking fluids may interfere with the testing being performed.

A sensor array 1230 may be placed onto the sensor array gasket. The sensor array may include one or more cavities, each of which includes one or more particles disposed within the cavities. The particles may react with an analyte present in a fluid to produce a detectable signal. Any of the sensor arrays described herein may be used in conjunction with the portable reader.

A second gasket 1240, may be positioned on the sensor array. The second gasket 1240, may be disposed between the sensor array 1230 and a window 1250. The second gasket 1240 may form a seal inhibiting leakage of the fluid from the sensor array. The window may be disposed above the gasket to inhibit damage to the sensor array.

The assembly may be completed by coupling a cover 1270 to the body 1210. A rubber spring 1260 may be disposed between the cover and the window to reduce pressure exerted by the cover on the window. The cover may seal the sensor array, gaskets, and window into the cartridge. The sensor array, gaskets and window may all be sealed together using a pressure sensitive adhesive. Examples of a pressure sensitive adhesive include Optimount 237 made by Seal products. Gaskets may be made from polymeric materials. In one example, Calon II—High Performance material from Arlon may be used. The rubber spring may be made form a silicon rubber material.

The cover may be removable or sealed. When a removable cover is used the cartridge may be reused by removing the cover and replacing the sensor array. Alternatively, the cartridge may be a one use cartridge in which the sensor array is sealed within the cartridge.

Figure 81:
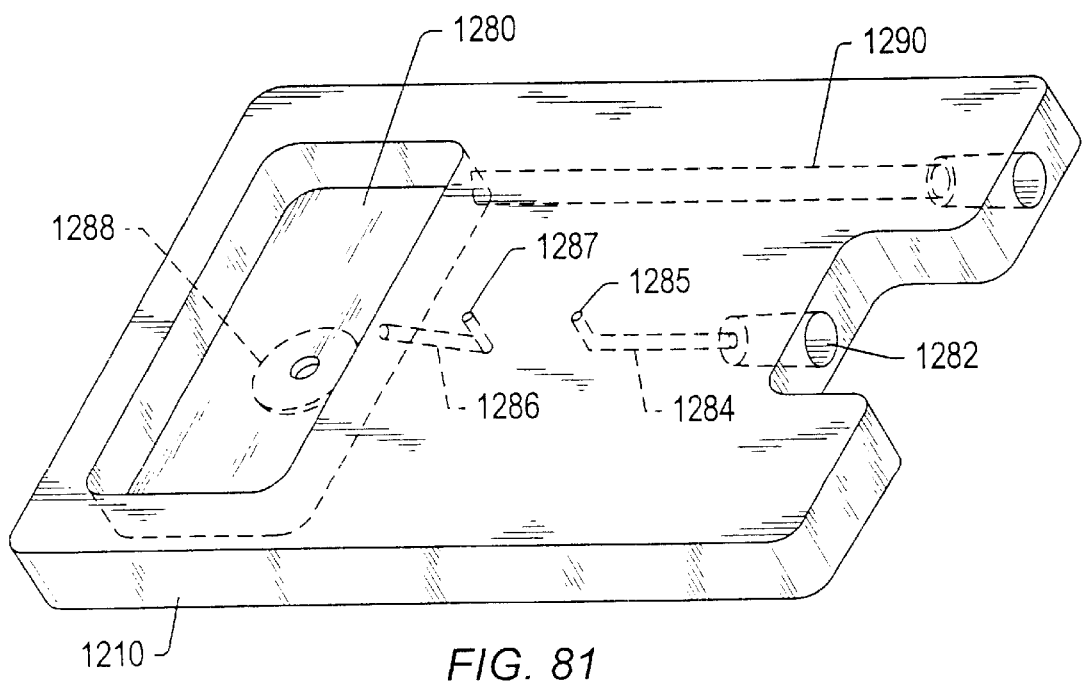
FIG. 81 depicts a cross sectional view of a cartridge for use in a portable sensor array.

The cartridge mar also include a reservoir 1280. The reservoir may be configured to hold the analyte containing fluid after the fluids pass though the sensor array. FIG. 81 depicts a cut away view of the cartridge that shows the positions of channels formed in the cartridge. The channels may allow the fluids to be introduced into the cartridge. The channels also may conduct the fluids from the inlet to the sensor array and to the reservoir.

In one embodiment, the cartridge body 1210, includes a number of channel throughout the body. An inlet port 1282 is configured to receive a fluid delivery device for the introduction of fluid samples into the cartridge. In one embodiment, the inlet port may include a luer lock adapter, configured to couple with a corresponding luer lock adapter on the fluid delivery device. For example, a syringe may be used as the fluid delivery device. The luer lock fitting on the syringe may be coupled with a mating luer lock fitting on the inlet port 1282. Luer lock adapters may also be coupled to tubing, so that fluid delivery may be accomplished by the introduction of fluids through appropriate tubing to the cartridge.

The introduced fluid passes through channel 1284 to channel outlet 1285. Channel outlet 1285 may be coupled to an inlet port on a sensor array (see description of sensor arrays herein). Channel outlet 1285 is also depicted on FIG. 80. The fluids travels into the sensor array and through the cavities. After passing through the cavities, the fluid exits the sensor array and enters channel 1286 via channel inlet 1287. Channel inlet 1287 is also depicted in FIG. 80. The fluid passes through channel 1286 to reservoir 1280 (depicted in both FIGS. 80 and 81). To facilitate the transfer of fluids through the cartridge, the reservoir may include an air outlet port 1288. Air outlet port 1288 may be configured to allow air to pass out of the reservoir, while retaining any fluids disposed within the reservoir. In one embodiment, the air outlet port 1288 may be an opening formed in the reservoir that is covered by a semipermeable membrane. A commercially available air outlet port includes a DURAVENT container vent, available from W. L. Gore. It should be understood, however, that any other material that allows air to pass out of the reservoir, while retaining fluids in the reservoir may be used. After extended use, the reservoir 1280 may become filled with fluids. An outlet channel 1290 may also be formed extending through the body 1210 to allow removal of fluids from the body. Fluid cartridges 1282 for introducing additional fluids into the sensor array may be incorporated into the cartridges.

Magnetic Particle Production and Use

Magnetic particles may be made by different methods. In an embodiment, a solution containing Fe(II) and Fe(III) (typically $FeCl_2$ and $FeCl_3$), and a polymer (e.g. a protein) having available coordination sites may be treated (by titration or otherwise) with a strong base such as aqueous ammonia in order to precipitate magnetic iron oxides such as magnetite ($Fe_3O_4$) in a form which is intimately combined with the polymer. The precipitation may be typically carried out with rapid stirring and optional agitation by sonication, in order to produce resuspendable magnetic-polymer particles.

After precipitation, the particles may be washed and subsequently resuspended in a buffer solution at approximately neutral pH. Other embodiments may involve the use of metals other than iron in the coprecipitation reaction. In particular, Fe(III) may be replaced by any of a wide range of transition metal ions. In some cases, iron may be completely supplanted by appropriately selected transition metal ions. In some cases, the use of metals other than iron produces colored particles ranging from white to dark brown.

Magnetic-polymer particles may be produced of varying size. Magnetic particles may be tailor-made to include specific biofunctional ligands useful in various analytical, diagnostic, and other biological/medical applications. Magnetic particles may be produced with select chemical reagents that may be useful in various analytical applications.

Subsequent to precipitation and resuspension of the magnetic-polymer particles, they may be treated with a bifunctional reagent in order to cross-link reactive sites present on the polymer. This cross-linking may be effective as either an intra-particulate cross-linking in which reactive sites are bound on the same particle, or may be a reaction of an extra-particulate ligand which may then be cross-linked to the polymer on a given particle. In the second case, a bifunctional reagent having a relatively short distance between its two functional groupings may be desirable to promote linkage between the particle polymer and the extra-particulate species. Conversely, intra-particulate cross-linking may be promoted by the use of a bifunctional reagent which may be longer and may not be sterically hindered from bending so that two reactive sites on a single particle may be linked by a single bifunctional molecule.

As an alternative to the use of sonication during either the precipitation or resuspension steps outlined above, another type of agitation (such as mechanical stirring) may be employed.

Resuspension of the magnetic-polymer particles may be typically carried out in a low ionic strength buffer system (e.g. 40 mM phosphate). The buffer system may enable resuspension of particles which are not resuspendable in non-ionic solutions. In addition to phosphate buffers, borate and sulfate systems may also be used. The association of polymer and metal may result from coordination of metal present during coprecipitation by coordination sites on the polymer. It may be that certain coordination sites are more "available" than others, based on both the strength of the coordinate bond which may be formed by the particular atom, and the spatial hindrances imposed by surrounding atoms. It is known, for instance, that oxygen atoms having a "free" electron pair complex iron more strongly than amine nitrogen atoms and, to an even greater degree, a hydroxyl oxygen atom. Thus, a polymer bearing oxy-acid functional groups may provide better product particles than an amine-substituted polymer. Similarly, coordination sites which may be freely approached to close distances may yield better performance than sites which are hindered in either a path of approach or in approach distance.

The above-described trends may be qualitatively observable in various experiments. The presence of "available coordination sites" appears necessary to the production of the resuspendable magnetic-polymer particles. For example, such diverse polymers as natural proteins, synthetic proteins, poly-amino acids, carboxy-poly-alkyls, alkoxy-poly-alkyls, amino-poly-alkyls, hydroxy-poly-alkyls, and various copolymers of these have all been demonstrated to produce suitable particles. In addition, other polymers such as sulfoxy-poly-alkyls, poly-acrylamines, poly-acrylic acid, and substituted poly-alkylenes may produce similar particles.

In selecting the transition metals to be employed in the coprecipitation reaction, several criteria may be important. First, the final compound must have one or more unpaired electrons in its structure. Second, one of the metals must possess an available coordination site for bonding to a polymer. Third, the coprecipitate must be capable of forming a cubic close-packed or hexagonal close-packed (e.g. for cubic: spinel or inverse spinel) crystalline structure. This last requirement may be due to the need for a very close packing in order for a compound to be magnetic.

In an embodiment, polymers useful in preparing the magnetic particles may be "tailor-made" to include monomers which may exhibit a specific biofunctional activity. Using such a polymer may permit direct precipitation of a biofunctional magnetic-polymer particle which may require little or no further treatment in order to be useful in assays which rely on the particular biofunctional activity of the polymer.

In some embodiments, larger, less stable particles may be useful. The particles may be made to agglomerate while still retaining both their biofunctional and magnetic characteristics. Agglomeration of the particles may be accomplished by treatment of a suspension with a predetermined amount of, for example, barium chloride solution. This treatment may be designed to cause the particles to settle out of suspension in a predetermined period of time in order to allow the performance of further procedures, or to allow the larger particles to be easily attracted by relatively small magnets. U.S. Pat. No. 4,795,698 to Owen et al., which is incorporated herein by reference, provides further details for producing magnetic particles.

Magnetic particles may also be produced from metallocenes and metal hydroxide compounds. These particles may then be incorporated into polymeric materials to produce magnetically active particles.

Metallocenes are cycopentadienyl coordinate complexes of metals. The cyclopentadienyl group, $C_5H_5$, has long been known to form complexes with metals or metalloidal atoms. In an embodiment, metallocenes may be cyclopentadienyl complexes of transition metals. The transition-metals may include, for example, iron (Fe), magnesium (Mg), manganese (Mn), cobalt (Co), nickel (Ni), zinc (Zn) and copper (Cu). Particularly useful metallocenes may be ferrocene $(C_5H_5)_2Fe$, nickelocene, $(C_5H_5)_2Ni$, and cobaltocene, $(C_5H_5)_2Co$. Metalloc formula $(C_5H_5)_2$ M, wherein M is the metal and have a "sandwich" configuration. The structure of metallocenes endows these molecules with high thermal stability (e.g., up to about 500° C. for ferrocene).

In an embodiment, an aqueous slurry of the metallocene may be produced. The slurry may be prepared, for example, by combining the metallocene compound and water, and mixing or by milling in a high energy mill, such as a sand mill or a ball mill. The length of time for which the slurries are milled will depend upon the particle size of the product which may be desired. The slurry may generally contain from about 0.1 to about 40 percent (%) by weight of the metallocene. A slurry containing from about 20 to about 25% by weight metallocene may be particularly useful.

The aqueous metallocene slurry may be combined with a second aqueous slurry of a metal hydroxide. The choice of metal hydroxide may depend upon the properties of the particles which may be desired. For example, to produce magnetite particles, iron (II) hydroxide (ferrous hydroxide) may be used. Other metal hydroxides which may be used to produce magnetic particles may include cobalt (II) hydroxide, cobalt (III) hydroxide, iron (III) hydroxide and nickel hydroxide. Slurries of these metal hydroxides may be prepared by precipitating a salt of the metal (e.g. chloride or sulfate salt) in an aqueous medium using a base, such as sodium hydroxide or ammonium hydroxide. An aqueous iron (II) hydroxide slurry may be prepared by precipitating an aqueous solution of ferrous chloride or ferrous sulfate with ammonium or sodium hydroxide to form ferrous hydroxide (FeO(OH)). The resulting gelatinous precipitate of iron (II) hydroxide may be filtered, and the solid material may be collected, combined with water and milled in a high energy mill to form the slurry. The metal hydroxide slurry may contain from about 0.1 to about 40 percent (%) by weight of the metal hydroxide.

The two slurries may be combined and the mixture may be milled in a high energy mill, such as a commercial ball or sand mill, for a period of time sufficient to form fine magnetic particles, generally for about 1 hour to about 60 hours. Generally, the longer the milling step, the smaller the particles which may be formed.

In an embodiment, magnetite particles may be formed from iron (II) hydroxide and ferrocene according to the following equation:

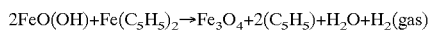

The iron (II) hydroxide powder may be milled in intimate contact with the ferrocene. Over a period of about 20 to 40 hours, the two materials may react by slow dissociation of the hydroxide to form magnetite, free cyclopentene, water and hydrogen. It may be necessary to allow sufficient void space in the mill, or to vent the mill periodically to accommodate the release of the hydrogen gas formed during the reaction. The particles may then be isolated and incorporated into polymeric materials to produce beads comprising magnetic particles. Additional production details may be found in U.S. Pat. No. 5,071,076 to Chagnon et al., which is incorporated herein by reference.

In an embodiment, colloidal polymer or protein magnetite may be prepared with highly controllable, polymer/protein magnetite ratios. Typically, the particles may be precipitated from solutions of hydrated ferric and ferrous chlorides at 3.5 and 1.5 mg/ml, respectively, with protein content ranging from 500 ug/ml to 1.5 mg/ml. After appropriate washing, resuspension and sonication of such precipitates, colloidal, magnetically responsive particles may be produced, wherein the mean diameter of particles may be approximately inversely proportional to starting protein concentrations. Particles about 20 nanometers or less in diameter may be obtained at the higher protein concentrations, whereas particles approximately 100 nanometers in diameter may be obtained at the lower end of the range of protein concentrations. It has been found that the ease with which various of these colloidal solutions may be salted out may be inversely related to the protein concentration of the solution and may be directly related to particle size. In other words, the smaller, higher protein containing particles may be more difficult to salt out. These results suggest that the particles having higher protein concentration may be more lyophilic, which might be expected because of the greater interaction between solvent water and protein, as compared with magnetite. Other possible explanations for this observed phenomenon may be that the magnetic cores of the larger colloidal particles may be easier to flocculate because of their magnetic moments, or that the smaller particles offer relatively larger surface area and consequently more surface charge to be neutralized.

In an embodiment, colloidal, magnetically responsive particles bearing (i) a biospecific binding material having binding affinity for the target substance of interest or (ii) a suitable retrieval agent, for example, anti-fluorescein, where a fluoresceinated receptor for the target substance may be used, may be incubated with an appropriately labeled specific binding substance and test sample suspected of containing the target substance, under conditions such that agglomeration of such particles may not occur. Agglomeration may not occur, for instance, because the binding capacity of the specific binding substance or the concentration of the target substance in the test medium may be too low. Following the binding of sufficient labeled substance (or inhibition thereof), an agglomerating agent, which may be either non-specific, or specific, preferably the former, e.g., a simple salt solution, may be added to the incubation mixture to cause agglomeration. Agglomeration may be brought about by the addition of a second non-specific agglomerating agent, e.g., an appropriately chosen colloid, if desired. Alternatively, agglomeration may be effected by means of a specific agglomerating agent capable of cross-linking a component of the colloidal magnetic particles, such as a specific antibody. The resulting agglomerate may be removed from solution via centrifugation, filtration or, via magnetic separation. It may also be possible to use a non-specific and/or specific agglomerating agents in various combinations, if desired. Thus, second colloid addition plus salting out may be feasible, as may the use of a second magnetically responsive colloidal particle bearing a receptor capable of cross-linking with a substance present on the colloidal protein magnetite initially added to the test sample.

Another useful application of the conversion of colloidal material to a magnetically separable form by the addition of a second colloid, may be to use protein colloidal magnetite as the agglomerating agent for some other non-magnetic colloidal material, where the latter bears the target substance of interest.

Colloidal reagents and non-specific or specific agglomerating agents may be added to the test medium simultaneously, rather than sequentially, as previously described. This may be accomplished by adding a suitable agglomerating agent to one of the colloidal reagents used in the assay, so that conversion of the colloid takes place after a substantial level of ligand/receptor interaction has occurred. Further information on production of magnetic colloidal particles may be found in U.S. Pat. No. 5,108,933 to Liberti et al., which is incorporated herein by reference.

In an embodiment, permanently magnetized materials may be used to produce magnetic particles. Previously discussed agglomeration techniques may be used to form particles in which the particle composition may encapsulate the magnetic material. In an embodiment, the magnetic material may be suspended in a solution from which the particles may be formed. As the particles begin to form, due to agglomeration or other methods, the suspended magnetic material may be encapsulated thereby forming a magnetic particle. Magnetic material may also be incorporated into particles by physical means. In an embodiment, magnetic materials may be intermixed with particles using methods such as, but not limited to ball mills, low intensity mixers, and pug mills. A wide variety of magnetized materials may be used in the magnetic particles. Examples of magnetized materials, besides those materials previously discussed, may include, but are not limited to materials such as alnico, ferrite, barium ferrite, strontium ferrite, neodymium iron boron, samarium cobalt, iron oxide, or other ferromagnetic materials.

Upon formation of the magnetic particle, the magnetic particle may be further modified with target analyte materials. Eventually, the magnetic particles may be placed within the sensor array. In an embodiment, the magnetic particles may be located within the cavity or cavities of a sensor array by placement of permanent magnets in such a manner that the magnetic particle may be directed to a particular location, in this instance, a cavity in the sensor array. In an embodiment, a permanent magnet may be located under a cavity of interest. A solution containing suspended magnetic particles may be allowed to flow over the cavity, wherein a magnetic particle may be directed into the cavity by the interaction of the magnetic particle and the permanent magnet. Depending upon the cavity size, other particles may or may not be directed into the cavity. For example, a cavity only large enough to include one magnetic particle, may capture one particle, but, based upon space limitation, no further particles may be directed into the cavity. Conversely, a cavity large enough to include several particles may have several particles directed toward it before the cavity may no longer capture particles. When the desired cavity or cavities may be filled, a cover layer may be added to the substrate to retain the particles as discussed in previous sections. Directing magnetic particles to magnets for collection or to a particular location are further discussed in U.S. Pat. No. 4,813,277 to Miller, et al, which is incorporated herein by reference.

Permanent magnets may be used to direct magnetic particles into cavities, but other embodiments may be possible. In an embodiment, electromagnets may be located at a desired cavity, such that the magnetic particle may be drawn into the desired cavity. For example, a flow of magnetic particles may be allowed to pass over the sensor array. An electromagnet may be located under a cavity such that as energy may be supplied to the electromagnet, a flowing magnetic particle may be directed into the desired cavity. A plurality of cavities may be located on the sensor array and a discrete electromagnet may be assigned to each cavity. Current flow to each electromagnet may be monitored such that a magnetic particle or particles may be directed to individual cavities. By controlling the electrical current to the electromagnets, some cavities may be filled with magnetic particles while other cavities may remain empty. A second flow of different magnetic particles may be allowed to flow over the sensor array, at which time other electromagnets may be activated thereby causing the different magnetic particles to be directed into the currently empty cavities. This procedure may continue using other different magnetic particles until the selected cavities may be filled. In this way, various cavities may be filled with different magnetic particles. Other embodiments may allow location of multiple magnetic particles within the same cavity thereby providing the ability to detect multiple analytes from the same cavity. Other variations of cavities and particles may be possible wherein the variations may not be limited by the foregoing embodiments. U.S. Pat. No. 5,981,297 to Baselt, which is incorporated herein by reference, further describes the recognition of magnetic particles with magnets.

Formation of Cavities With Retaining Projections

In an embodiment, a mask may be deposited on a bulk crystalline (100) silicon substrate to form an integrated cover layer. The cover layer may be, but is not limited to, silicon nitride, a plastic, silicon dioxide, or a dry film photoresist material. The cover layer may be formed or etched in such a way that, after etching of the silicon substrate, various flexible micromachined projections may be present in the cover layer. Many types of structures formed on the cover layer may provide for development of flexible projections after etching. Examples of structures that may be formed on the cover layer may be, but are not limited to: star; cross; circle; square; or any other type of formation that provides for flexible projections after etching. In an embodiment, a cross, formed by an equal length upright with a transverse beam may be formed in the cover layer. An amount of the cover layer may be removed such that the substrate may be exposed to an etchant material. After removing the desired amount of cover layer, the substrate may be etched anisotropically. The etchant may continue to remove the silicon substrate until the bounding (111) planes may be reached. The resulting cavity may be a pyramidal shape into the silicon substrate. The pyramidal shaped cavity may enhance fluid flow. The cavity may be formed such that a bottom opening may also be present.

The flexible projections formed from the undercutting of the silicon substrate beneath the cover layer may provide a method of retention of the particle. In an embodiment, the flexible projections may be produced from a mask opening which may be smaller than the underlying cavity. The particle may then be manipulated past the flexible projections into the cavity. As the particle passes the flexible projections, the flexible projections may be displaced downward until the particle passes completely by the flexible projections and into the cavity. As the particle passes the flexible projections, the flexible projections may return to their original position, thereby providing retention of the particle in the cavity. Retention of the particle in the cavity may be maintained by the flexible projections during subsequent handling of the sensor array.

Figure 82:
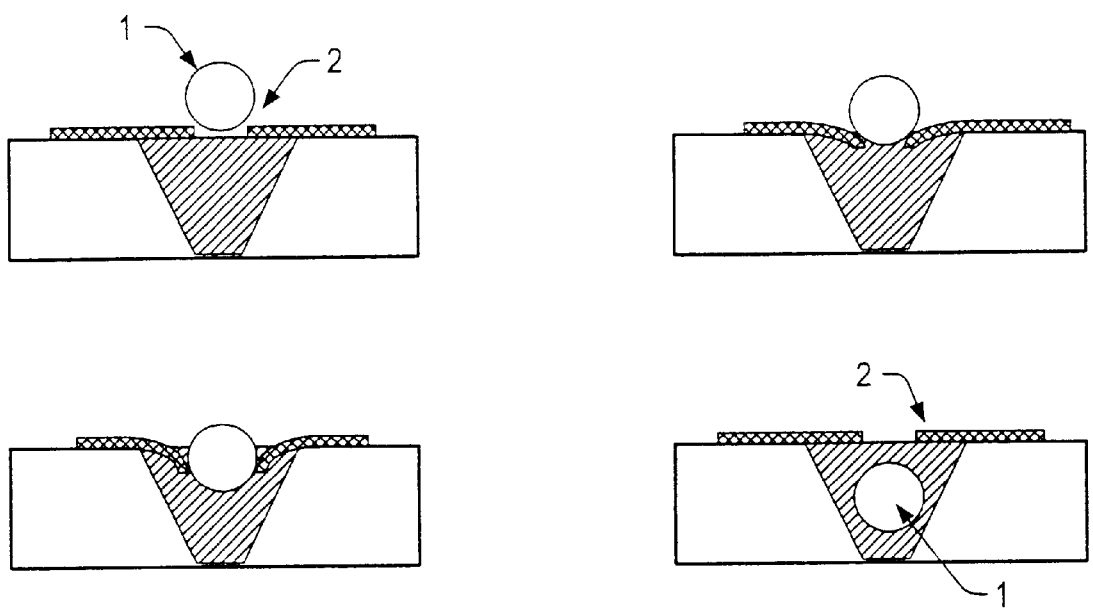
FIG. 82 depicts the placement of a particle into a cavity.

FIG. 82 shows the placement of a particle (1) into a cavity. The particle may be placed proximate to the cavity on top of the flexible projections (2) as shown in (a), at which time a micromanipulator may be used to press the particle past the flexible projections. The flexible projections may bend as the particle may be pressed past the projections, as shown in (b) and (c), until the particle may be placed within the cavity. The flexible projections may return to their normal position, as shown in (d), as the particle moves past the flexible projections and is substantially retained within the cavity.

The flexible projections may provide for specific size selection of particles to be placed into the cavity. In an embodiment, it may be assumed the particles may have a gaussian distribution. In a non-limiting example, an opening may be provided in the cover layer by the flexible projections which may be an opening larger than the mean size of the particle times a sigma value. The sigma value as defined hereinafter is the variability in size of a particle around a mean particle diameter of a gaussian distribution of particles. The bottom opening of the cavity may be an opening smaller than the mean size of the particle times a sigma value. If a 10% sigma value of the particle diameters may be assumed and a 10% sigma value of the top and bottom cavity openings, only the next size up or down may have a chance of filling the cavity. Assuming these variables, the probability for placing a particle the next size up in the cavity may be about one part in one thousand. The probability of placing a particle the next size down in the cavity may be about 1 in 300. Reduction in the variability of the particle size and reduction in the variability in the top and bottom openings of the cavity may result in a higher percentage of correctly sized particles being placed in the cavity.

In an embodiment, another strategy which may be employed with bead capture selectivity probability may be the use of three cavities of a desired size to provide triple redundancy. In this strategy, three cavities of the selected size may be used and selection criteria designed such that if two cavities contain the correct particle size, the cavities may be considered correctly filled. An error may result if two-same sized cavities may be incorrectly filled. The foregoing criteria may provide for a selection of the probability of placing a too large particle of about 1 in $10^6$ and placement of a too small particle of about 1 in 77,000. Error rates may be further reduced by decreasing the variability of the particle diameter and variability in the cavity top and bottom openings.

In an embodiment, a particle may be placed in a cavity using various techniques such as individual placement of particles. Micromanipulators may be used in the individual placement of a particle. A vacuum or flow system may be used to provide for more rapid production of cavity arrays compared to individual placement of particles into cavities. In an embodiment, a wafer may be fabricated with the correct top and bottom cavity openings to select the desired particle size. A solution of particles with a wide range of size distribution may be produced. The wafer may then be dipped into the solution whereupon a vacuum or flow may pull the particles past the cavity top flexible projections. A too large particle may not pass the top opening and a too small particle may pass through the cavity and out the cavity bottom. A correctly sized particle may pass the top opening flexible projections and be retained on the cavity bottom. In the embodiment, the flexible projections may be used as cavity opening discriminators. Flexing of the projections as the particle passes may not be necessary.

A combination of correctly sized flexible projections and particles may be used to produce a backflow preventer and pump. In an embodiment, a cavity may be fabricated such that the slits in the cover layer produce a rectangular bottom opening. The top layer may be fabricated such that a round opening slightly smaller than the particle may be produced. The flexible projections of the bottom opening may be designed for placement of a particle into the cavity. The fluid flow may be inhibited or stopped if the flow direction forces the particle against the round top opening. If the flow is reversed, the particle may be forced against the flexible projections and depending upon the design of the flexible projections, flow may occur or may be significantly inhibited. For example, the flexible projections may be designed such that the slits may be as small as possible resulting in a significant decrease in back-flow capabilities. The effect of this embodiment may produce a valve with a high flow coefficient for flow in one direction and a low flow coefficient in the opposite direction.

The flexible projections may be designed to bend in one direction more favorably than in the opposite direction. In an embodiment, multiple lithography or deposition steps for producing the cover layer may provide a flexible projection which may flex preferably in the direction to allow placement of a particle within the cavity. The flexibility may be reduced in the direction in which the projections may be required to flex for removal of the particle. Providing enhanced flexibility in only one flexural direction may allow reduction of slit size in the cover layer needed to provide etch access to the silicon substrate.

In an embodiment, the flexible projections may be produced by undercutting the silicon substrate as described previously. The top cover flexible projections and bottom cover opening may be fabricated to the diameter desired, such that a particle may only be accepted in a shrunken state. The particle to be placed within the cavity may be exposed to a medium in which the particle may be caused to shrink. The shrunken particle may then be placed within the cavity at which point the particle may be exposed to a medium which causes the particle to return to it's normal diameter state. The particle may then be captured within the cavity. Correctly designing the swollen state of the particle and the flexible projections, the particle may be retained within the cavity subsequent to further processing of the array.

The sensor array may be used as a method for sorting various sized particles. In an embodiment, the sensor array may be fabricated with various sized cavities which may capture various sized particles. Depending upon etch time, the cavity sizes may be configured to different sizes. A shorter etch time may produce a smaller cavity size based upon the depth of the cavity into the substrate.

In an embodiment to provide selection of only one particle size from a distribution of particle sizes, a solution of particles with a wide range of particle size distribution may be allowed to flow over the substrate. A vacuum or flow may be used to pull the particles past the cavities etched into the substrate support. Those particles with a too large diameter may not be captured by a cavity where the top opening may be smaller than the particle diameter. The too large particle may continue to flow across the sensor array. Those particles with a smaller diameter than the bottom opening may be drawn into the cavity as they pass the top opening, but the small diameter particle may pass through the bottom opening and out of the substrate support. Particle sizes smaller than the top opening, but larger than the bottom opening may be drawn into the cavity and retained within the cavity. Those particles larger than the top opening and smaller than the bottom opening may not be retained on the substrate support. The non-retained particles may flow away from the substrate support. The flow may then be stopped and the substrate along with the captured particles may be removed from the flow. A reverse flow may then be used to dislodge the particles into a desired location.

In an embodiment, the array may provide an ability to pick and place many particles at once. The substrate may be fabricated with top and bottom openings designed to select a certain desired particle size. A solution of particles may be flowed over the substrate. Those particles of the desired particle size may be captured by the cavities as discussed in the previous section. The flow may then be stopped and the substrate, along with the captured particles, may be removed from the flow. A reverse flow may then be used to dislodge the particles into a desired location.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for forming a sensor array configured to detect an analyte in a fluid, comprising:

forming a cavity in a supporting member;

placing a particle in the cavity, wherein the particle is configured to produce a signal when the particle interacts with the analyte, and wherein the particle is placed in the cavity using an automated particle dispensing machine; and positioning a cover over the supporting member, wherein the cover is positioned at a fixed distance over the cavity such that a channel is formed between the supporting member and the cover to allow the fluid to enter the cavity via the formed channel wherein the fixed distance is such that the cover inhibits dislodgment of the particle from the cavity during use.

2. The method of claim 1, wherein forming the cavity comprises anisotropically etching a silicon wafer.

3. The method of claim 1, wherein forming the cavity comprises anisotropically etching a silicon wafer such that sidewalls of the cavity are tapered at an angle from about 50 degrees to about 60 degrees.

4. The method of claim 1, wherein the automated particle dispensing machine comprises a vacuum dispenser head.

5. The method of claim 1, wherein the automated particle dispensing machine comprises a vacuum dispenser head, and wherein placing a particle in the cavity comprises:

placing the vacuum dispenser head over the particle;

applying vacuum to the vacuum dispenser head, wherein the applied vacuum causes the particle to become removably attached to the dispenser head;

moving the dispenser head to a position proximate to the cavity; and removing the vacuum, wherein the removal of the vacuum causes the particle to drop into the cavity.

6. The method of claim 1, wherein the automated particle dispensing machine comprises a solid dispenser head.

7. The method of claim 1, wherein the automated particle dispensing machine comprises a solid dispenser head, and wherein placing a particle in the cavity comprises:

placing the solid dispenser head over the particle, wherein the electrostatic interaction between the particle and the dispenser head causes the particle to become removably attached to the dispenser head; and moving the dispenser head to a position proximate to the cavity, wherein the electrostatic interaction between the particle and the cavity causes the particle to fall into the cavity.

8. The method of claim 1, wherein the automated particle dispensing machine comprises a pipette type dispenser head.

9. The method of claim 1, wherein the automated particle dispensing machine comprises a pipette type dispenser head, and wherein placing a particle in the cavity comprises:

placing the particle in a compartment of the pipette type dispenser head, suspending the particle in a liquid;

moving the dispenser head to a position proximate to the cavity; and forcing a portion of the liquid out of the dispenser head, wherein forcing liquid out of the dispenser head causes the particle to drop into the cavity.

10. The method of claim 1, wherein the cover comprises a developed layer of a dry photoresist film.

11. The method of claim 1, wherein the cover comprises plastic, glass, quartz, silicon nitride, or silicon oxide.

12. The method of claim 1, wherein the formed cavity is configured to allow the fluid to pass through the supporting member.

13. The method of claim 1, further comprising forming channels in the supporting member wherein the channels are configured to allow the fluid to pass through the supporting member to and from the cavity.

14. The method of claim 1, further comprising forming a pump on the supporting member, the pump being configured to pump the fluid to the cavity.

15. The method of claim 1, wherein the supporting member comprises a plastic material.

16. The method of claim 1, wherein the supporting member comprises a plastic material, and wherein the cavity is formed by drilling the supporting member.

17. The method of claim 1, wherein the supporting member comprises a plastic material, and wherein the cavity is formed by transfer molding the supporting member.

18. The method of claim 1, wherein the supporting member comprises a plastic material, and wherein the cavity is formed by a punching device.

19. The method of claim 1, wherein the size of the particle ranges from about 0.05 micron to about 500 microns.

20. The method of claim 1, wherein a volume of the particle changes when contacted with the fluid.

21. The method of claim 1, wherein the particle comprises a receptor molecule coupled to a polymeric resin.

22. The method of claim 1, wherein the particle comprises a receptor molecule coupled to a polymeric resin, and wherein the polymeric resin comprises polystyrene-polyethylene glycol-divinyl benzene.

23. The method of claim 1, wherein the particle comprises a receptor molecule coupled to a polymeric resin, and wherein the particles further comprises a first indicator and a second indicator, the first and second indicators being coupled to the receptor, wherein the interaction of the receptor with the analyte causes the first and second indicators to interact such that the signal is produced.

24. The method of claim 1, wherein the particle comprises a receptor molecule coupled to a polymeric resin, and wherein the particles further comprises an indicator, wherein the indicator is associated with the receptor such that in the presence of the analyte the indicator is displaced from the receptor to produce the signal.

25. The method of claim 1, further comprising coating an inner surface of the cavity with a material to increase adhesion of the particle to the inner surface of the cavity.

26. The method of claim 1, further comprising coating an inner surface of the cavity with a material to increase reflectivity of the inner surface of the cavity.

27. The method of claim 1, further comprising forming an optical detector upon a bottom surface of the supporting member below the cavity.

28. The method of claim 1, wherein the fixed distance over the cavity is substantially less than a width of the particle.

* * * * *

UNITED STATES PATENT AND TRADEMARK OFFICE
CERTIFICATE OF CORRECTION

PATENT NO. : 6,649,403 B1  
DATED : November 18, 2003  
INVENTOR(S) : McDevitt et al.

It is certified that error appears in the above-identified patent and that said Letters Patent is hereby corrected as shown below:

Title page,
Item [75], Inventor, "John T. McDevitt", please delete "Travis, TX (US)" and substitute therefor -- Austin, TX (US) --; and "Dean P. Neikirk", please delete "Travis, TX (US)" and substitute therefor -- Austin, TX (US) --.

Column 120,
Lines 26 and 33, please delete "particles" and substitute therefor -- particle --.

Signed and Sealed this

Twenty-seventh Day of April, 2004

JON W. DUDAS  
*Acting Director of the United States Patent and Trademark Office*